United States Patent
Kato et al.

(10) Patent No.: US 10,411,192 B2
(45) Date of Patent: Sep. 10, 2019

(54) AROMATIC AMINE COMPOUND, ORGANIC ELECTROLUMINESCENT ELEMENT AND ELECTRONIC DEVICE

(71) Applicant: IDEMITSU KOSAN CO., LTD., Chiyoda-ku (JP)

(72) Inventors: Tomoki Kato, Ichihara (JP); Masakazu Funahashi, Chiba (JP); Takahiro Fujiyama, Kisarazu (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 472 days.

(21) Appl. No.: 14/910,591

(22) PCT Filed: Oct. 10, 2014

(86) PCT No.: PCT/JP2014/077266
§ 371 (c)(1),
(2) Date: Feb. 5, 2016

(87) PCT Pub. No.: WO2015/053403
PCT Pub. Date: Apr. 16, 2015

(65) Prior Publication Data
US 2016/0181526 A1 Jun. 23, 2016

(30) Foreign Application Priority Data
Oct. 11, 2013 (JP) .................. 2013-214094

(51) Int. Cl.
| | | |
|---|---|---|
| H01L 51/00 | (2006.01) | |
| C07C 211/61 | (2006.01) | |
| C07D 307/91 | (2006.01) | |
| C09K 11/06 | (2006.01) | |
| C07D 405/14 | (2006.01) | |
| C07D 487/14 | (2006.01) | |
| C07D 333/76 | (2006.01) | |
| C07D 235/08 | (2006.01) | |
| C07D 403/14 | (2006.01) | |
| C07D 405/10 | (2006.01) | |
| C07D 407/10 | (2006.01) | |
| C07D 407/12 | (2006.01) | |
| C07D 407/14 | (2006.01) | |

(Continued)

(52) U.S. Cl.
CPC .......... *H01L 51/006* (2013.01); *C07C 211/55* (2013.01); *C07C 211/61* (2013.01); *C07D 235/08* (2013.01); *C07D 307/91* (2013.01); *C07D 333/76* (2013.01); *C07D 403/14* (2013.01); *C07D 405/10* (2013.01); *C07D 405/14* (2013.01); *C07D 407/10* (2013.01); *C07D 407/12* (2013.01); *C07D 407/14* (2013.01); *C07D 487/14* (2013.01); *C09K 11/06* (2013.01); *H01L 51/0052* (2013.01); *H01L 51/0061* (2013.01); *H01L 51/0072* (2013.01); *H01L 51/0073* (2013.01); *C07C 2603/18* (2017.05); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1088* (2013.01); *C09K 2211/1092* (2013.01); *H01L 51/0054* (2013.01); *H01L 51/0058* (2013.01); *H01L 51/0065* (2013.01); *H01L 51/0067* (2013.01); *H01L 51/5012* (2013.01); *H01L 51/5016* (2013.01); *H01L 51/5056* (2013.01); *H01L 51/5064* (2013.01)

(58) Field of Classification Search
CPC ..... H01L 5/0052; H01L 5/006; H01L 5/0061; H01L 5/0065; H01L 5/0072; H01L 5/0073; H01L 5/5056; H01L 5/5064; H01L 5/5068; C07C 211/55; C07C 211/61; C07D 307/91; C07D 333/76; C09K 11/06; C09K 2211/1007; C09K 2211/1011; C09K 2211/1088; C09K 2211/1092
USPC .................. 428/690, 917; 257/40, E51.051; 548/440; 549/460; 564/308
See application file for complete search history.

(56) References Cited

U.S. PATENT DOCUMENTS

| | | | |
|---|---|---|---|
| 2006/0069287 | A1 | 3/2006 | Kubo et al. |
| 2009/0200926 | A1 | 8/2009 | Lee et al. |
| 2009/0302758 | A1 | 12/2009 | Saitoh et al. |

(Continued)

FOREIGN PATENT DOCUMENTS

| | | | |
|---|---|---|---|
| EP | 2 067 767 A1 | 6/2009 | |
| EP | 2 075 309 A2 | 7/2009 | |

(Continued)

OTHER PUBLICATIONS

International Search Report dated Dec. 16, 2014 in PCT/JP14/077266 Filed Oct. 10, 2014.

(Continued)

*Primary Examiner* — Ruiyun Zhang
(74) *Attorney, Agent, or Firm* — Oblon, McClelland, Maier & Neustadt, L.L.P.

(57) ABSTRACT

An aromatic amine derivative having a specific structure, an organic electroluminescence device, and an electronic equipment are provided. The organic electroluminescence device includes organic thin film layers which include a light emitting layer and are disposed between a cathode and an anode. At least one layer of the organic thin film layers includes the aromatic amine derivative. The organic electroluminescence device can be operated at low driving voltage and has high efficiency. The compound achieves the above organic electroluminescence device.

31 Claims, No Drawings

(51) Int. Cl.
*C07C 211/55* (2006.01)
*H01L 51/50* (2006.01)

(56) References Cited

U.S. PATENT DOCUMENTS

| | | |
|---|---|---|
| 2010/0019657 A1 | 1/2010 | Eum et al. |
| 2012/0012832 A1* | 1/2012 | Yabunouchi .......... C07C 211/61 257/40 |
| 2013/0207046 A1 | 8/2013 | Pflumm et al. |
| 2014/0312287 A1 | 10/2014 | Stoessel et al. |
| 2014/0374722 A1 | 12/2014 | Kim et al. |
| 2015/0155491 A1 | 6/2015 | Mujica-Fernaud et al. |
| 2015/0179940 A1 | 6/2015 | Mujica-Fernaud et al. |
| 2015/0179953 A1 | 6/2015 | Mujica-Fernaud et al. |
| 2015/0207075 A1 | 7/2015 | Mujica-Fernaud et al. |
| 2015/0287921 A1 | 10/2015 | Kato et al. |
| 2015/0295181 A1 | 10/2015 | Mujica-Fernaud et al. |

FOREIGN PATENT DOCUMENTS

| | | |
|---|---|---|
| KR | 101251451 | 4/2013 |
| KR | 10-2013-0078439 | 7/2013 |
| KR | 10-2013-0121516 | 11/2013 |
| WO | 2004/024670 A1 | 3/2004 |
| WO | 2007/123259 A1 | 11/2007 |
| WO | 2012/034627 A1 | 3/2012 |
| WO | 2013/087142 A1 | 6/2013 |
| WO | 2013/109027 A1 | 7/2013 |
| WO | 2013/118846 A1 | 8/2013 |
| WO | WO 2013/182263 A1 | 12/2013 |
| WO | 2014/015935 A2 | 1/2014 |
| WO | 2014/015937 A1 | 1/2014 |
| WO | 2014/015938 A1 | 1/2014 |
| WO | 2014/072017 A1 | 5/2014 |

OTHER PUBLICATIONS

Extended European Search Report dated Feb. 20, 2017 in Patent Application No. 14852470.5.
Office Action dated Aug. 23, 2016, in Japanese Patent Application No. 2015-541658.
Office Action dated Mar. 13, 2019, in Korean Patent Application No. 10-2016-700291, filed Oct. 10, 2014 w/English translation.

\* cited by examiner

AROMATIC AMINE COMPOUND, ORGANIC ELECTROLUMINESCENT ELEMENT AND ELECTRONIC DEVICE

TECHNICAL FIELD

The present invention relates to aromatic amine compounds and organic electroluminescence devices employing the compounds, and also relates to electronic equipment including the organic electroluminescence devices.

BACKGROUND ART

An organic EL device is a spontaneous light emitting device which utilizes the principle that holes injected from an anode and electrons injected from a cathode are recombined in response to the applied electric field and the recombination energy causes the light emission from a fluorescent substance. Therefore, it is important for increasing the efficiency of an organic EL device to develop a compound which transports electrons or holes into a light emitting zone efficiently and facilitates the recombination of electrons and holes.

The device performance of organic EL devices has been improved by making a hole transporting layer into two-layered structure which includes a first hole transporting layer and a second hole transporting layer from the anode side. The first hole transporting layer is generally required to be excellent in the hole injection ability into the second hole transporting layer.

For example, Patent Literature 1 discloses an organic EL device wherein a monoamine compound having an ortho-substituted phenyl group is used as the material for the layer adjacent to the light emitting layer.

Patent Literature 2 discloses an organic EL device wherein a monoamine having a fluorene group is used as the material for the first hole transporting layer.

CITATION LIST

Patent Literature

PATENT LITERATURE 1: WO 2013/087142
PATENT LITERATURE 1: WO 2013/118846

SUMMARY OF INVENTION

Technical Problem

The present invention intends to provide an organic EL device which is operated by a low voltage drive and has higher efficiency, electronic equipment including such an organic EL device, and a compound which provides such an organic EL device.

Solution to Problem

As a result of extensive research in view of developing a compound having the above favorable properties and an organic EL device employing such a compound, the inventors have found that the above problem is solved by the compound represented by formula 01 The present invention is based on this finding.

In an aspect of the invention, a compound represented by formula (1) is provided:

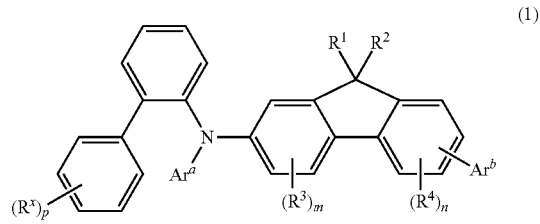

wherein $Ar^a$ represents an aryl group having 6 to 50 ring carbon atoms, a heteroaryl group having 5 to 50 ring atoms, or a group in which two to four groups selected from the aryl group and the heteroaryl group are linked;

$R^1$ and $R^2$ each independently represent a hydrogen atom, an alkyl group having 1 to 10 carbon atoms, or an aryl group having 6 to 12 ring carbon atoms, and $R^1$ and $R^2$ may be bonded to each other to form a hydrocarbon ring;

$R^x$, $R^3$ and $R^4$ each represent an alkyl group having 1 to 10 carbon atoms, a cycloalkyl group having 3 to 10 ring carbon atoms, or an aryl group having 6 to 30 ring carbon atoms;

p represents an integer of 0 to 3, m and n each independently represent an integer of 0 to 2, $R^3$ and $R^4$ may be bonded to each other to form a hydrocarbon ring, and when m or n is 2, adjacent groups $R^3$ or adjacent groups $R^4$ may be bonded to each other to form a hydrocarbon ring; and $Ar^b$ represents an aryl group having 6 to 18 ring carbon atoms.

In another aspect, the invention provides a material for organic EL devices and a hole transporting material for organic EL devices each comprising the compound mentioned above. The hole transporting material for organic EL devices is particularly useful as a hole transporting material for an organic EL device having an hole transporting layer adjacent to an acceptor layer.

In still another aspect, the invention provides an organic EL device which comprises an organic thin film layer between a cathode and an anode, wherein the organic thin film layer comprises one or more layers comprising a light emitting layer and at least one layer of the organic thin film layer comprises the compound represented by formula (1) alone or in combination.

In still another aspect, the invention provides an electronic equipment comprising the organic EL device mentioned above.

Advantageous Effects of Invention

An organic EL device employing the compound of the invention as the material for organic EL devices can be operated by lower voltage drive and has high emission efficiency.

The compound of the invention is a hole transporting material having a high mobility enough to prevent the increase in the driving voltage even when the thickness of a hole transporting layer in organic EL device is increased, and therefore, makes it easy to adjust the optical path length of organic EL device and is capable of providing an organic EL device with a high efficiency.

In particular, when the compound is used as a hole transporting material for an organic EL device wherein an acceptor layer is bonded to an anode, the amount of hole injection from the acceptor layer to the hole transporting layer is increased because of a high compatibility of the compound with the acceptor material, thereby enhancing the above effect.

DESCRIPTION OF EMBODIMENTS

The term "a to b carbon atoms" referred to by "a substituted or unsubstituted group X having a to b carbon atoms" used herein is the number of carbon atoms of the unsubstituted group X and does not include any carbon atom in the substituent of the substituted group X.

The number of "ring carbon atoms" referred to herein is the number of the carbon atoms which form a saturated ring, an unsaturated ring, or an aromatic ring, and the carbon atom in a substituent on the ring is not included in the ring carbon atom.

The number of "ring atom" referred to herein is the number of the atoms which form a saturated ring, an unsaturated ring, or an aromatic ring, and a hydrogen atom and the atom in a substituent on the ring are not included in the ring atom.

The definition of "hydrogen atom" used herein includes isotopes different in the neutron numbers, i.e., light hydrogen (protium), heavy hydrogen (deuterium), and tritium.

The optional substituent referred to by "substituted or unsubstituted" used herein is, unless otherwise defined, preferably selected from the group consisting of an alkyl group having 1 to 20, preferably 1 to 10, more preferably 1 to 6 carbon atoms; a cycloalkyl group having 3 to 20, preferably 3 to 6, more preferably 5 or 6 ring carbon atoms; an aryl group having 6 to 30, preferably 6 to 24, more preferably 6 to 12 ring carbon atoms; an aralkyl group having 7 to 30, preferably 7 to 10, more preferably 7 to 12 carbon atoms having an aryl group having 6 to 30, preferably 6 to 24, more preferably 6 to 12 ring carbon atoms; an amino group; a mono- or dialkylamino group having an alkyl group having 1 to 20, preferably 1 to 10, more preferably 1 to 6 carbon atoms; a mono- or diarylamino group having an aryl group having 6 to 30, preferably 6 to 24, more preferably 6 to 12 ring carbon atoms; an alkoxy group having an alkyl group having 1 to 30, preferably 1 to 10, more preferably 1 to 6 carbon atoms; an aryloxy group having an aryl group having 6 to 30, preferably 6 to 24, more preferably 6 to 12 ring carbon atoms; a mono-, di- or tri-substituted silyl group, wherein the substituent is selected from an alkyl group having 1 to 20, preferably 1 to 10, more preferably 1 to 6 and an aryl group having 6 to 30, preferably 6 to 24, more preferably 6 to 12 ring carbon atoms; a heteroaryl group having 5 to 30, preferably 5 to 24, more preferably 5 to 12 ring atoms, which comprise 1 to 5, preferably 1 to 3, more preferably 1 to 2 heteroatoms, such as a nitrogen atom, an oxygen atom, and a sulfur atom; a haloalkyl group having 1 to 20, preferably 1 to 10, more preferably 1 to 6 carbon atoms; a halogen atom, such as a fluorine atom, a chlorine, a bromine atom, and a iodine atom; a cyano group; and a nitro group.

Of the above, a substituent selected from the group consisting of an alkyl group having 1 to 6 carbon atoms, a cycloalkyl group having 5 or 6 carbon atom, and an aryl group having 6 to 12 ring carbon atoms is more preferred.

These optional substituents may further include a substituent mentioned above.

The number of the substituent referred to by "substituted or unsubstituted" may be one or more. When two or more substituents occur, these substituents may be the same or different.

In the present invention, the features which are defined as being preferred can be selected arbitrarily and a combination thereof is a more preferred embodiment.

The compound of the invention is represented by formula (1):

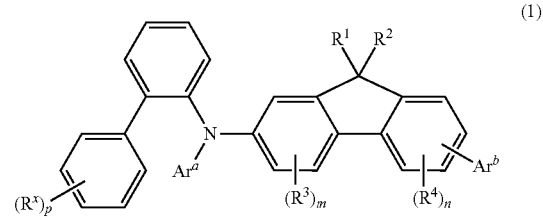

wherein $Ar^a$ represents an aryl group having 6 to 50 ring carbon atoms, a heteroaryl group having 5 to 50 ring atoms, or a group in which two to four groups selected from the aryl group and the heteroaryl group are linked;

$R^1$ and $R^2$ each independently represent a hydrogen atom, an alkyl group having 1 to 10 carbon atoms, or an aryl group having 6 to 12 ring carbon atoms, and $R^1$ and $R^2$ may be bonded to each other to form a hydrocarbon ring;

$R^x$, $R^3$ and $R^4$ each represent an alkyl group having 1 to 10 carbon atoms, a cycloalkyl group having 3 to 10 ring carbon atoms, or an aryl group having 6 to 30 ring carbon atoms;

p represents an integer of 0 to 3, m and n each independently represent an integer of 0 to 2, $R^3$ and $R^4$ may be bonded to each other to form a hydrocarbon ring, and when m or n is 2, adjacent groups $R^3$ or adjacent groups $R^4$ may be bonded to each other to form a hydrocarbon ring; and $Ar^b$ represents an aryl group having 6 to 18 ring carbon atoms.

The compound represented by formula (1) is preferably represented by formula (1'):

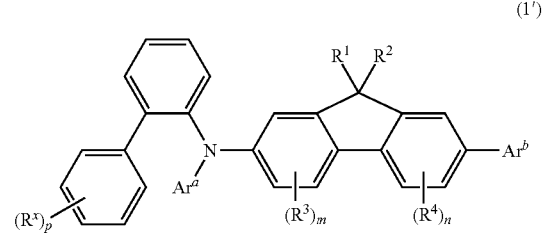

wherein $Ar^a$, $Ar^b$, $R^x$, $R^1$, $R^2$, $R^3$, $R^4$, p, m, and n are as defined above.

The definition of each group of formulae (1) and (1') will be described in more detail below.

Examples of the aryl group for $Ar^a$ include a phenyl group, a biphenylyl group, a terphenylyl group, a naphthyl group, an anthryl group, a fluorenyl group, and 9,9-dimethylfluorenyl group. The number of ring carbon atoms of the aryl group is preferably 6 to 30, more preferably 6 to 20, and still more preferably 6 to 14. Preferred aryl groups are a biphenylyl group, a fluorenyl group, and 9,9-dimethylfluorenyl group, with 9,9-dimethylfluorenyl group being more preferred.

Examples of the heteroaryl group for $Ar^a$ include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a triazolyl group, a pyrazolyl group, an isoxazolyl group, an isothiazolyl group, an oxadiazoyl group, a thiadiazolyl group, a triazolyl group, a tetrazolyl group, an indolyl group, an isoindolyl group, a benzofuranyl group, a dibenzofuranyl group, an isobenzofuranyl group, a benzothiophenyl group, a dibenzothiophenyl group, a dibenzothiophenylphenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a phenanthridinyl group, an acridinyl group, a phenanthrolinyl group, a phenazinyl group, a phenothiazinyl group, a phenoxazinyl group, and a xanthenyl group, with a dibenzofuranyl group and a dibenzothiophenyl group being preferred.

As described above, Ar$^a$ may be a group wherein two to four groups selected from the above aryl group and the above heteroaryl group are linked, for example, heteroaryl group-aryl group, aryl group-heteroaryl group, aryl group-heteroaryl group-aryl group, heteroaryl group-aryl group-heteroaryl group, an group-heteroaryl group-aryl group-heteroaryl group, and heteroaryl group-aryl group-heteroaryl group-aryl group, with a group wherein one aryl group and one heteroaryl group are linked, i.e., heteroaryl group-aryl group and aryl group-heteroaryl group being preferred. Examples of the aryl group and the heteroaryl group are the same as those described above.

In view of achieving the low voltage drive and high efficiency of the organic EL device, Ar$^a$ is preferably a phenyl group.

Ar$^a$ preferably comprises a fused aryl group having 10 to 50 ring carbon atoms, a non-fused aryl group having 13 to 50 ring carbon atoms, a heteroaryl group having 5 to 50 ring atoms, or a group in which two to four groups selected from the aryl group and the heteroaryl group are linked, and more preferably comprises a fused aryl group having 10 to 50 ring carbon atoms.

In another embodiment, Ar$^a$ is preferably a fused aryl group having 10 to 50 ring carbon atoms, a non-fused aryl group having 13 to 50 ring carbon atoms, a heteroaryl group having 5 to 50 ring atoms, or a group in which two to four groups selected from the aryl group and the heteroaryl group are linked, and more preferably a fused aryl group having 10 to 50 ring carbon atoms.

Examples of the fused aryl group having 10 to 50 ring carbon atoms for Ar$^a$ include a naphthyl group, an anthryl group, a fluorenyl group, a phenanthryl group, and a 9,9-dimethylfluorenyl group. The number of ring carbon atoms of the fused aryl group is preferably 10 to 30, more preferably 10 to 20, and still more preferably 10 to 14. Preferred aryl groups are a naphthyl group, a fluorenyl group, and a 9,9-dimethylfluorenyl group, with a 9,9-dimethyifluorenyl group being more preferred.

Examples of the non-fused aryl group having 13 to 50 ring carbon atoms for Ar$^a$ include a terphenylyl group and a quaterphenylyl group. The number of ring carbon atoms of the aryl group is preferably 18 to 30 and more preferably 18 to 20. Preferred non-fused aryl group is a terphenylyl group.

Examples of the heteroaryl group for Ar$^a$ are as described above.

Examples of the alkyl group having 1 to 10 carbon atoms for R$^x$ and R$^1$ to R$^4$ include a methyl group, an ethyl group, various propyl groups ("various" means that any of straight chain and branched chain analogues are included, the same applies below), various butyl groups, various octyl groups, and various decyl groups. The number of carbon atoms of the alkyl group is preferably 1 to 6.

Examples of the aryl group having 6 to 12 ring carbon atoms for R$^1$ and R$^2$ include a phenyl group, a biphenylyl group, and a naphthyl group, with a phenyl group being preferred.

As described above, R$^1$ and R$^2$ may be bonded to each other to form a hydrocarbon ring. When forming a hydrocarbon ring, the group attached to the nitrogen atom is represented, for example, by the flowing formula. Preferably, R$^1$ and R$^2$ do not form a hydrocarbon ring.

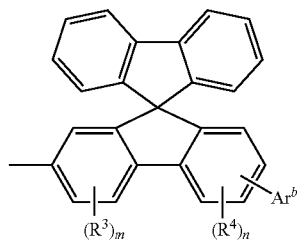

Examples of the cycloalkyl group having 3 to 10 ring carbon atoms for R$^x$, R$^3$ and R$^4$ include a cyclopropyl group, a cyclopentyl group, a cyclohexyl group, and a cyclooctyl group. The number of ring carbon atoms of the cycloalkyl group is preferably 5 to 8.

Examples of the aryl group having 6 to 30 ring carbon atoms for R$^x$, R$^3$ and R$^4$ include a phenyl group, a biphenylyl group, a terphenylyl group, a naphthyl group, and an anthryl group. The number of ring carbon atoms of the aryl group is preferably 6 to 20, more preferably 6 to 14, and still more preferably 6 to 12.

The subscript p is an integer of 0 to 3, preferably an integer of 0 to 2, more preferably 0 or 1, and still more preferably 0, and m and n are each independently an integer of 0 to 2, preferably 0 or 1, and more preferably 0.

Examples of the aryl group having 6 to 18 ring carbon atoms for Ar$^b$ include a phenyl group, a naphthyl group, a biphenylyl group, a terphenylyl group, and a phenanthryl group, with an aryl group having 6 to 14 ring carbon atoms being preferred, an aryl group having 6 to 12 ring carbon atoms being more preferred, and a biphenylyl group being still more preferred.

In view of achieving the low voltage drive and high efficiency of the organic EL device, preferably Ar$^b$ comprises a fused aryl group having 10 to 18 ring carbon atoms and more preferably Ar$^b$ is a fused aryl group having 10 to 18 ring carbon atoms.

Examples of the fused aryl group having 10 to 18 ring carbon atoms for Ar$^b$ include a naphthyl group, an anthryl group, and a phenanthryl group, with a fused aryl group having 10 to 14 ring carbon atoms being preferred.

As described above, R$^3$ and R$^4$ may be bonded to each other to form a hydrocarbon ring. When forming a hydrocarbon ring, the group attached to the nitrogen atom is represented, for example, by any of the flowing formulae:

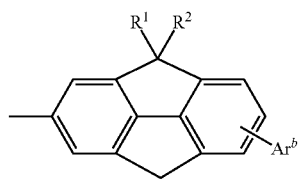

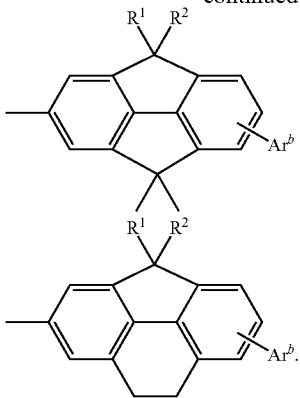

When m or n is 2, adjacent groups R³ or adjacent groups R⁴ may be bonded to each other to form a hydrocarbon ring. When forming a hydrocarbon ring, the group attached to the nitrogen atom is represented, for example, by any of the flowing formulae:

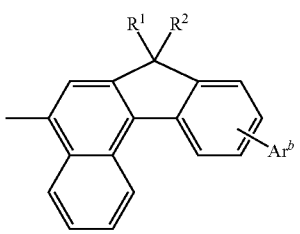

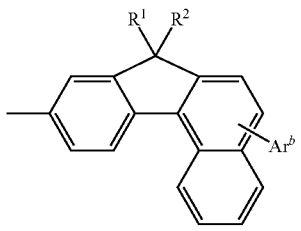

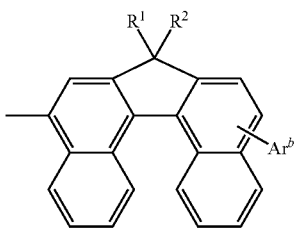

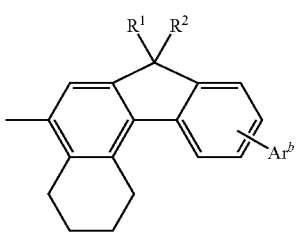

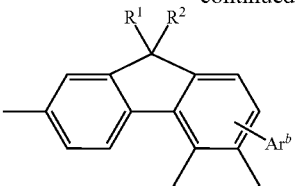

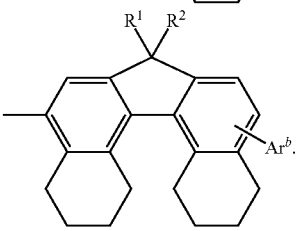

In view of achieving the low voltage drive and high efficiency of the organic EL device, $R^1$ and $R^2$ each preferably represent a hydrogen atom or an alkyl group having 1 to 10 carbon atoms.

In view of achieving the low voltage drive and high efficiency of the organic EL device, $Ar^a$ is particularly preferably represented by formula (A-1):

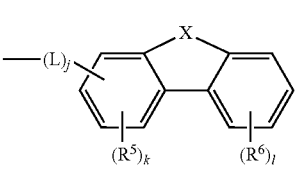

(A-1)

wherein L represents an arylene group having 6 to 20 ring carbon atoms or a heteroarylene group having 5 to 20 ring atoms, and J is 0 or 1;

X represents an oxygen atom, a sulfur atom, or a divalent group represented by $>CR^7R^8$, wherein $R^7$ and $R^8$ each independently represent a hydrogen atom, an alkyl group having 1 to 10 carbon atoms, or an aryl group having 6 to 12 ring carbon atoms; and $R^5$ and $R^6$ each independently represent an alkyl group having 1 to 10 carbon atoms, a cycloalkyl group having 3 to 10 ring carbon atoms, an aryl group having 6 to 14 ring carbon atoms, or a heteroaryl group having 5 to 14 ring atoms, k represents an integer of 0 to 2, 1 represents an integer of 0 to 3, when k is 2, adjacent groups $R^5$ may be bonded to each other to form a hydrocarbon ring, when l is 2 or 3, adjacent groups $R^6$ may be bonded to each other to form a hydrocarbon ring, and $R^5$ and $R^6$ may be bonded to each other to form a hydrocarbon ring.

Examples of the arylene group having 6 to 20 ring carbon atoms for L include a phenylene group, a naphthylene group, a biphenylylene group, an anthrylene group, an acenaphthylenylene group, an anthranylene group, a phenanthrylene group, a phenalenylene group, a quinolylene group, an isoquinolylene group, a s-indacenylene group, an as-indacenylene group, a chrysenylene group, with a phenylene group, a naphthylene group, and a biphenylylene group being preferred. The number of ring carbon atoms of the arylene group is preferably 6 to 14, more preferably 6 to 12, and still more preferably 6 to 10.

Examples of the heteroarylene group having 5 to 20 ring atoms for L include a pyrrolylene group, a furylene group, a thienylene group, a pyridylene group, an imidazopyridylene group, a pyridazinylene group, a pyrimidinylene group, a pyrazinylene group, a triazinylene group, an imidazolylene group, an oxazolylene group, a thiazolylene group, a pyrazolylene group, an isoxazolylene group, an isothiazolylene group, an oxadiazolylene group, a thiadiazolylene group, a triazolylene group, a tetrazolylen group, an indolylene group, an isoindolylene group, a benzofuranylene group, an isobenzofuranylene group, a benzothiophenylene group, an isobenzothiophenylene group, an indolizinylene group, a quinolizinylene group, a quinolylene group, an isoquinolylene group, a cinnolylene group, a phthalazinylene group, a quinazolinylene group, a quinoxalinylene group, a benzimidazolylene group, a benzoxazolylene group, a benzothiazolylene group, an indazolylene group, a benzisoxazolylene group, a benzisothiazolylene group, a dibenzofuranylene group, a dibenzothiophenylene group, a phenanthridinylene group, an acridinylene group, a phenanthrolinylene group, a phenazinylene group, a phenothiazinylene group, a phenoxazinylene group, and a xanthenylene group. Preferred are a furylene group, a thienylene group, a pyridylene group, an imidazopyridylene group, a pyridazinylene group, a pyrimidinylene group, a pyrazinylene group, a benzimidazolylene group, a dibenzofuranylene group, a dibenzothiophenylene group, and a phenanthrolinylene group. The number of ring carbon atoms of the heteroarylene group is preferably 5 to 14, more preferably 5 to 12, and still more preferably 5 to 10.

The subscript j is 0 or 1, and preferably 0 in view of achieving the low voltage drive and high efficiency of the organic EL device. When j is 0, L represents a single bond.

X may be a divalent group represented by $>CR^7R^8$, wherein $R^7$ and $R^8$ each independently represent a hydrogen atom, an alkyl group having 1 to 10 carbon atoms or an aryl group having 6 to 12 ring carbon atoms. Examples of the alkyl group having 1 to 10 carbon atoms for $R^7$ and $R^8$ include those mentioned above with respect to $R^1$ to $R^4$. The number of carbon atoms of the alkyl group is preferably 1 to 6, more preferably 1 to 3, and still more preferably 1. Examples and preferred examples of the aryl group having 6 to 12 ring carbon atoms for $R^7$ and $R^8$ are the same as those described with respect to $R^1$ to $R^4$.

The divalent group represented by $>CR^7R^8$ is preferably $>C(CH_3)_2$.

X is preferably an oxygen atom or a group represented by $>CR^7R^8$.

Examples and preferred examples of the alkyl group having 1 to 10 carbon atoms and the cycloalkyl group having 3 to 10 ring carbon atoms for $R^5$ and $R^6$ are the same as those described with respect to $R^3$ and $R^4$.

Examples of the aryl group having 6 to 14 ring carbon atoms for $R^5$ and $R^6$ include a phenyl group, a naphthyl group, a biphenylyl group, and an anthryl group. The number of ring carbon atoms of the aryl group is preferably 6 to 12, and more preferably 6 to 10.

Examples of the heteroaryl group having 5 to 14 ring atoms for $R^5$ and $R^6$ are those having 5 to 14 ring atoms selected from those described above with respect to the heteroaryl group for L. The number of ring atoms of the heteroaryl group is preferably 5 to 12 and more preferably 5 to 10.

The subscript k is an integer of 0 to 2, preferably 0 or 1, and more preferably 0, and 1 is an integer of 0 to 3, preferably 0 or 1, and more preferably 0.

When k is 2, adjacent groups $R^5$ may be bonded to each other to form a hydrocarbon ring, and when 1 is 2 or 3, adjacent groups $R^6$ may be bonded to each other to form a hydrocarbon ring. When forming a hydrocarbon ring, the group attached to the nitrogen atom is represented, for example, by any of the flowing formulae:

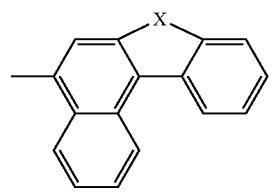

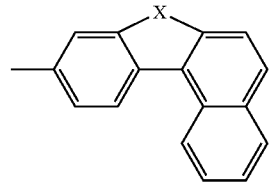

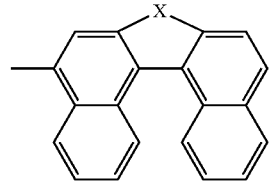

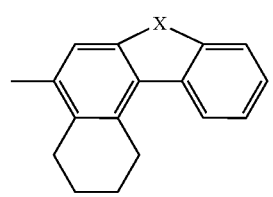

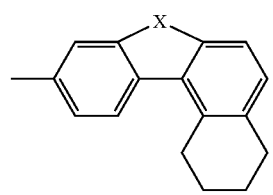

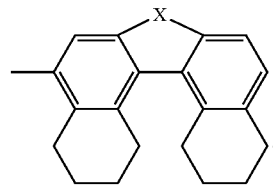

A compound wherein $Ar^0$ is represented by any of formulae (A-1-1) to (A-1-5) is more preferred:

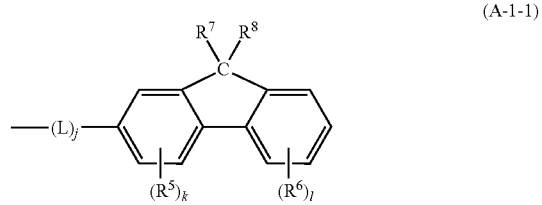

(A-1-1)

-continued

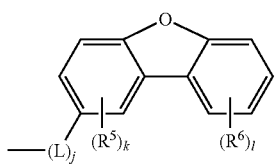
(A-1-2)

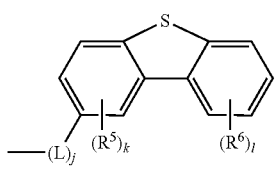
(A-1-3)

(A-1-4)

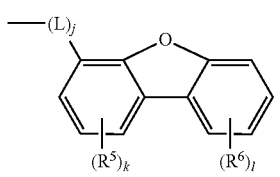

(A-1-5)

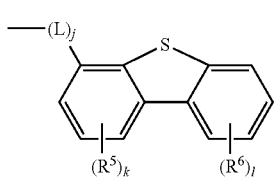

wherein L, $R^5$ to $R^8$, j, k, and l are as defined above and preferred examples thereof are also the same as those described above.

$R^5$ and $R^6$ may be bonded to each other to form a hydrocarbon ring. When forming a hydrocarbon ring, the group attached to the nitrogen atom is represented, for example, by any of the flowing formulae:

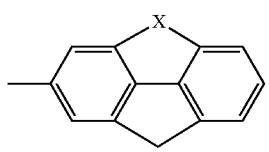

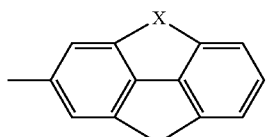

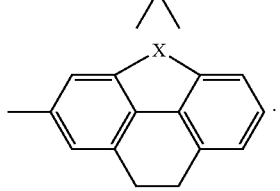

In view of achieving the low voltage drive and high efficiency of the organic EL device, a compound wherein $Ar^a$ is represented by formula (A-2) is more preferred and a compound wherein $Ar^a$ is represented by any of formulae (A-2-1) to (A-2-3) is still more preferred:

(A-2)

wherein X, $R^5$, $R^6$, k, and l are as defined above and preferred examples thereof are also the same as those described above; and (A-2-1)

(A-2-2)

(A-2-3)

wherein $R^5$ to $R^8$, k, and l are as defined above and preferred examples thereof are also the same as those described above.

The method of producing the compound represented by formula (1) of the invention is not particularly limited and it can be produced in accordance with the following examples while referring to a known method.

The compound of the invention is, as described below, useful as a material for organic EL devices, particularly, as a hole transporting material for organic EL devices. In addition, the compound of the invention is useful as a material for the hole transporting layer which is adjacent (bonded) to an acceptor layer.

In the compound of the invention, a 2-biphenylyl group (o-biphenylyl group) and the following fluorene skeleton:

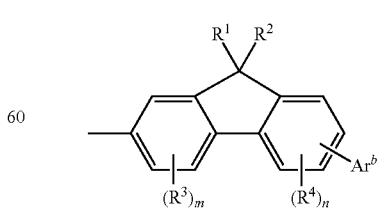

are "directly" bonded to the nitrogen atom. With this structure, advantageous effects, such as low driving voltage and high efficiency, are obtained by using the compound as a material for organic EL devices. Particularly, it has been found that the fluorene skeleton directly bonded to the nitrogen atom tends to increase the hole transporting ability. It has been also found that the 2-biphenylyl group (o-biphenylyl group) which is directly bonded to the nitrogen atom results in the low driving voltage of an organic EL device and improves the emission efficiency.

Examples of the compound of the invention are shown below, although not limited thereto.

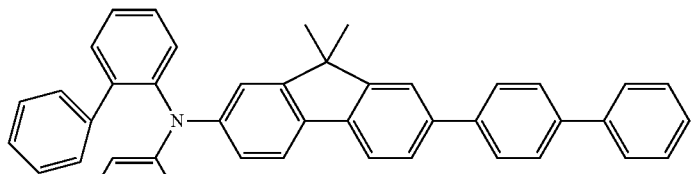

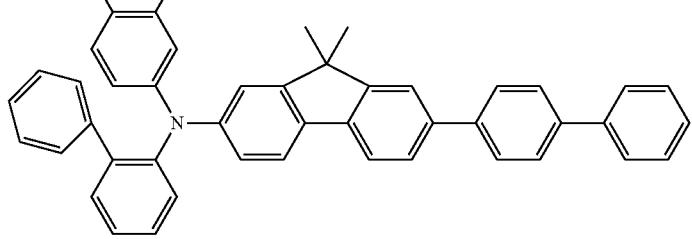

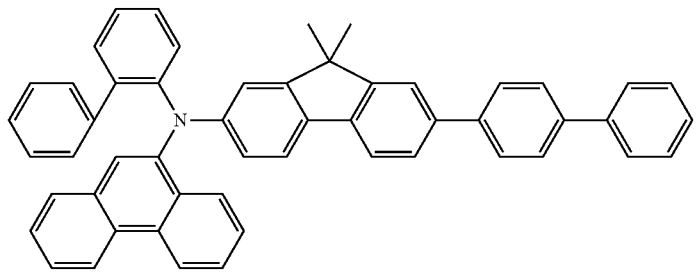

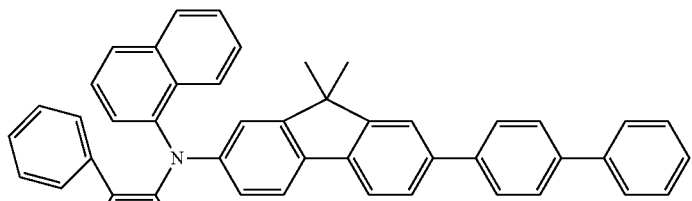

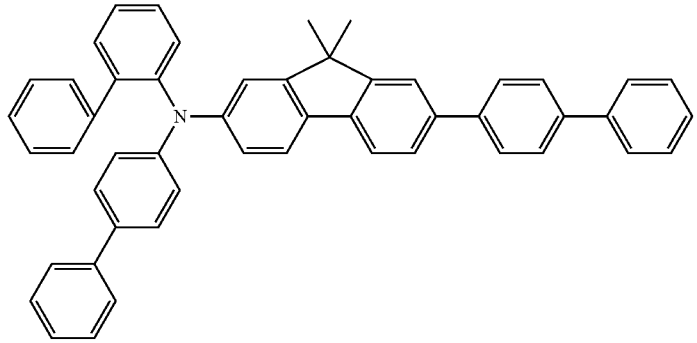

-continued
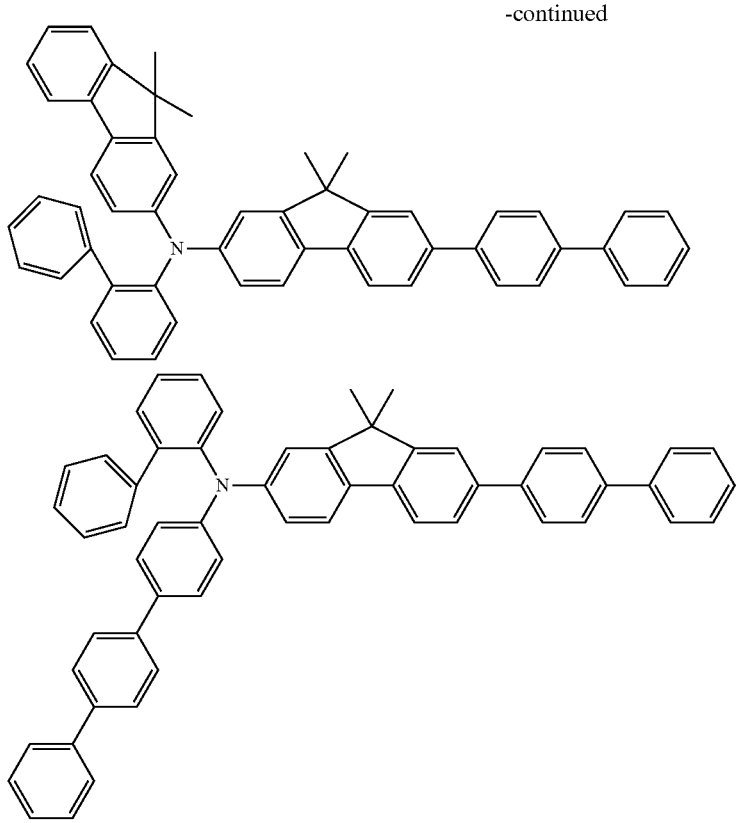
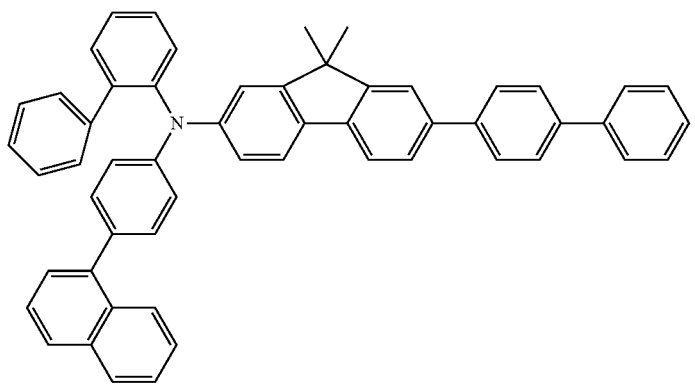
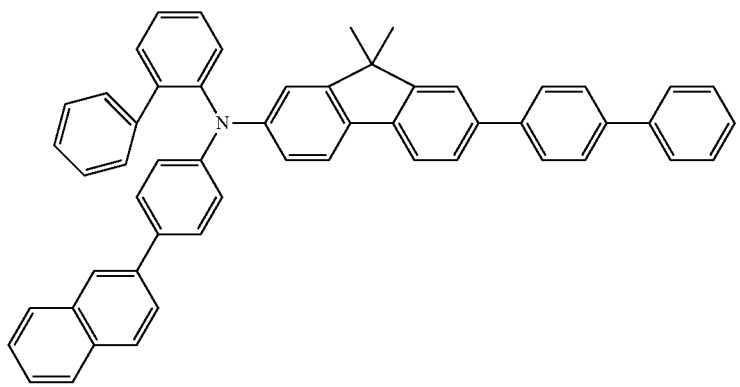

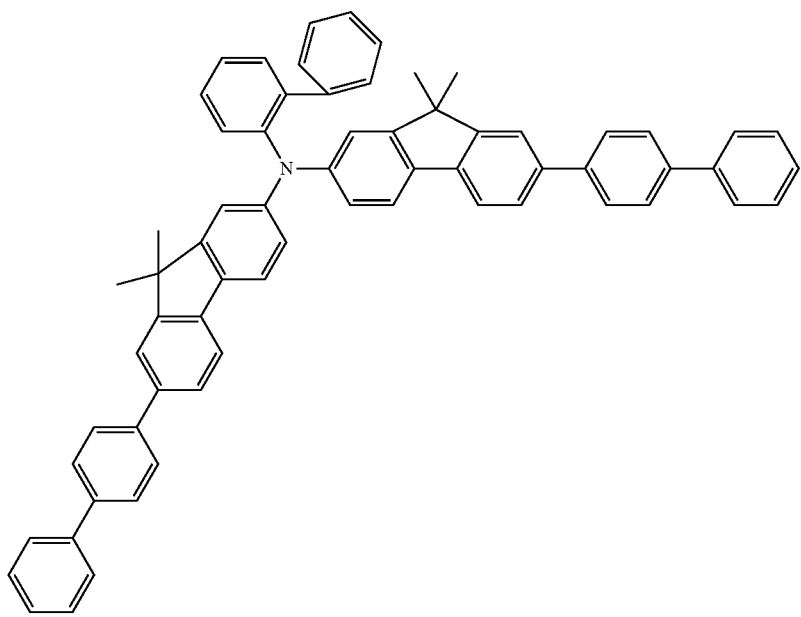
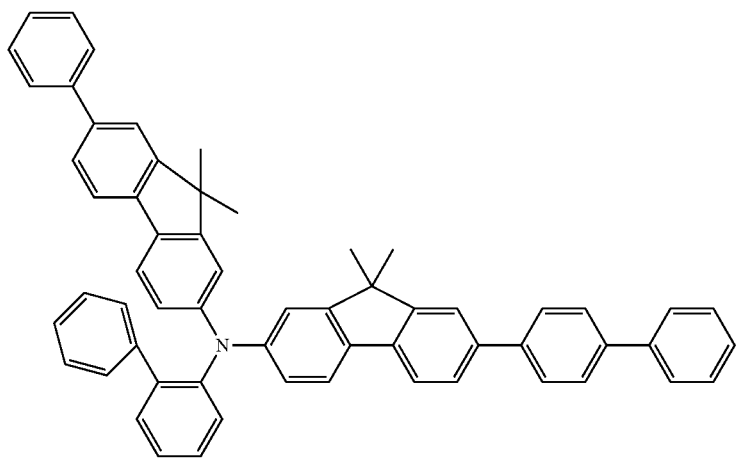
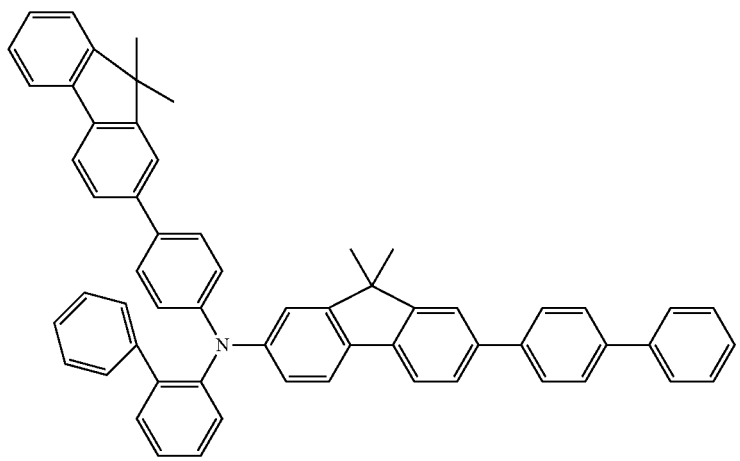

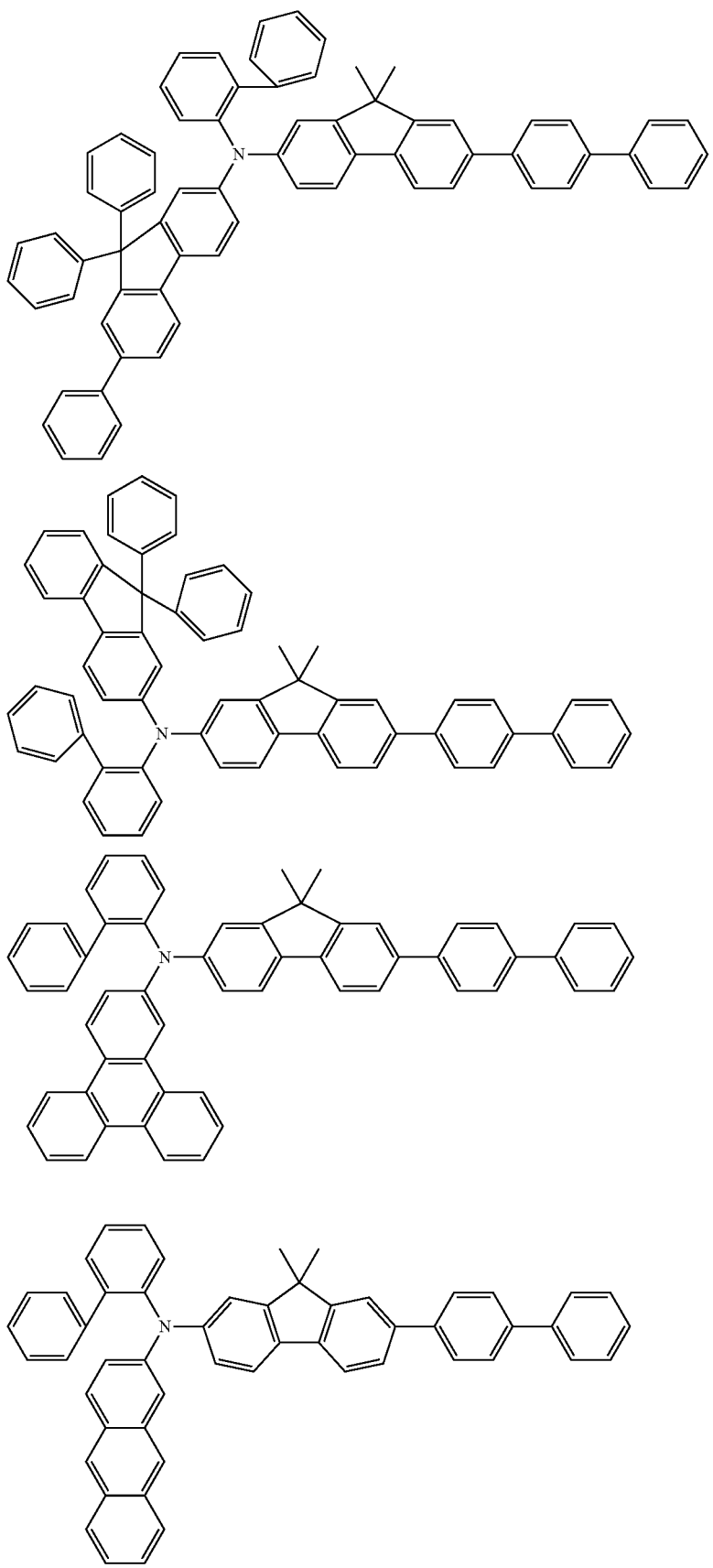

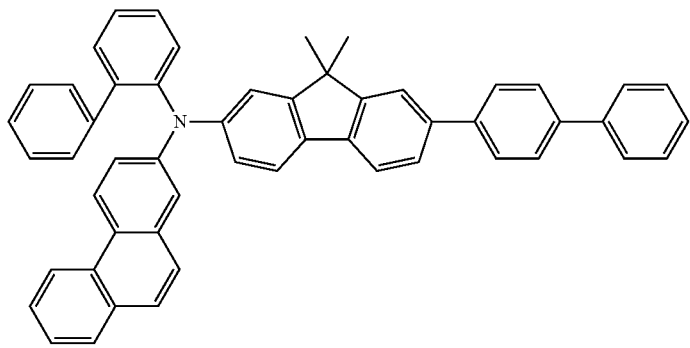
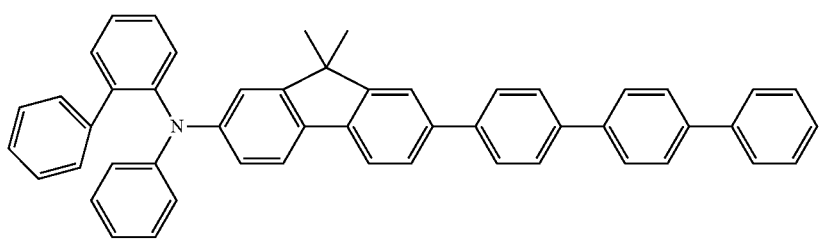
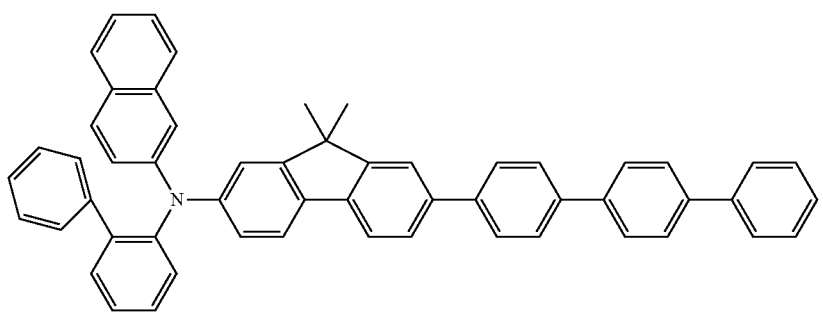
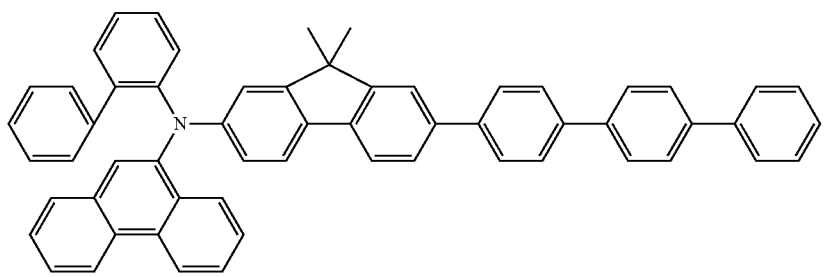
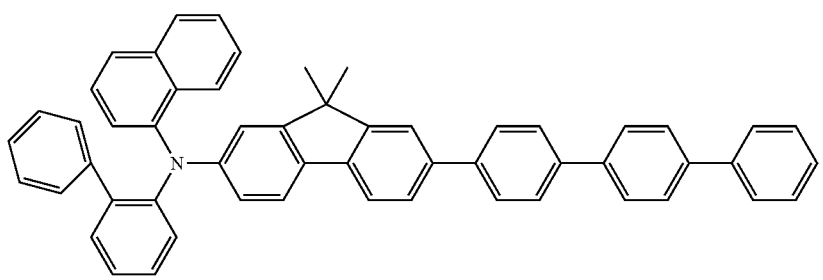

-continued
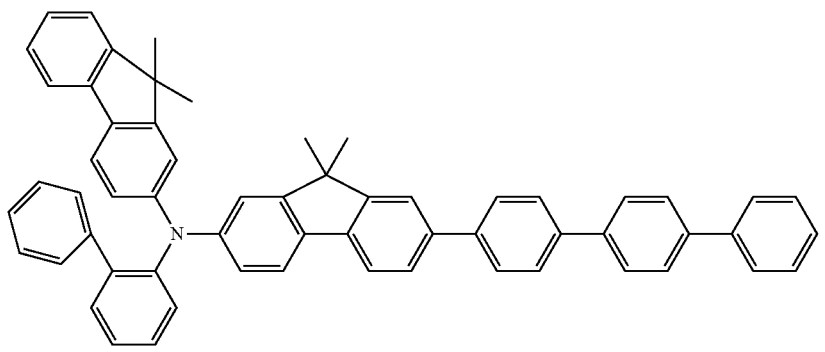
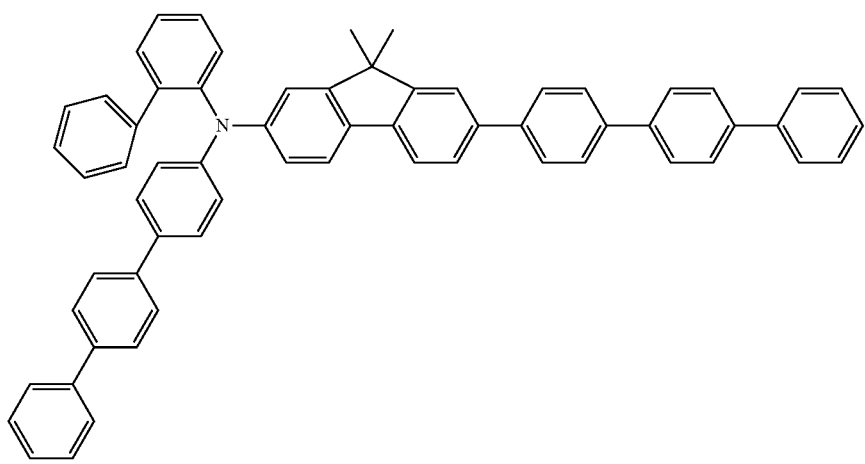
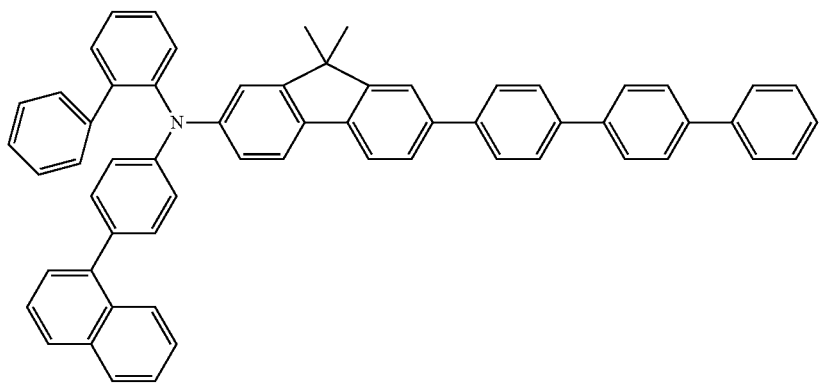

-continued
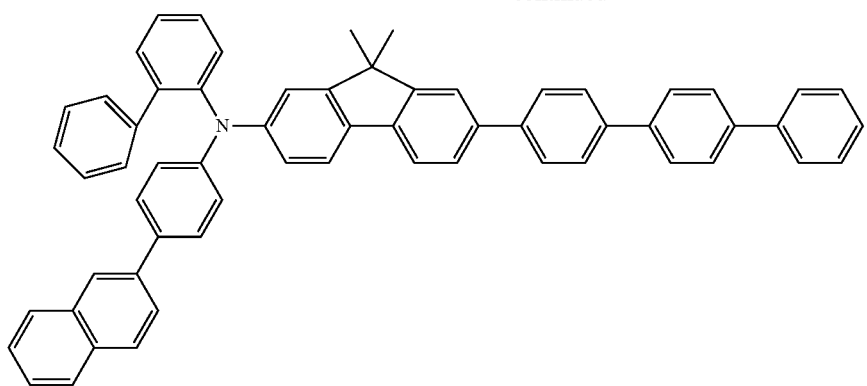
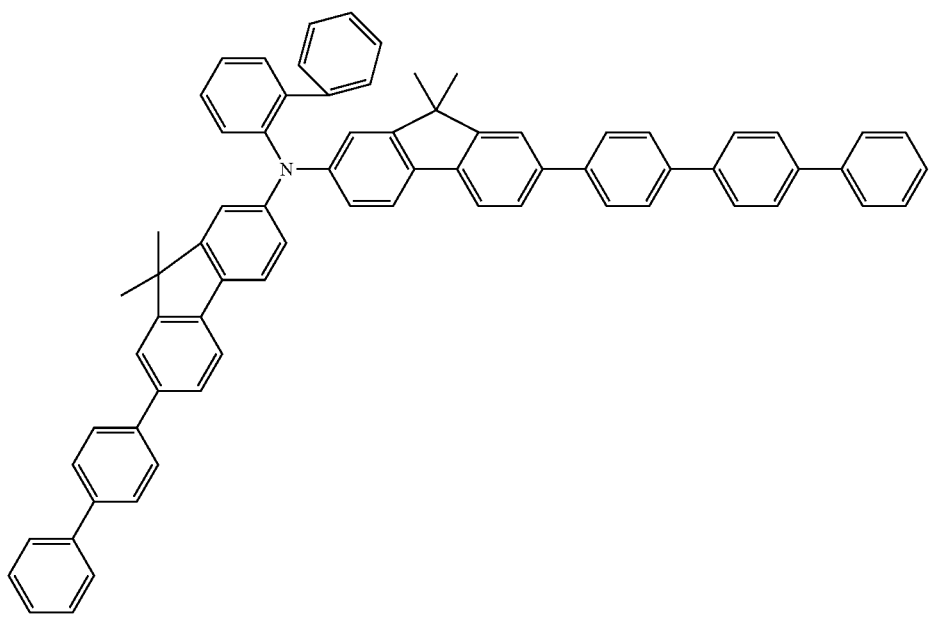
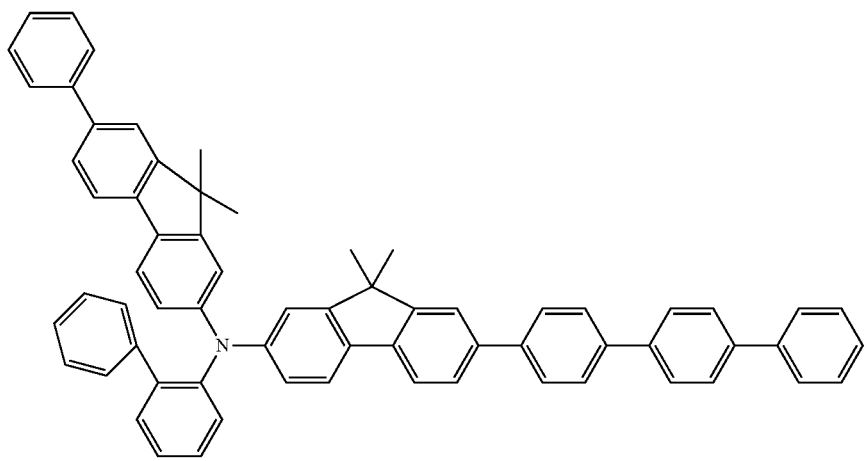

-continued
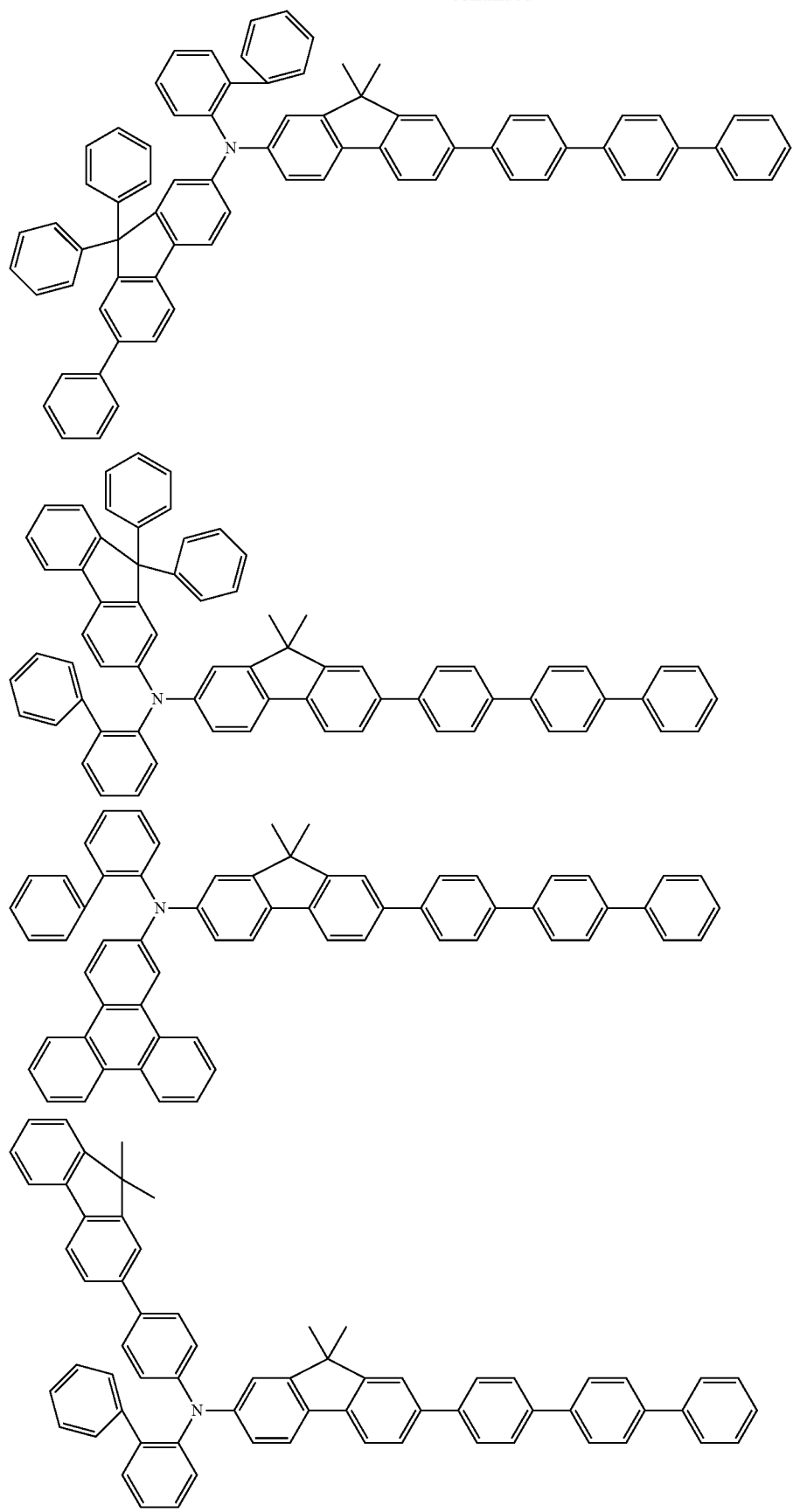

-continued
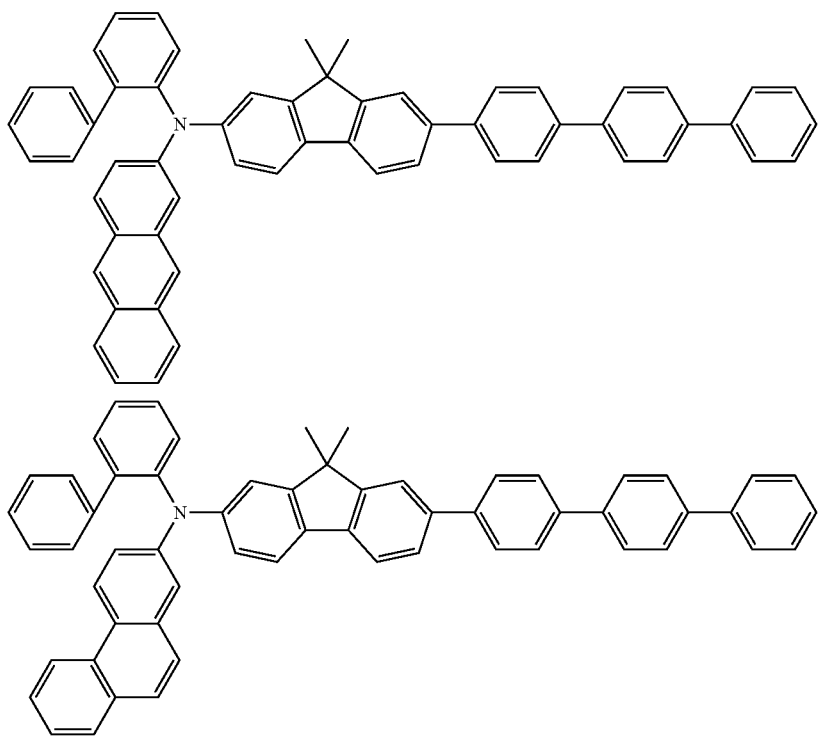
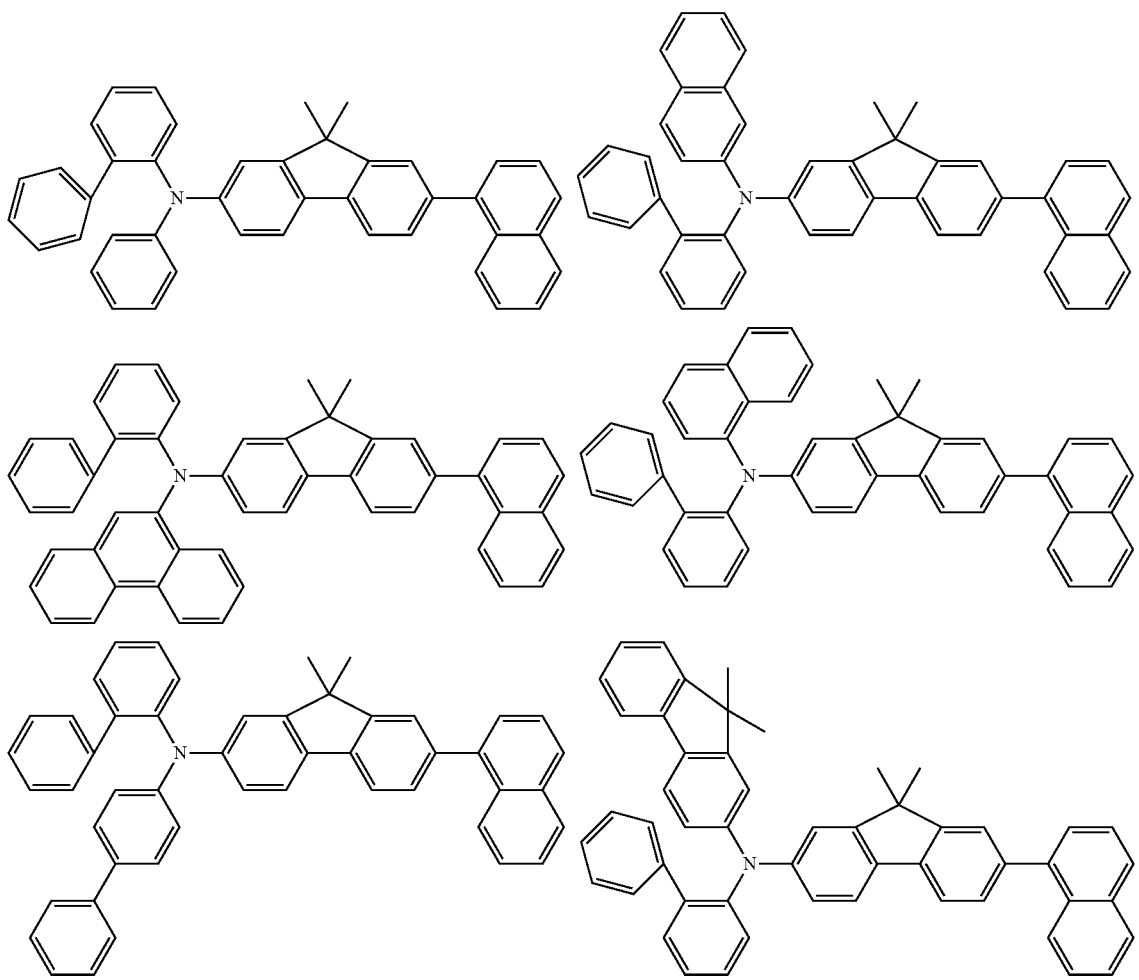

-continued
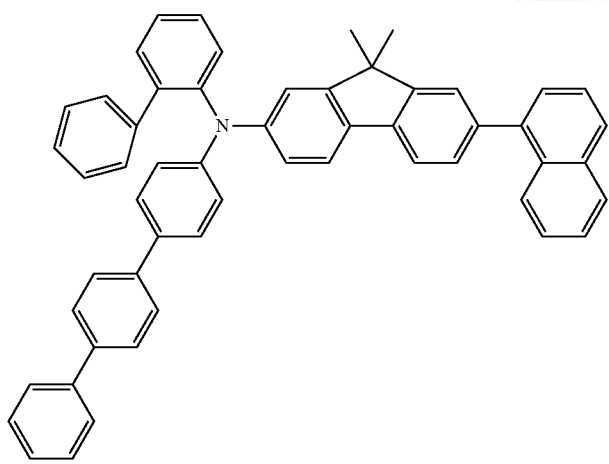
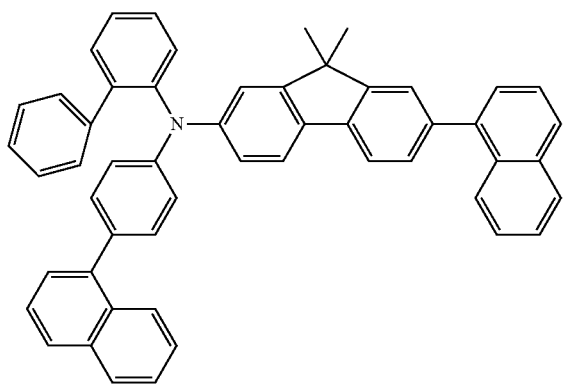
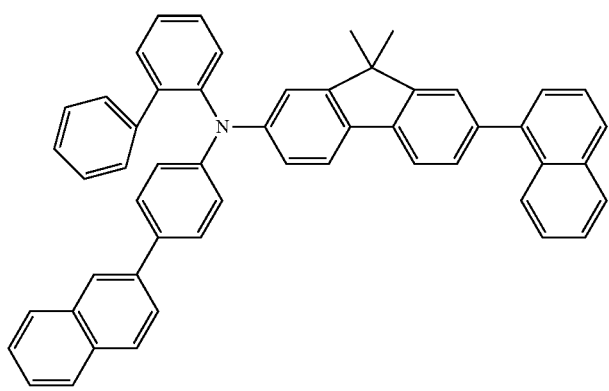

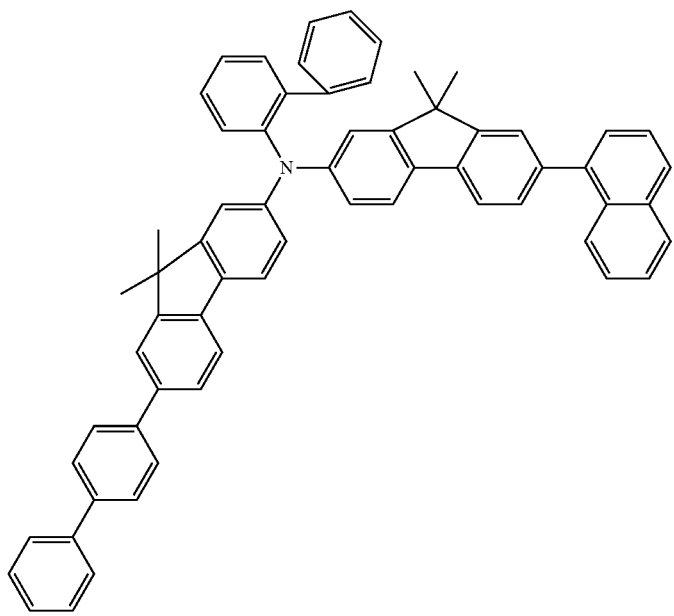
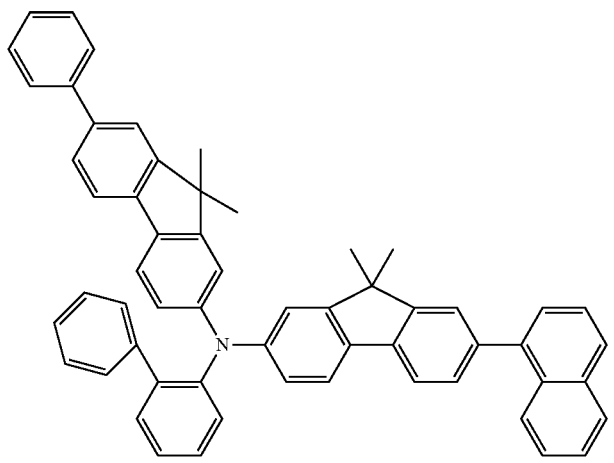
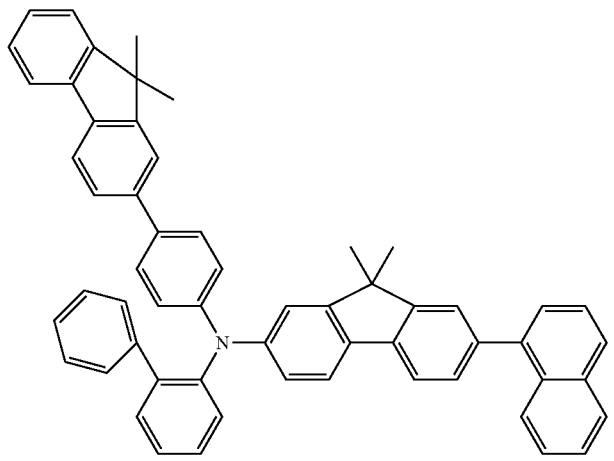

-continued
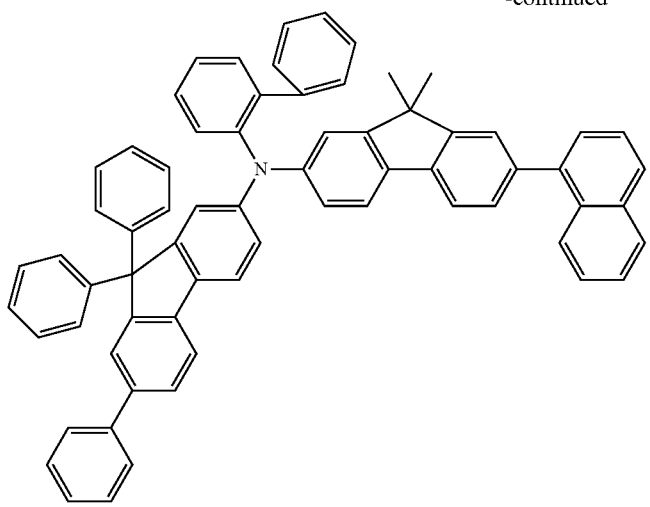
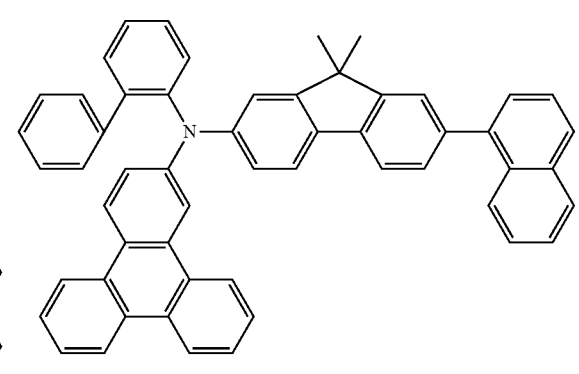
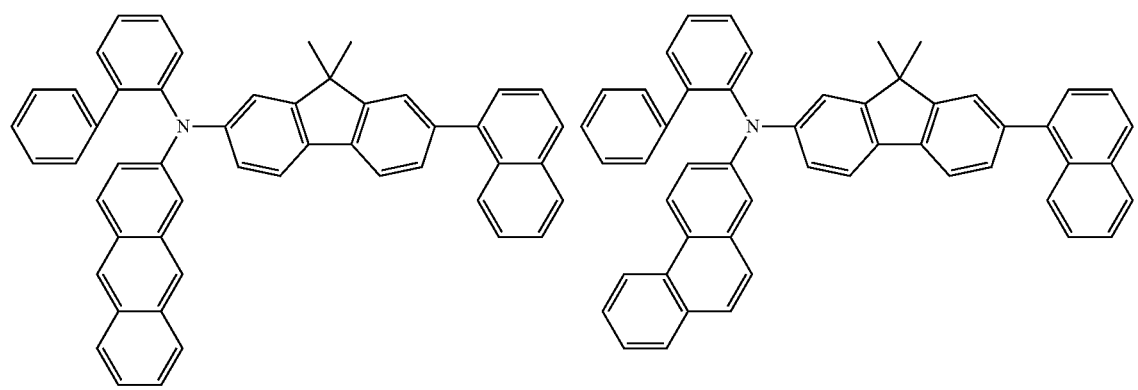
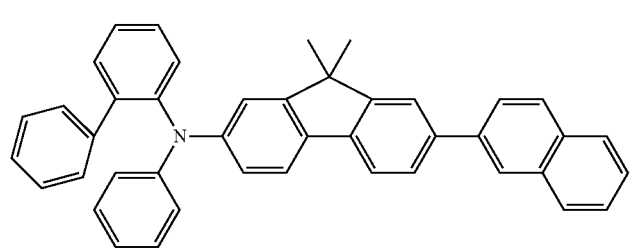

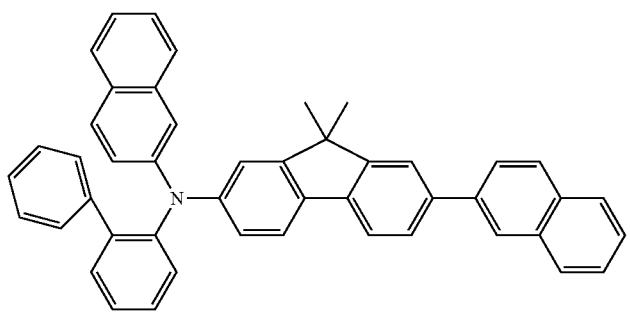
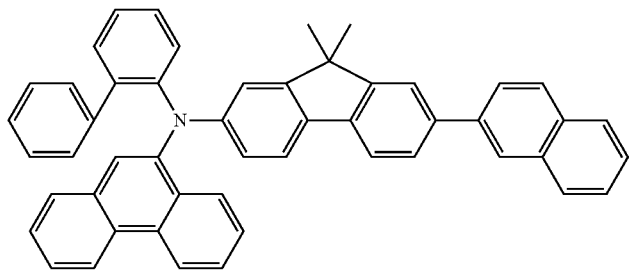
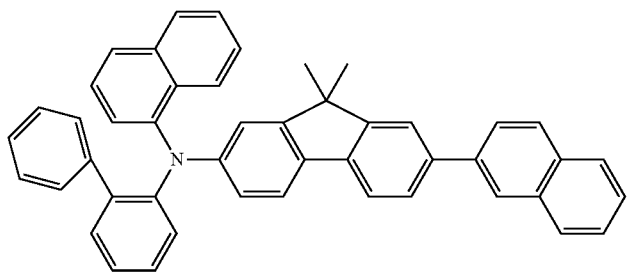
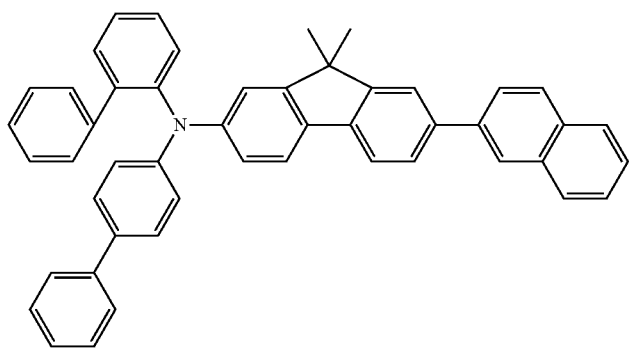
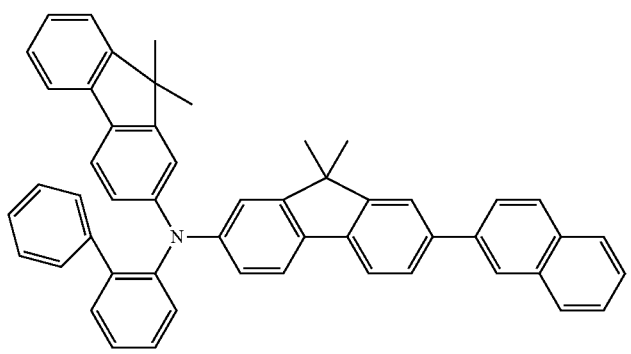

-continued
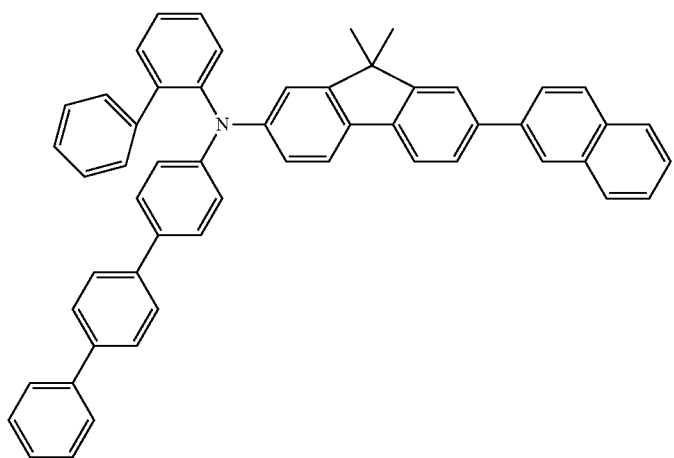
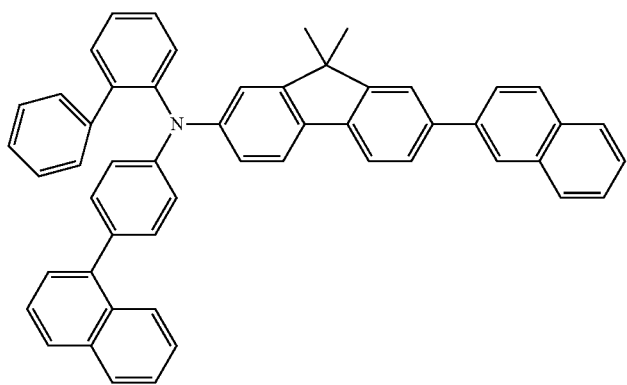
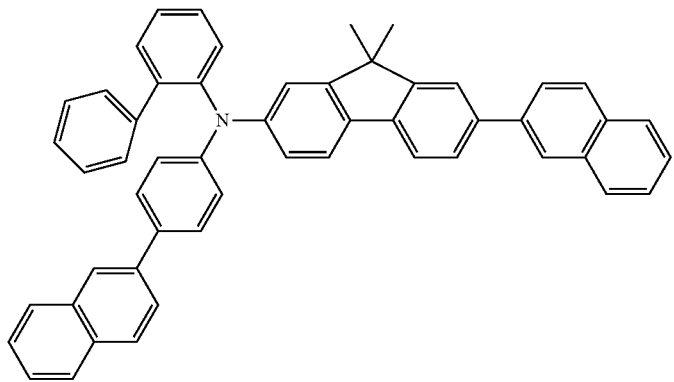

-continued
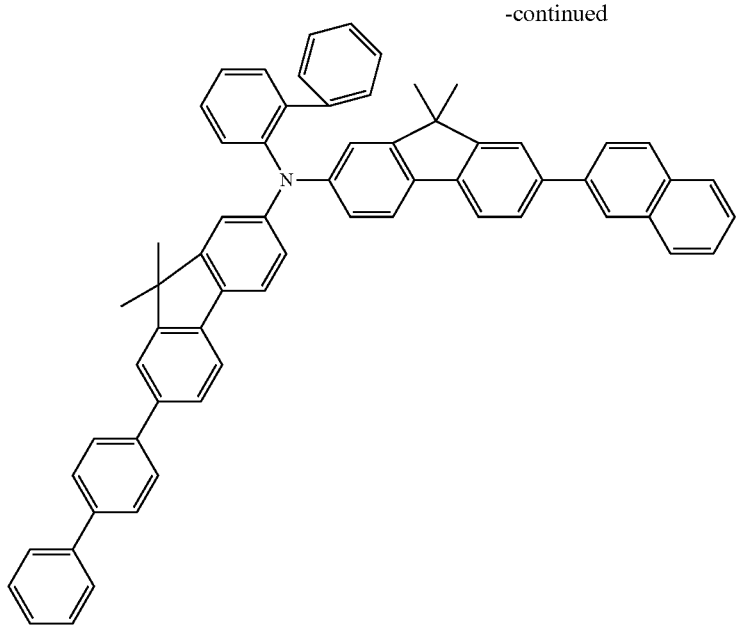
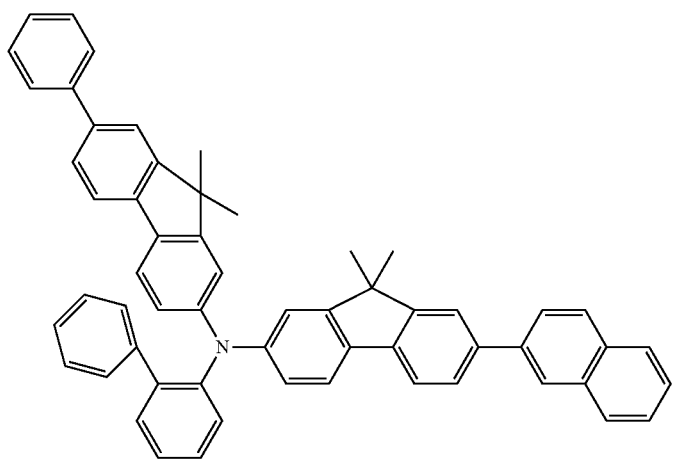
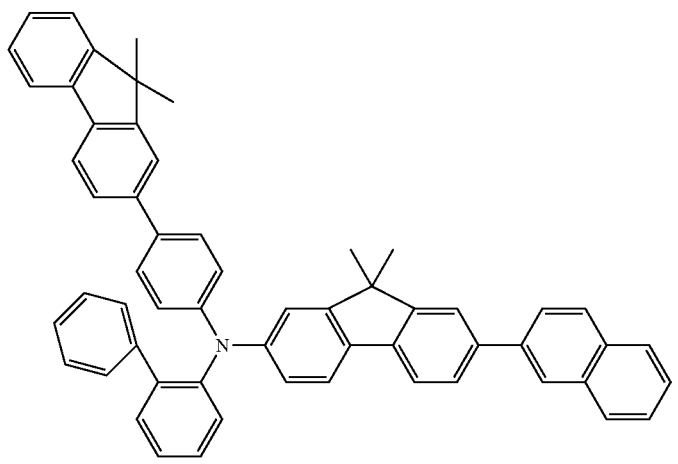

-continued
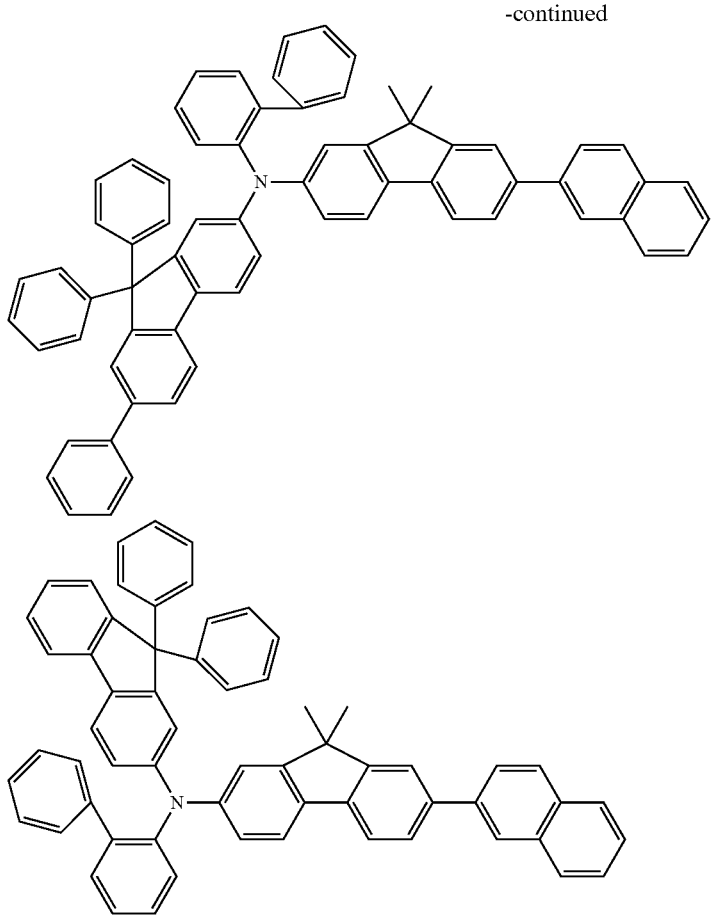
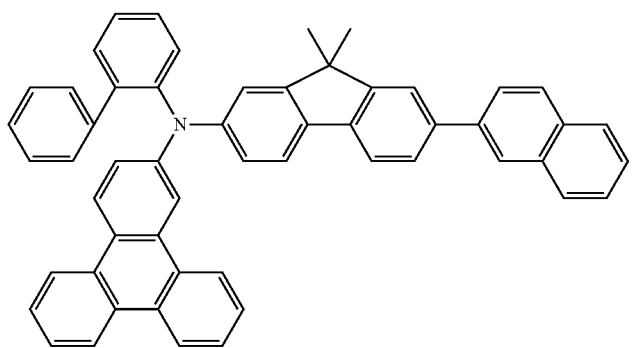
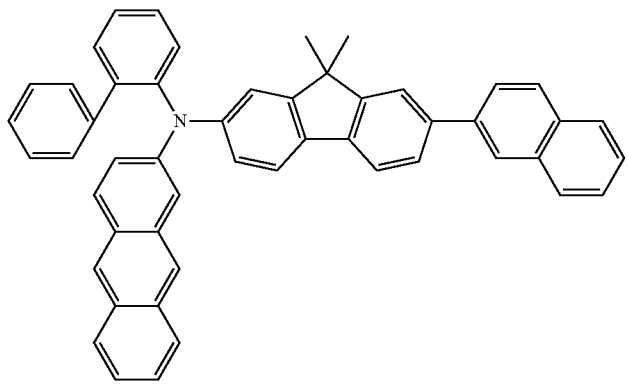

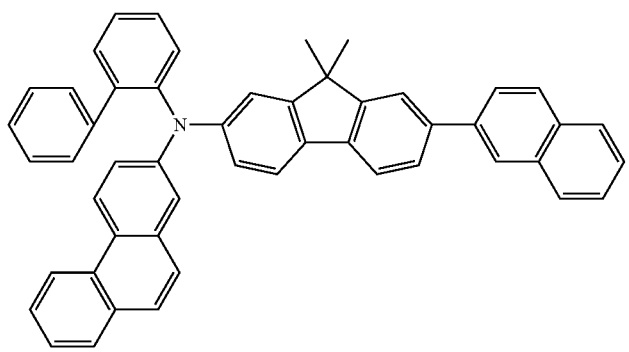
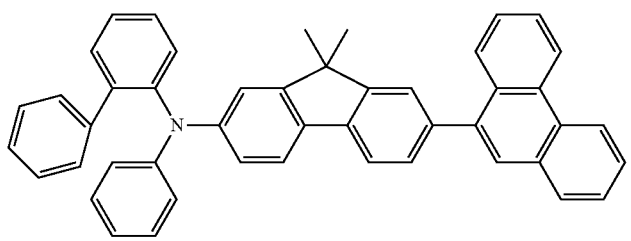
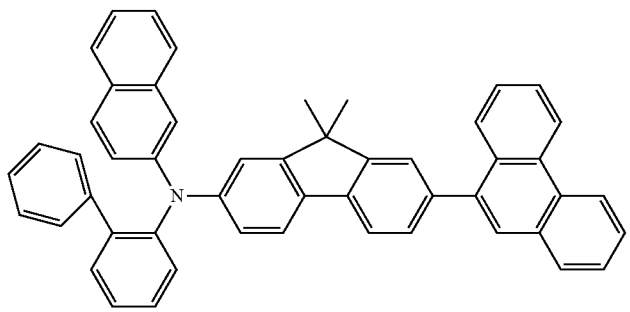
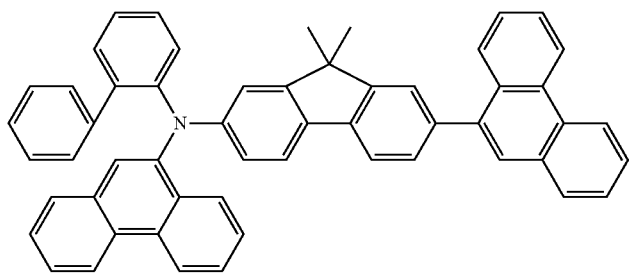
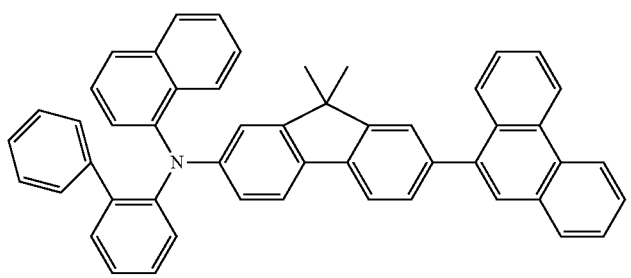

-continued
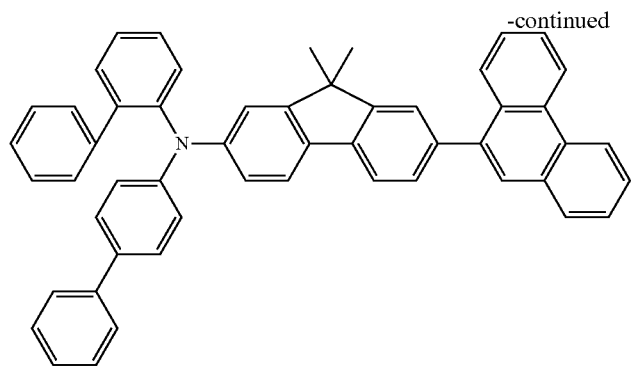
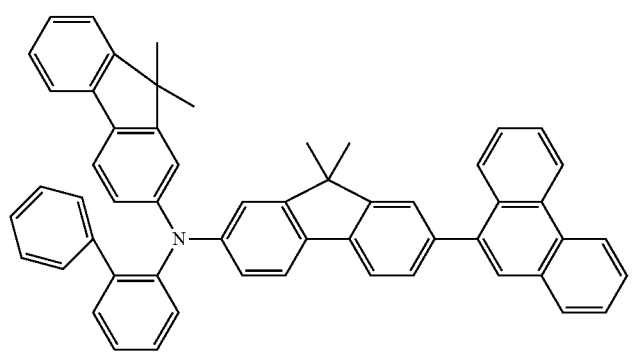
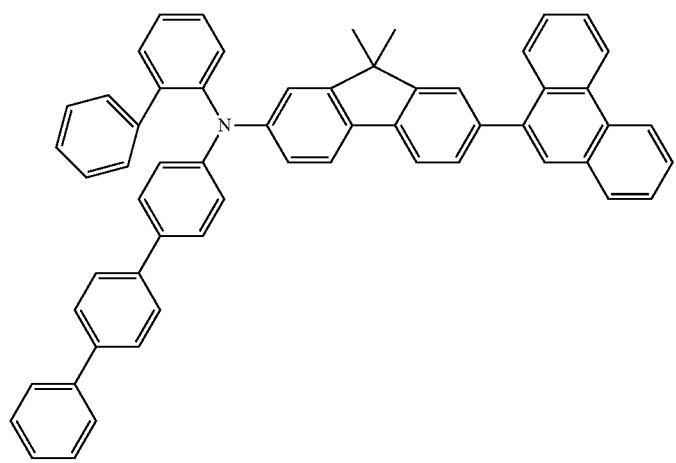
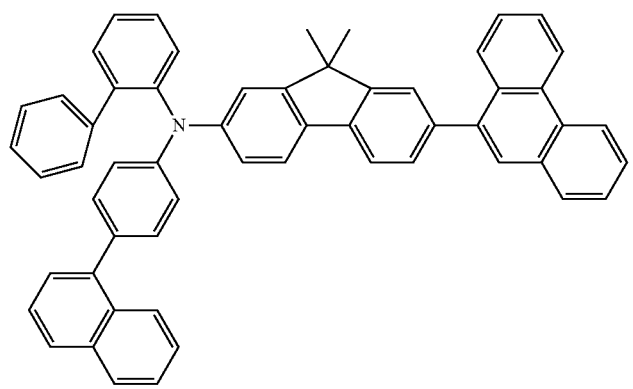

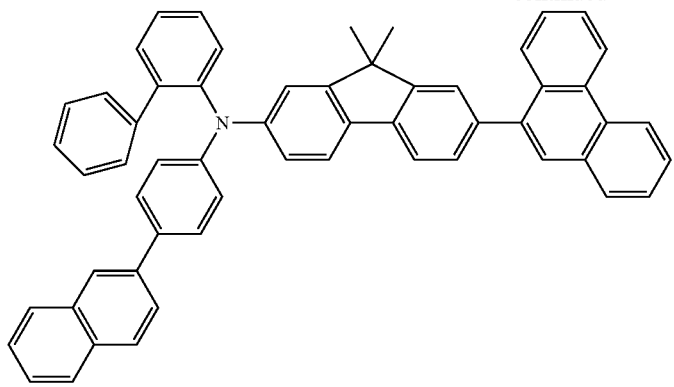
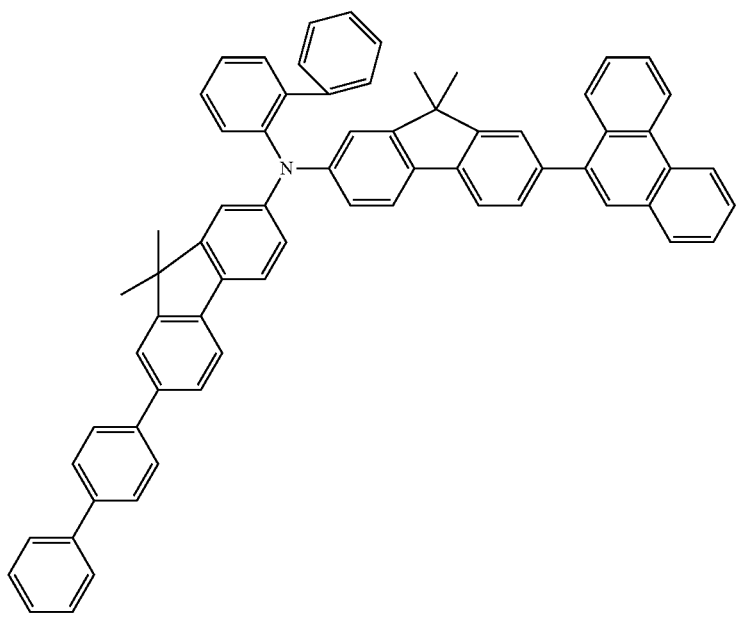
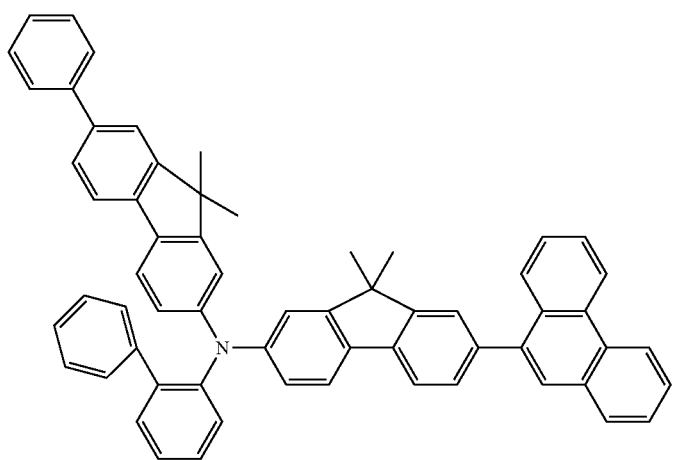

-continued
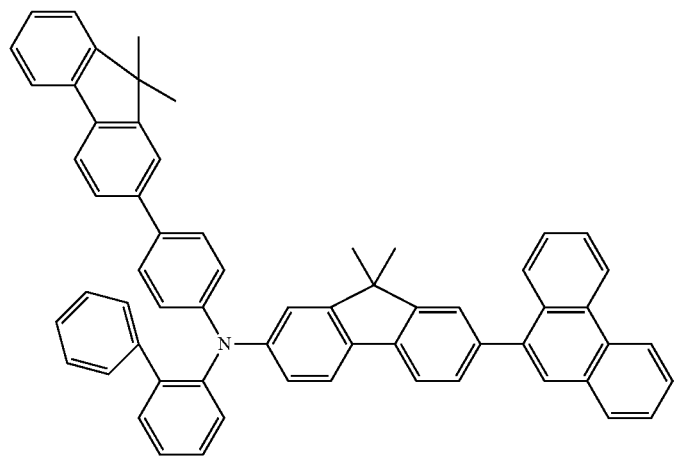
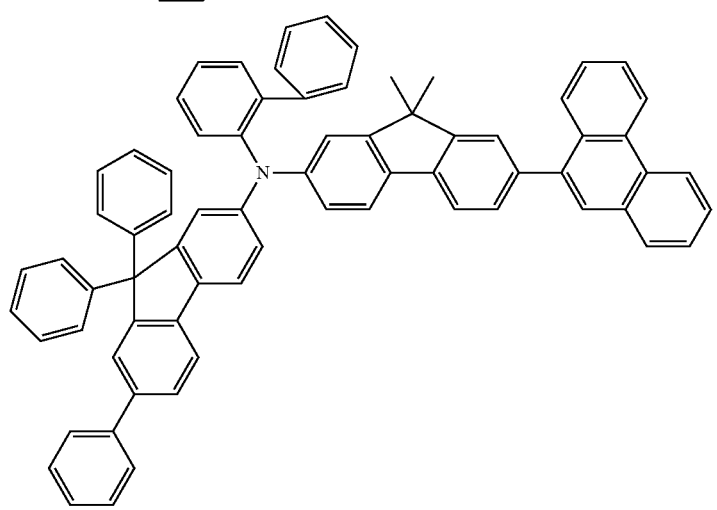
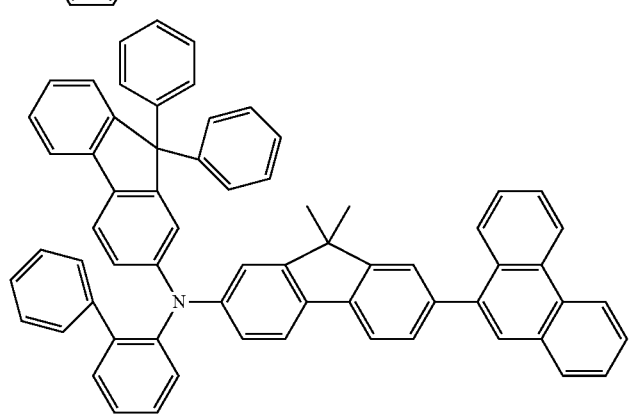
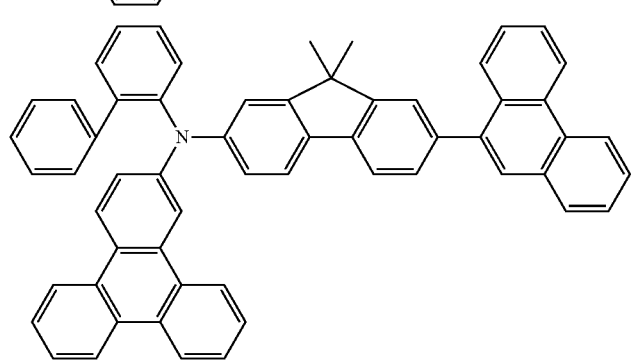

-continued
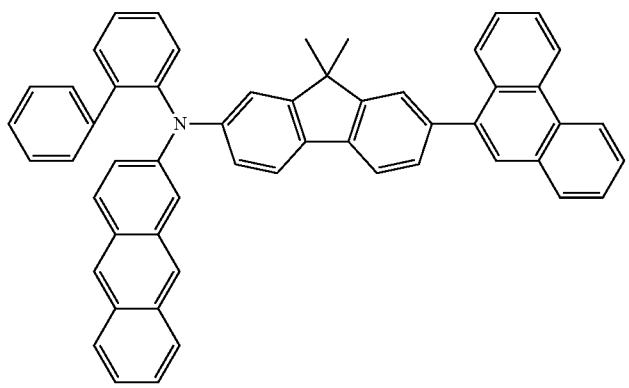
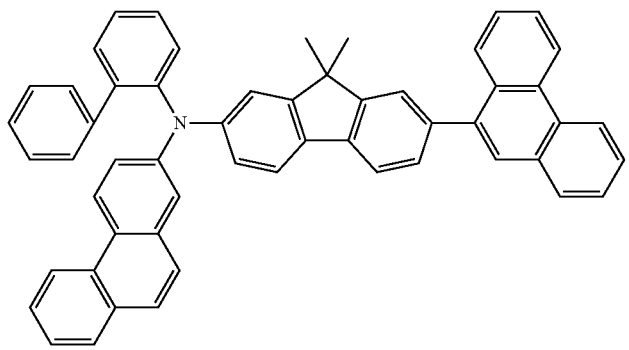
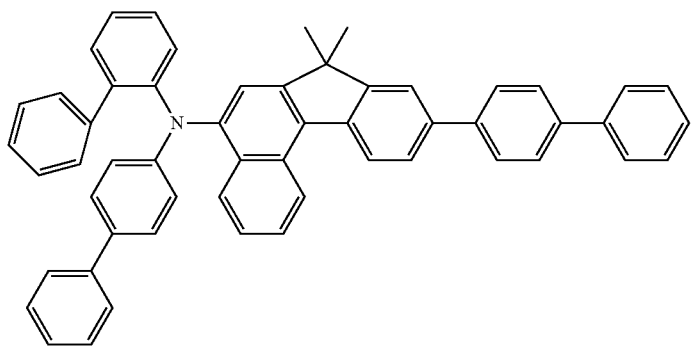
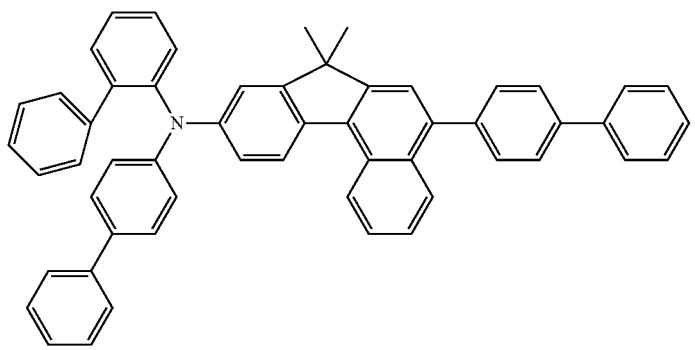

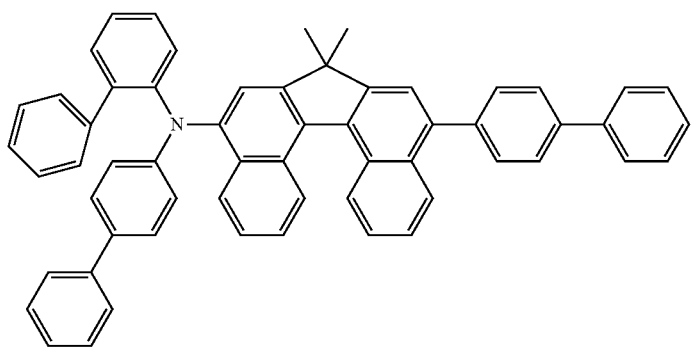
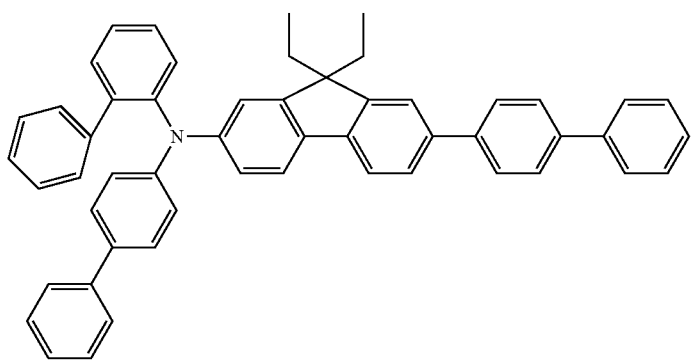
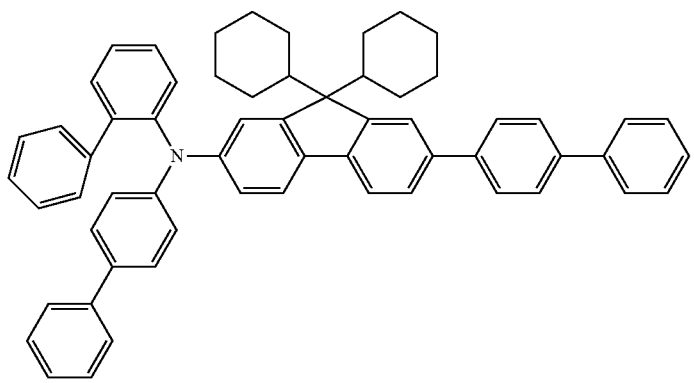
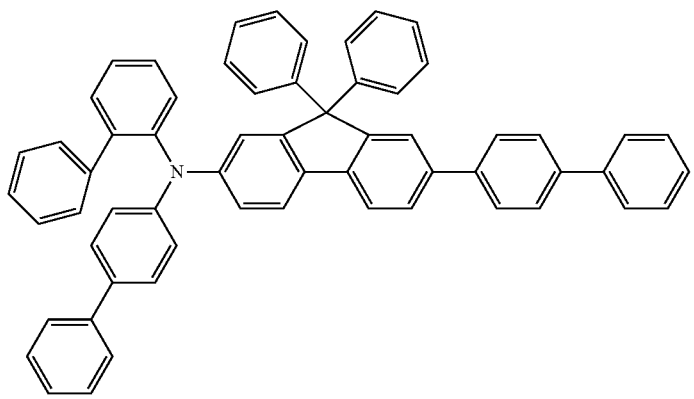

-continued
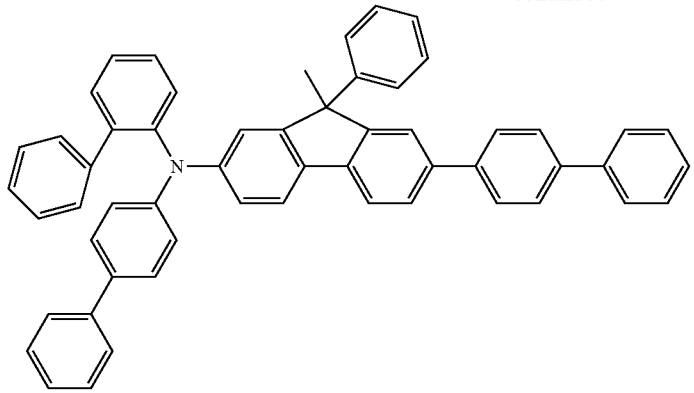
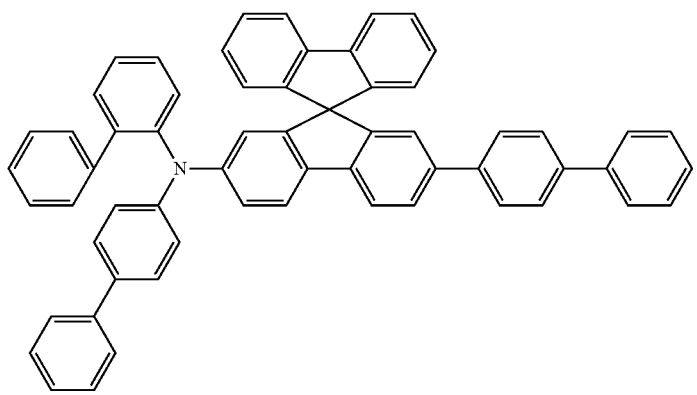
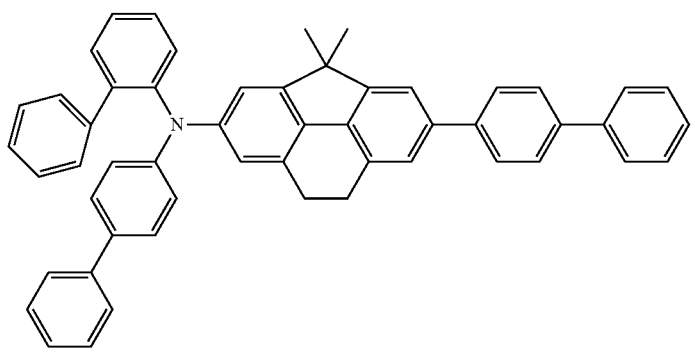
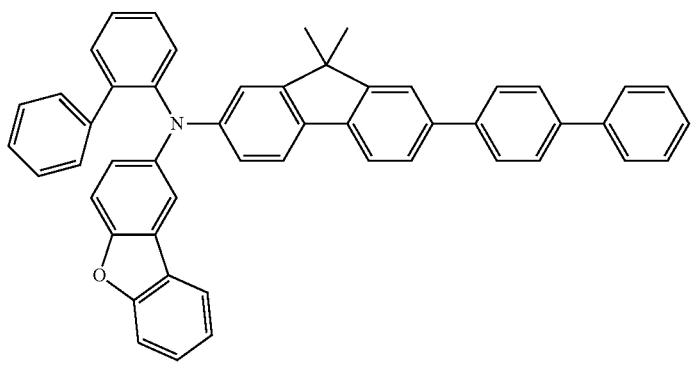

-continued
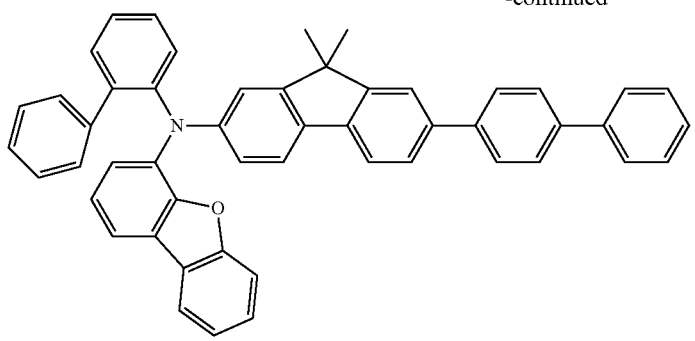
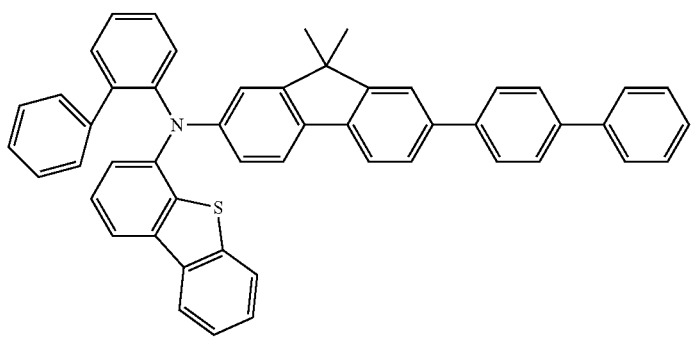
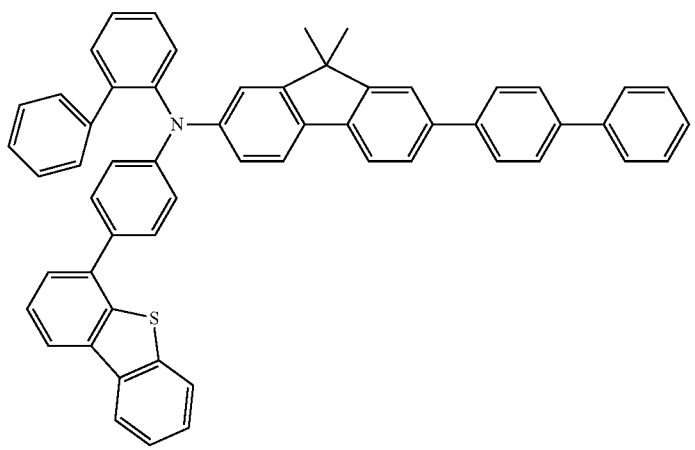
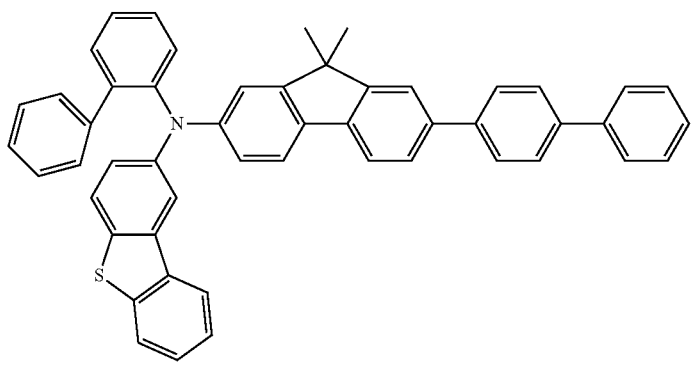

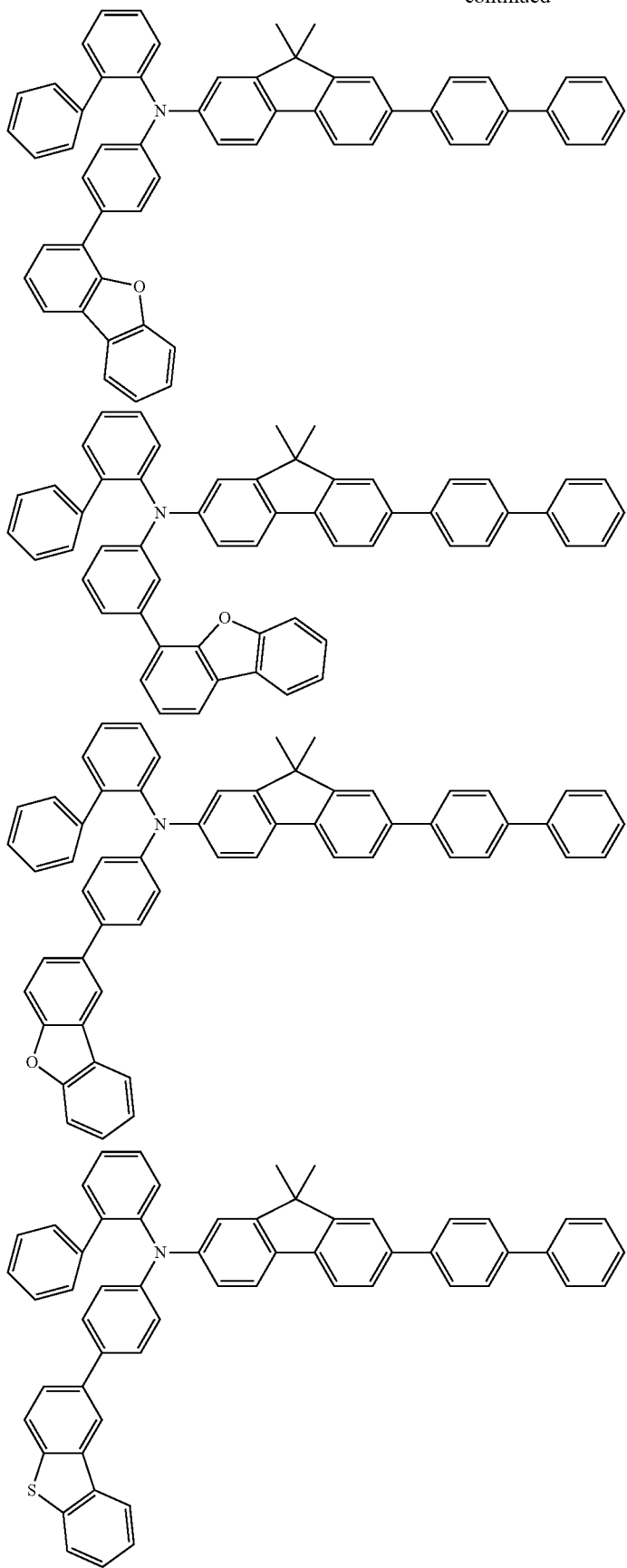

-continued
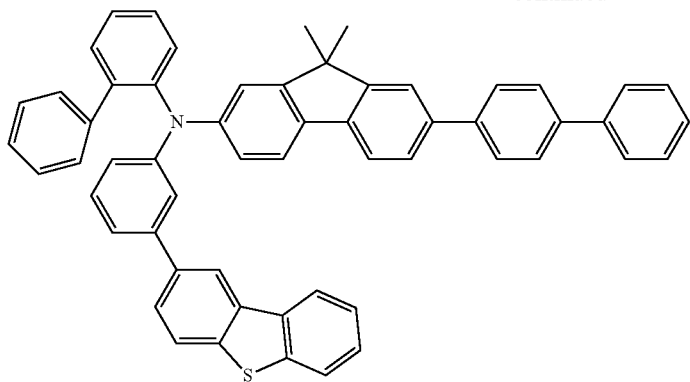
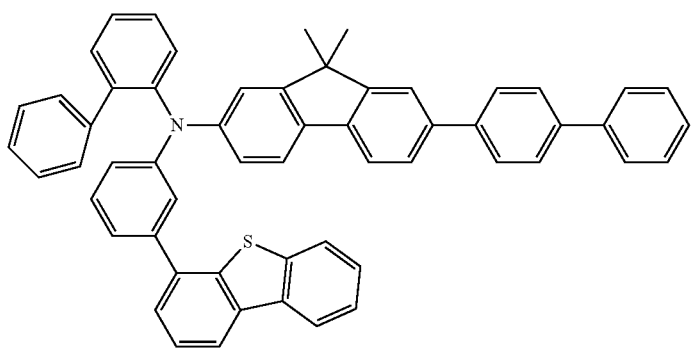
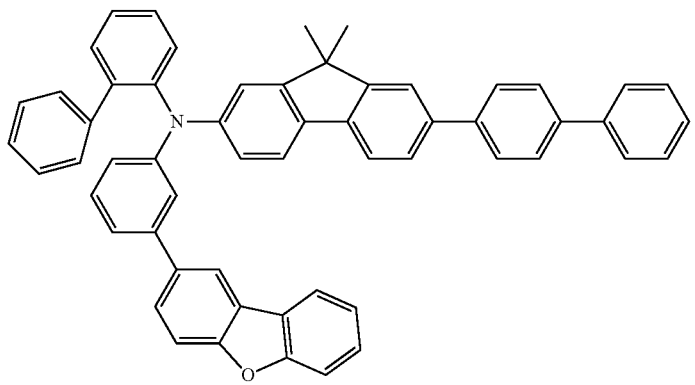
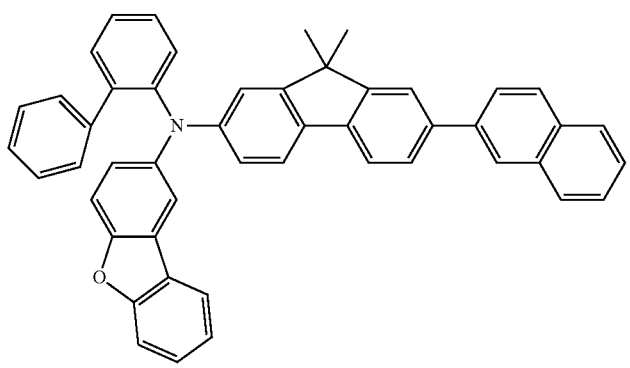

-continued
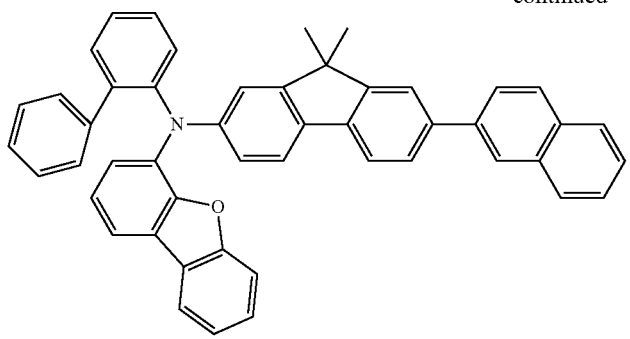
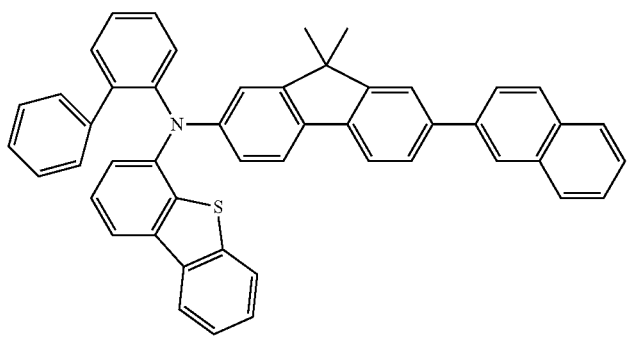
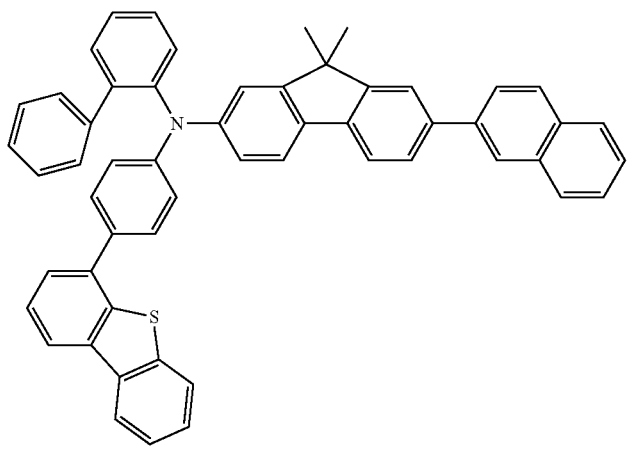
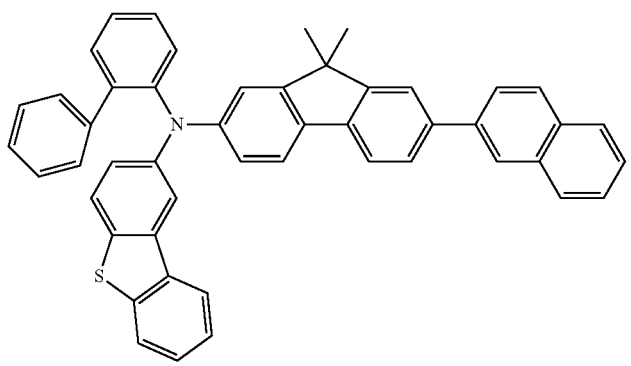

-continued
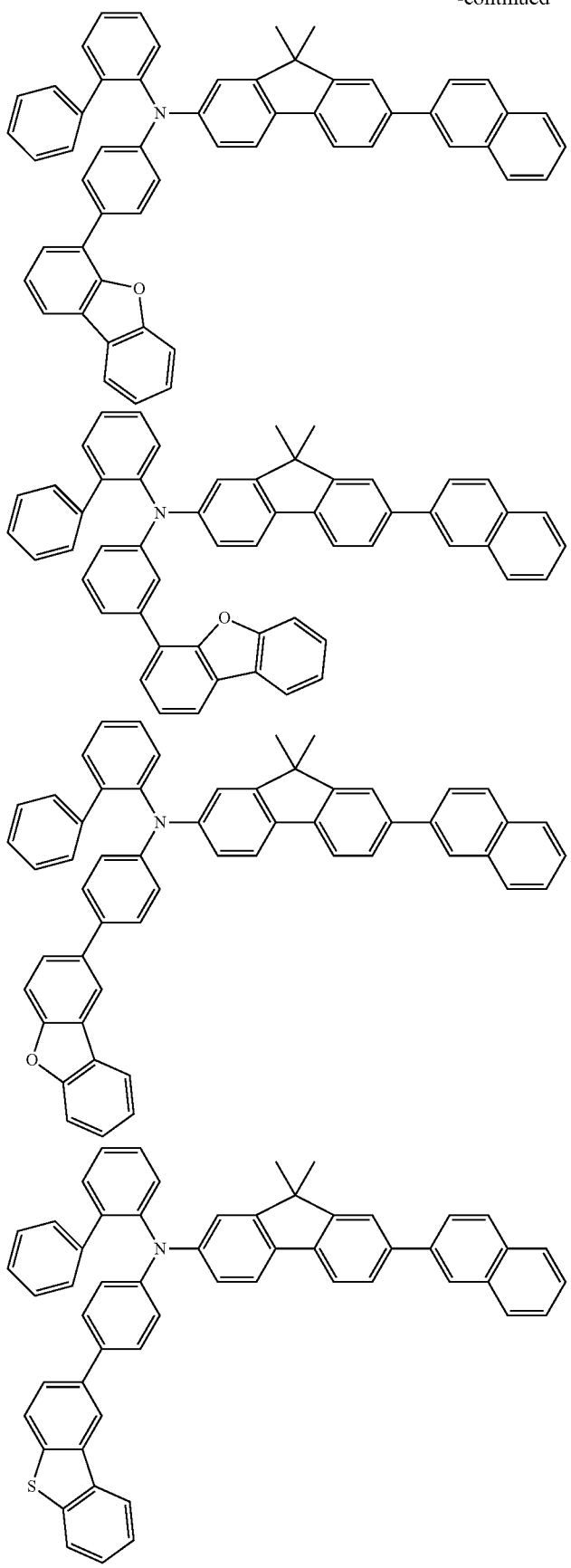

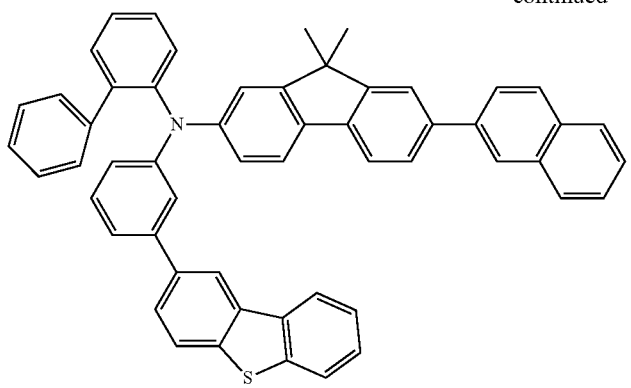
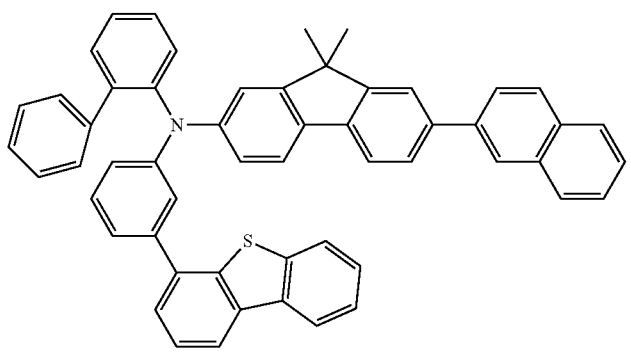
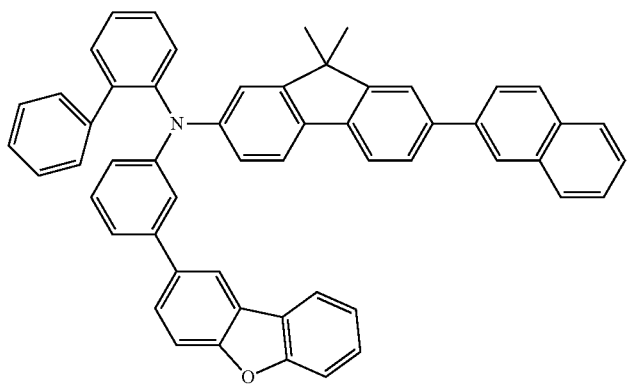
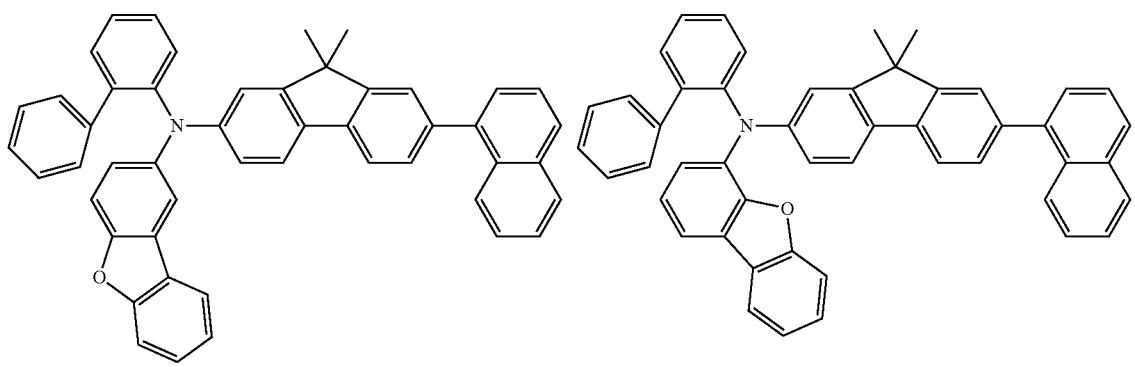

71
72
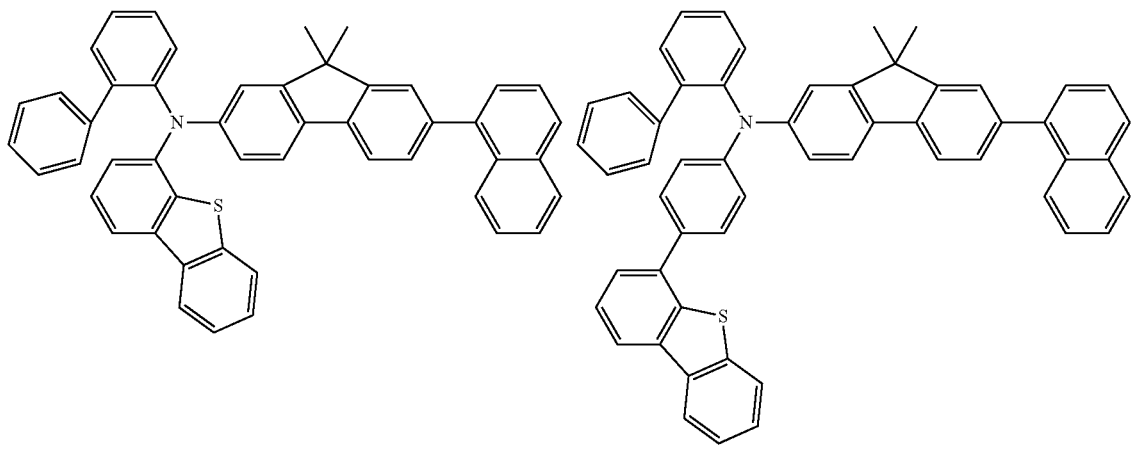
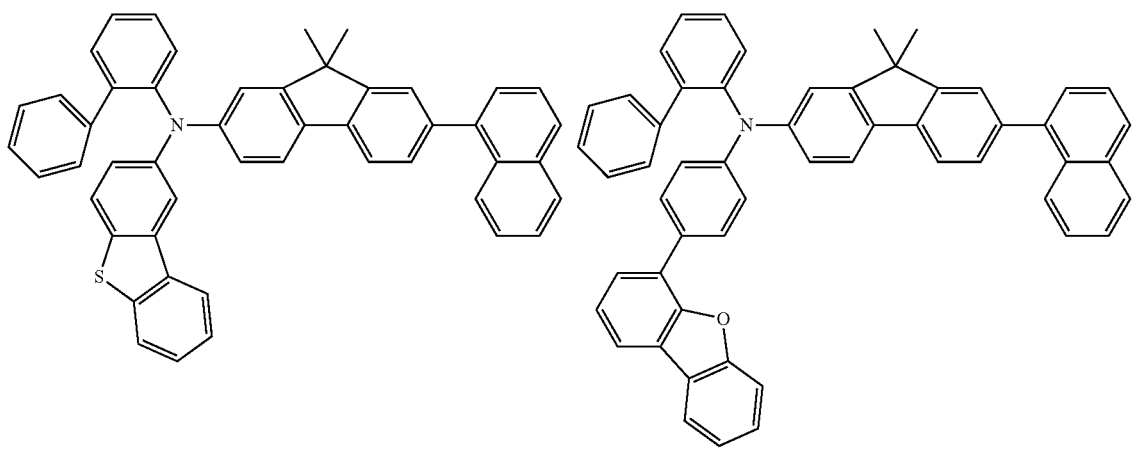
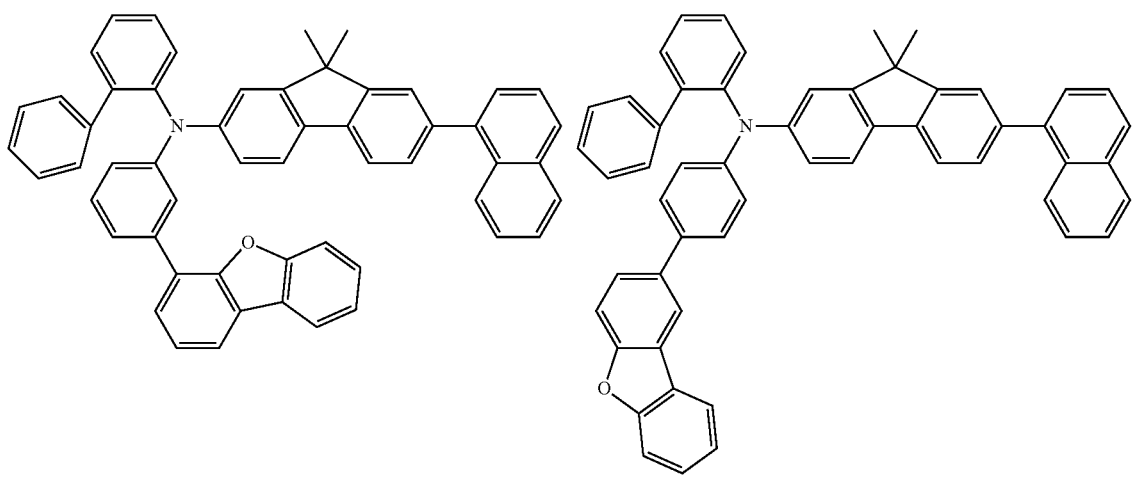

-continued
73 74
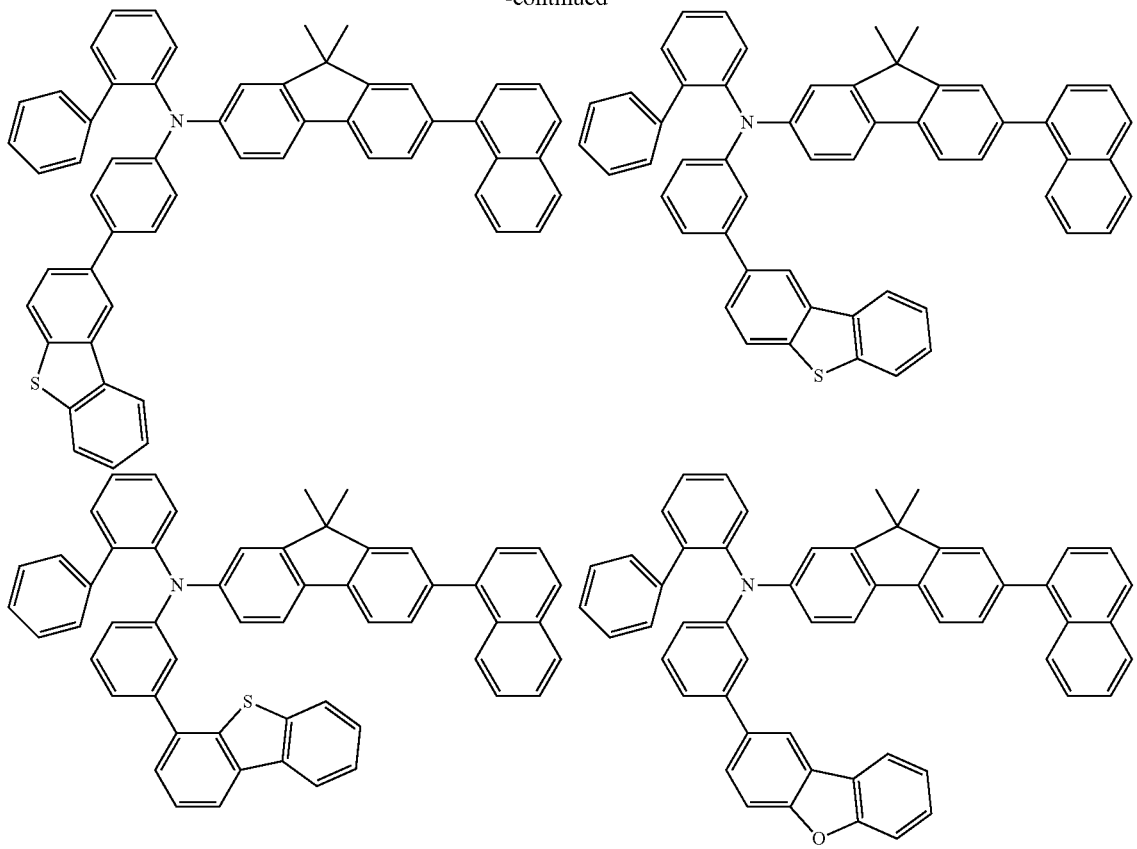
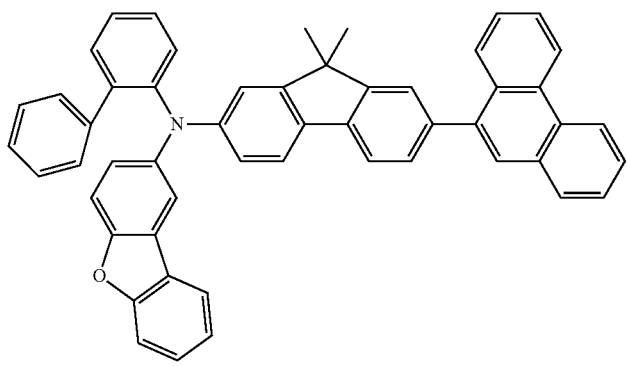
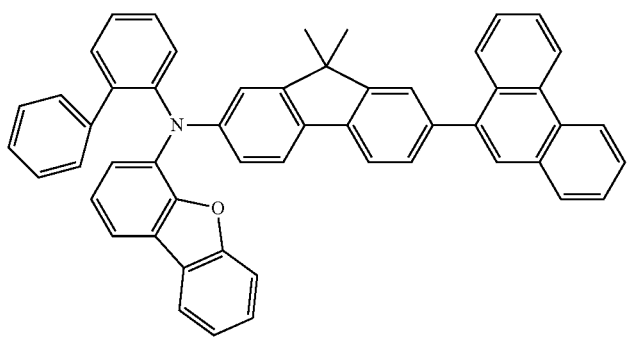

-continued
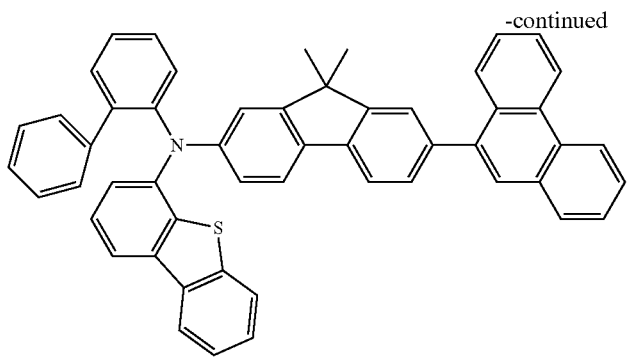
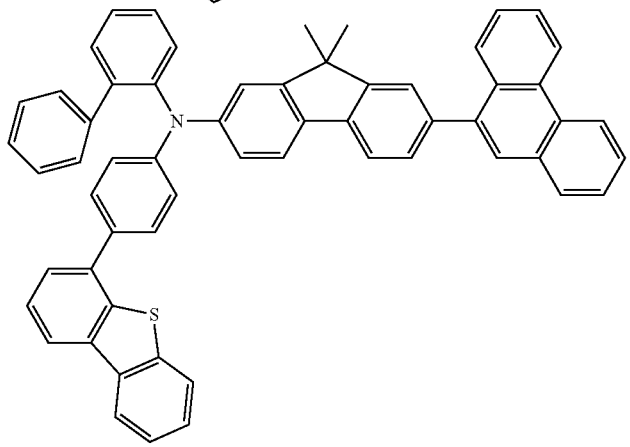
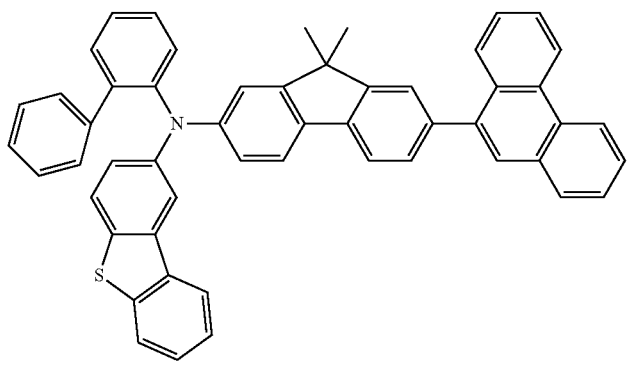
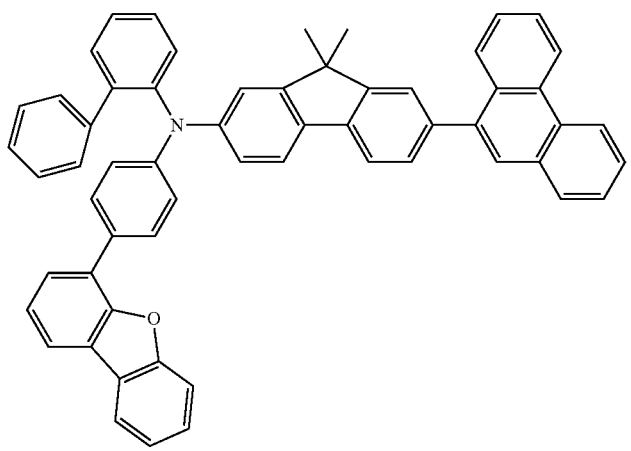

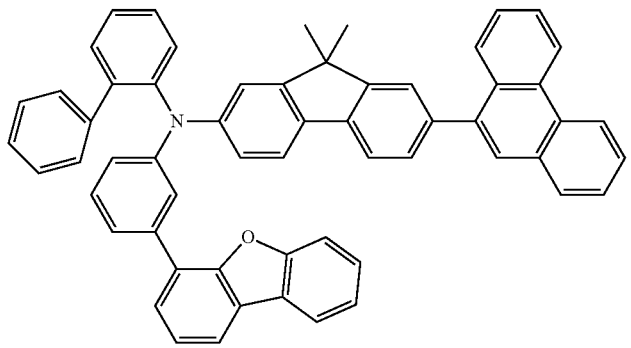
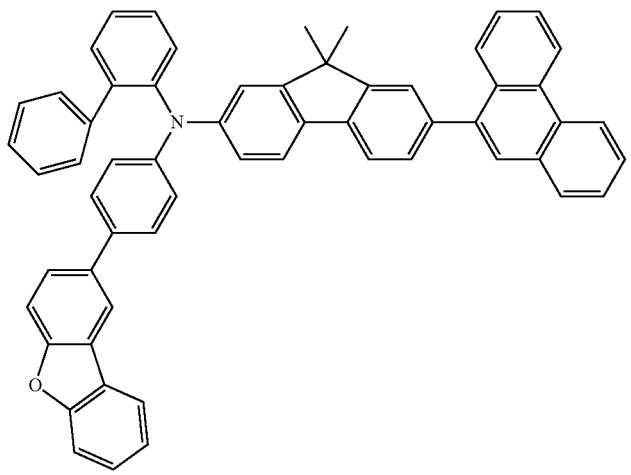
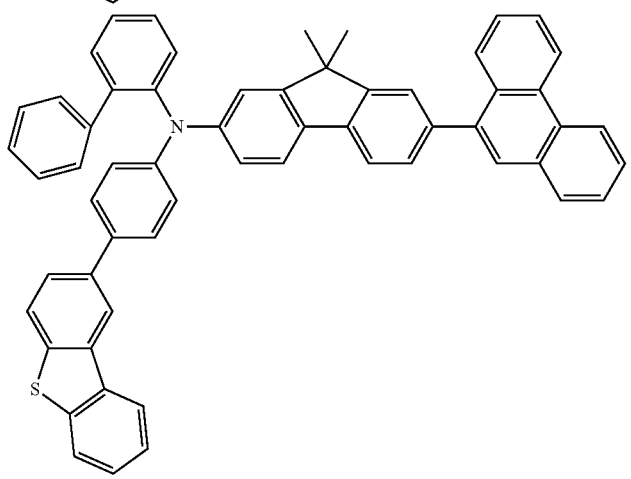
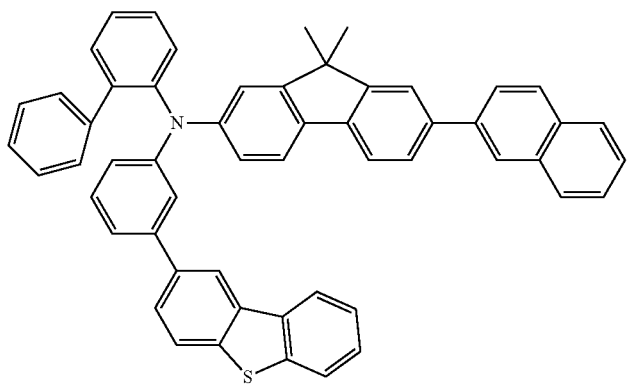

-continued
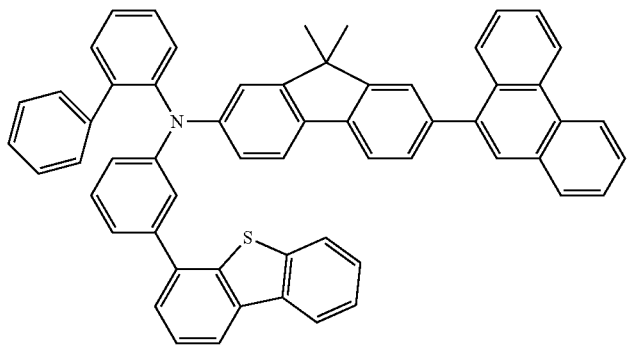
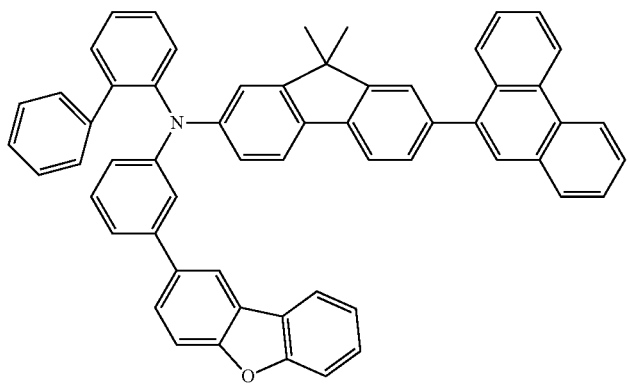
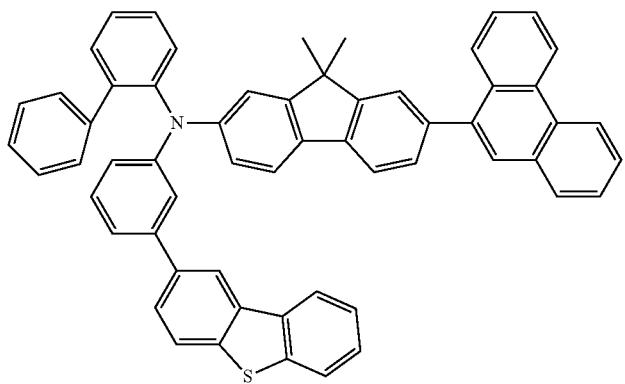
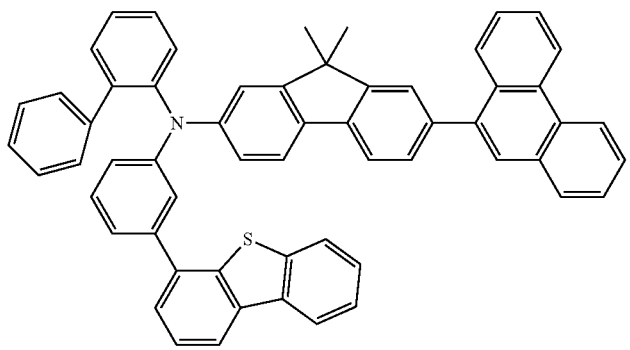

-continued
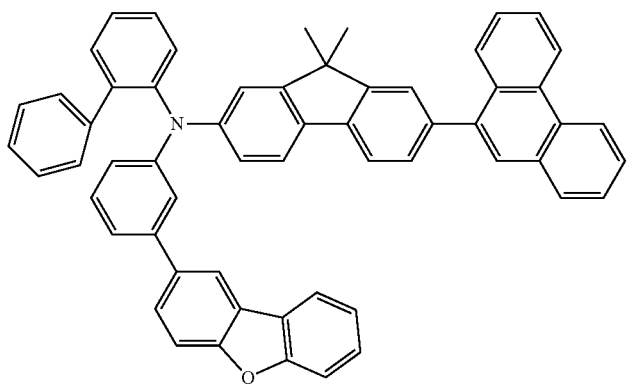
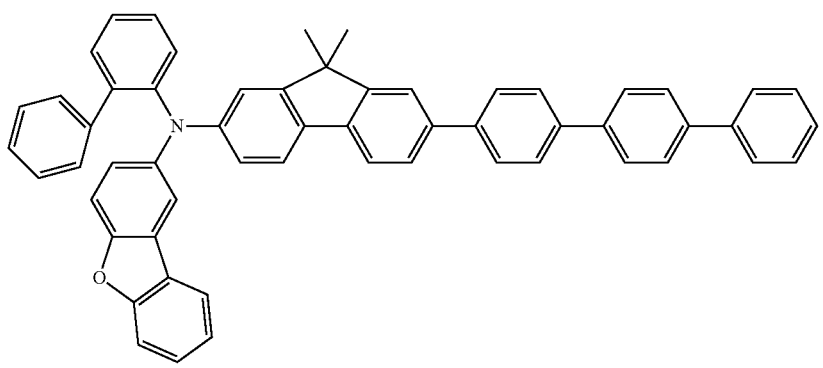
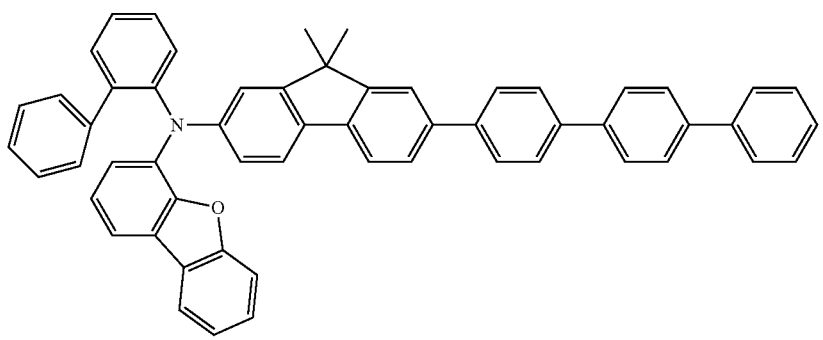
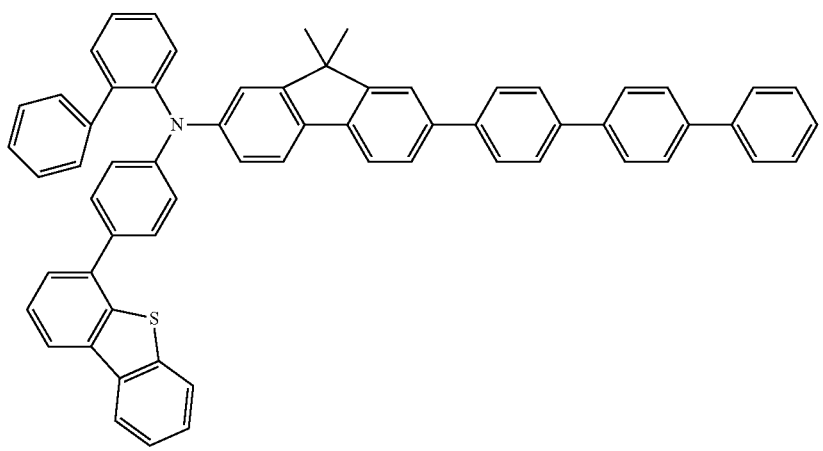

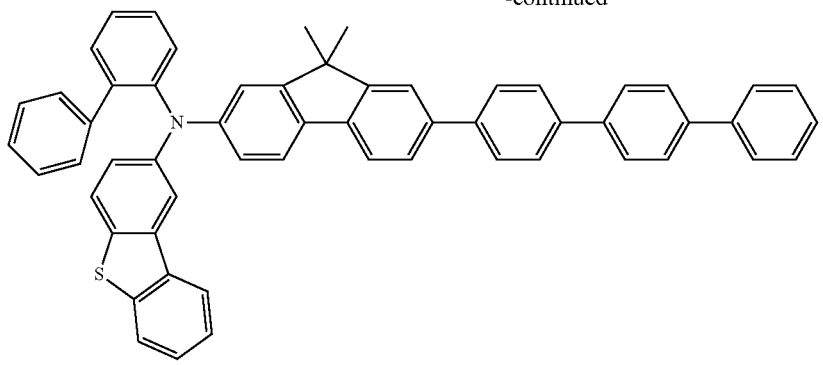
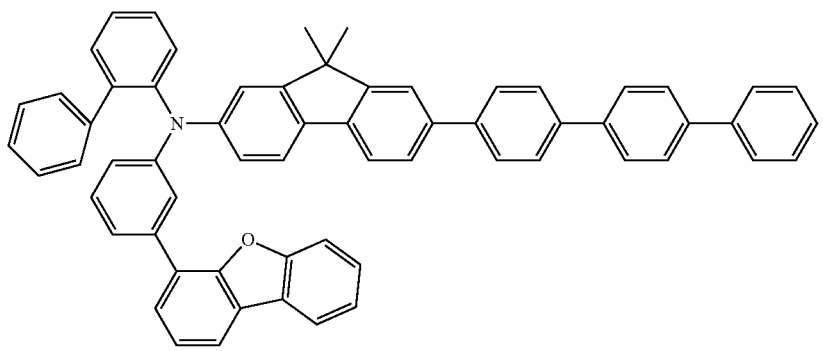
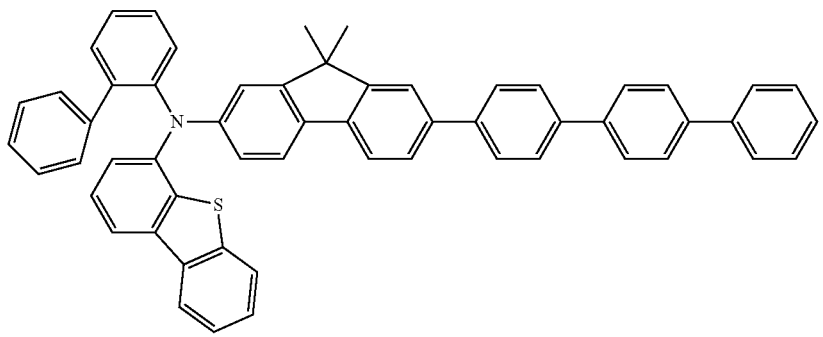
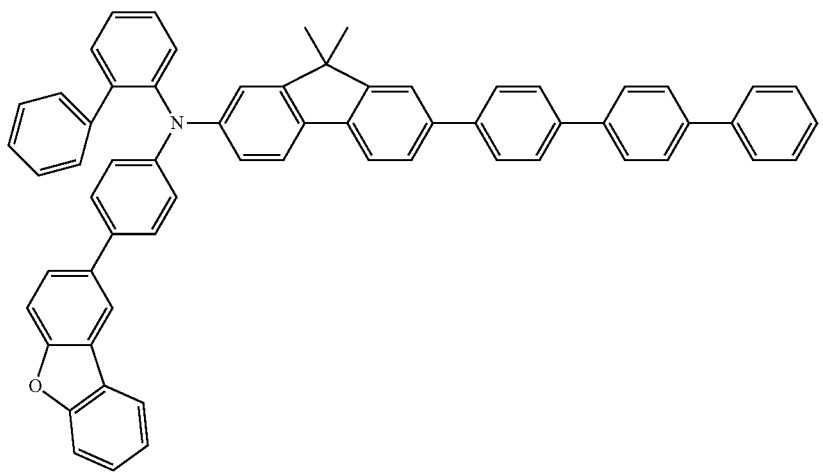

-continued
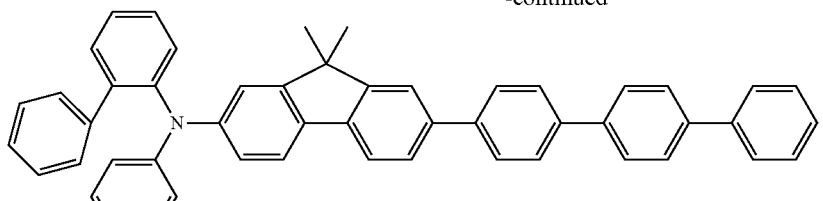
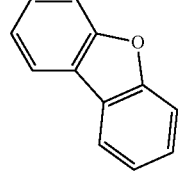
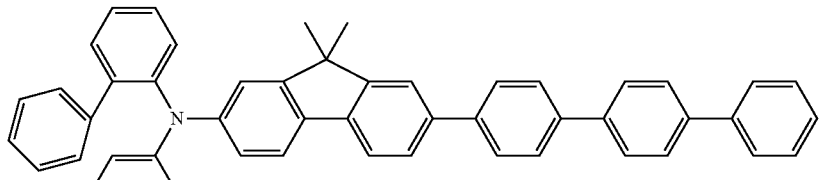
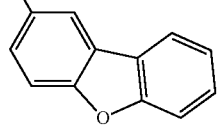
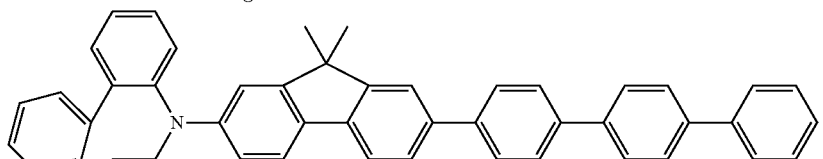
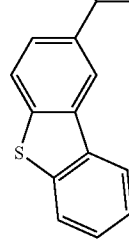
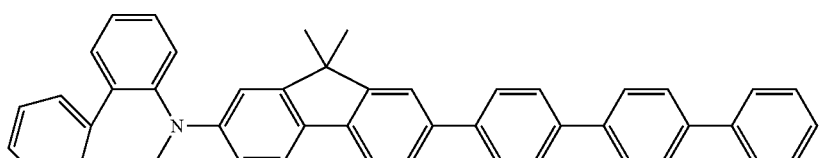
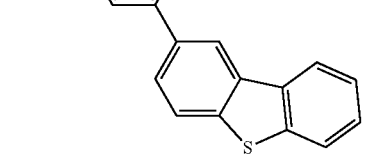

-continued
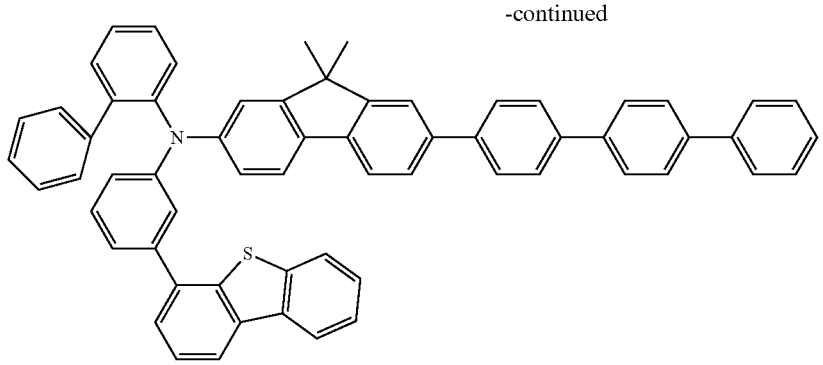
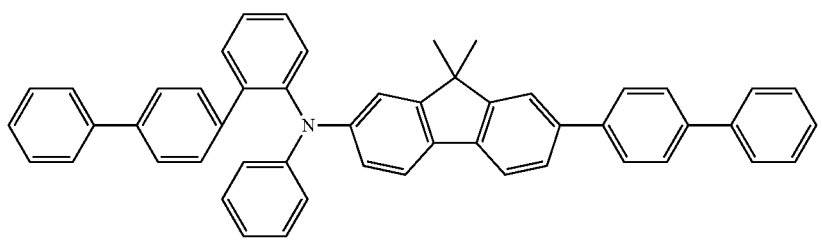
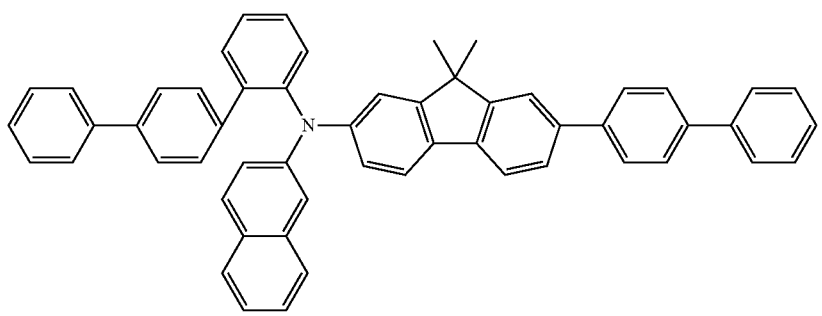
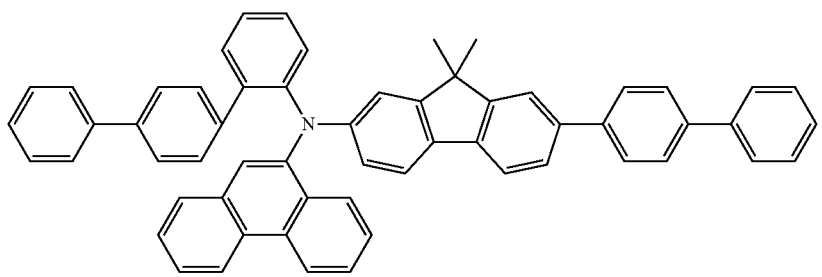
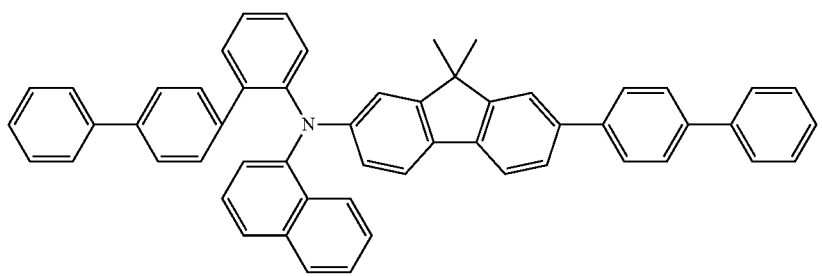

-continued
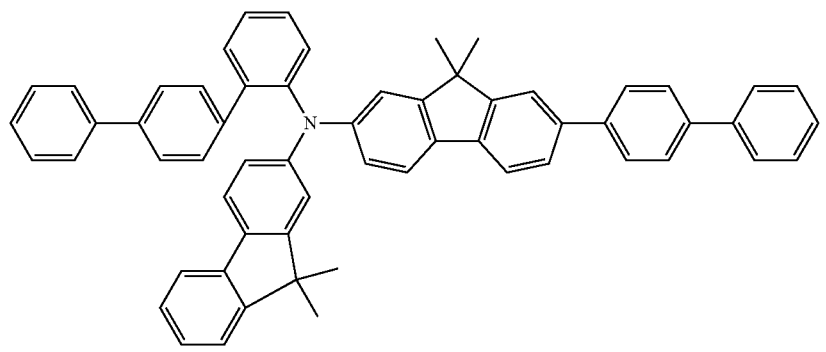
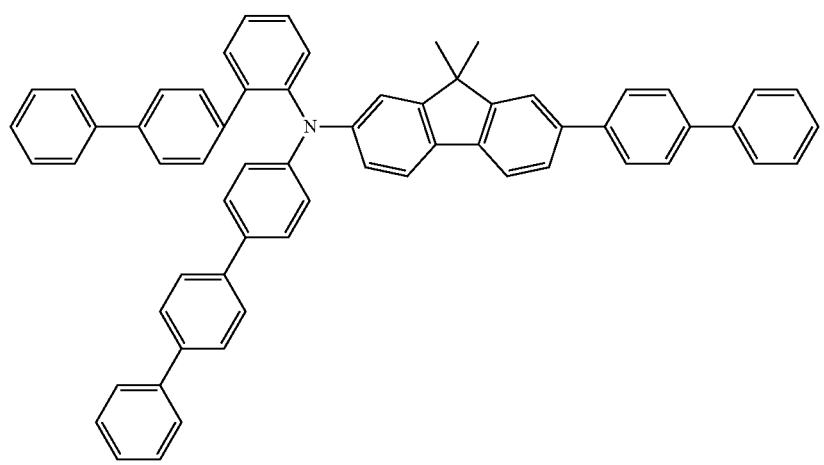
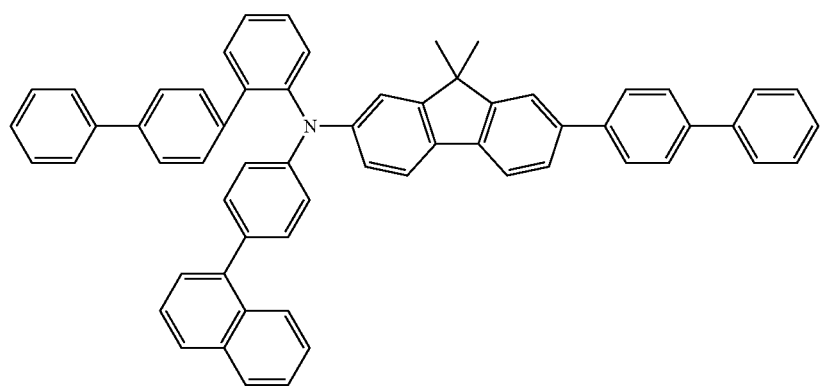

-continued
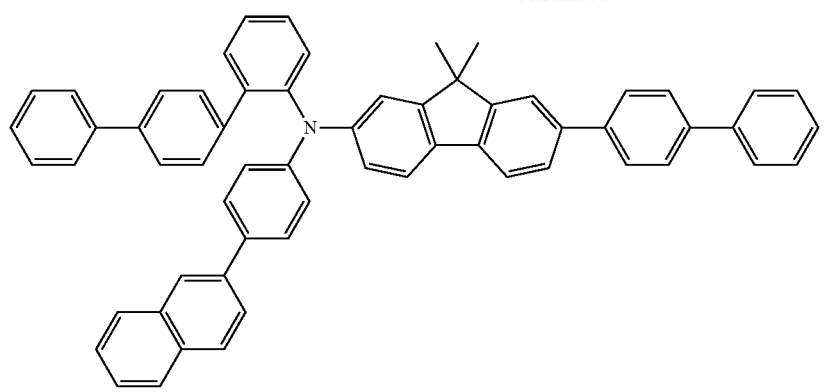
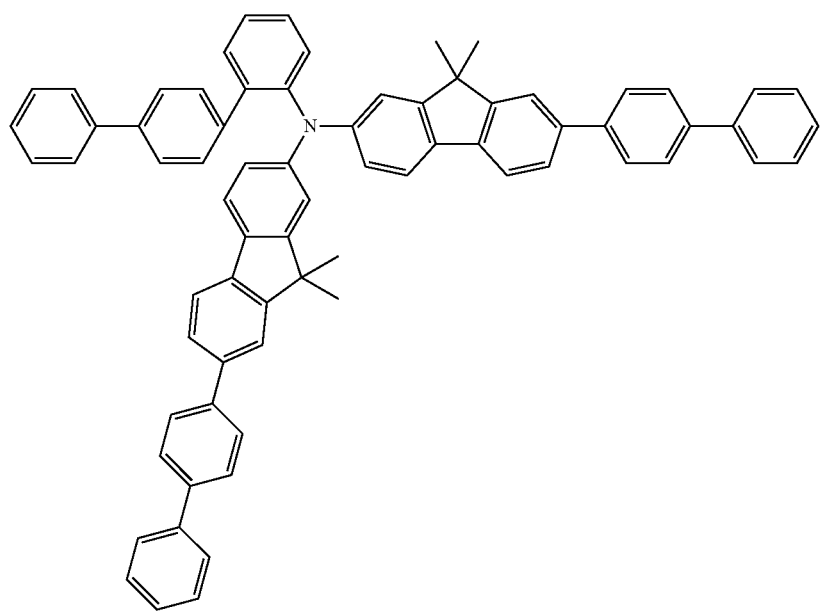
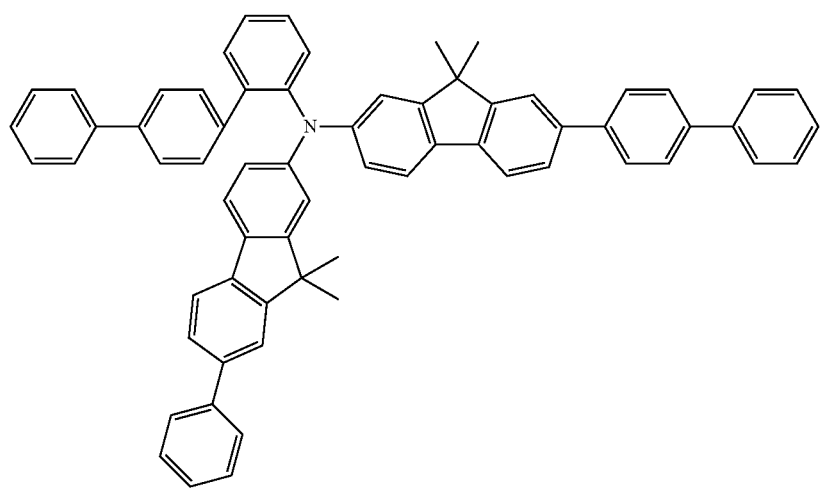

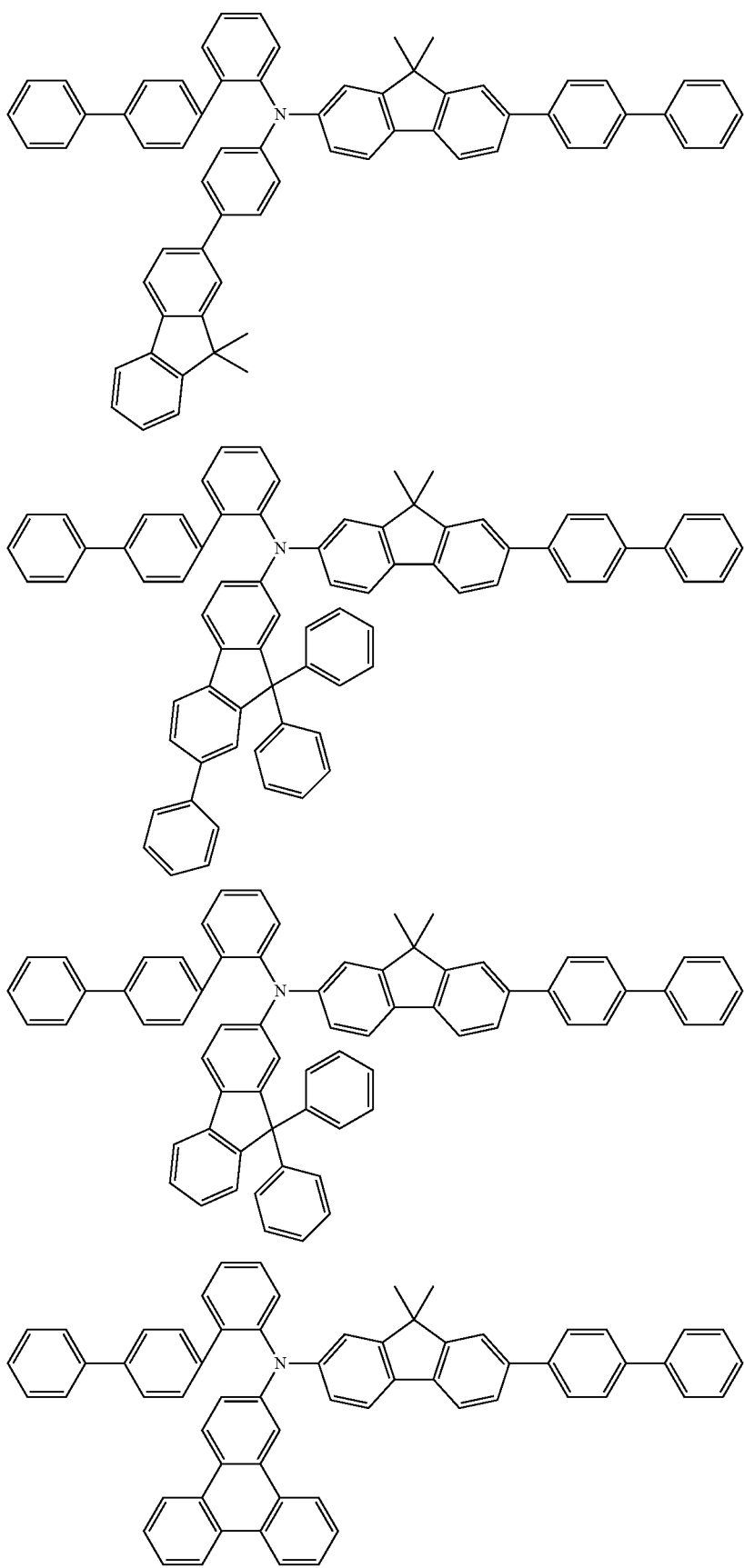

-continued
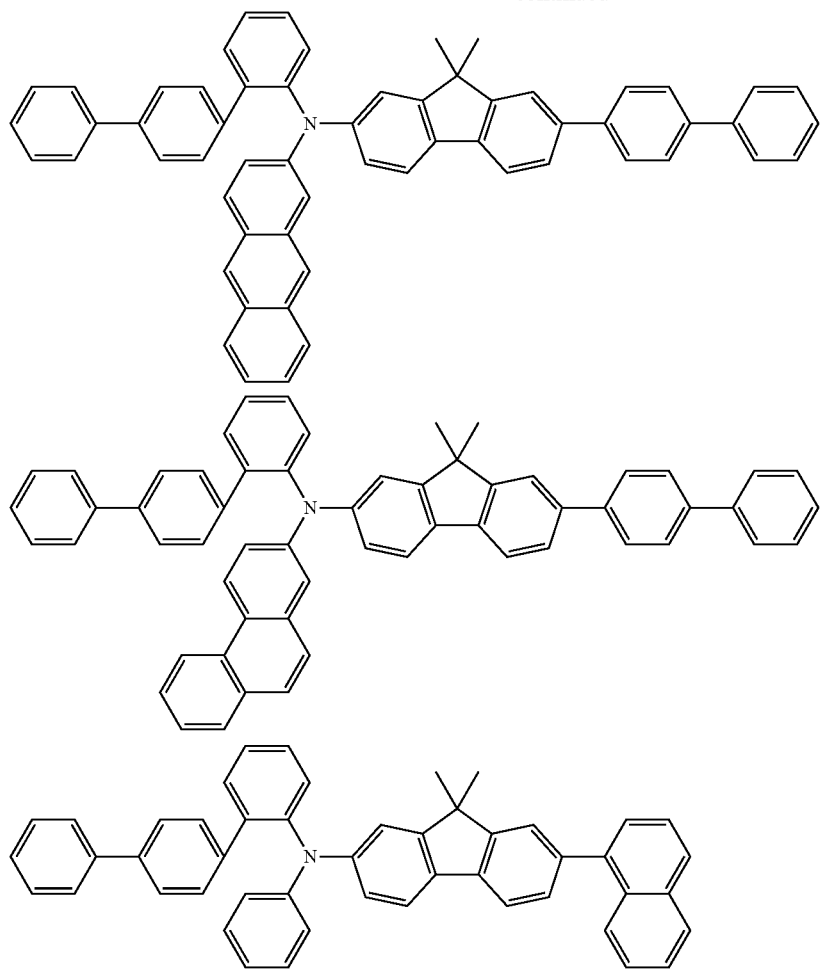
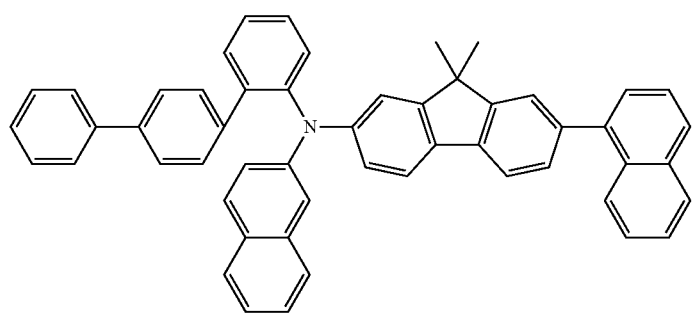
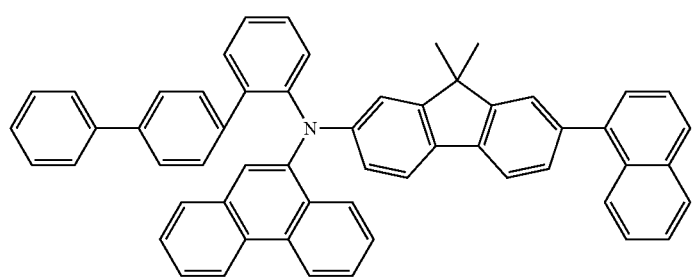

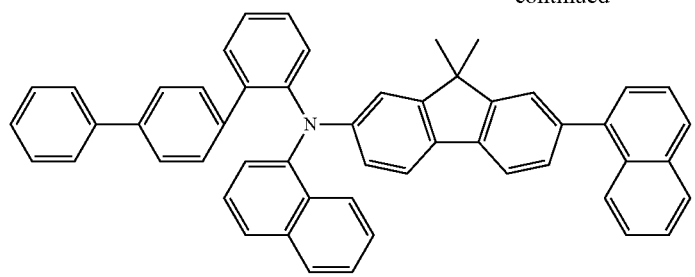
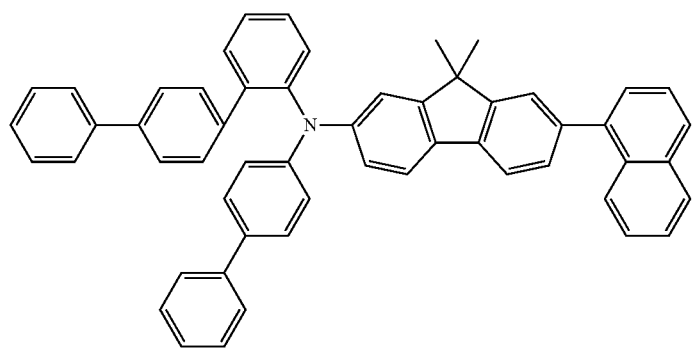
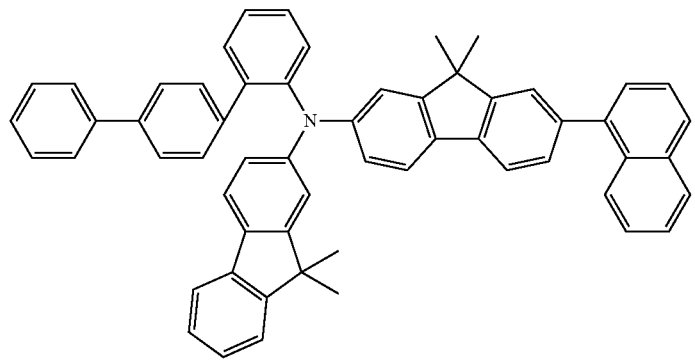
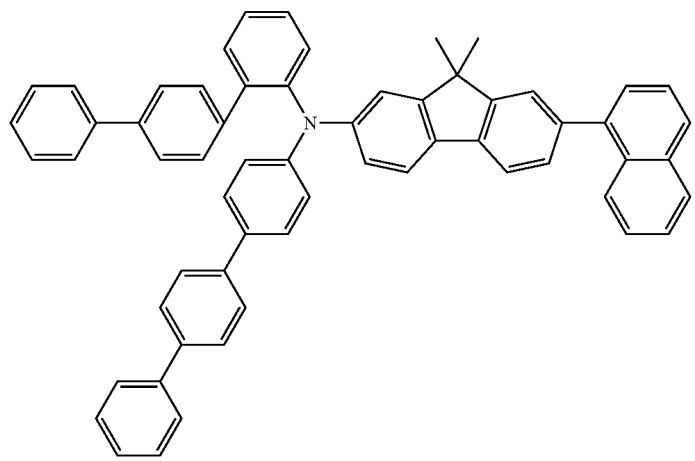

-continued
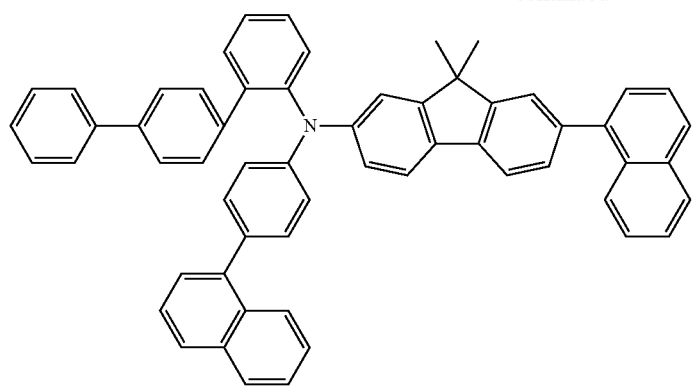
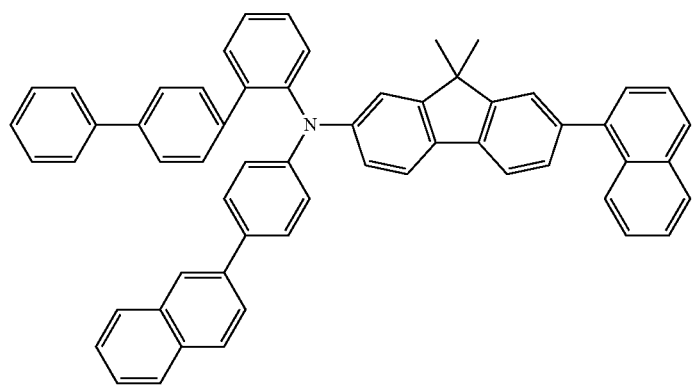
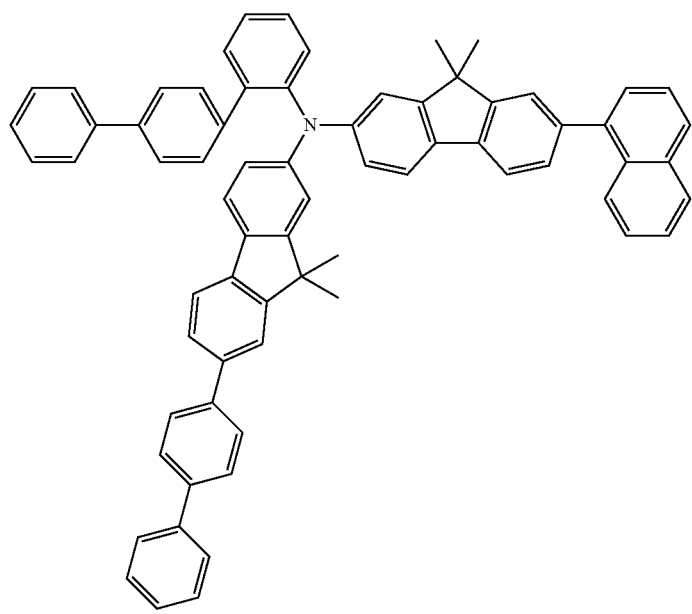

-continued
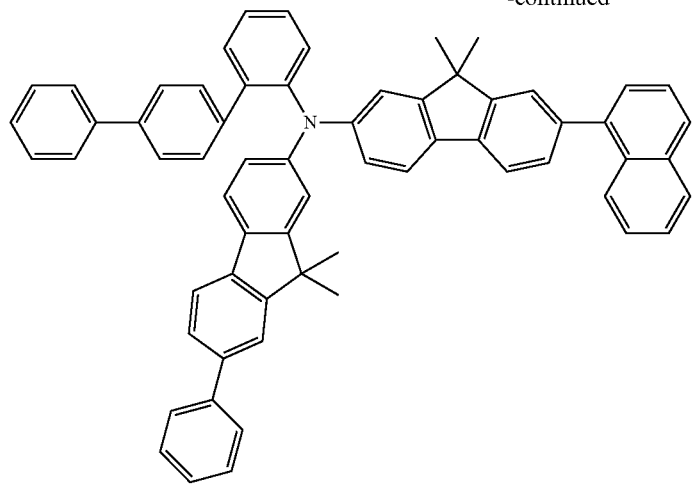
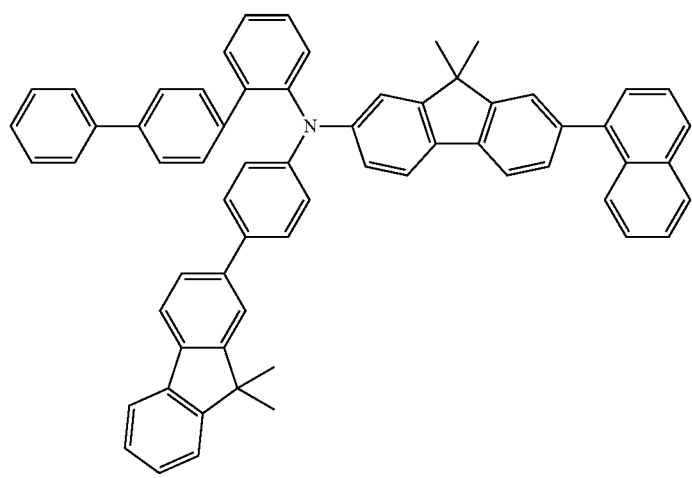
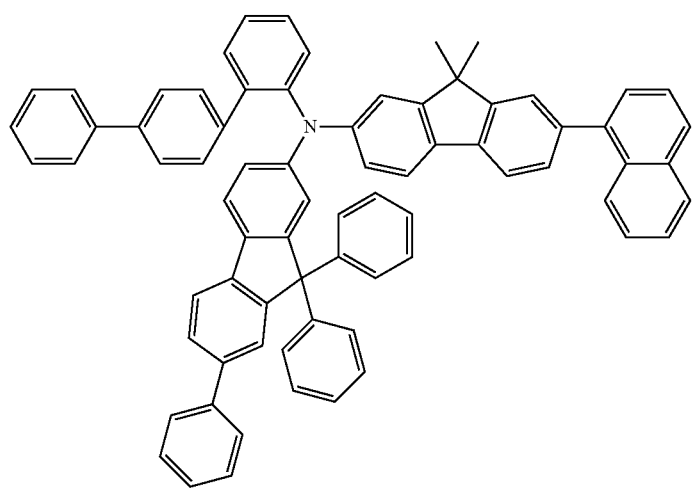

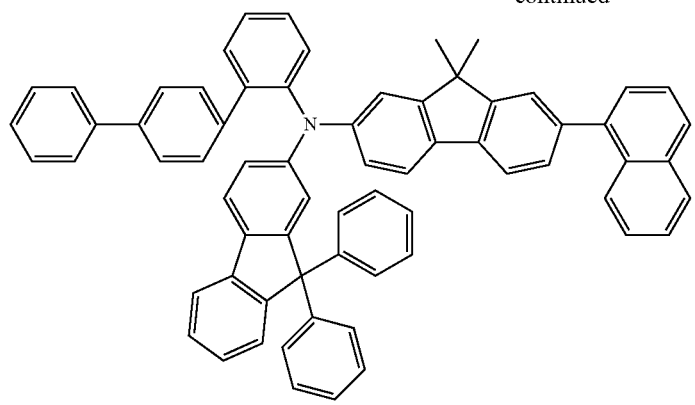
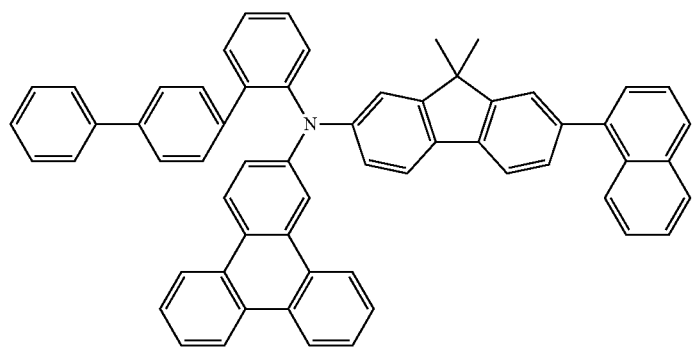
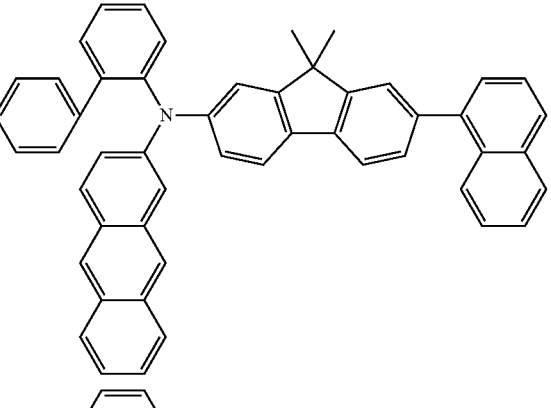
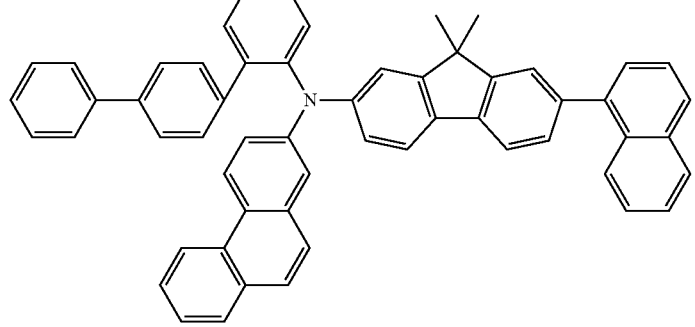
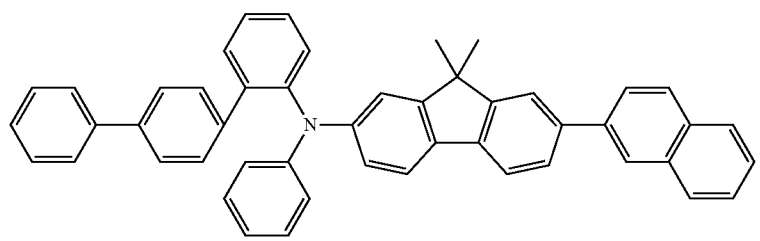

-continued
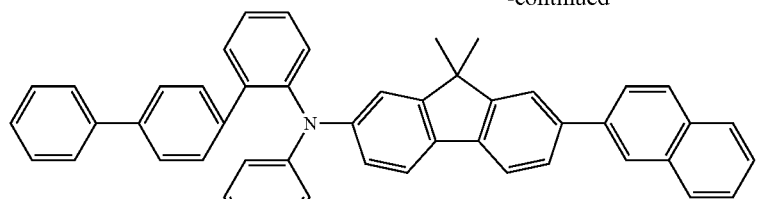
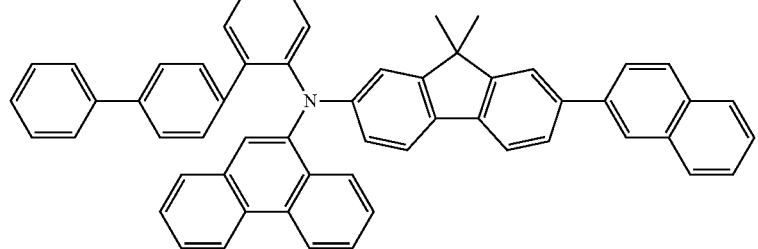
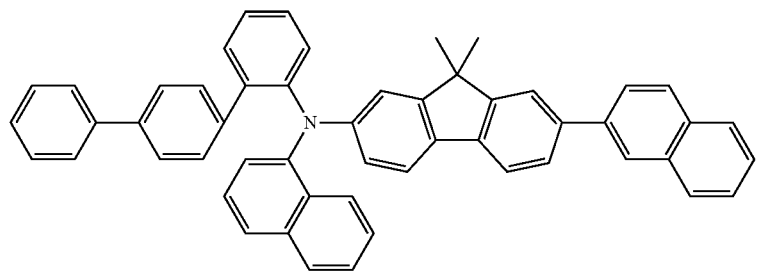
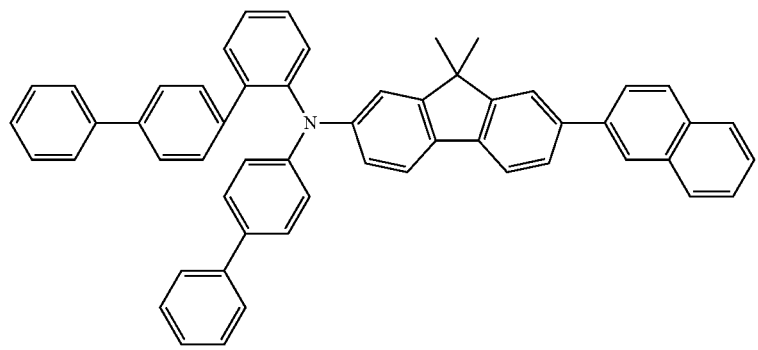
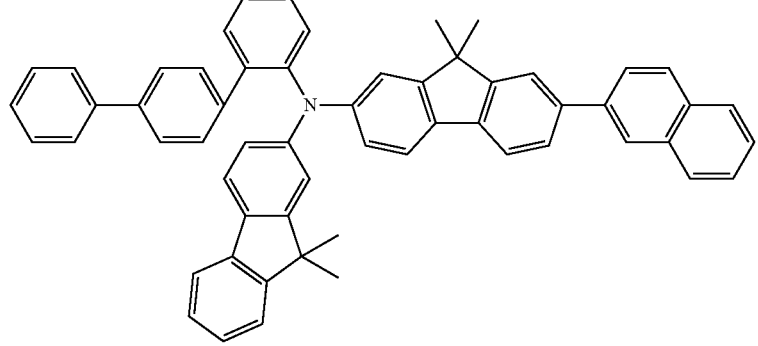

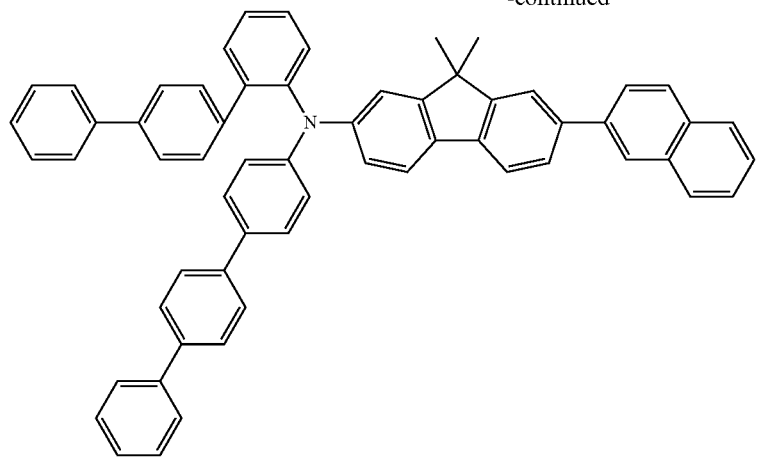
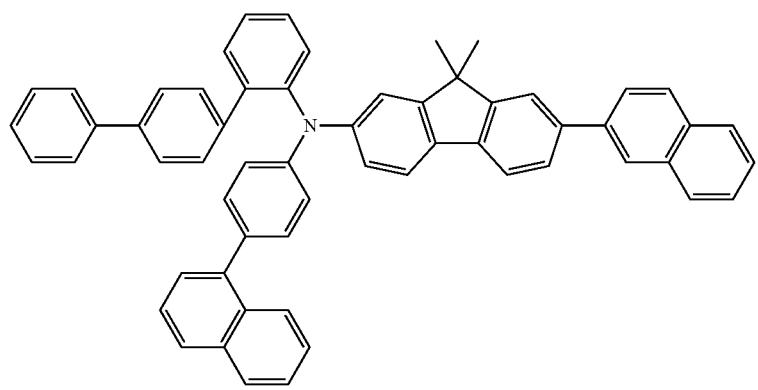
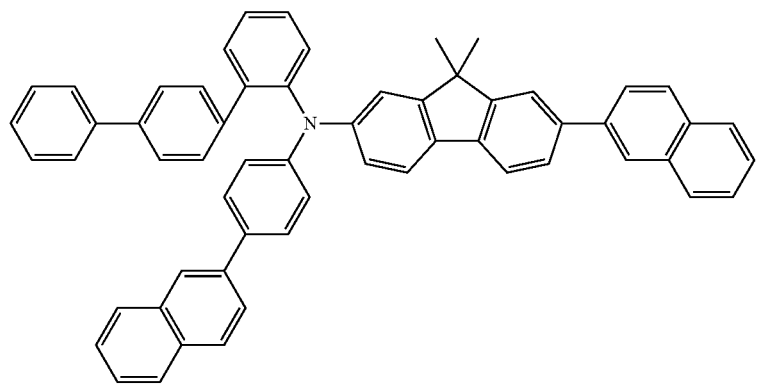

-continued
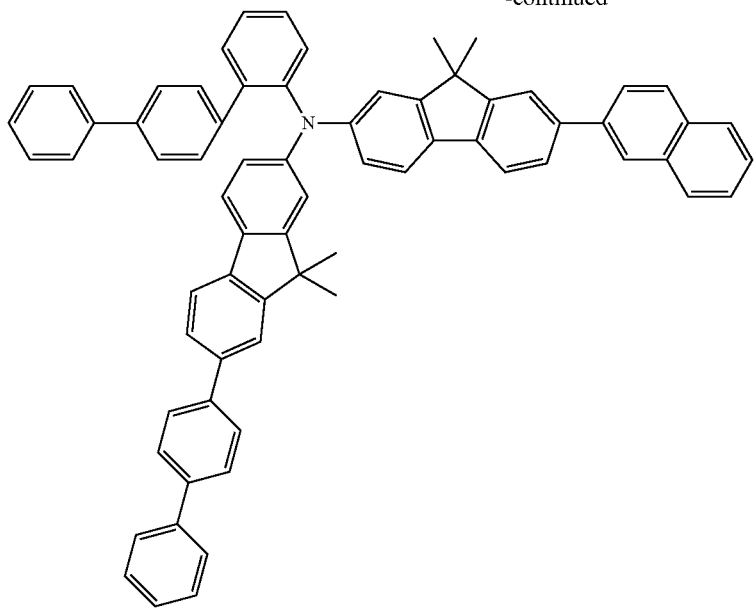
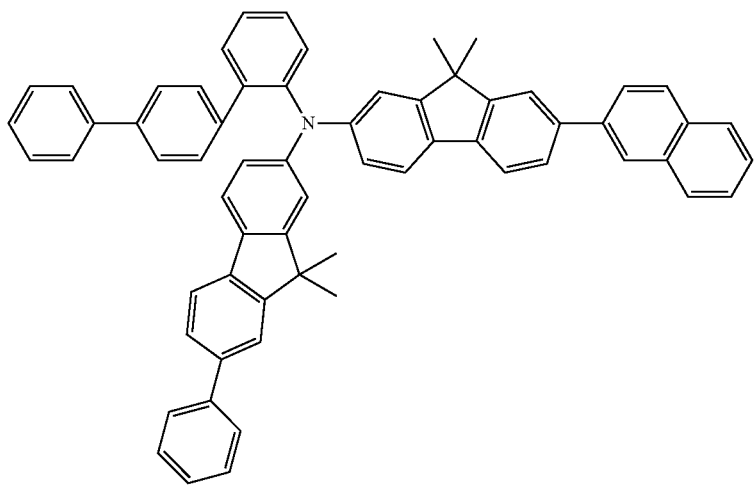
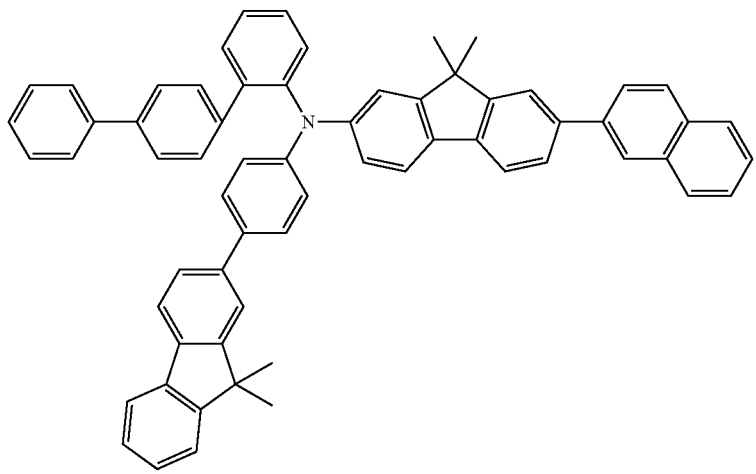

-continued
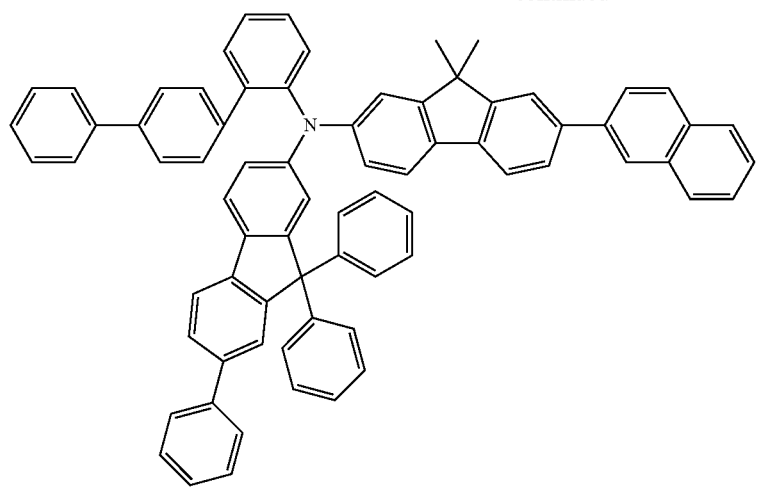
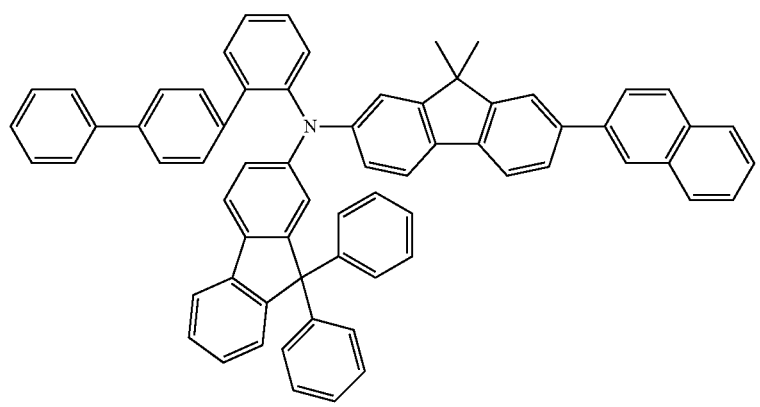
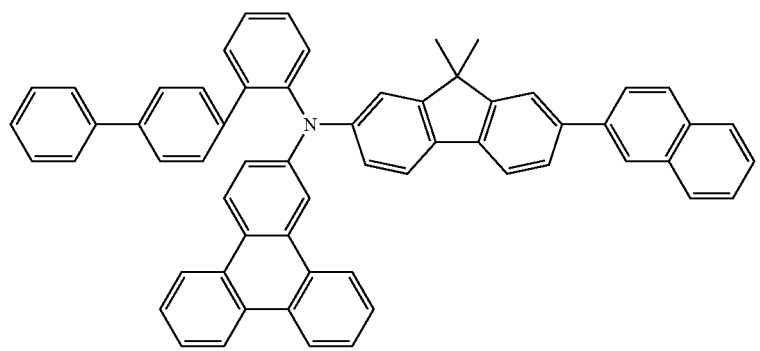
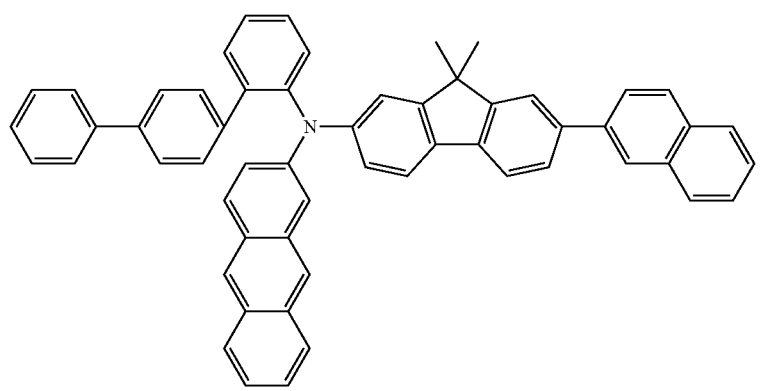

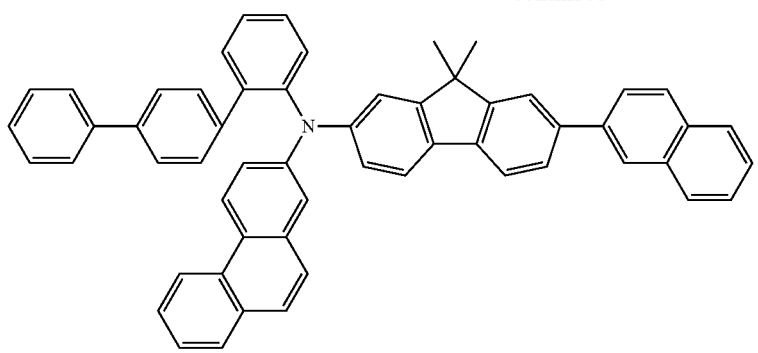
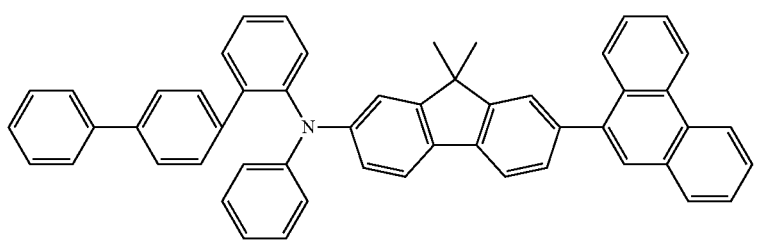
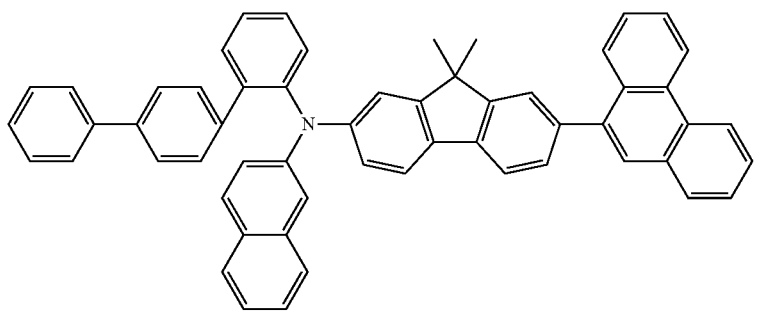
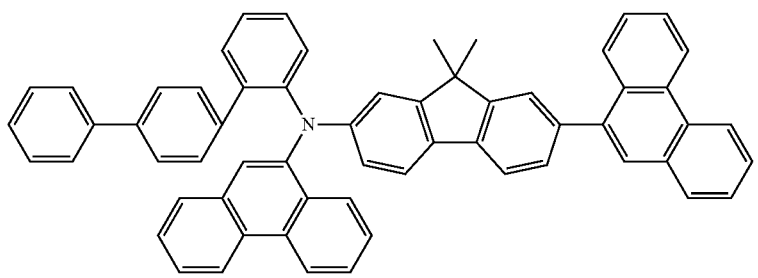
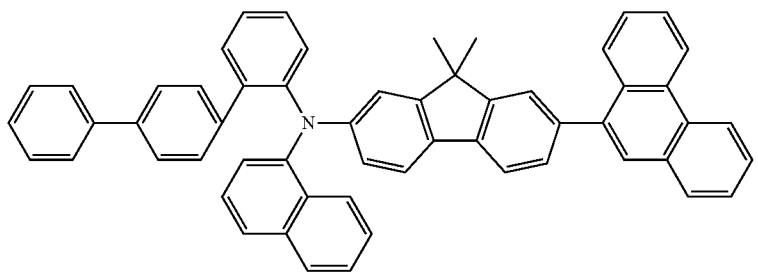

-continued
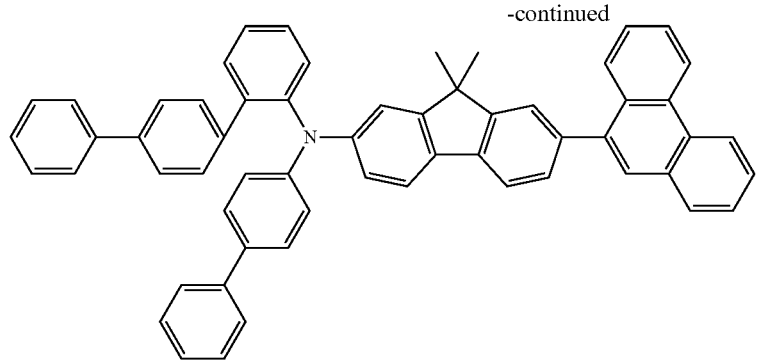
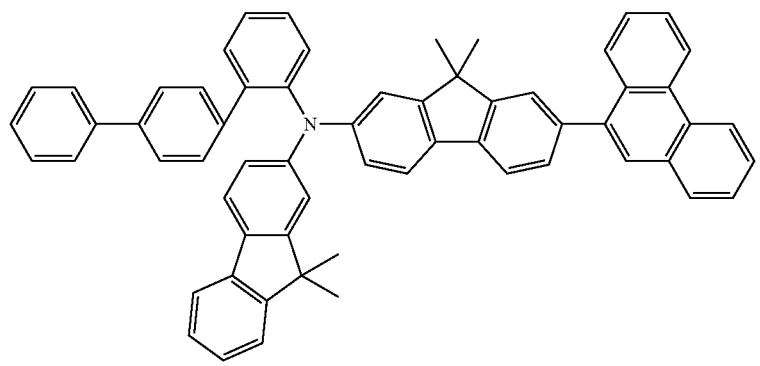
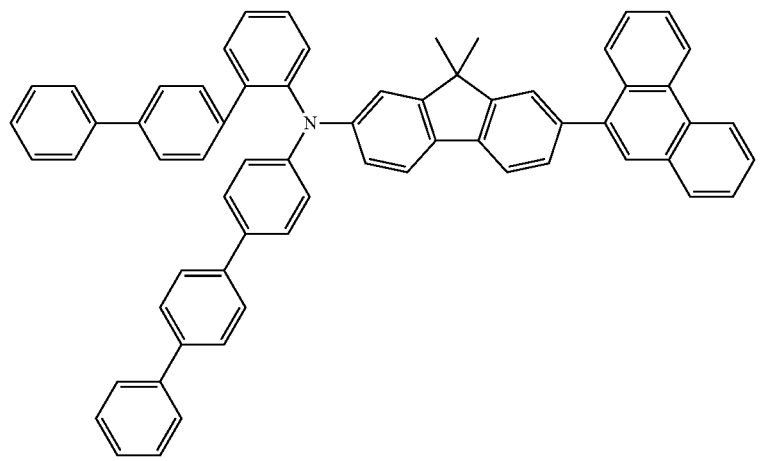
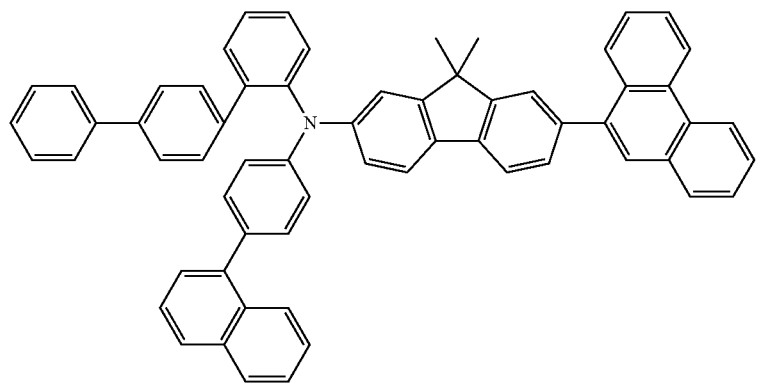

-continued
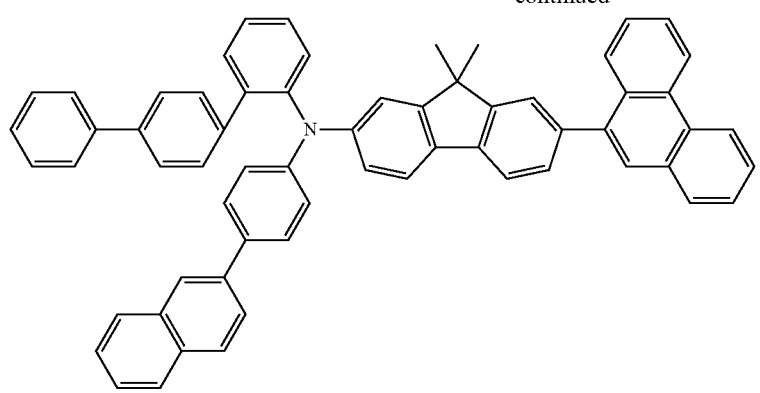
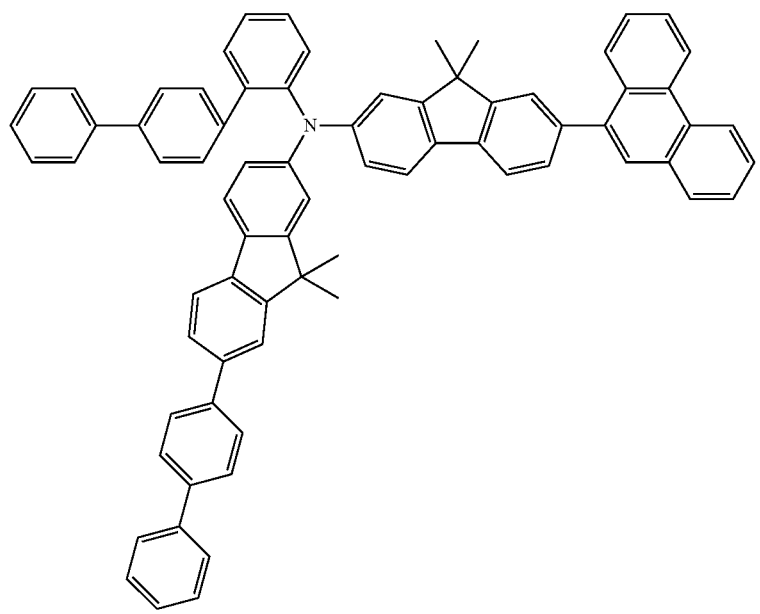
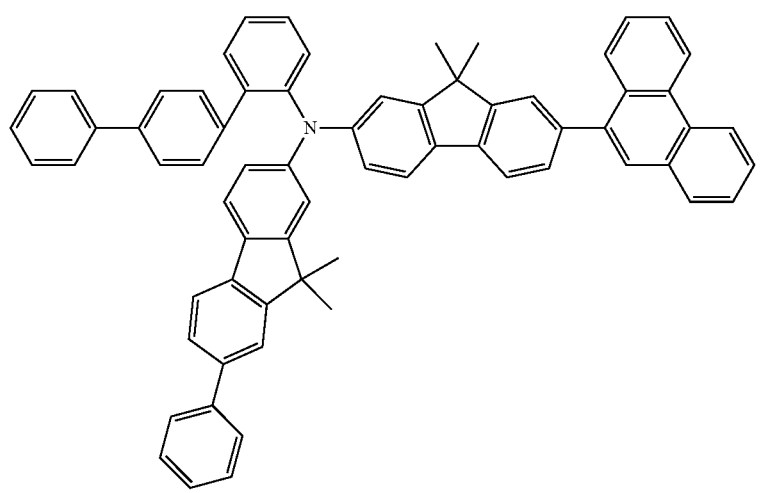

-continued
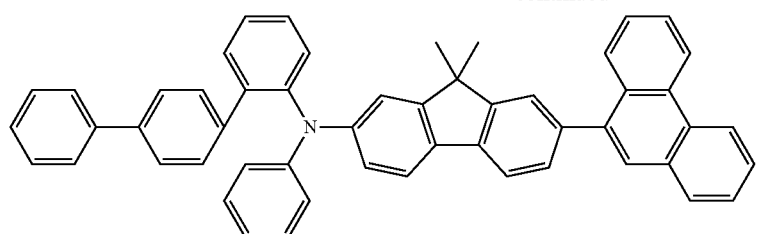
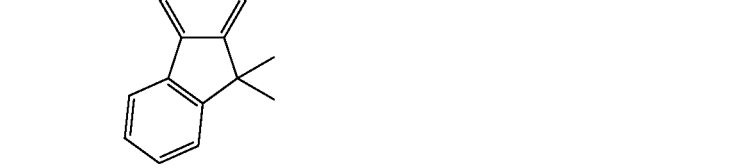
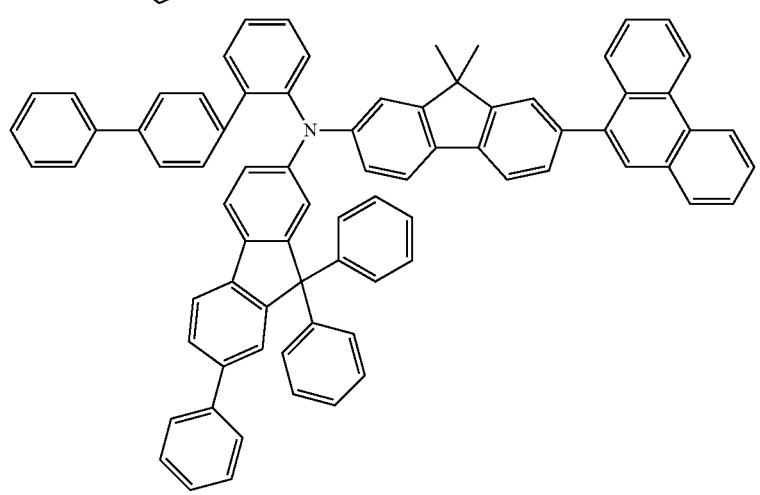
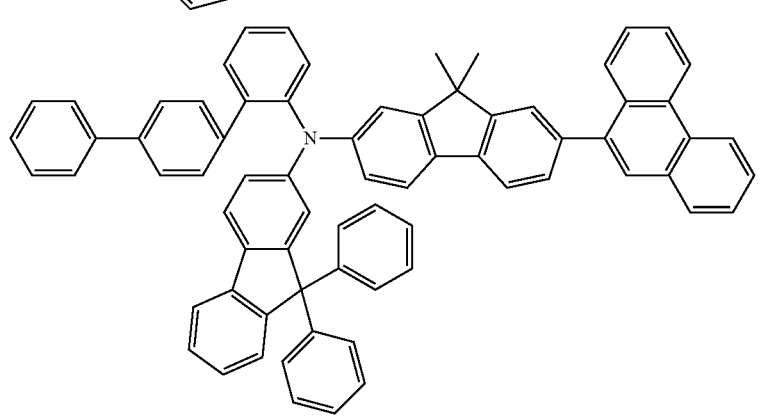
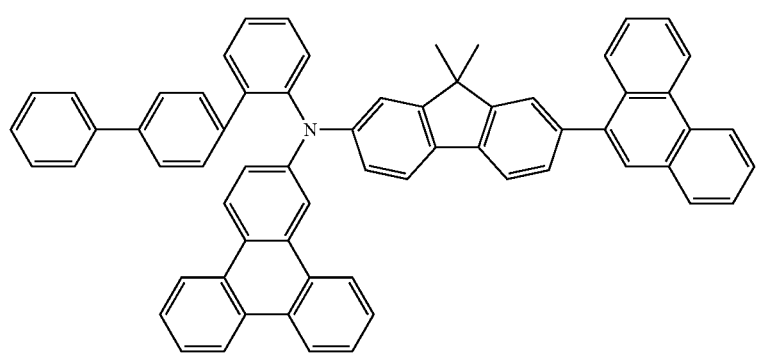

-continued
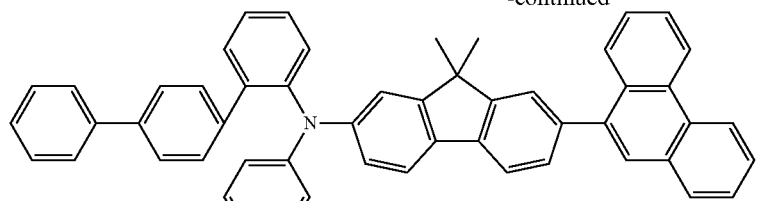
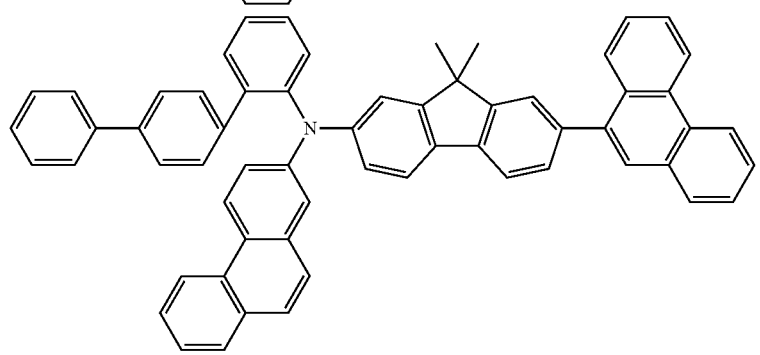
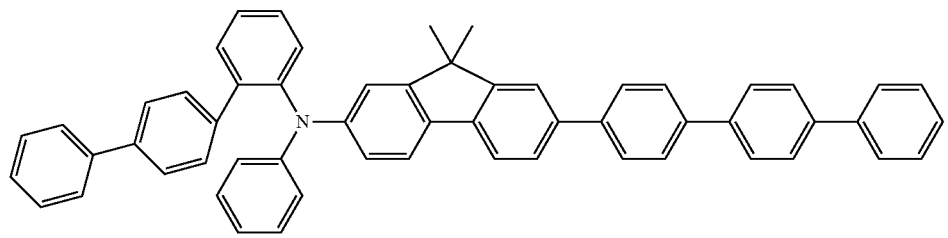
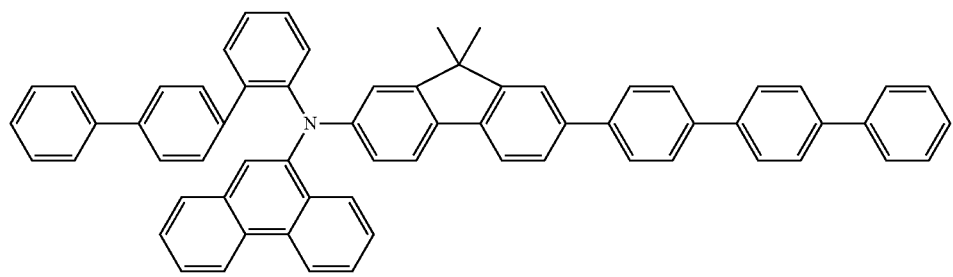
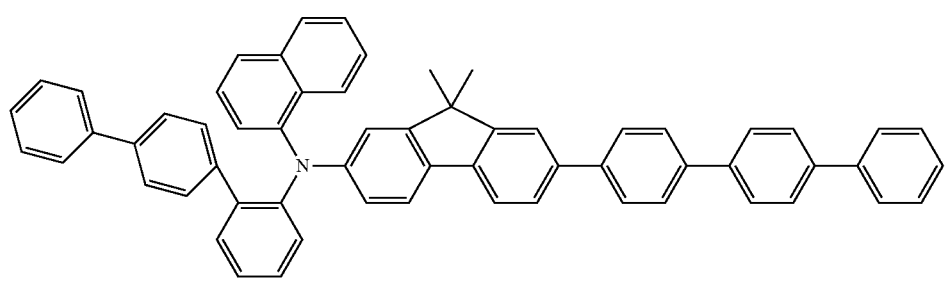

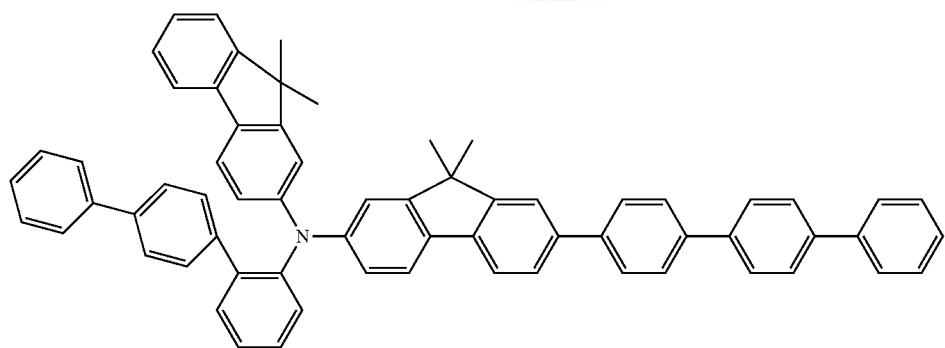
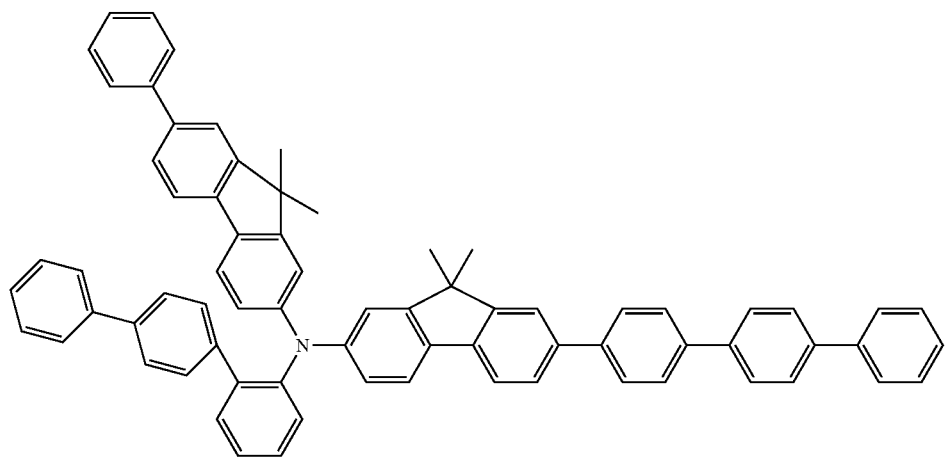
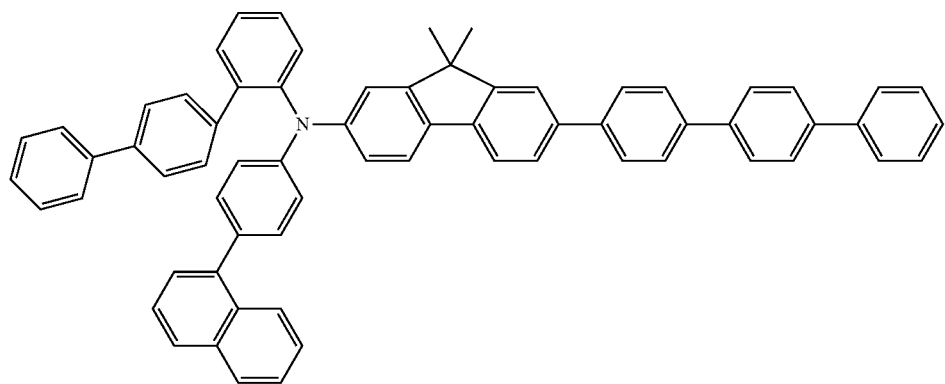

-continued
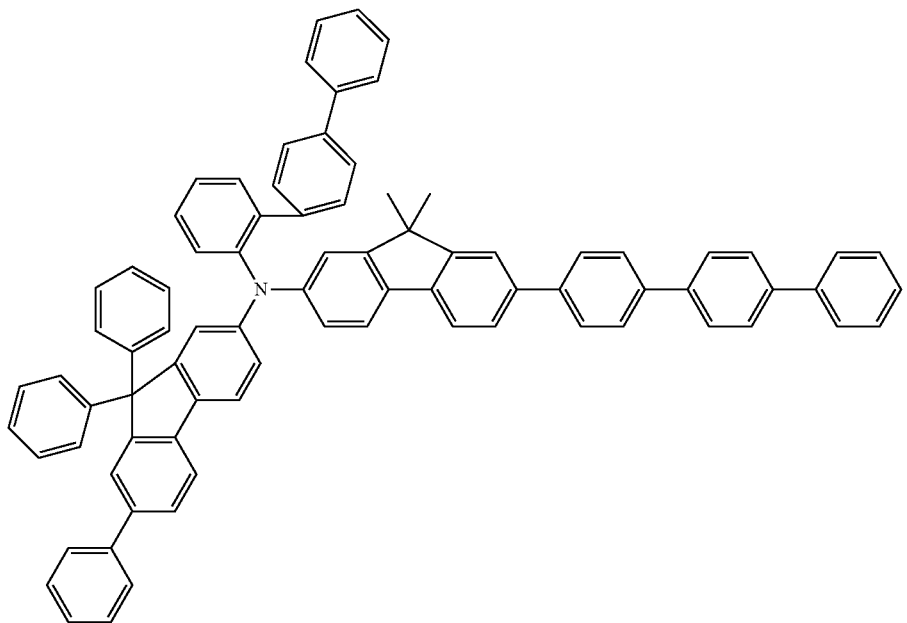
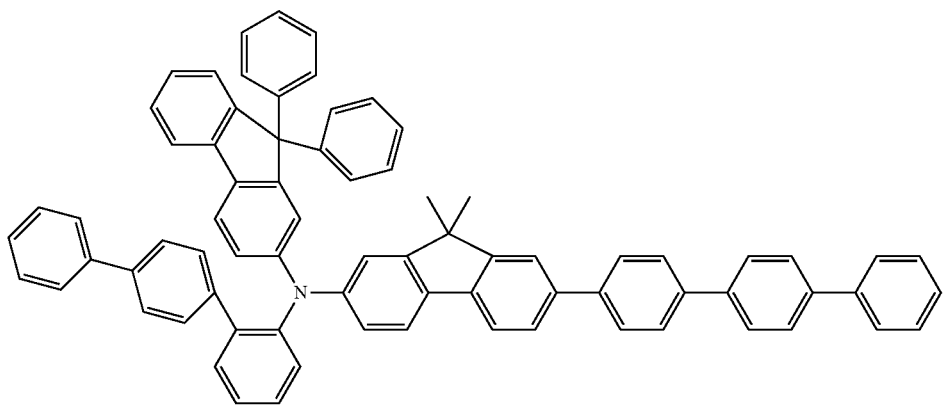
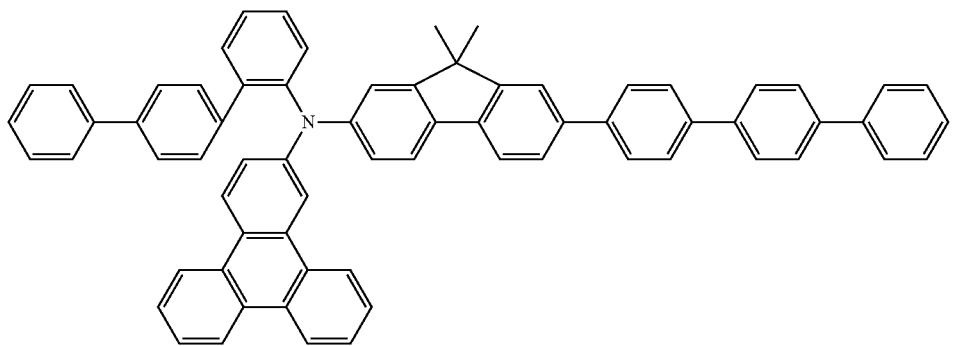

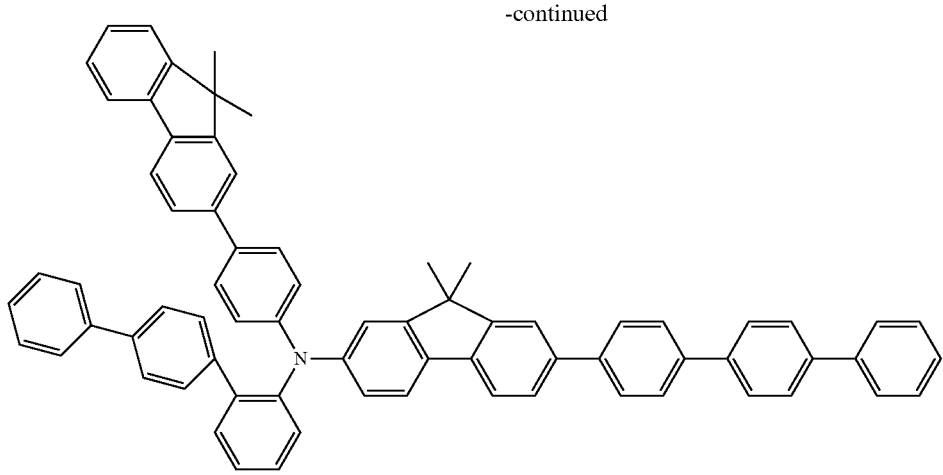
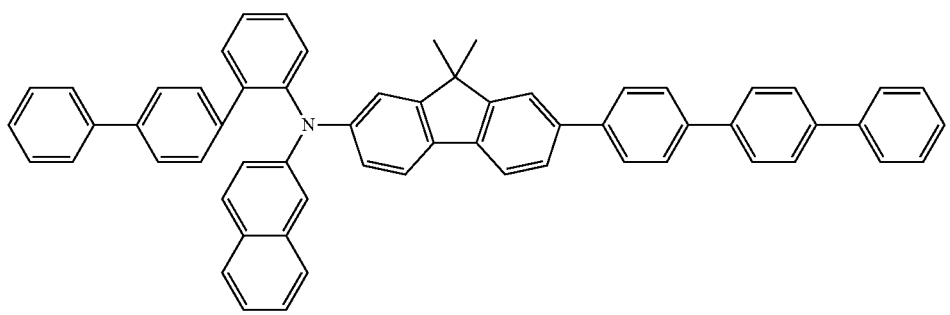
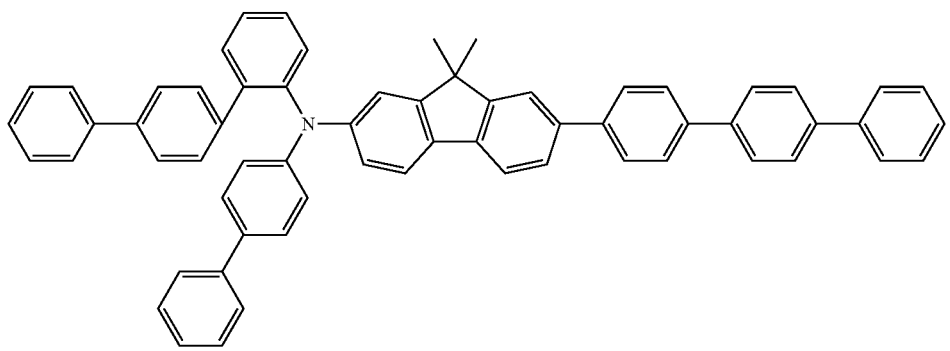
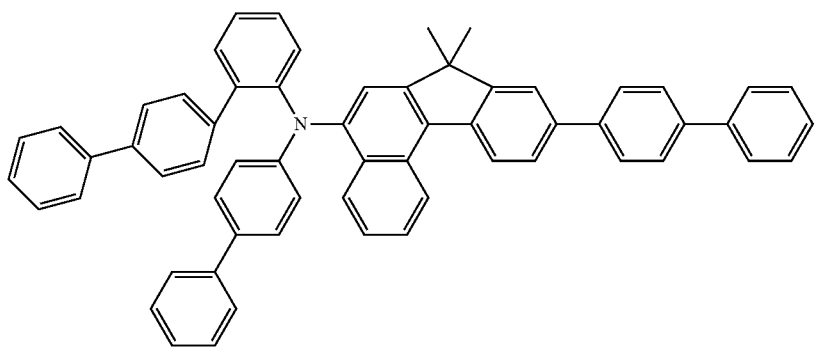

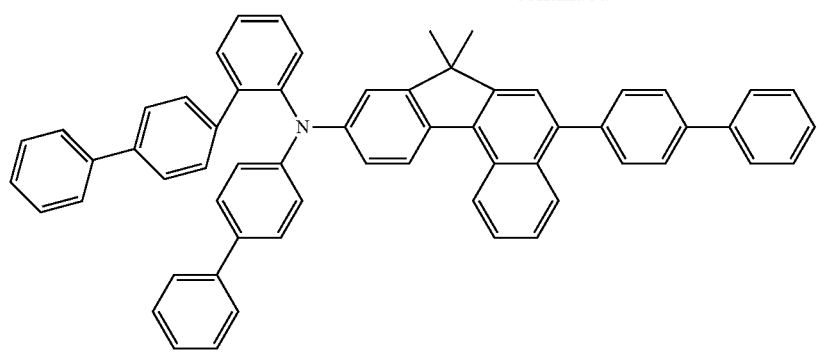
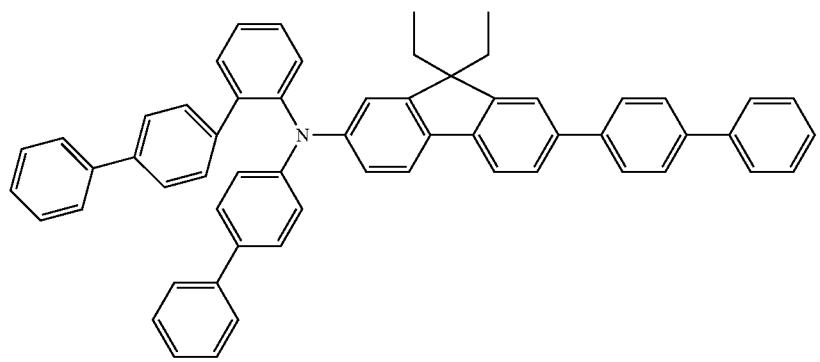
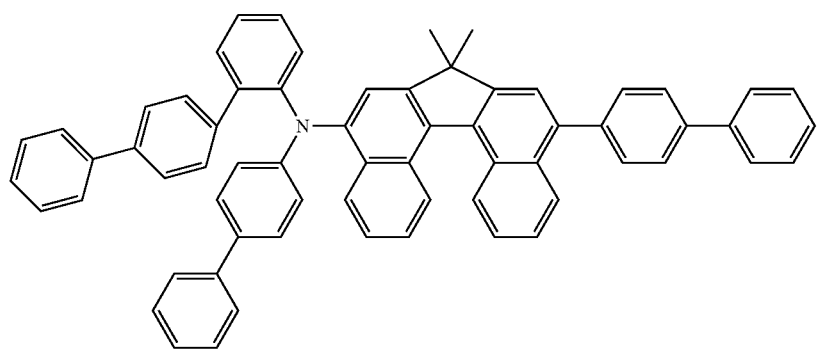
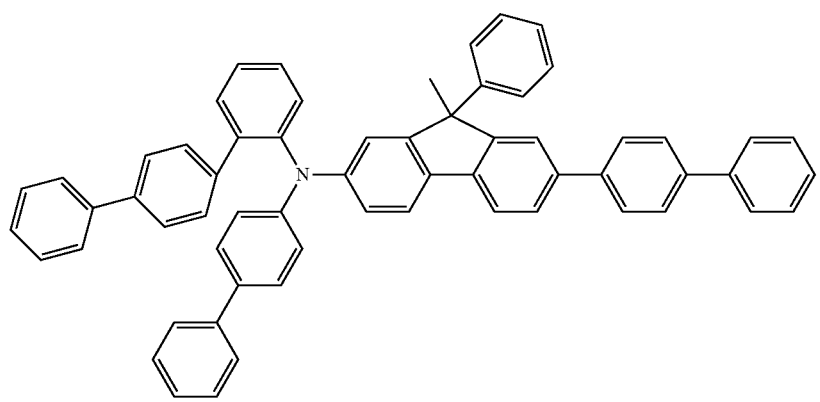

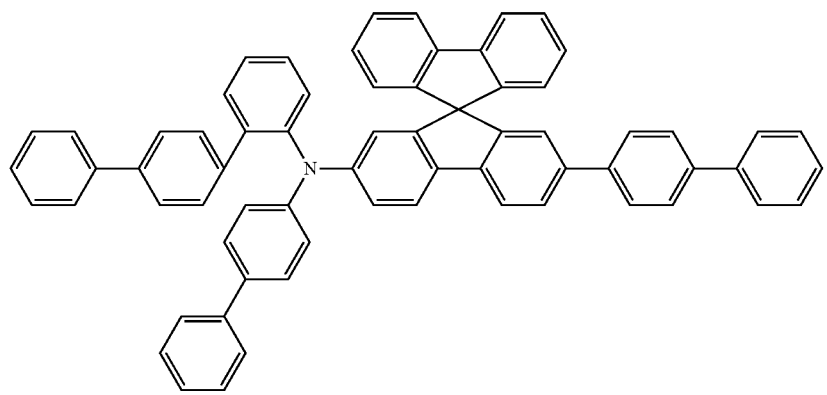
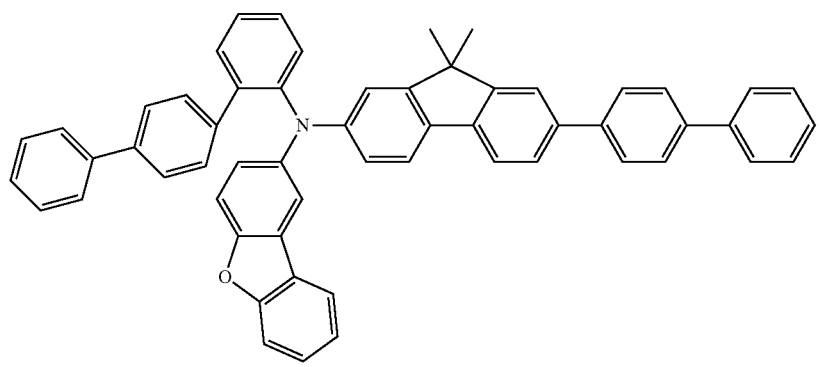
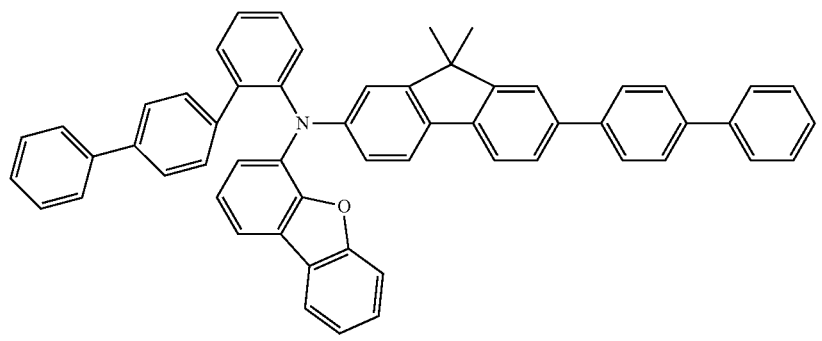
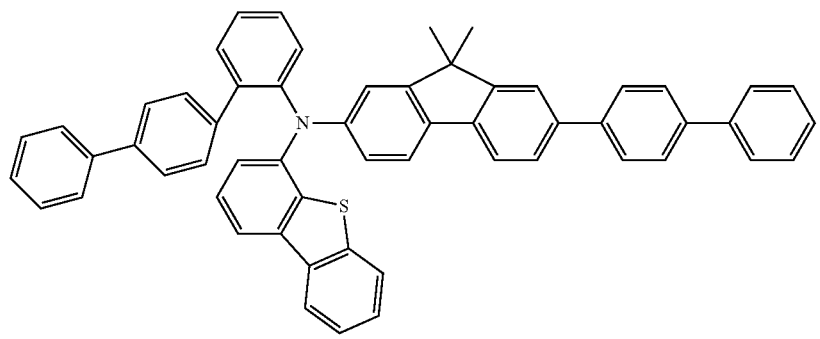

-continued
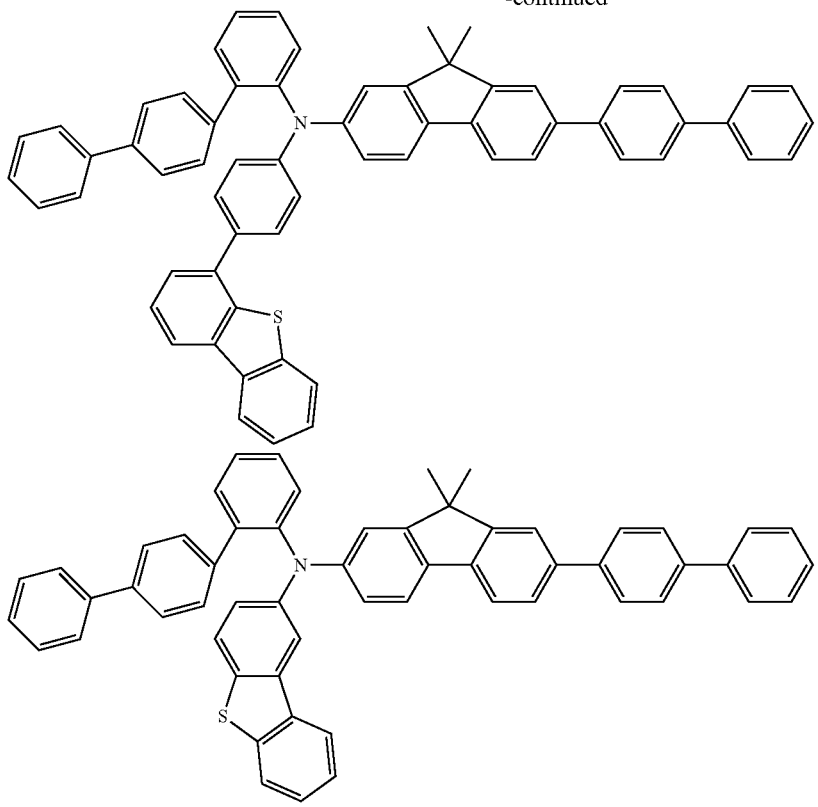
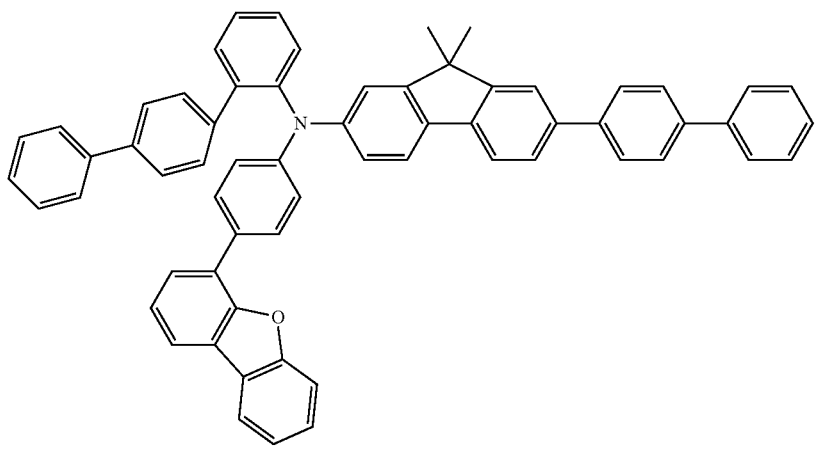
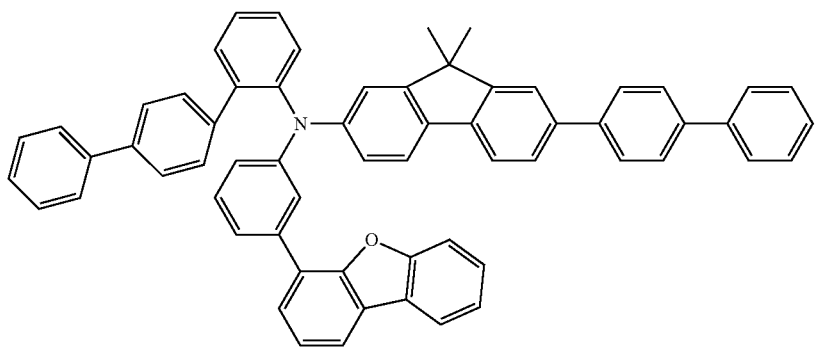

-continued
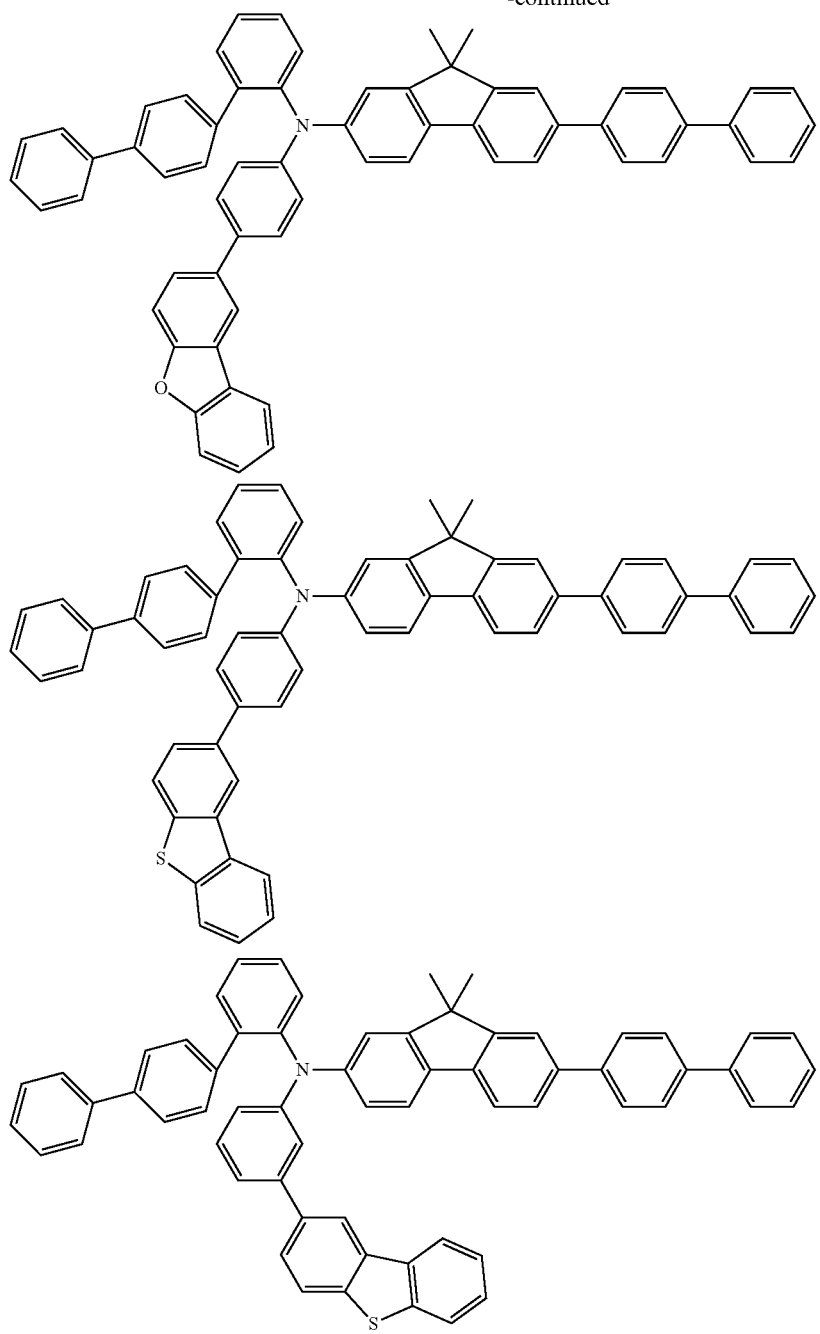
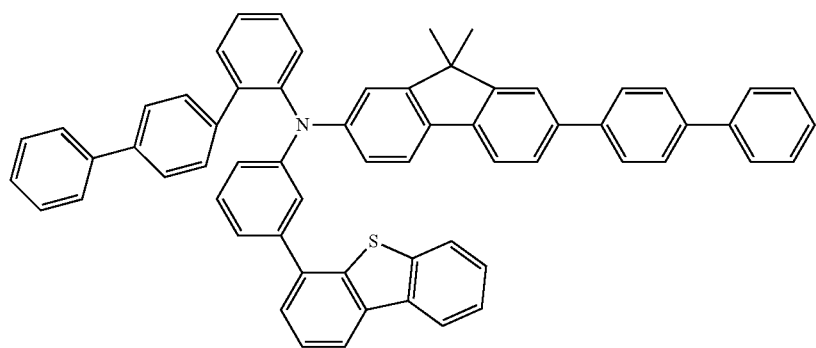

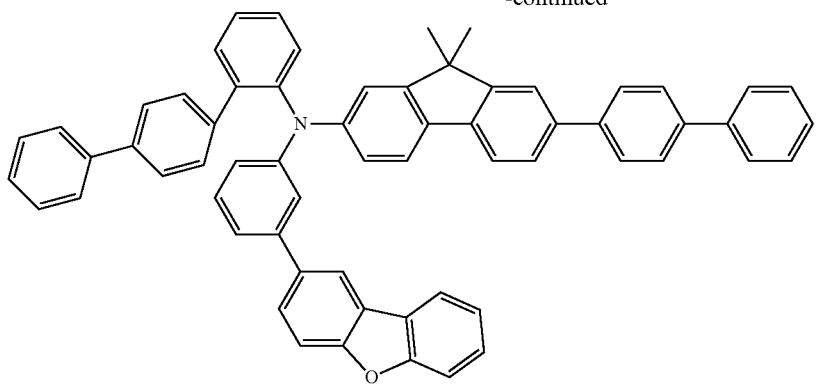
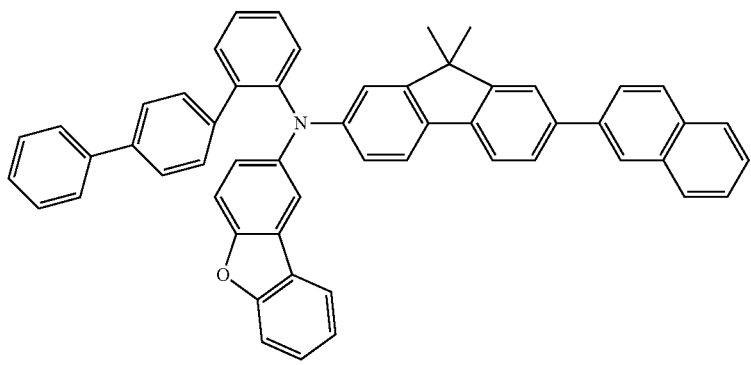
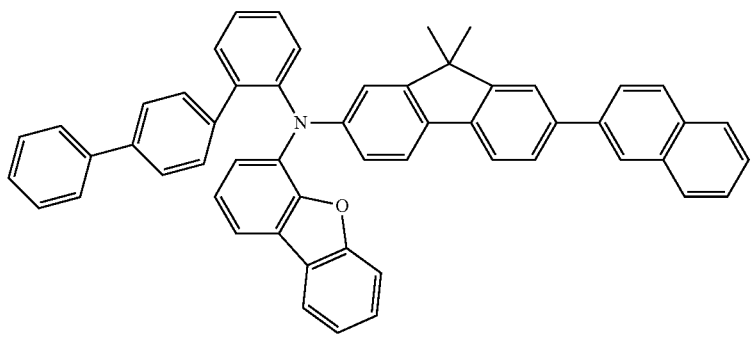
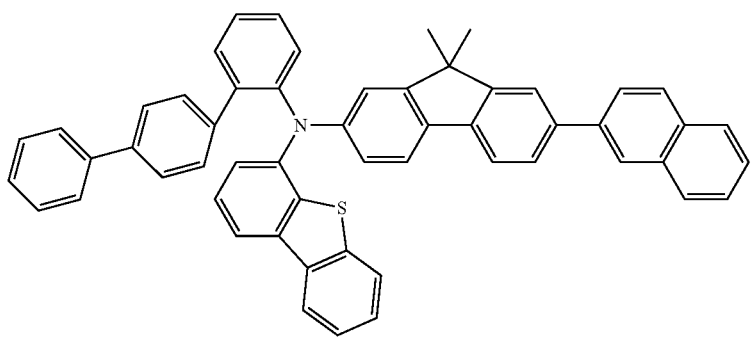

-continued
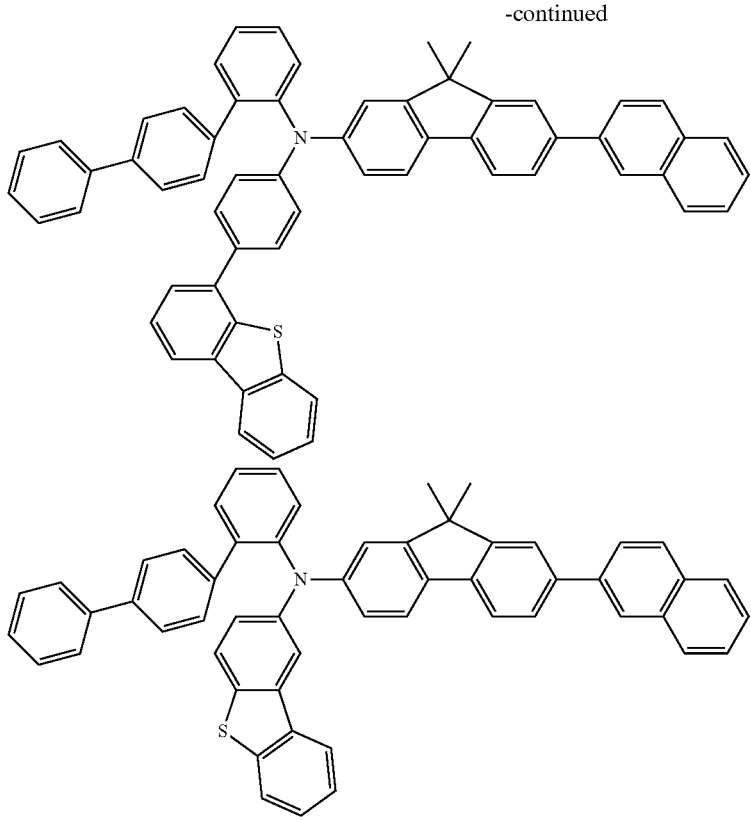
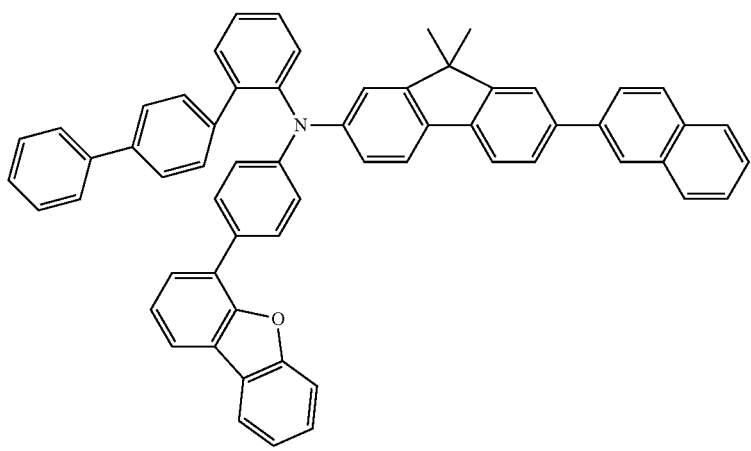
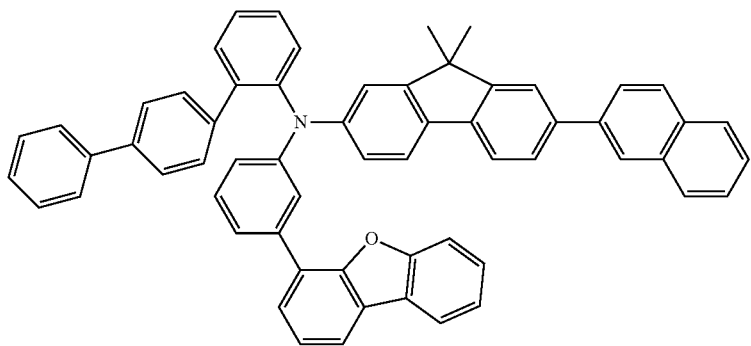

-continued
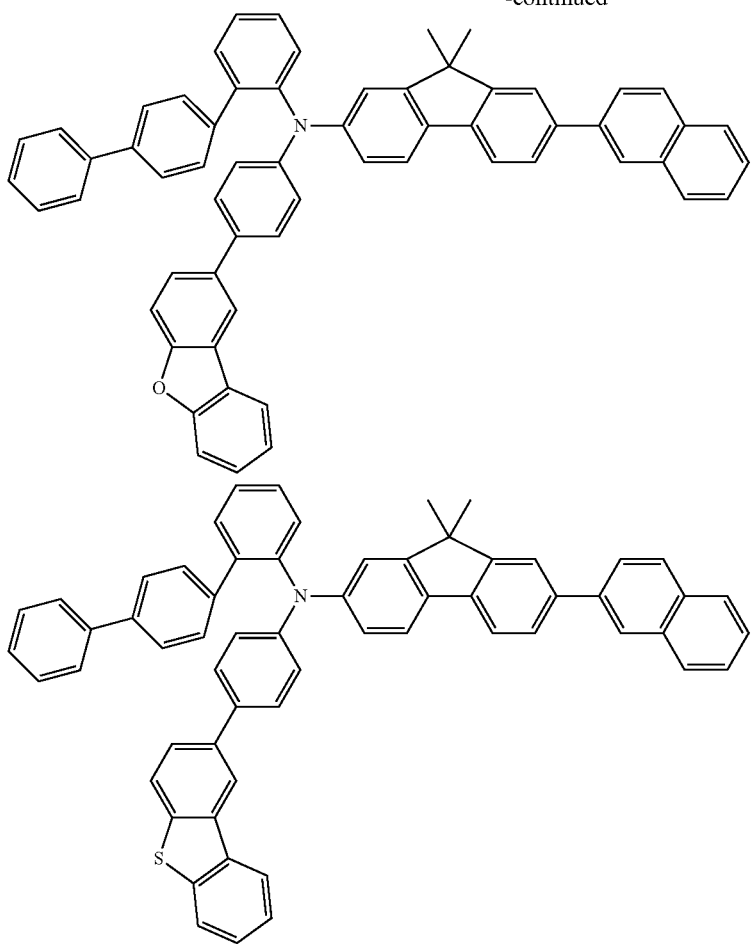
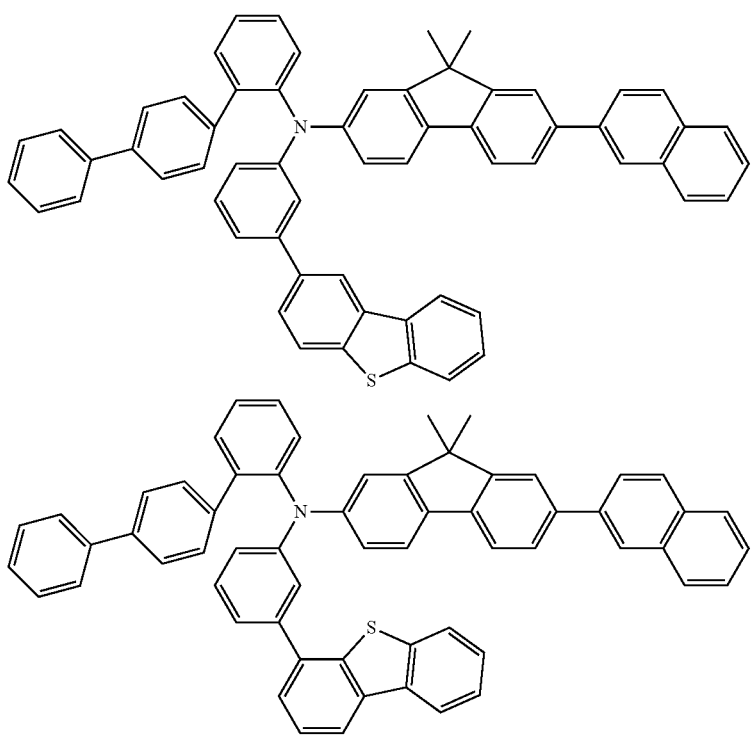

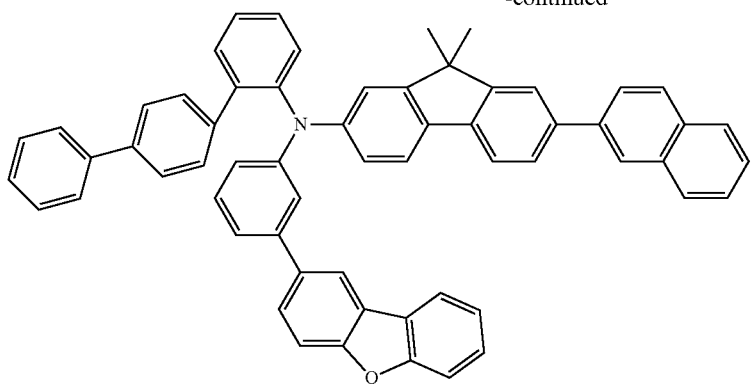
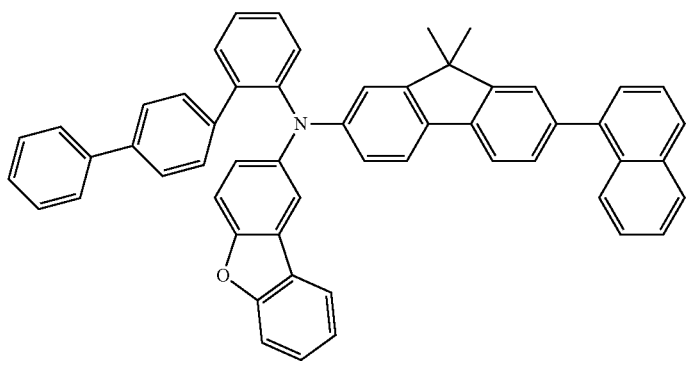
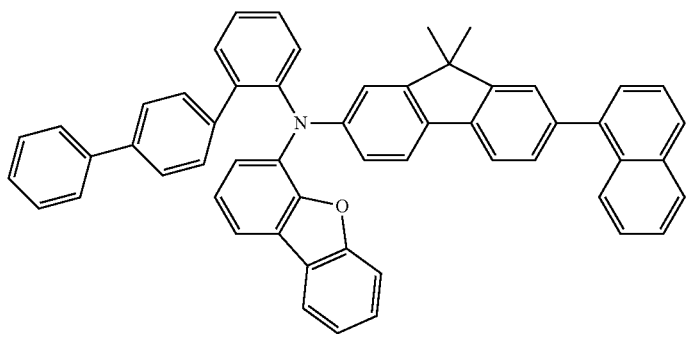
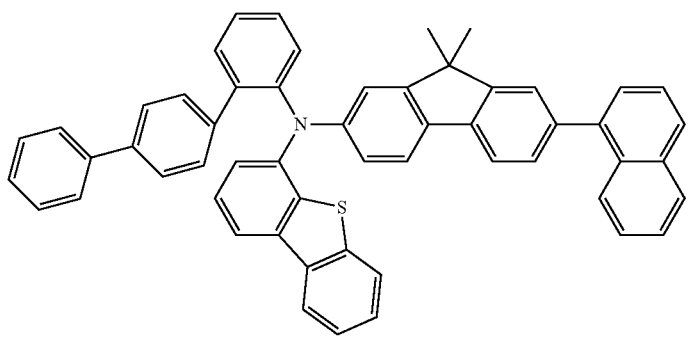

-continued
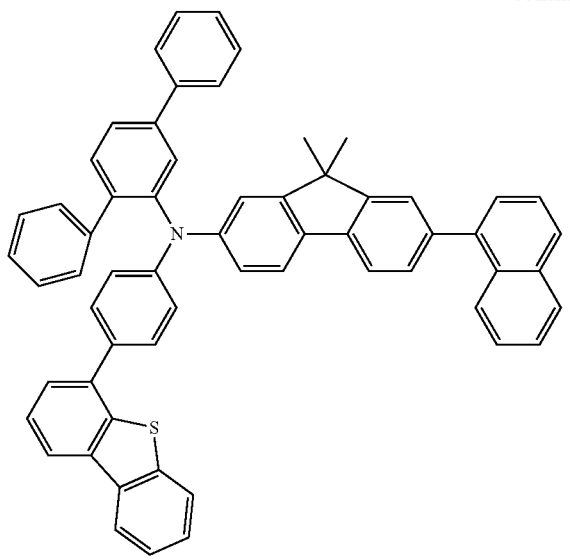
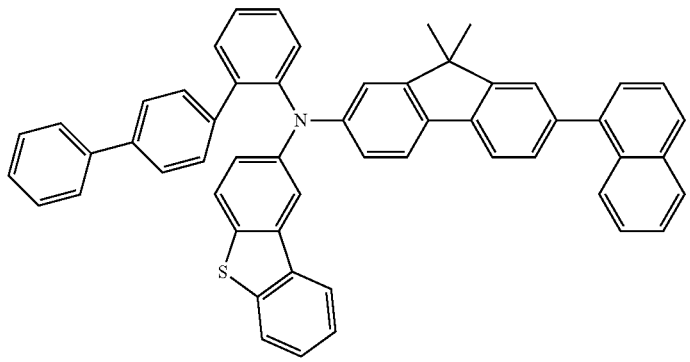
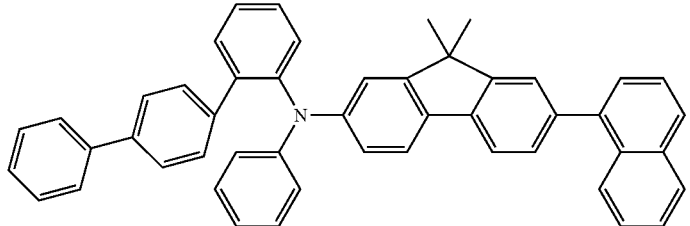
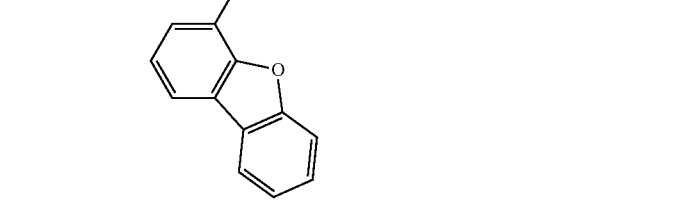
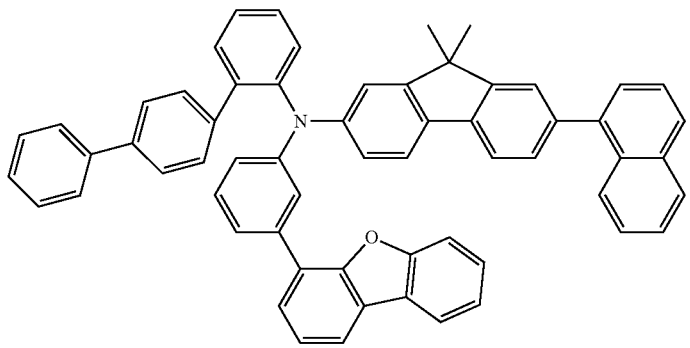

-continued
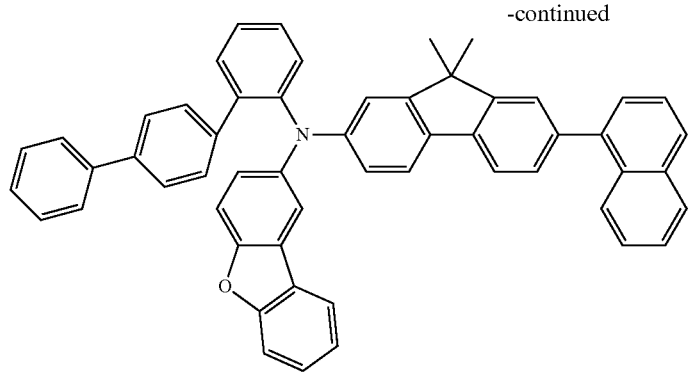
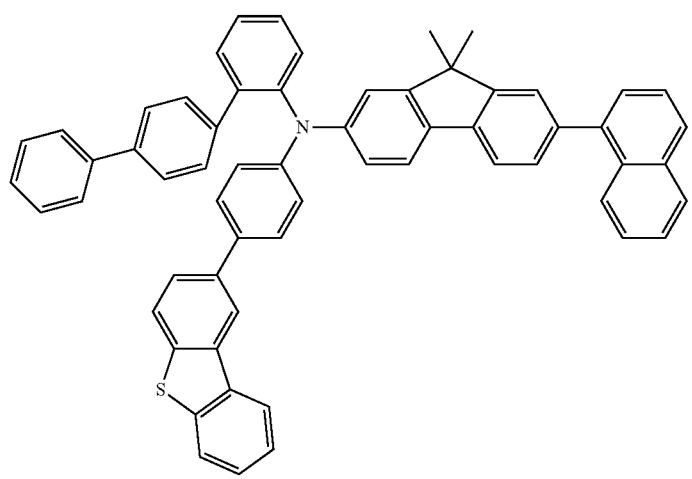
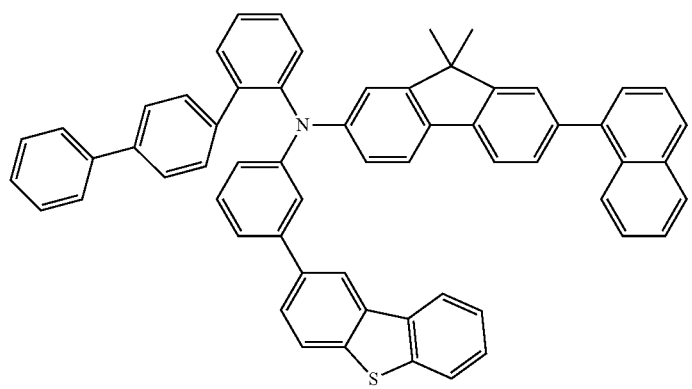
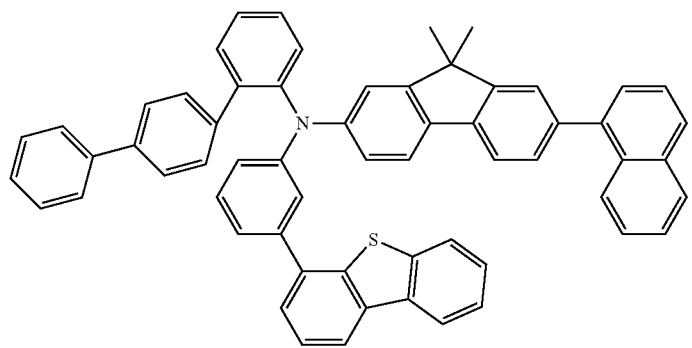

-continued
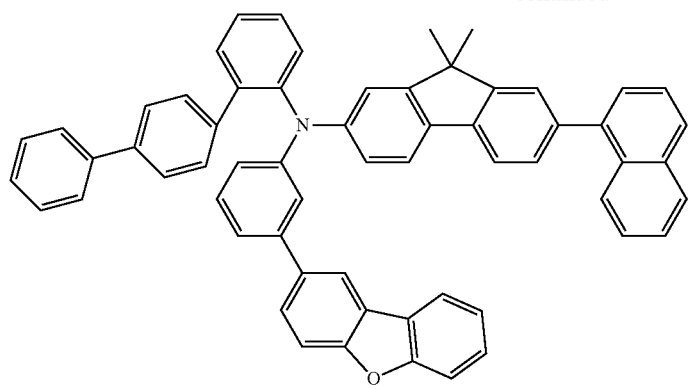
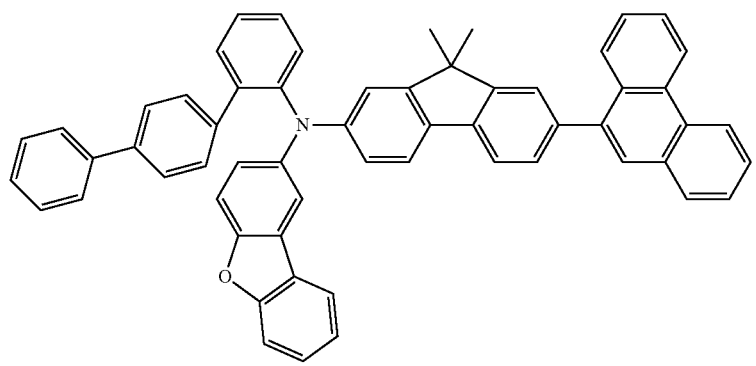
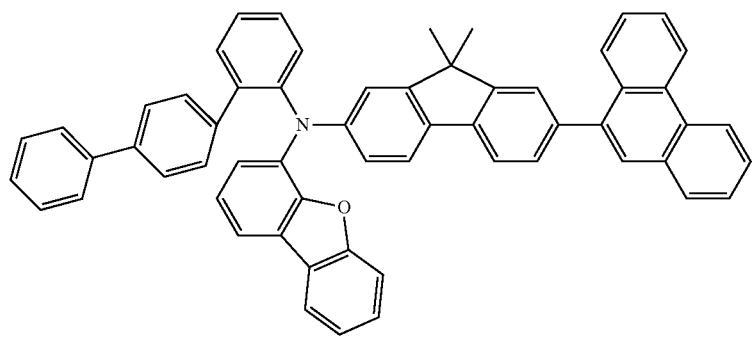
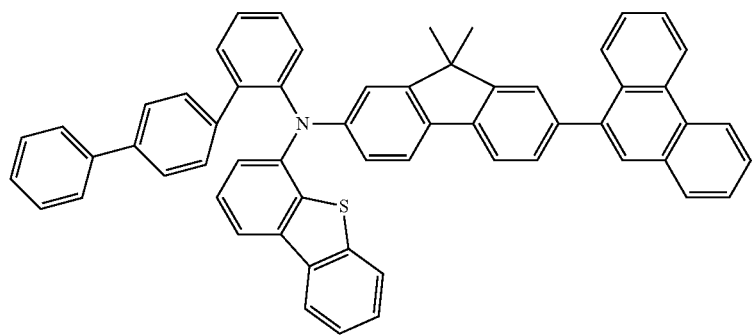

-continued
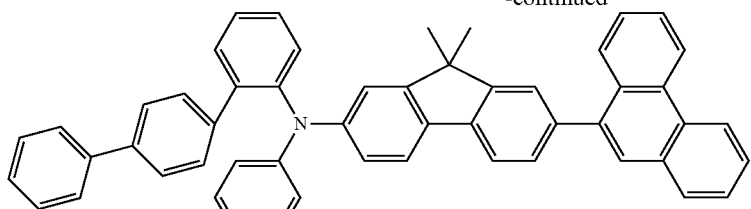
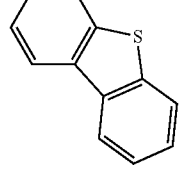
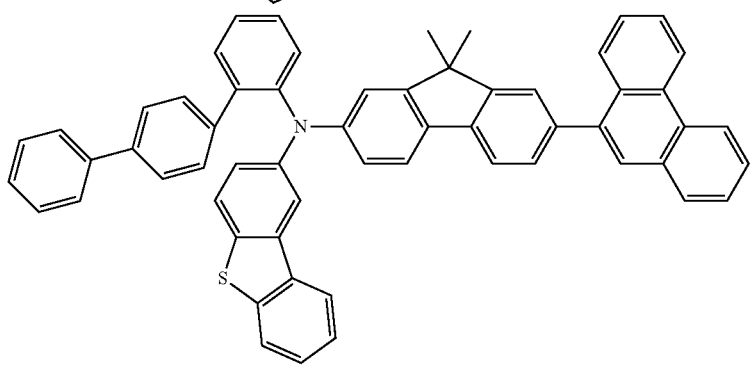
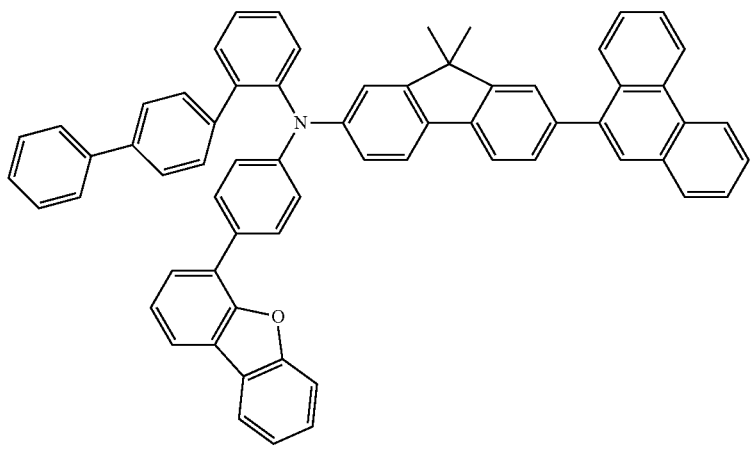
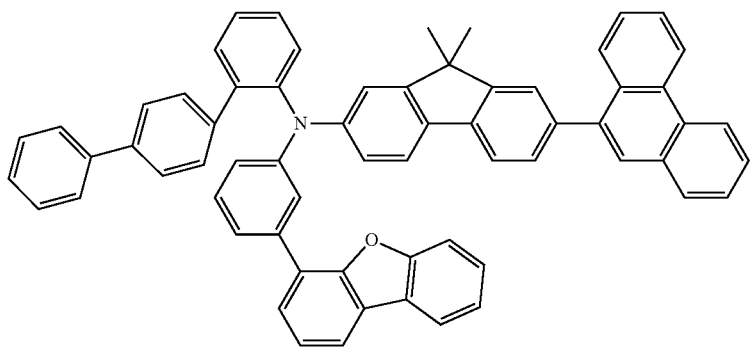

-continued
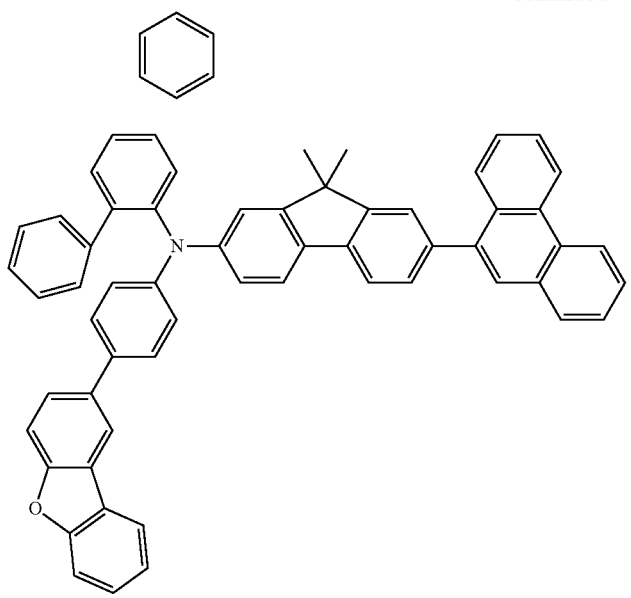
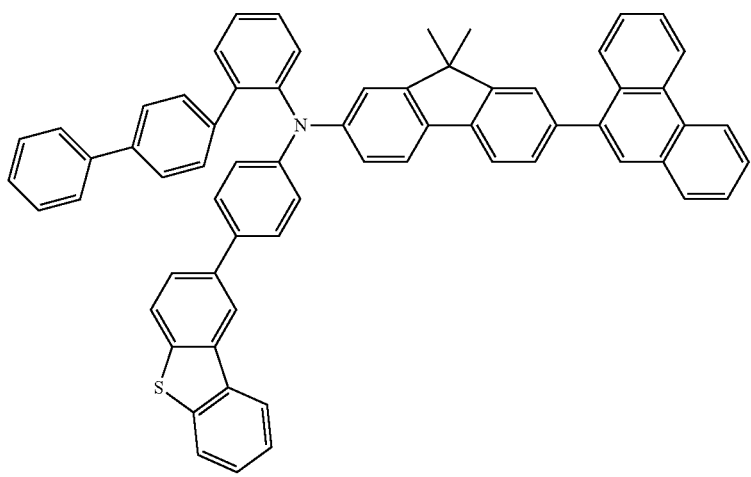
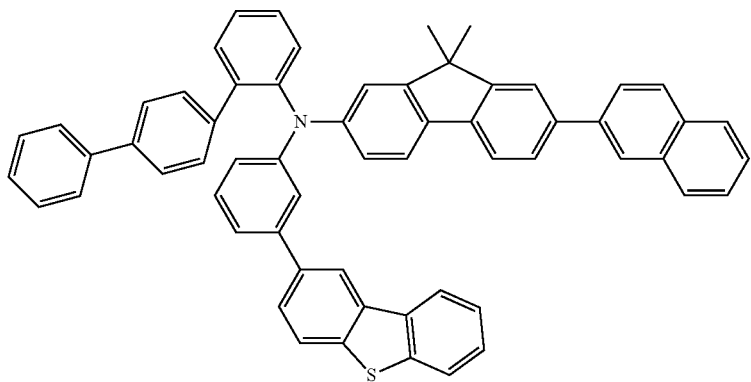

-continued
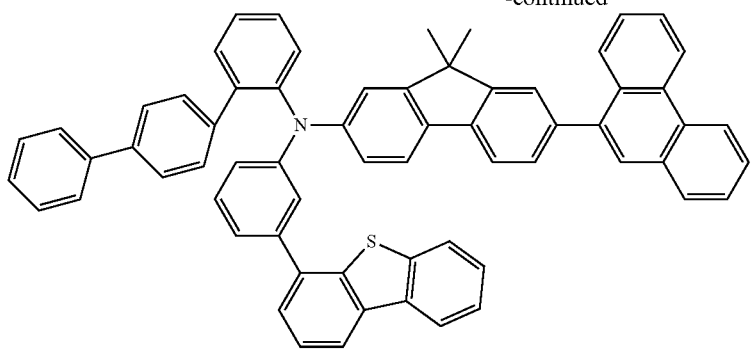
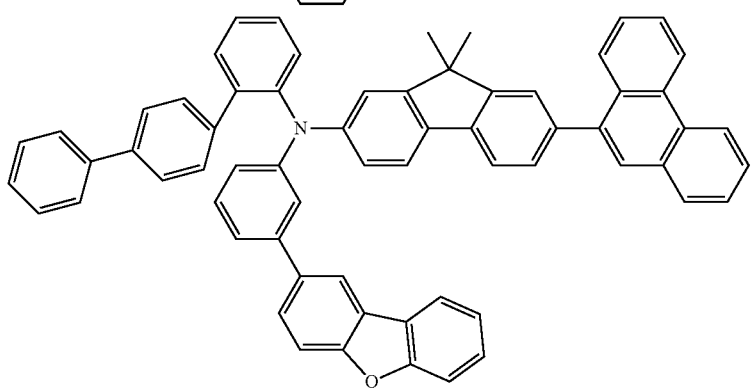
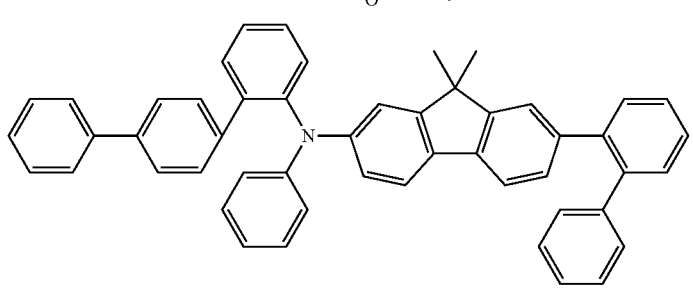
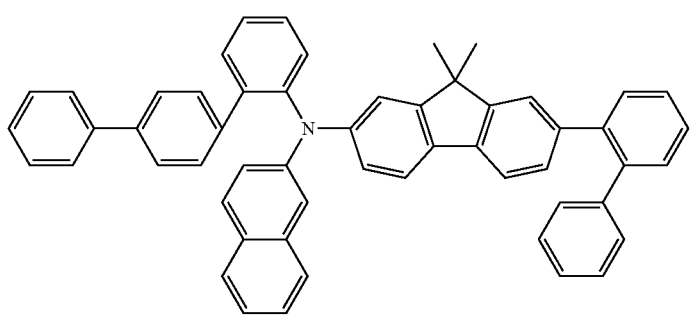
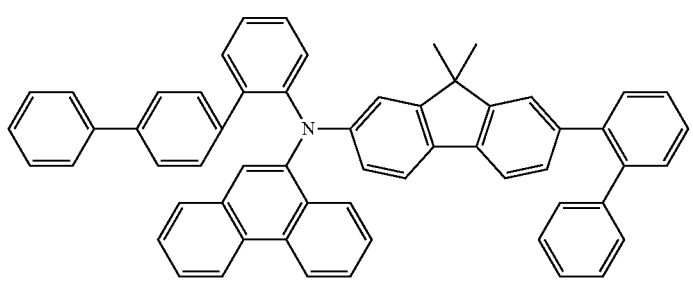

-continued
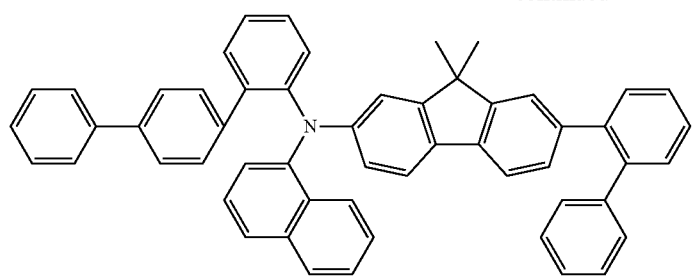
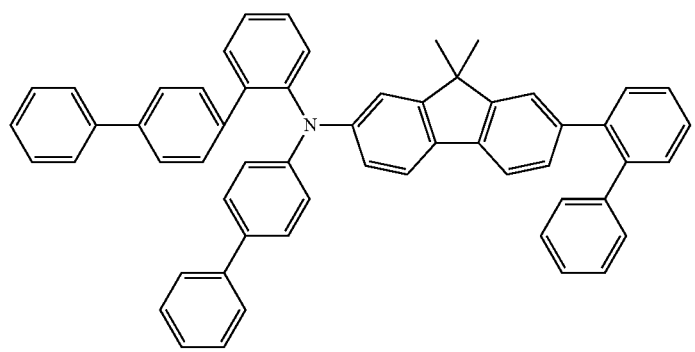
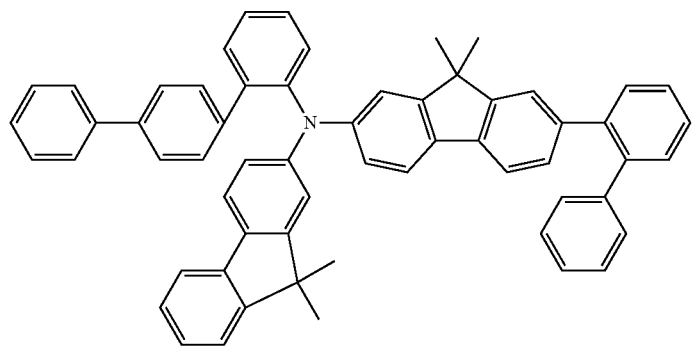
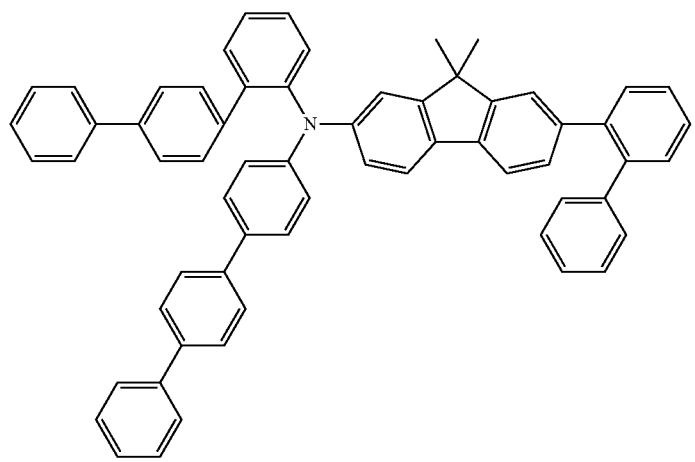

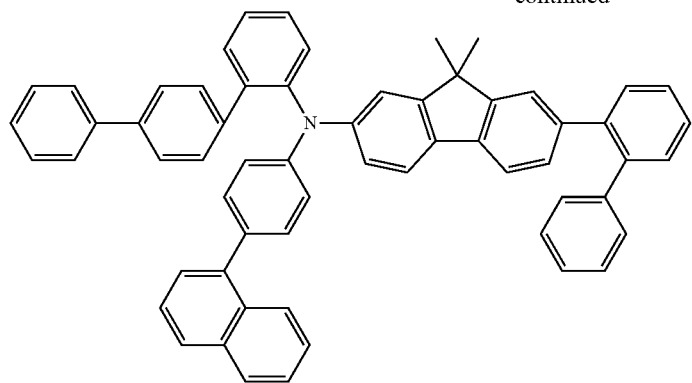
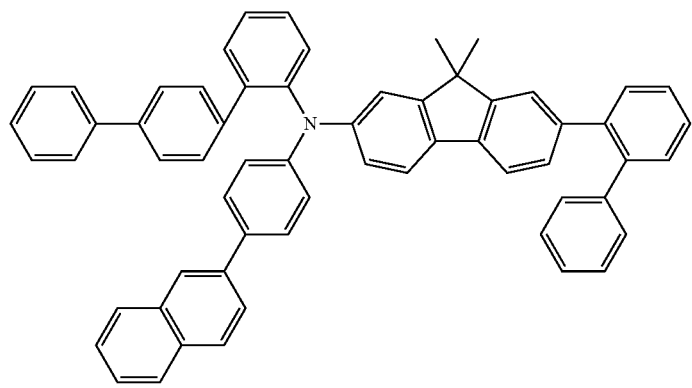
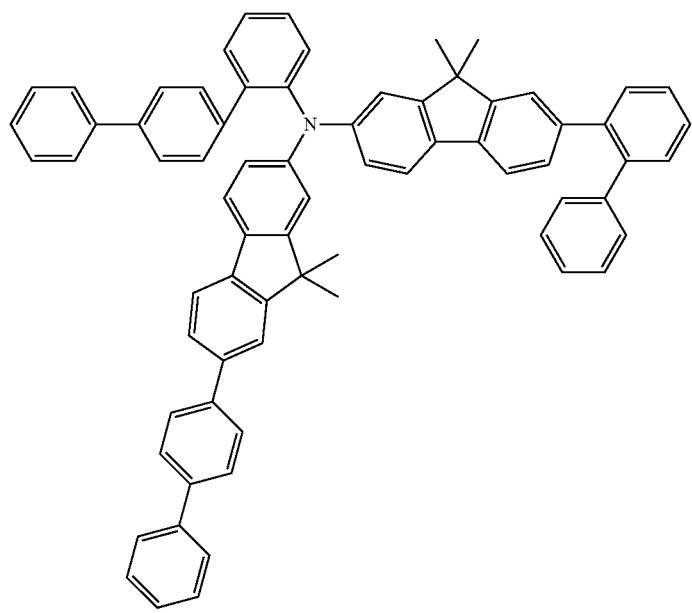

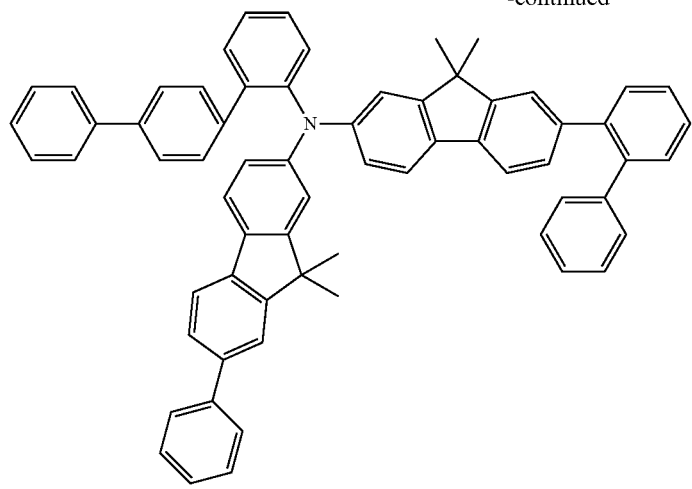
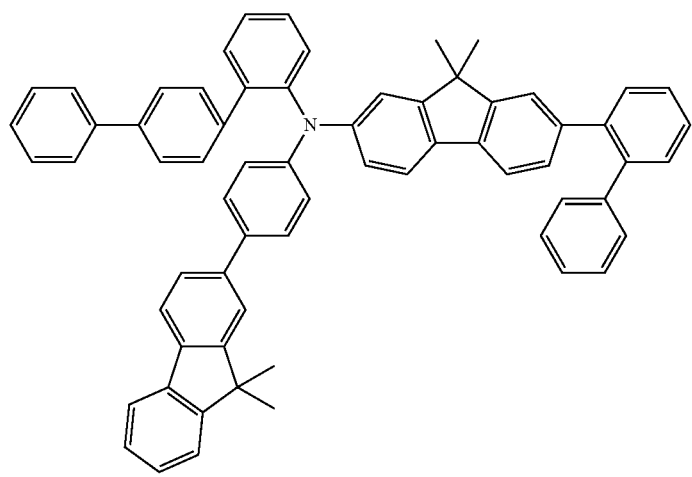
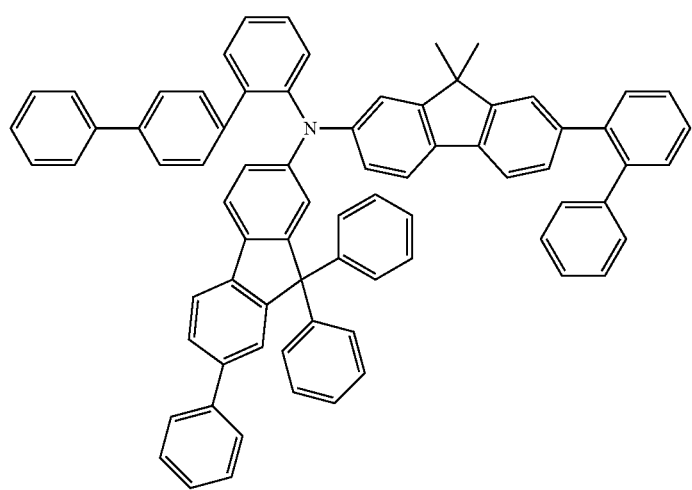

-continued
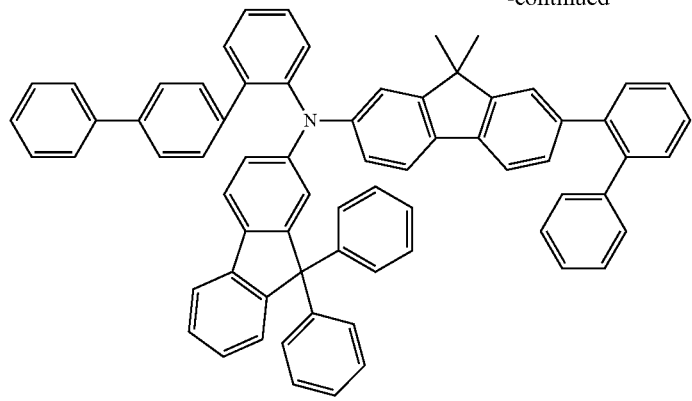
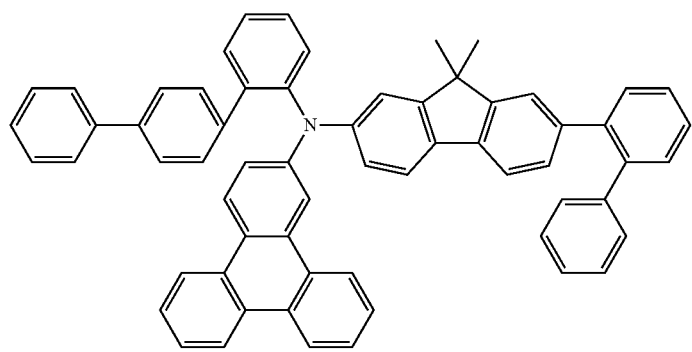
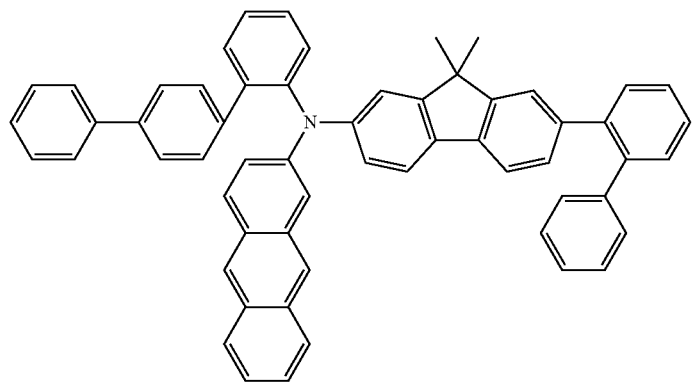
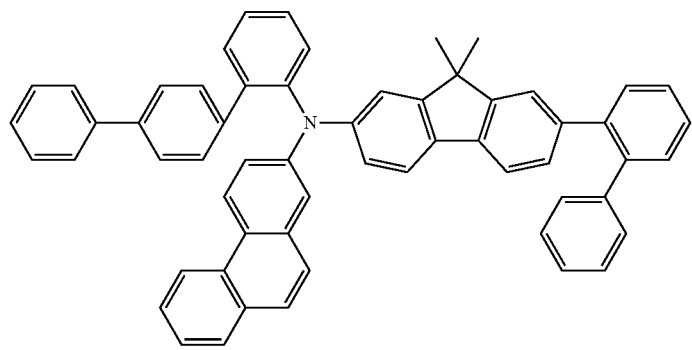
Of the above exemplary compounds, preferred are the following compounds.

(H1)
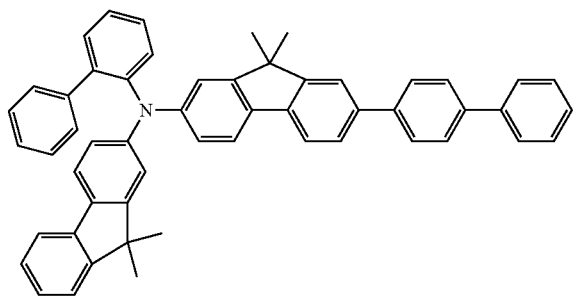

(H5)
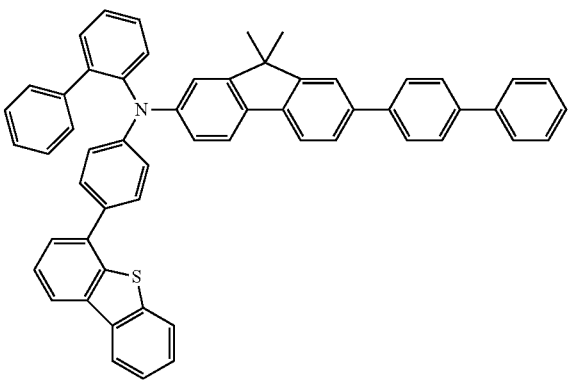

(H2)
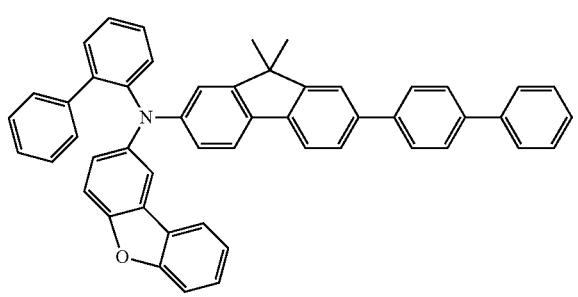

(H6)
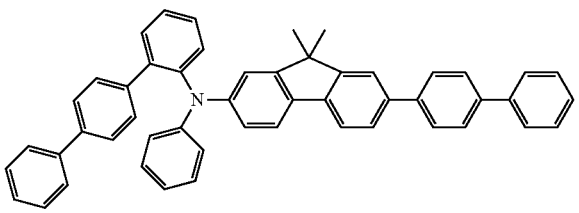

(H3)
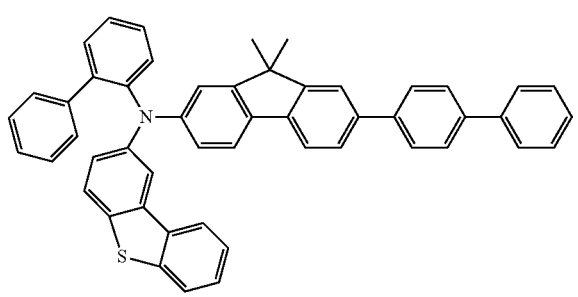

(H7)
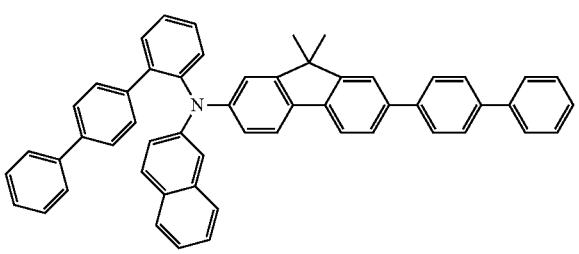

(H8)
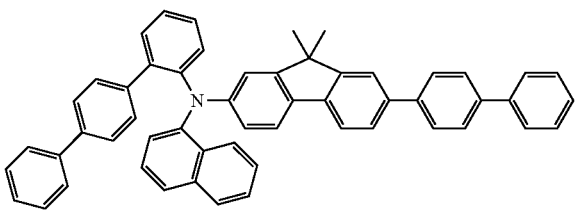

(H4)
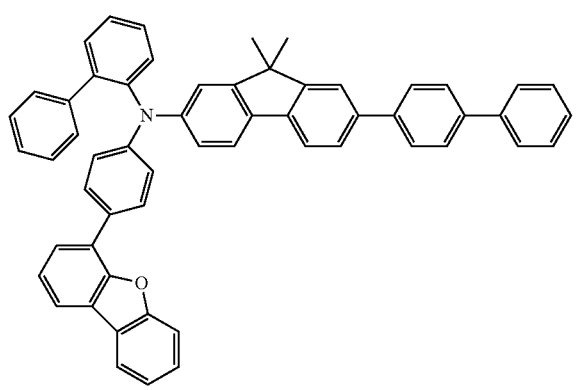

(H9)
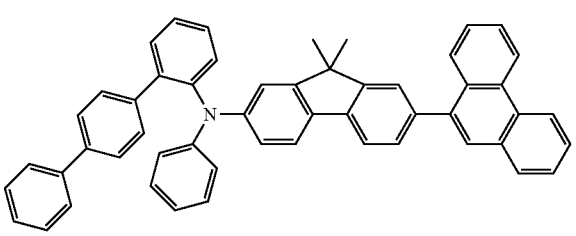

The Organic Electroluminescence Device

Next, an embodiment of the organic electroluminescence device (organic EL device) of the invention will be described.

The organic EL device of the invention comprises an organic thin film layer between an anode and a cathode opposite to the anode. At least one layer of the organic thin film layer comprises the compound represented by formula (1).

In a preferred embodiment of the invention, the organic EL device comprises at least two hole transporting layers and a light emitting layer sequentially between an anode and a cathode opposite to the anode. One of the hole transporting layers comprises the compound represented by formula (1) and is not adjacent to the light emitting layer.

For example, the at least two hole transporting layers comprise a first hole transporting layer on an anode side and a second hole transporting layer on a light emitting layer side, and the first hole transporting layer more preferably comprises the compound represented by formula (1).

Thus, in the present invention, two or more hole transporting layers are formed and the hole transporting layer which is not adjacent to the light emitting layer comprises the compound having a high mobility represented by formula (1) as a hole transporting material. Therefore, the driving voltage does not increase even when the thickness of the hole transporting layer is increased, thereby making it easy to adjust the optical path length of organic EL device to result in high efficiency. Since the compound represented by formula (1) is well compatible with an acceptor material having a high hole injecting ability, the amount of the carrier to be generated is increased, therefore, more holes can be transported and injected into the light emitting layer, resulting in improvement of the efficiency of a device.

The organic EL device of the invention may be any of a single color emitting fluorescent or phosphorescent device, a white-emitting fluorescent/phosphorescent hybrid device, a simple emitting device having a single emission unit, and a tandem emitting device having two or more emission units. The "emission unit" referred to herein is the smallest unit for emitting light by the recombination of injected holes and injected electrons, which comprises one or more organic layers wherein at least one layer is a light emitting layer.

The device structure of the organic EL device of the invention is described below.

(I) Structure of Organic EL Device

Representative device structures of organic EL device of the invention are:

(1) anode/acceptor material-containing layer (acceptor layer)/first hole transporting layer/second hole transporting layer/light emitting layer/cathode;

(2) anode/acceptor material-containing layer (acceptor layer)/first hole transporting layer/second hole transporting layer/light emitting layer/electron injecting layer/cathode;

(3) anode/acceptor material-containing layer (acceptor layer)/first hole transporting layer/second hole transporting layer/light emitting layer/electron transporting layer/electron injecting layer/cathode;

(4) anode/first hole transporting layer/second hole transporting layer/light emitting layer/electron injecting layer/cathode; and (5) anode/first hole transporting layer/second hole transporting layer/light emitting layer/electron transporting layer/electron injecting layer/cathode.

A third, fourth hole . . . transporting layer may be disposed between the second hole transporting layer and the light emitting layer. An electron blocking layer or an exciton blocking layer may be disposed between the light emitting layer and the hole transporting layer, and the hole transporting layer adjacent to the light emitting layer may work as an electron blocking layer or an exciton blocking layer. In addition, an insulating layer may be disposed between the pair of electrodes.

The hole transporting layer adjacent to the acceptor layer, for example, the first hole transporting layer adjacent to the acceptor layer in the above device structures (1) to (3) is also referred to as a hole transporting layer adjacent to an acceptor layer.

The organic EL device of the invention preferably comprises an acceptor layer comprising an acceptor material between the anode and two or more hole transporting layers mentioned above, particularly a hole transporting layer closest to the anode.

The hole transporting layer comprising the compound represented by formula (1) may further comprise an acceptor material.

The compound represented by formula (A), (B) or (C) having a highly planar skeleton is preferably used as the acceptor material, because the acceptor layer is well boned to the hole transporting layer comprising the compound represented by formula (1) so that a further improvement of device performance is expected.

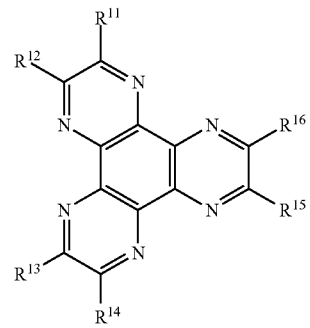

(A)

In formula (A), $R^{11}$ to $R^{16}$ each independently represent a cyano group, —$CONH_2$, a carboxyl group, or —$COOR^{17}$, wherein $R^{17}$ represents an alkyl group having 1 to 20 carbon atoms, provided that $R^{11}$ and $R^{12}$, $R^{13}$ and $R^{14}$, or $R^{15}$ and $R^{16}$ may be bonded to each other to form a group represented by —CO—O—CO—.

Examples of the alkyl group for $R^{17}$ include a methyl group, an ethyl group, a n-propyl group, an isopropyl group, a n-butyl group, an isobutyl group, a tert-butyl group, a cyclopentyl group, and a cyclohexyl group.

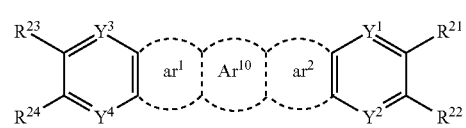

(B)

I formula (B), $R^{21}$ to $R^{24}$ may be the same or different and each independently represent a hydrogen atom, a substituted or unsubstituted alkyl group having 1 to 20 carbon atoms, a substituted or unsubstituted aryl group having 6 to 50, preferably 6 to 30, more preferably 6 to 20, and still more preferably 6 to 14 ring carbon atoms, a substituted or unsubstituted heterocyclic group having 5 to 50, preferably 5 to 30, more preferably 5 to 20, and still more preferably 5 to 14 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted aryloxy group having 6 to 50, preferably 6 to 30, more preferably 6 to 20, and still more preferably 6 to 14 ring carbon atoms, or a cyano group, provided that adjacent groups selected from $R^{21}$ and $R^{24}$ may be bonded to each other to form a ring.

$Y^1$ to $Y^4$ may be the same or different and each independently represent —N=, —CH=, or —C($R^{25}$)=, wherein $R^{25}$ represents a substituted or unsubstituted alkyl group having 1 to 20 carbon atoms, a substituted or unsubstituted aryl group having 6 to 50, preferably 6 to 30, more preferably 6 to 20, and still more preferably 6 to 14 ring carbon atoms, a substituted or unsubstituted heterocyclic group having 5 to 50, preferably 5 to 30, more preferably 5 to 20, and still more preferably 5 to 14 ring atoms, a halogen atom, a substituted or unsubstituted alkoxy group having 1 to 20 carbon atoms, a substituted or unsubstituted aryloxy group having 6 to 50, preferably 6 to 30, more preferably 6 to 20, and still more preferably 6 to 14 ring carbon atoms, or a cyano group $Ar^{10}$ represents a fused ring having 6 to 24 ring carbon atoms or a heterocyclic ring having 6 to 24 ring atoms, and $ar^1$ and $ar^2$ each independently represent a ring represented by formula (i) or (ii):

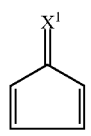

(i)

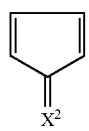

(ii)

wherein $X^1$ and $X^2$ may be the same or different and each independently represent a divalent group represented by any of formulae (a) to (g):

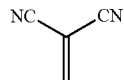

(a)

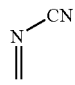

(b)

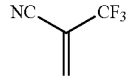

(c)

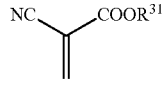

(d)

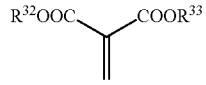

(e)

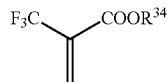

(f)

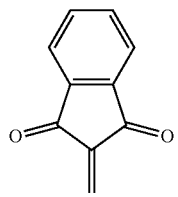

(g)

wherein $R^{31}$ to $R^{34}$ may be the same or different and each represent a hydrogen atom, a substituted or unsubstituted alkyl group having 1 to 20 carbon atoms, a substituted or unsubstituted aryl group having 6 to 50 ring carbon atoms, or a substituted or unsubstituted heterocyclic group having 5 to 50 ring atoms, and $R^{32}$ and $R^{33}$ may be bonded to each other to form a ring.

Examples of the groups for $R^{21}$ to $R^{24}$ and $R^{31}$ to $R^{34}$ are described below.

The alkyl group may include a methyl group, an ethyl group, a n-propyl group, an isopropyl group, a n-butyl group, an isobutyl group, a tert-butyl group, a cyclopentyl group, and a cyclohexyl group.

The aryl group may include a phenyl group, a biphenyl group, and a naphthyl group.

The heterocyclic group may include residues of pyridine, pyrazine, furan, imidazole, benzimidazole, and thiophene.

The halogen atom may include a fluorine atom, a chlorine atom, a bromine atom, and an iodine atom.

The alkoxy group may include a methoxy group and an ethoxy group.

The aryloxy group may include a phenyloxy group.

The above groups may have a substituent. The substituted aryl group may include a haloaryl group, such as a monofluorophenyl group and a trifluoromethylphenyl group, and an alkyl-substituted aryl group having an alkyl group having 1 to 10, preferably 1 to 5 carbon atoms, such as a tolyl group and a 4-t-butylphenyl group. The substituted alkyl group may include a haloalkyl group, such as a trifluoromethyl group, a pentafluoroethyl group, a perfluorocyclohexyl group, and a perfluoroadamantyl group. The substituted aryloxy group may include an aryloxy group having a halogen atom or a haloalkyl group having 1 to 5 carbon atoms, such as a 4-trifluoromethylphenyloxy group and a pentafluorophenyloxy group, and an aryloxy group having an alkyl group having 1 to 10, preferably 1 to 5 carbon atoms, such as a 4-t-butylphenoxy group.

Adjacent groups selected from $R^{21}$ to $R^{24}$ may be bonded to each other to form a ring, such as a benzene ring, a naphthalene ring, a pyrazine ring, a pyridine ring, and a furan ring.

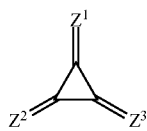

(C)

wherein $Z^1$ to $Z^2$ each independently represent a divalent group represented by formula (h):

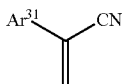
(h)

wherein $Ar^{31}$ represents a substituted or unsubstituted aryl group having 6 to 50 ring carbon atoms or a substituted or unsubstituted heteroaryl group having 5 to 50 ring atoms.

The aryl group may include a phenyl group and a naphthyl group.

The heteroaryl group may include a pyridine, a pyrazine, a pyrimidine, a quinoline, and an isoquinoline.

The substituent of these groups may include an electron-accepting group, such as a cyano group, a fluorine atom, a trifluoromethyl group, a chlorine atom, and a bromine atom.

(2) Light-Transmissive Substrate

The organic EL device of the invention is formed on a light-transmissive substrate. The light-transmissive substrate serves as a support for the organic EL device and preferably a flat substrate having a transmittance of 50% or more to 400 to 700 nm visible light.

Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

(3) Anode

The anode of the organic EL device injects holes to the hole transporting layer or the light emitting layer, and an anode having a work function of 4.5 eV or more is effective. Examples of material for anode include indium tin oxide alloy (ITO), tin oxide (NESA), indium-zinc oxide alloy (IZO), gold, silver, platinum, and copper.

The anode is formed by making the electrode material into a thin film by a method, such as a vapor deposition method or a sputtering method.

When getting the light emitted from the light emitting layer through the anode, the transmittance of anode to visible light is preferably 10% or more. The sheet resistance of anode is preferably several hundreds $\Omega/\square$ or less. The film thickness of anode depends upon the kind of material and generally 10 nm to 1 μm, preferably 10 to 200 nm.

(4) Hole Transporting Layer

As described above, the organic EL device in more preferred embodiment of the invention comprises two or more hole transporting layers.

The hole transporting layer not adjacent to the light emitting layer is often made thicker for the optical adjustment. To reduce the driving voltage, such a hole transporting layer is needed to have a high hole mobility. In addition, the hole transporting layer is often laminated with an acceptor layer for efficient generation of carriers, and therefore, is needed to have a large interaction with the acceptor layer.

The compound represented by formula (1) has a high hole mobility, because its molecular is highly planar due to the fluorene structure as compared with a compound having a biphenyl stricture. In addition, the compound is capable of transporting and injecting more holes into the light emitting layer, because a large amount of carriers is generated by a large interaction with the highly planar acceptor material.

Namely, the compound represented by formula (1) satisfies the properties required for the hole transporting layer not adjacent to the light emitting layer (first hole transporting layer when two hole transporting layers are formed), and therefore, is preferably used as the material for the hole transporting layer not adjacent to the light emitting layer.

It has been known that the hole transporting layer adjacent to the light emitting layer (second hole transporting layer when two hole transporting layer are formed) is required to have (i) a high triplet energy (preferably 2.6 eV or more) to prevent the diffusion of excitation energy from the phosphorescent emitting layer; an electron resistance because the layer is adjacent to the light emitting layer; a small affinity (preferably 2.4 eV or less) to prevent the leak of electrons from the light emitting layer; and a large ionization potential (preferably 5.5 eV or more) to facilitate the hole injection into the light emitting layer. Preferred example of a material meeting these properties include a heteroaryl-substituted amine derivative, with a compound represented by any of formulae (4) to (8) shown below being more preferred, because an excellent phosphorescent organic EL device and also an excellent fluorescent organic EL device are obtained.

Material for hole transporting layer adjacent to light emitting layer (second hole transporting material) represented by formula (4):

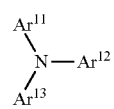
(4)

wherein at least one selected from $Ar^{11}$ to $Ar^{13}$ represents a group represented by formula (4-2) or (4-4), a group not represented by formula (4-2) represents a group represented by formula (4-3) or (4-4) or a substituted or unsubstituted aryl group having 6 to 40 ring carbon atoms, and a group not represented by formula (4-4) represents a group represented by formula (4-2) or (4-3) or a substituted or unsubstituted aryl group having 6 to 40 ring carbon atoms.

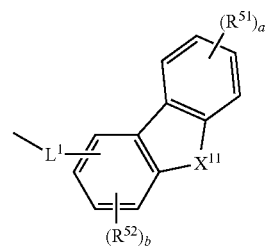
(4-2)

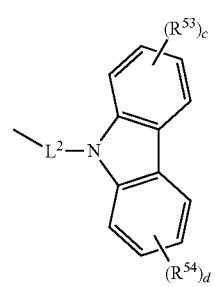
(4-3)

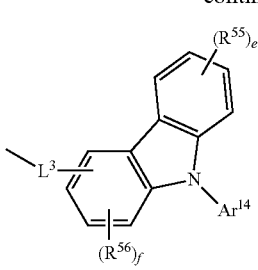

(4-4)

wherein:

$X^{11}$ represents an oxygen atom or a sulfur atom;

$L^1$ to $L^3$ each independently represent a single bond or a substituted or unsubstituted arylene group having 6 to 50 ring carbon atoms;

an optional substituent of $L^1$ to $L^3$ is selected from a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms wherein the alkyl portion has 1 to 5 carbon atoms and the aryl portion has 6 to 14 ring carbon atoms, an aryl group having 6 to 50 ring carbon atoms, a halogen atom, and a cyano group;

$Ar^{14}$ represents a substituted or unsubstituted aryl group having 6 to 50 ring carbon atoms;

an optional substituent of $Ar^{14}$ is selected from a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms wherein the alkyl portion has 1 to 5 carbon atoms and the aryl portion has 6 to 14 ring carbon atoms, an aryl group having 6 to 50 ring carbon atoms, a halogen atom, and a cyano group;

$R^{51}$ to $R^{56}$ each independently represent a substituted or unsubstituted, linear or branched alkyl group having 1 to 10 carbon atoms, a substituted or unsubstituted cycloalkyl group having 3 to 10 ring carbon atoms, a substituted or unsubstituted trialkylsilyl group having 3 to 10 carbon atoms, a substituted or unsubstituted triarylsilyl group having 18 to 30 ring carbon atoms, a substituted or unsubstituted alkylarylsilyl group having 8 to 15 carbon atoms wherein the alkyl portion has 1 to 5 carbon atoms and the aryl portion has 6 to 14 ring carbon atoms, a substituted or unsubstituted aryl group having 6 to 50 ring carbon atoms, a halogen atom, and a cyano group;

adjacent groups selected from $R^{51}$ to $R^{56}$ may be bonded to each other to form a ring;

b and f each independently represent an integer of 0 to 3; and a, c, d, and e each independently represent an integer of 0 to 4.

Examples of the arylene group for $L^1$ to $L^3$ include a phenylene group, a naphthylene group, a biphenylene group, an anthrylene group, an acenaphthylenylene group, an anthranylene group, a phenanthrenylene group, a phenalenylene group, a quinolylene group, an isoquinolylene group, a s-indacenylene group, an as-indacenyiene group, and a chrysenylene group, with an arylene group having 6 to 30 ring carbon atoms being preferred, an arylene group having 6 to 20 ring carbon atoms being more preferred, and an arylene group having 6 to 12 ring carbon atoms being still more preferred, and a phenylene group being particularly preferred.

The other groups will be described below, in which the group having the same name are defined in the same manner.

Examples of the alkyl group include a methyl group, an ethyl group, a n-propyl group, an isopropyl group, n-butyl group, an isobutyl group, t-butyl group, and n-hexyl group, with an alkyl group having 1 to 5 carbon atoms being preferred and an alkyl group having 1 to 3 carbon atoms being more preferred.

The alkyl group in the trialkylsilyl group and its preferred examples are as defined above. Examples of the aryl group for the triarylsilyl group include a phenyl group, a naphthyl group, and a biphenylyl group.

Examples of the alkylarylsilyl group include a dialkylmonoarylsilyl group, wherein the alkyl group has 1 to 5, preferably 1 to 3 carbon atoms, and the aryl group has 6 to 14, preferably 6 to 10 ring carbon atoms.

Examples of the aryl group having 6 to 50 ring carbon atoms include a phenyl group, a naphthyl group, a biphenylyl group, an anthryl group, a phenanthryl group, and a terphenylyl group, with an aryl group having 6 to 30 ring carbon atoms being preferred, an aryl group having 6 to 20 ring carbon atoms being more preferred, and an aryl group having 6 to 12 ring carbon atoms being still more preferred.

Examples of the halogen atom include a fluorine atom, a chlorine atom, and an iodine atom.

Each of a to f is preferably 0 or 1 and more preferably 0.

The group represented by formula (4-2) is preferably represented by formula (4-2') or (4-2"), wherein each variable is as defined above:

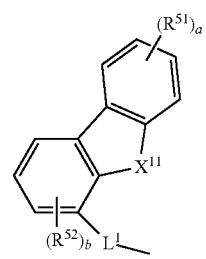

(4-2')

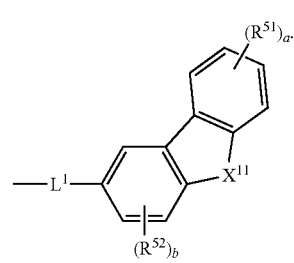

(4-2")

The group represented by formula (4-4) is preferably represented by formula (4-4'), wherein each variable is as defined above:

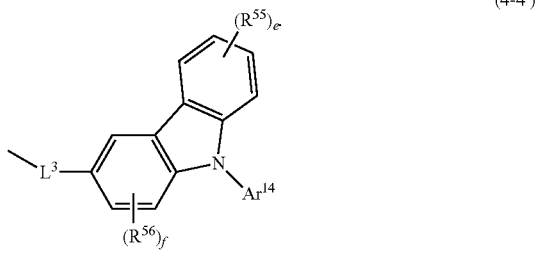

(4-4')

In formula (4), at least one selected from $Ar^{11}$ to $Ar^{13}$ is preferably a group represented by formula (4-2). In formula (4-2), $X^{11}$ is preferably an oxygen atom.

Also preferred are a compound wherein two of $Ar^{11}$ to $Ar^{13}$ are represented by formula (4-2), a compound wherein one thereof is represented by formula (4-2) and another one is represented by formula (4-3), and a compound wherein tree thereof are represented by formula (4-2).

When $L^1$ of formula (4-2) is an arylene group or $L^3$ of formula (4-4) is an arylene group, the increase in the electron density of the compound represented by formula (4) is prevented to increase Ip, therefore, the hole injection into the light emitting layer is promoted to reduce the driving voltage of the device. In addition, when a dibenzofuran structure or a carbazole structure is bonded to the nitrogen atom via an arylene group, the amine is made resistant to oxidation and stable in many cases to make it easy to prolong the lifetime of the device. When $L^3$ of formula (4-4) is an arylene group, the compound is made stable and its synthesis is easy. The arylene groups mentioned above is particularly preferably a phenylene group.

In formula (4), when a group selected from $Ar^{11}$ to $Ar^{13}$ is not a group represented by any of formulae (4-2) to (4-4), it represents a substituted or unsubstituted aryl group having 6 to 40 ring carbon atoms which is preferably represented by any one of formulae (4-5) to (4-7):

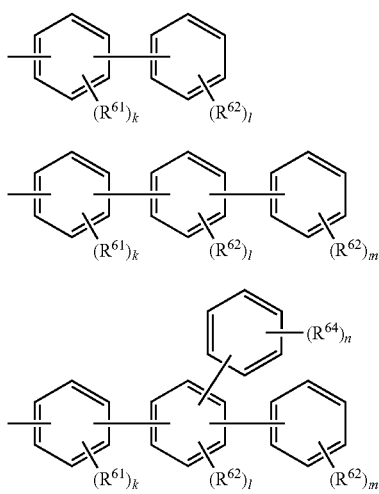

wherein:

$R^{61}$ to $R^{64}$ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms wherein the aryl portion has 6 to 14 ring carbon atoms, an aryl group having 6 to 50 ring carbon atoms, a halogen atom, or a cyano group;

adjacent groups selected from $R^{61}$ to $R^{64}$ may be bonded to each other to form a ring; and k, l, m, and n each independently represent an integer of 0 to 4.

Formulae (4-5) to (4-7) are preferably represented by formulae (4-5') to (4-7'), respectively, wherein each valuable is as defined above.

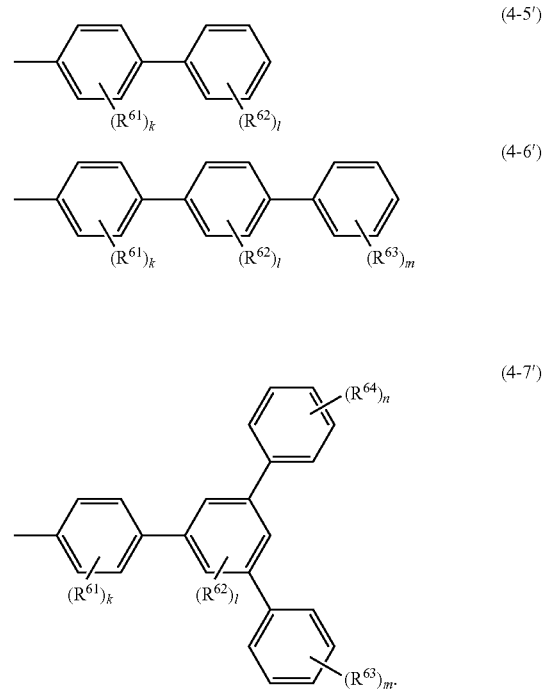

The group represented by formula (4-5') includes the following groups:

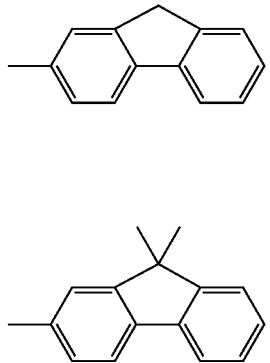

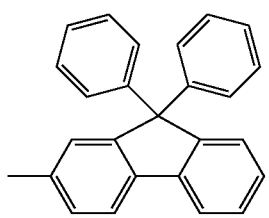
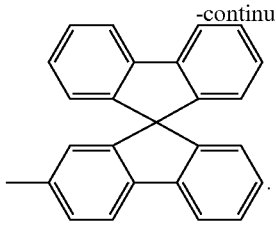
Examples of the compound represented by formula (4) are shown below, although not limited to the following compounds.
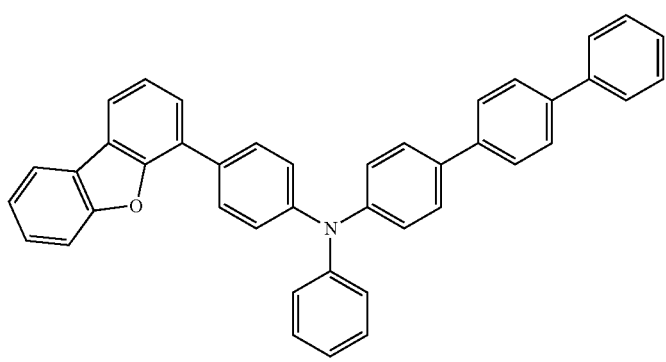
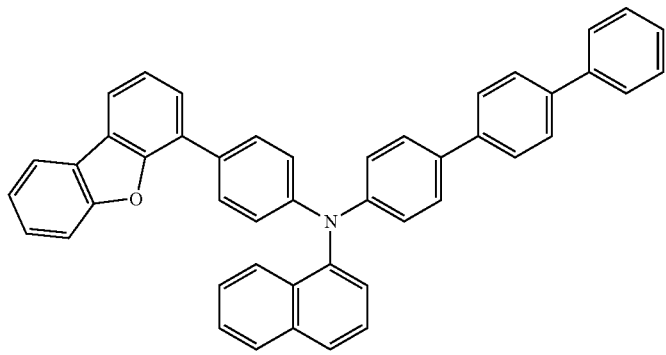
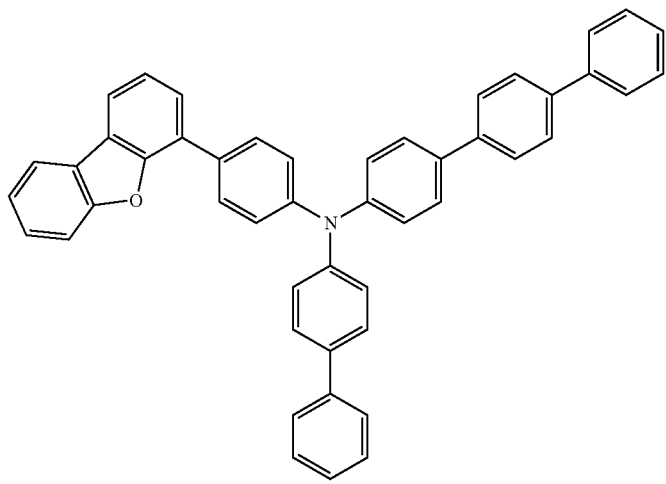

-continued
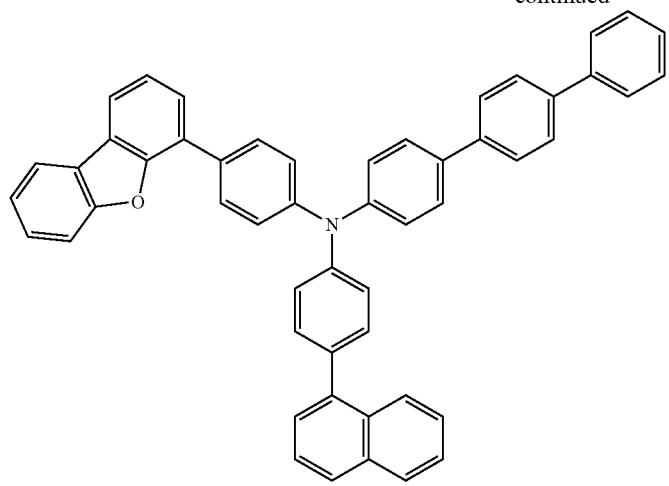
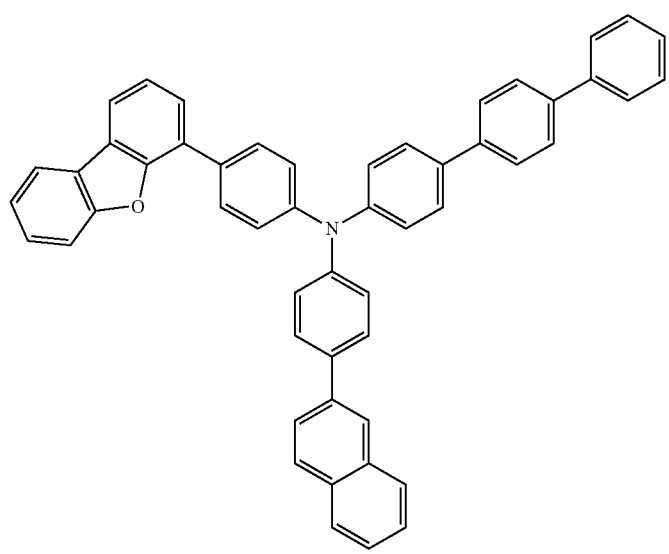
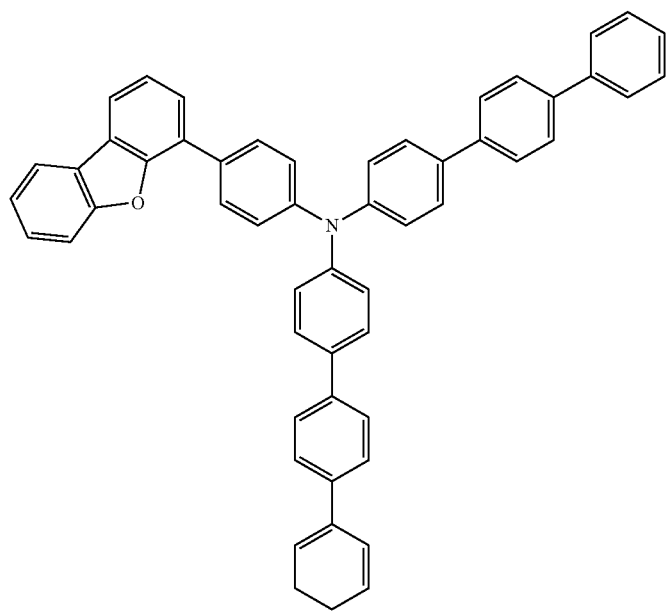

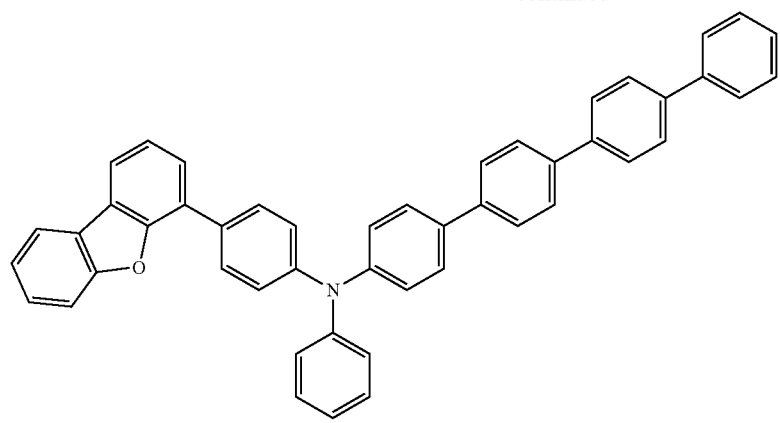
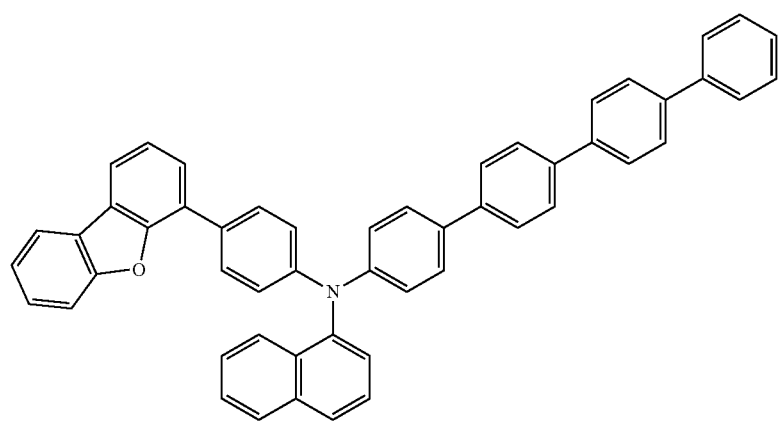
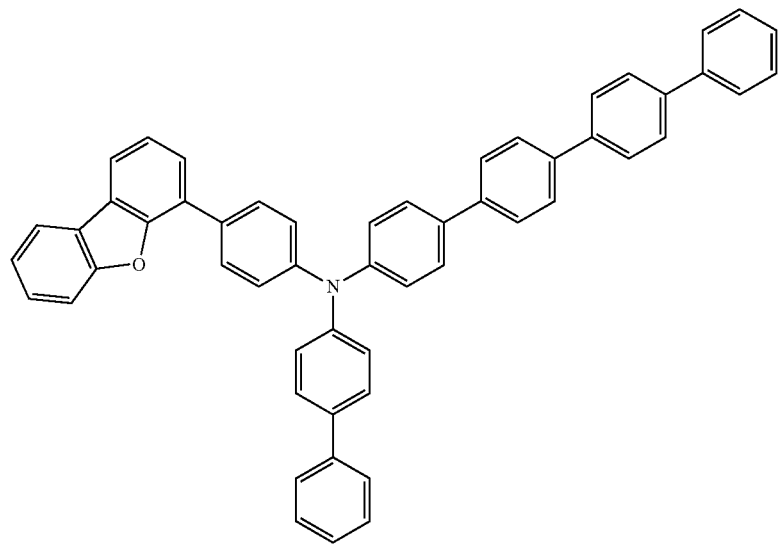

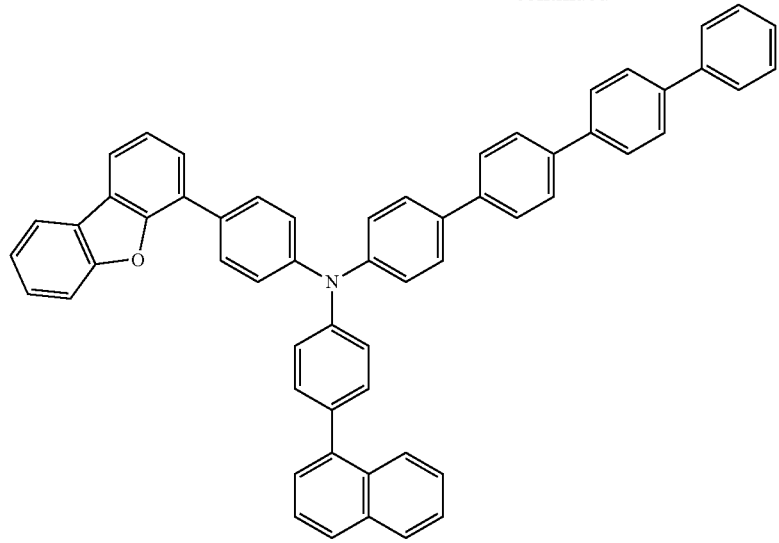
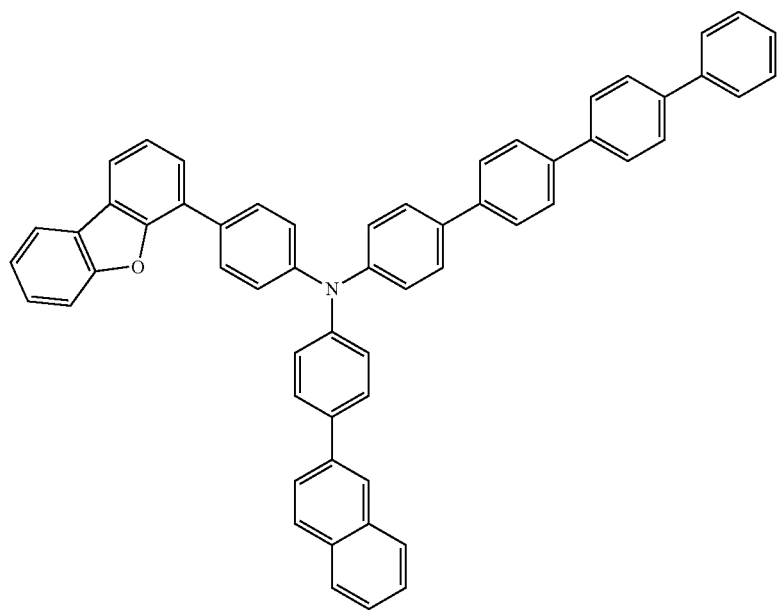

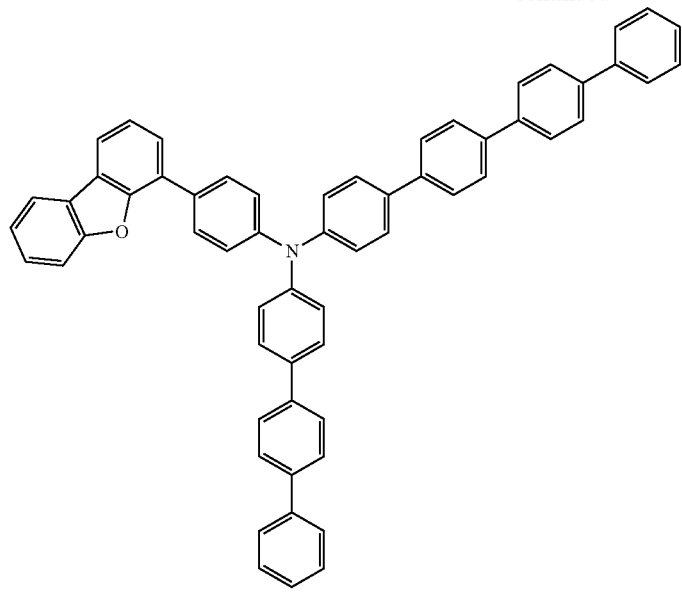
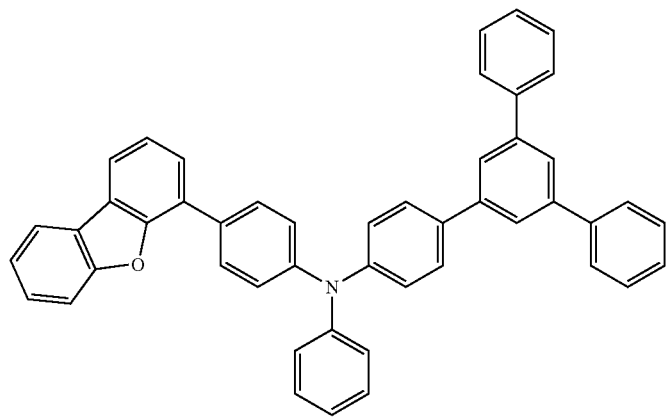
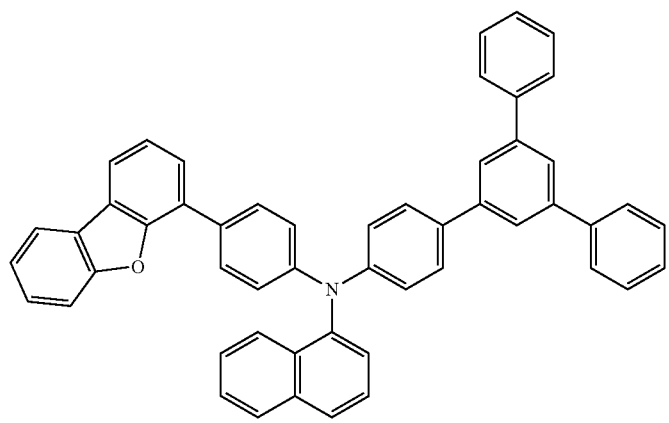

-continued
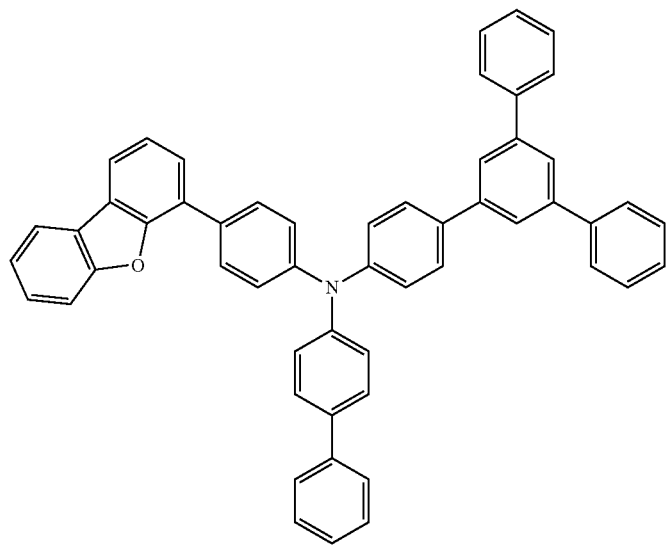
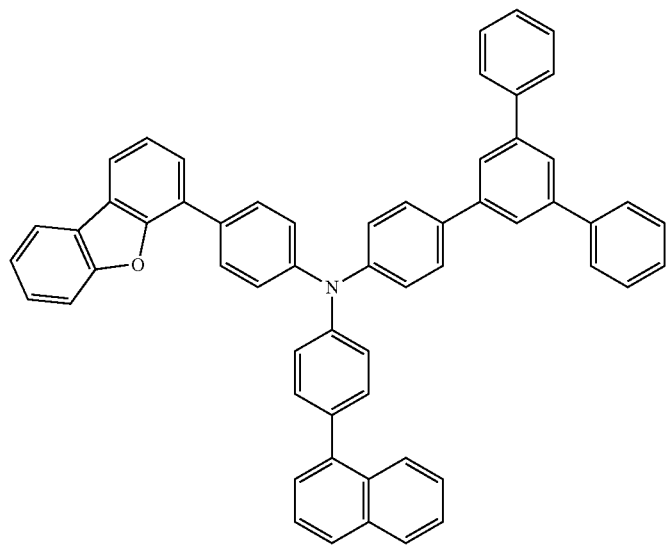
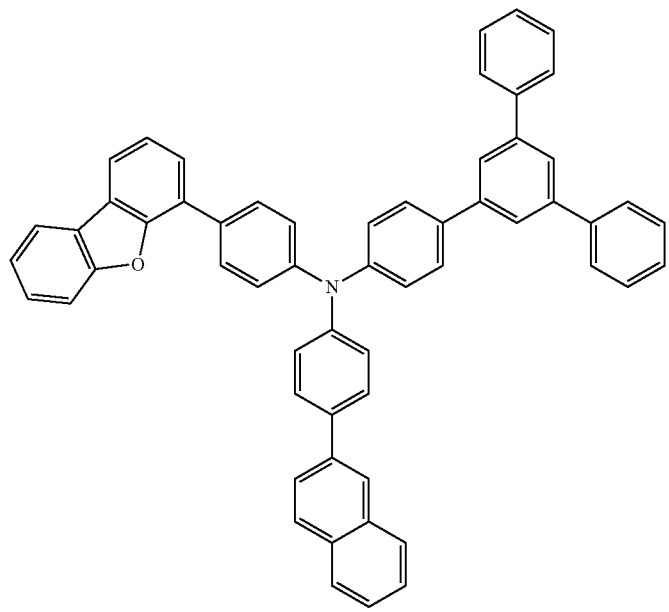

-continued
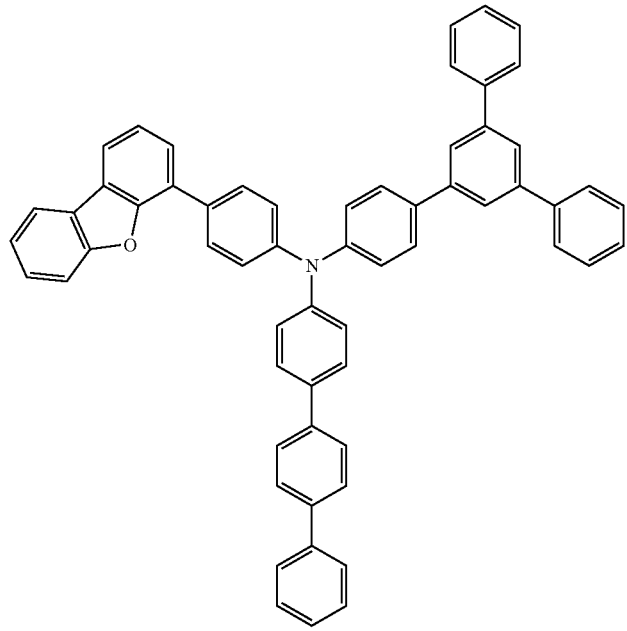
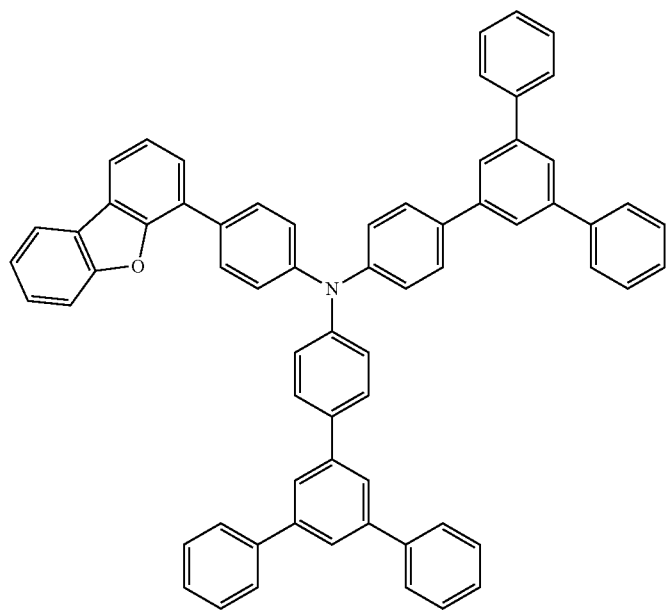
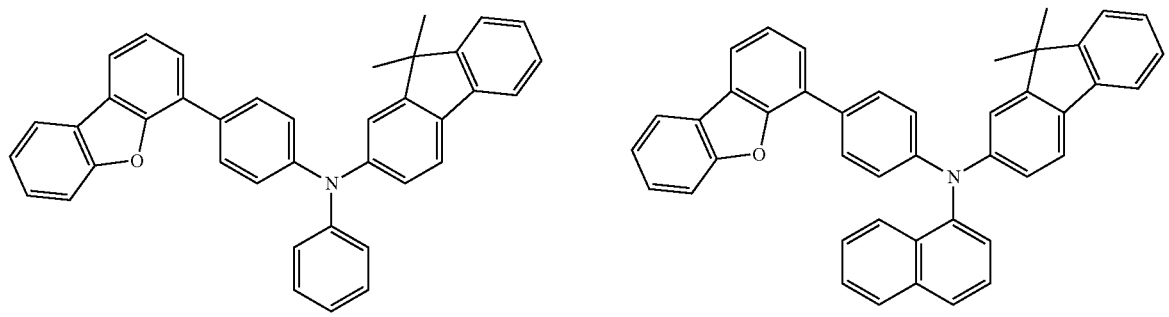

191 192
-continued
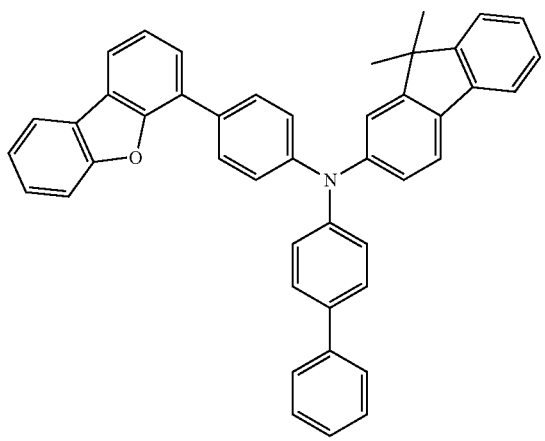
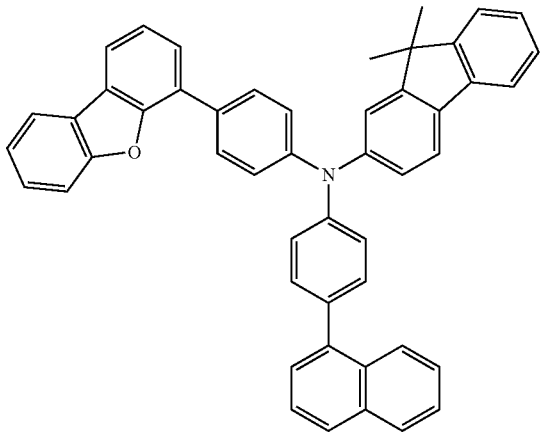
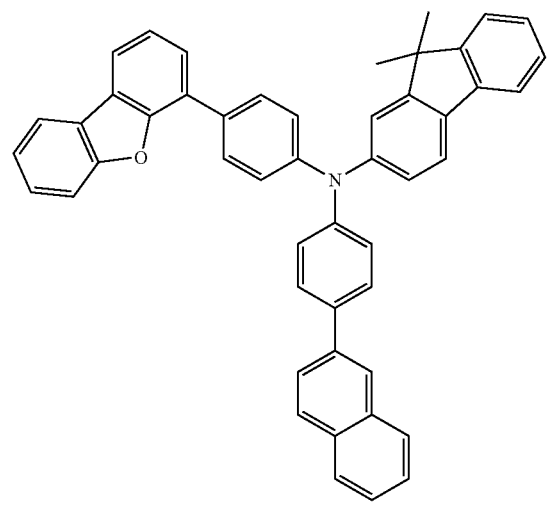
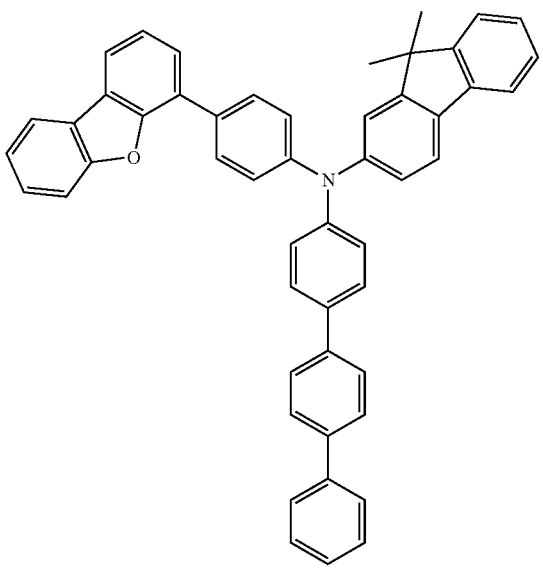
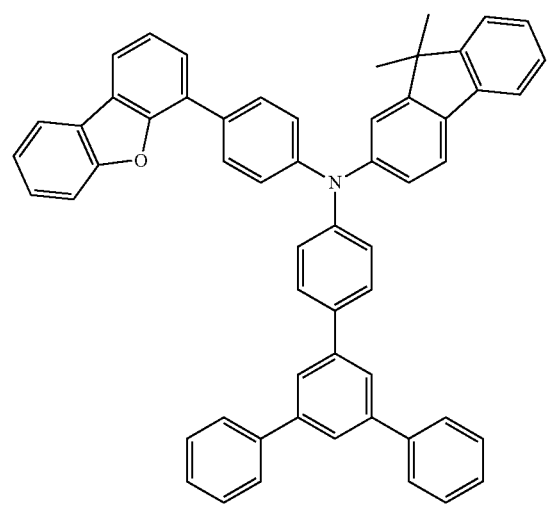
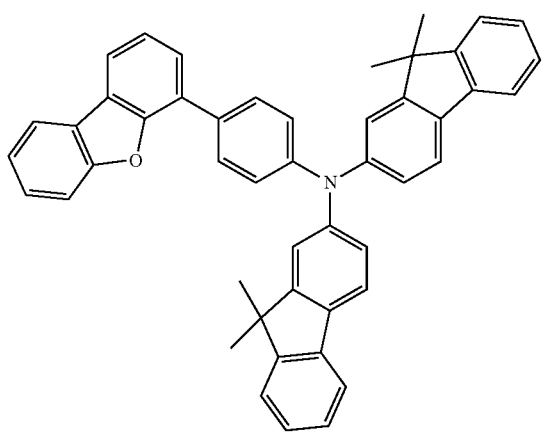

-continued
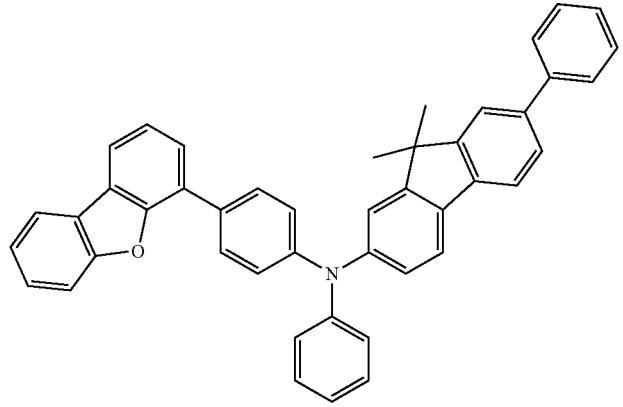
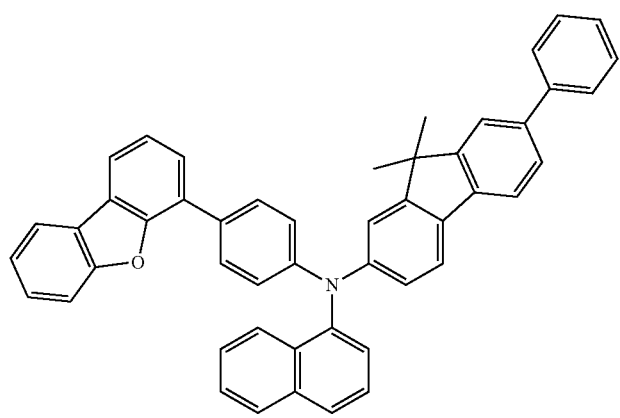
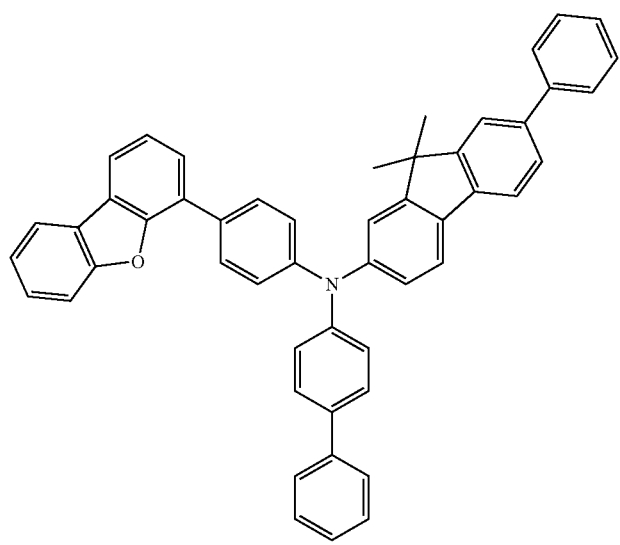

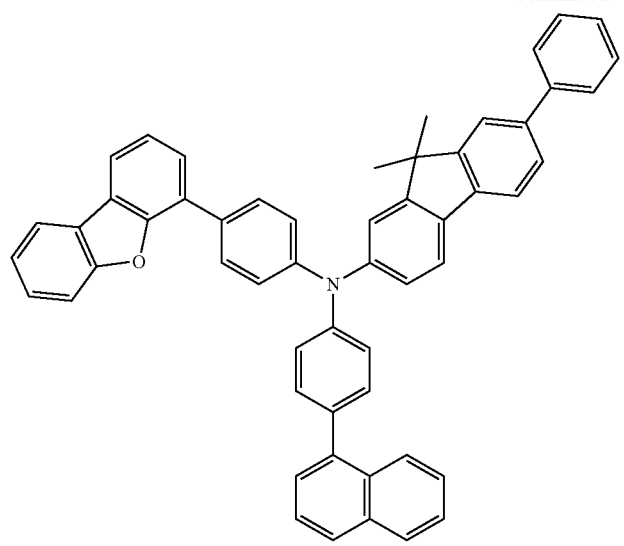
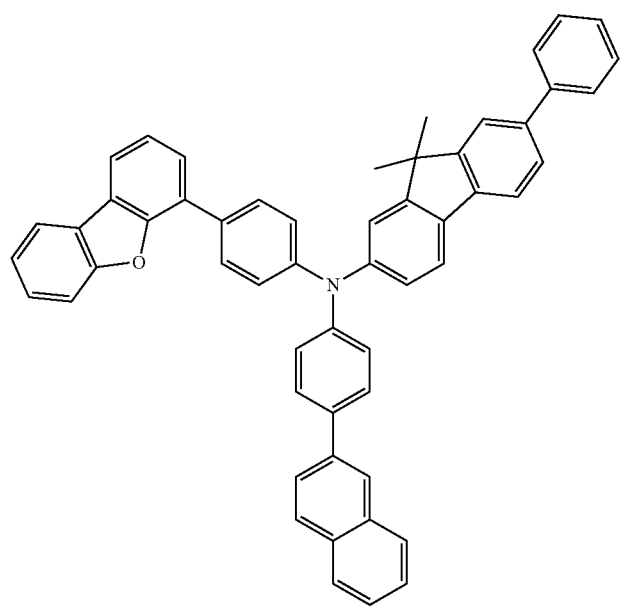

-continued
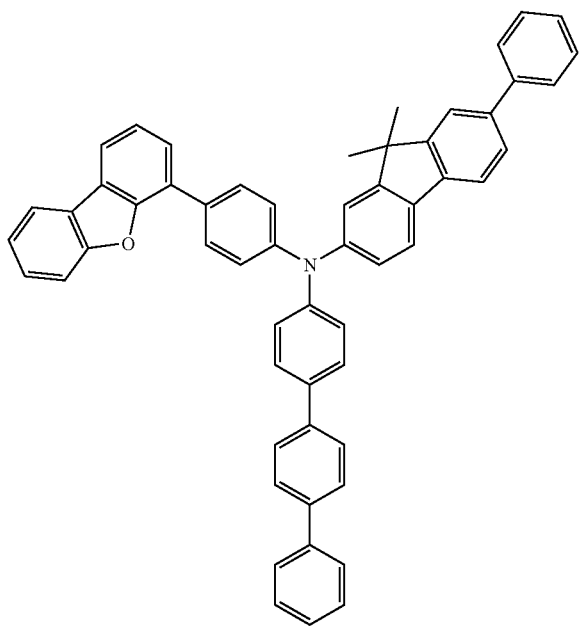
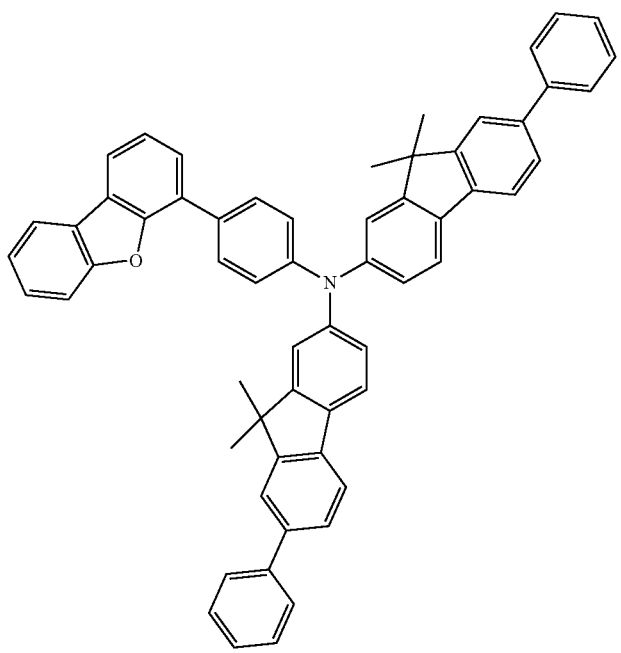
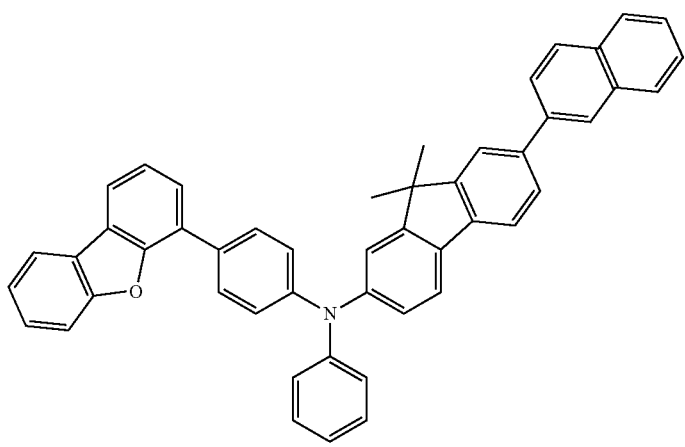

-continued
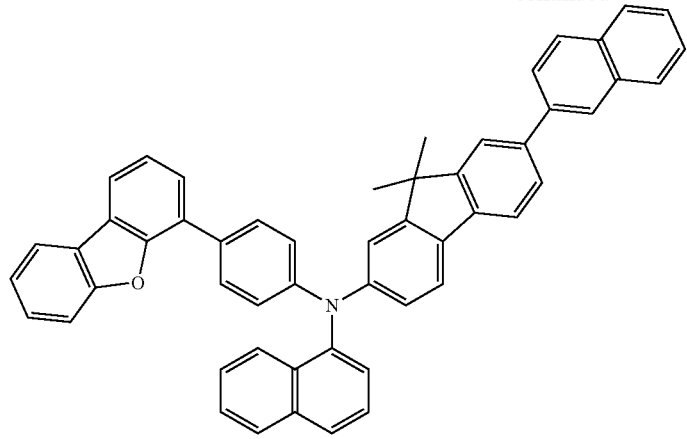
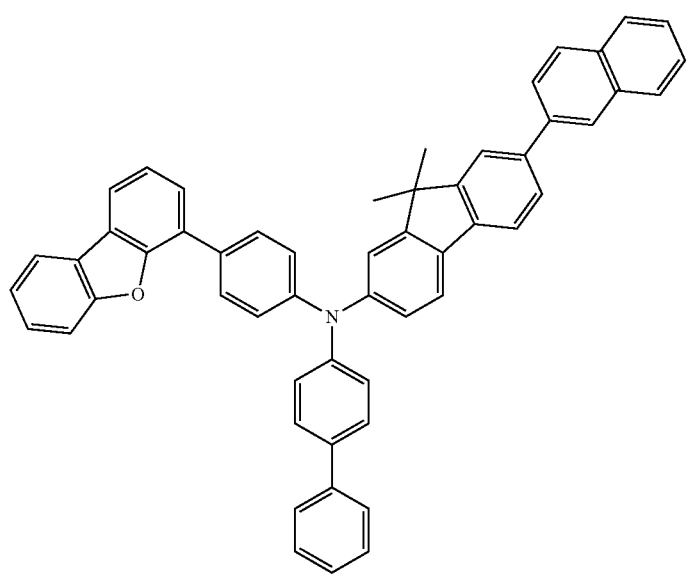
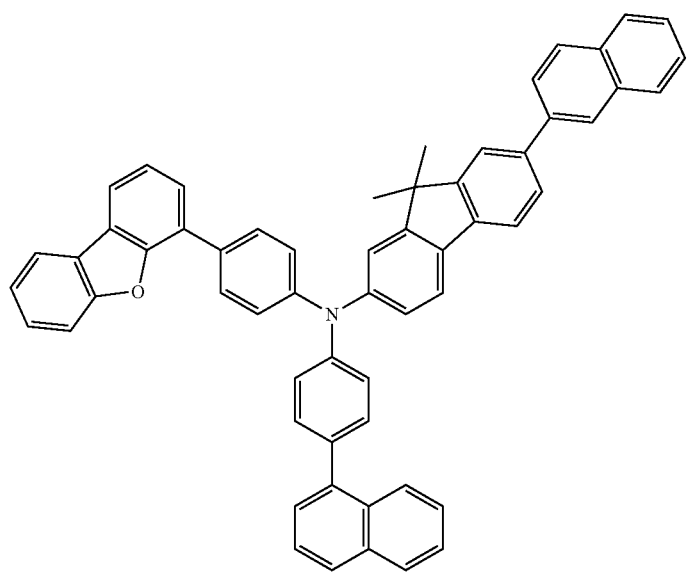

-continued
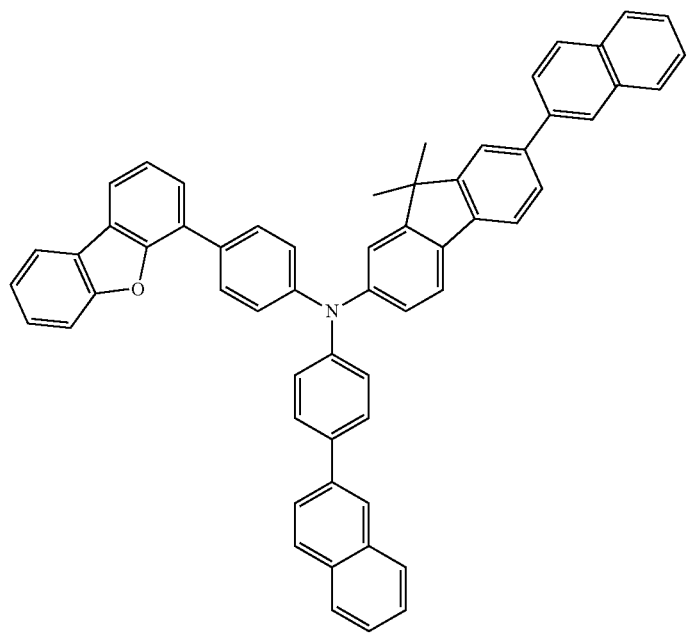
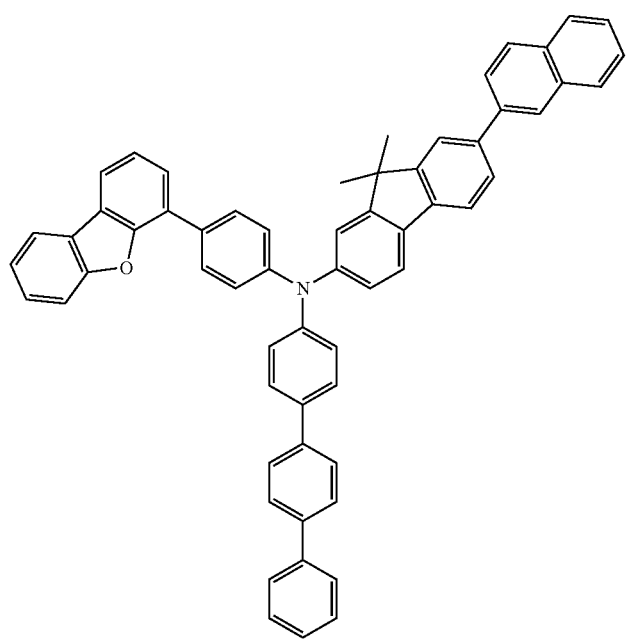

-continued
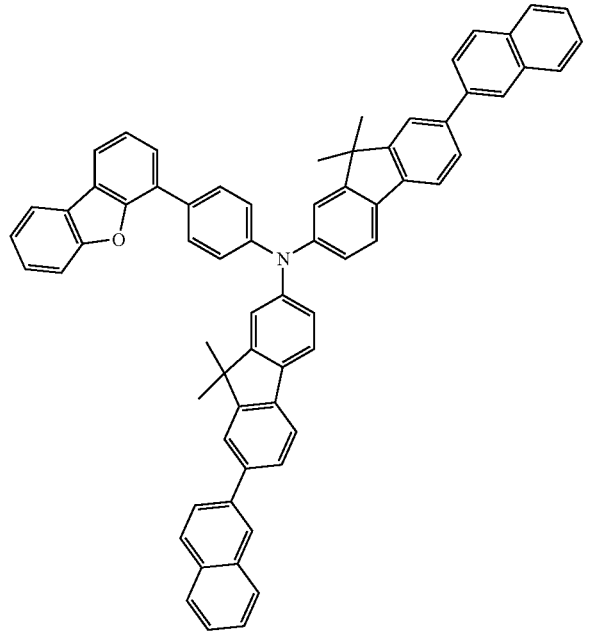
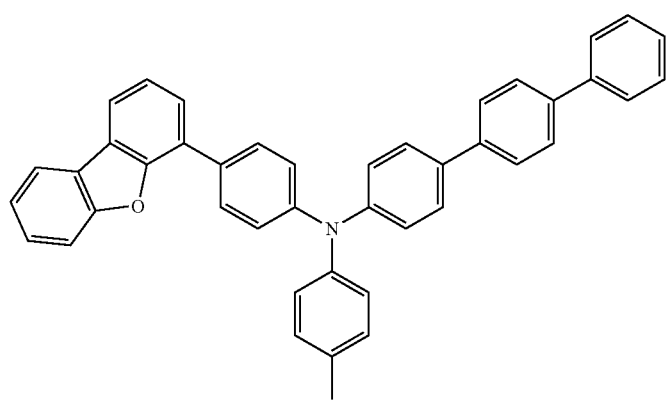
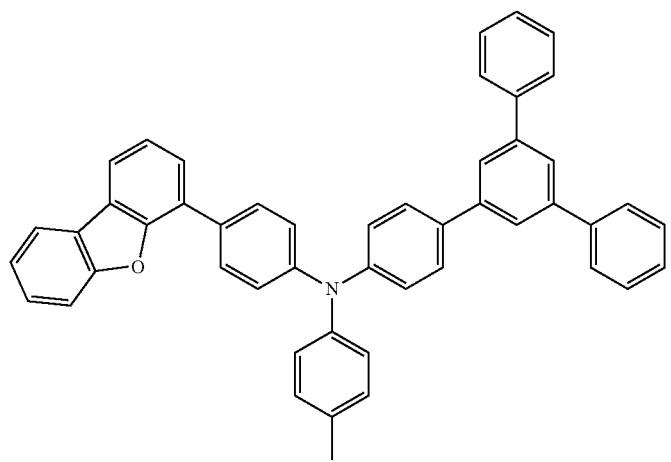

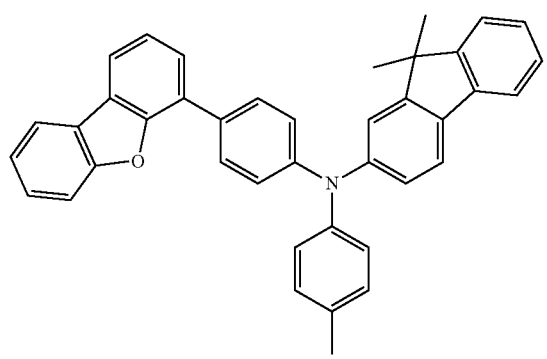
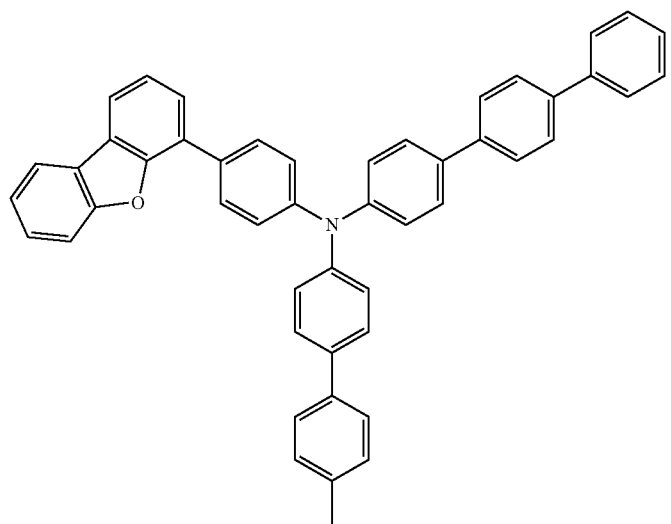
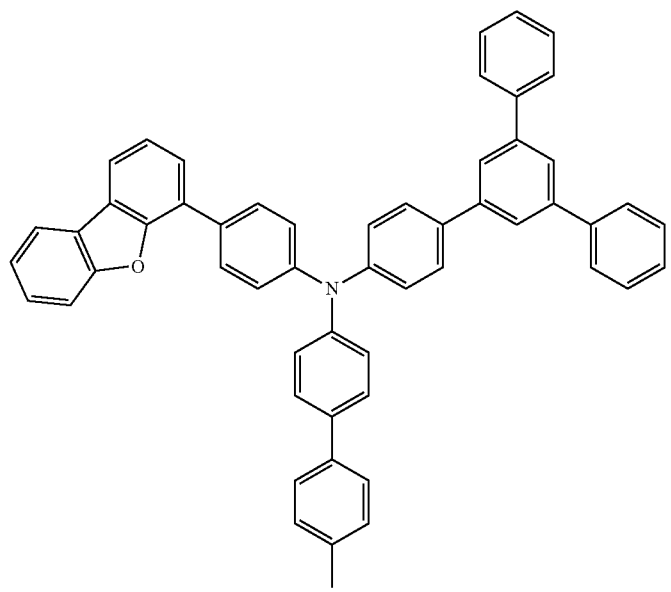

-continued
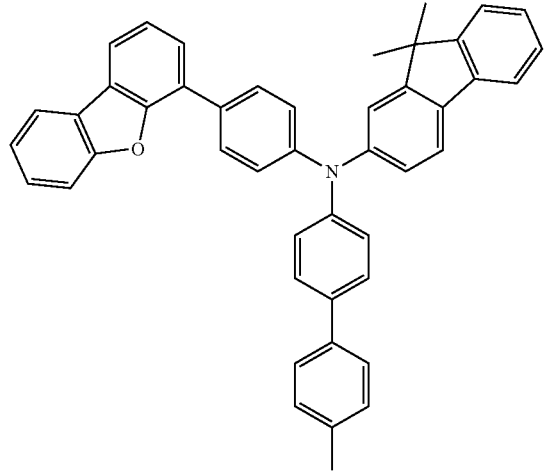
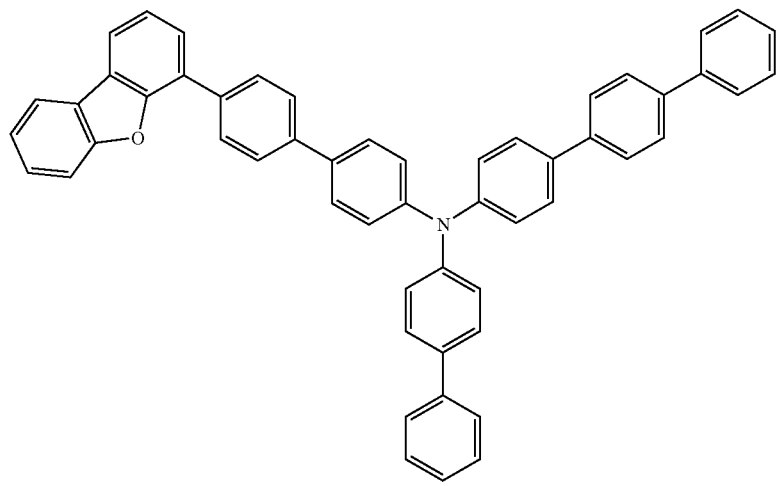
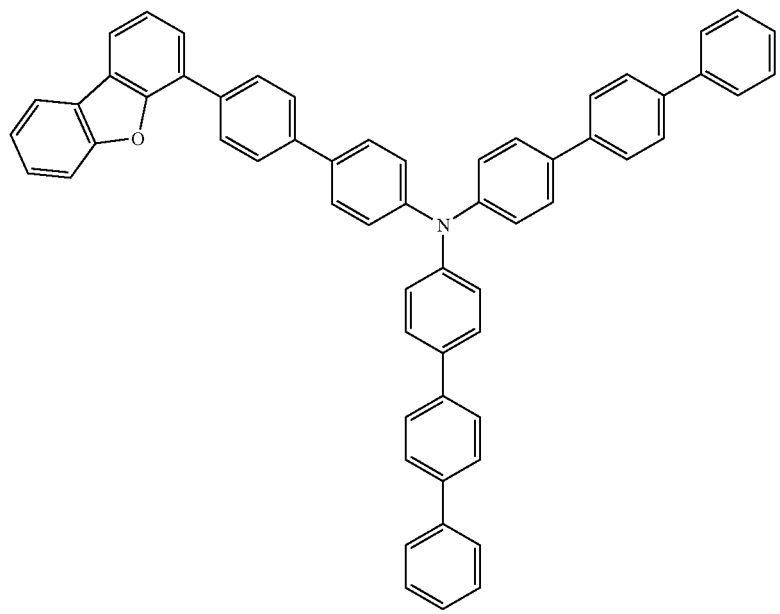

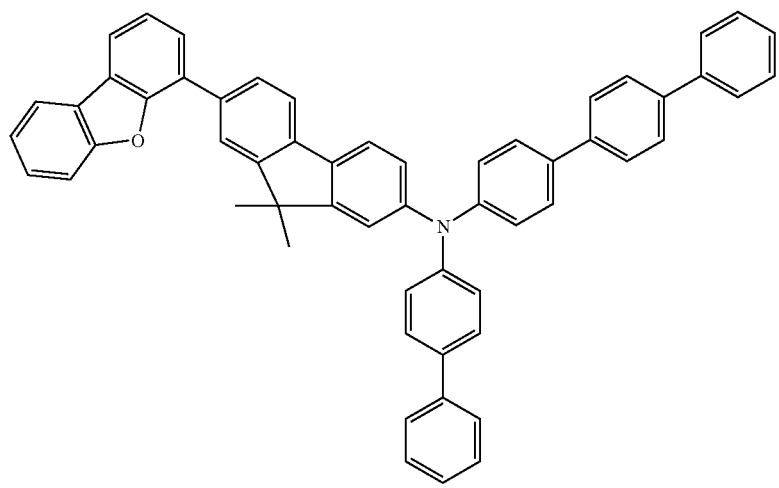
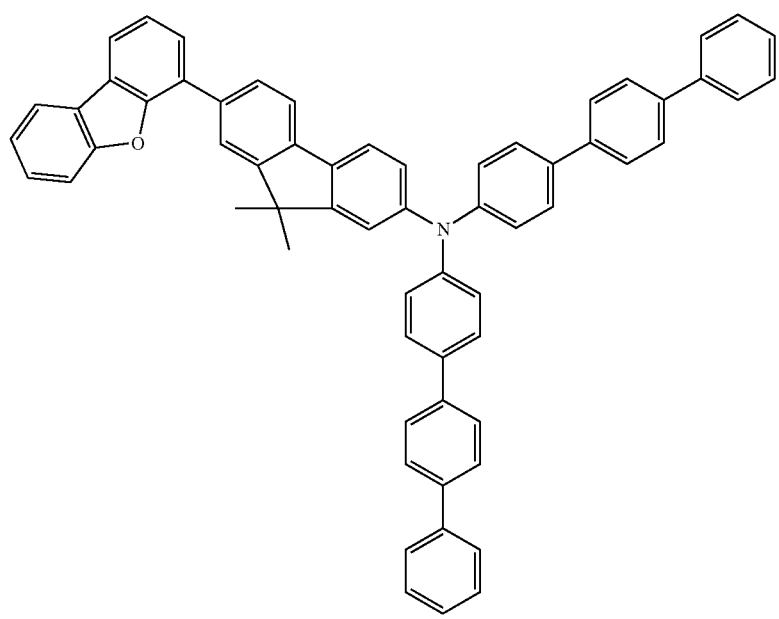
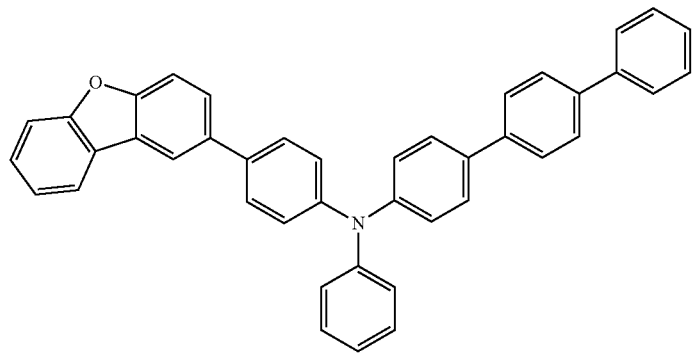

-continued
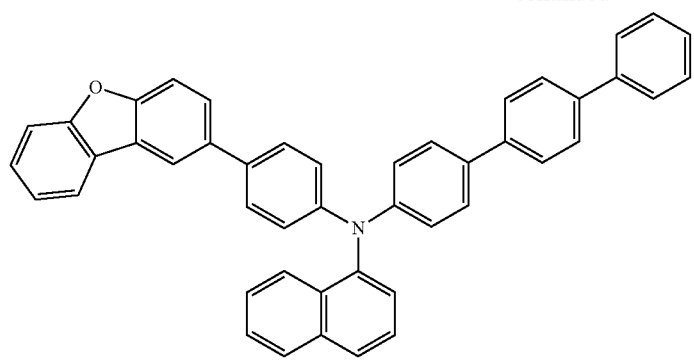
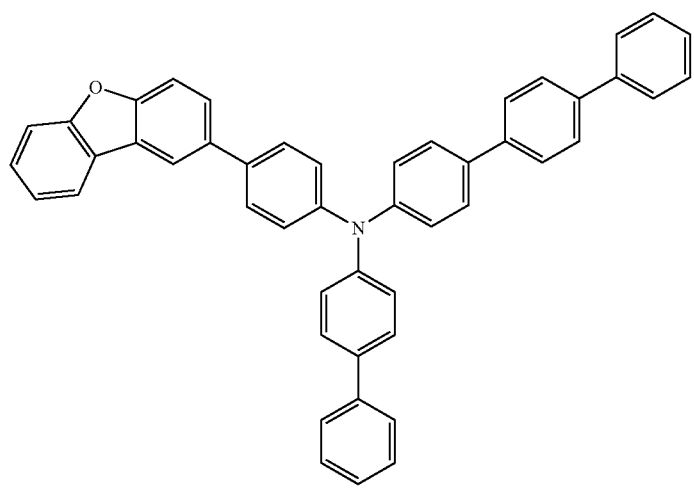
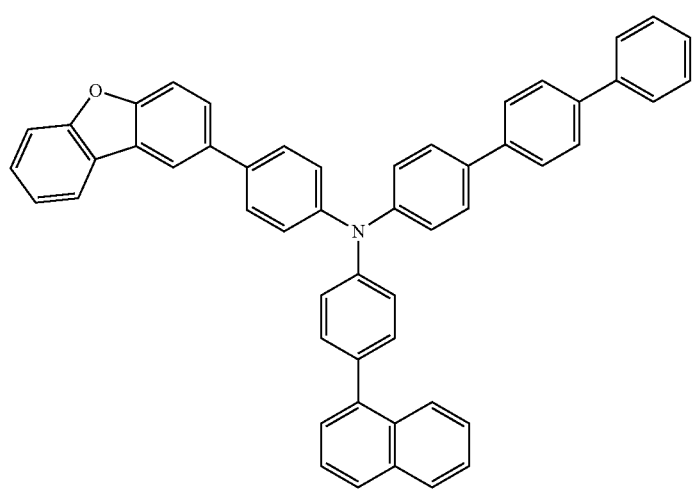

-continued
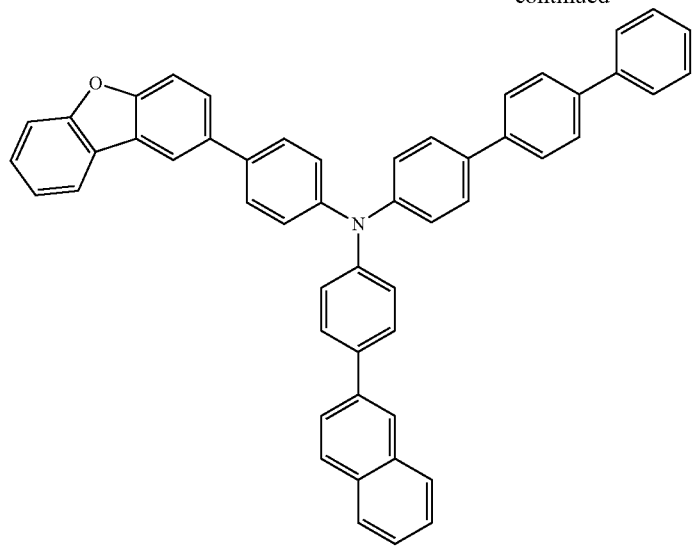
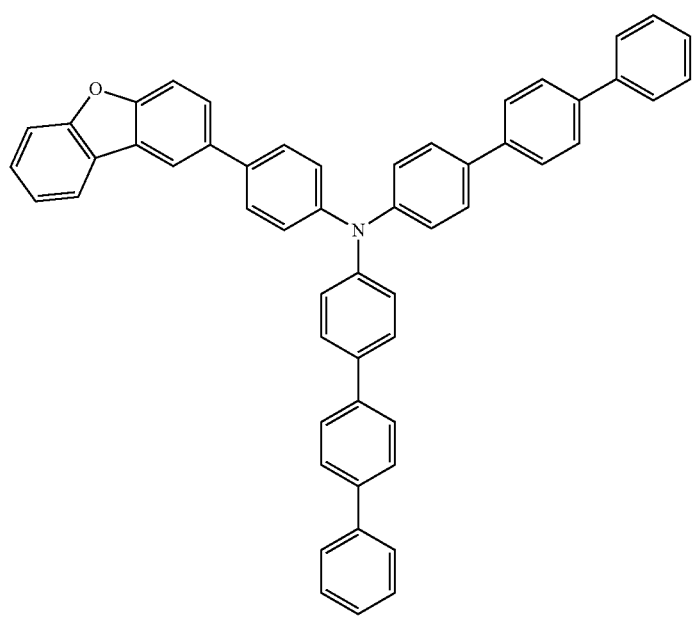
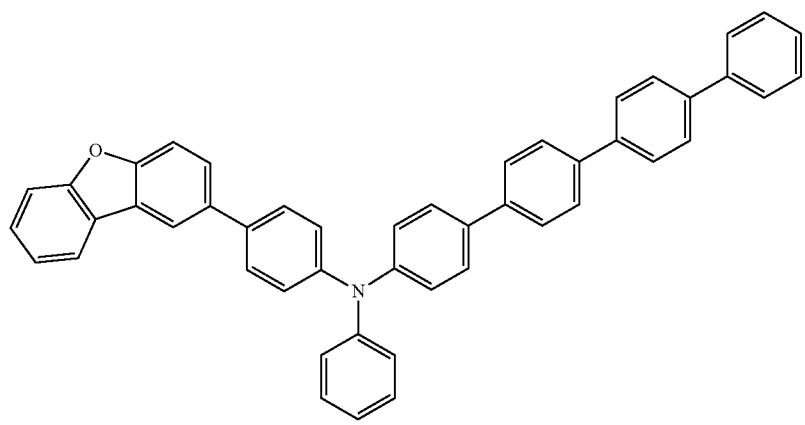

-continued
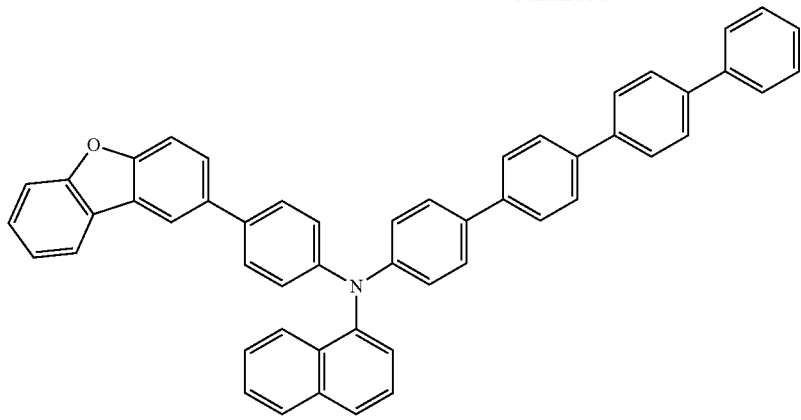
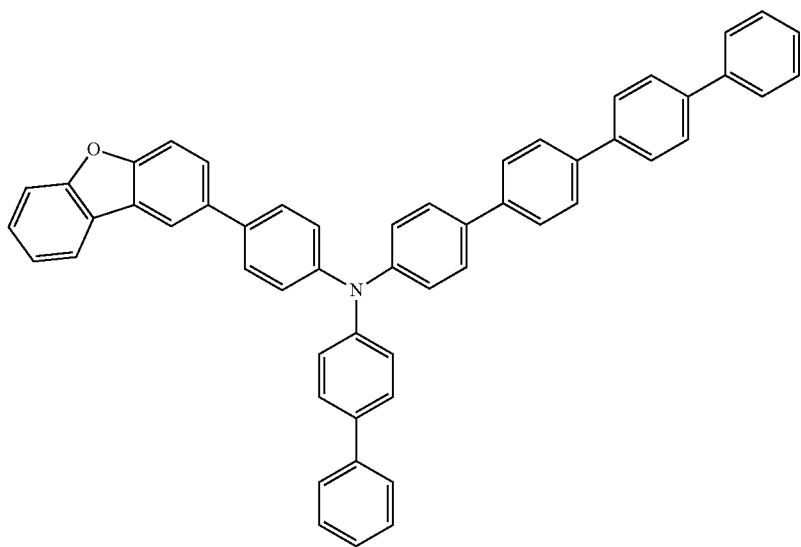
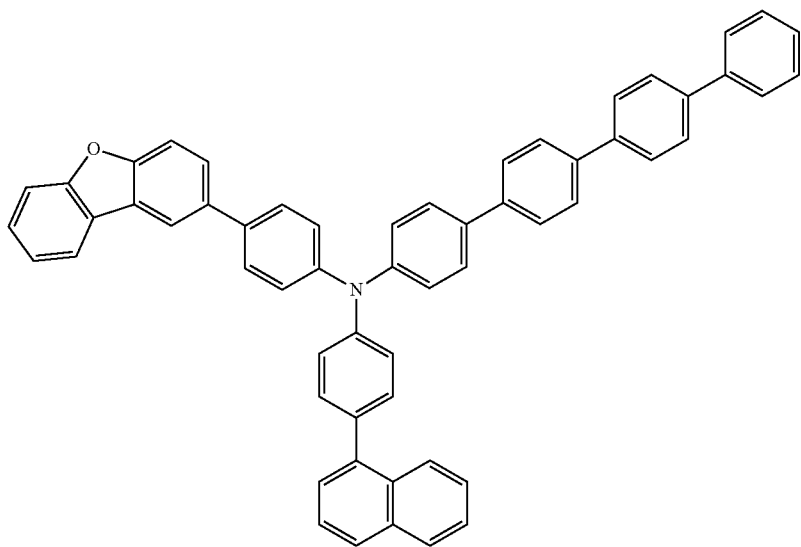

-continued
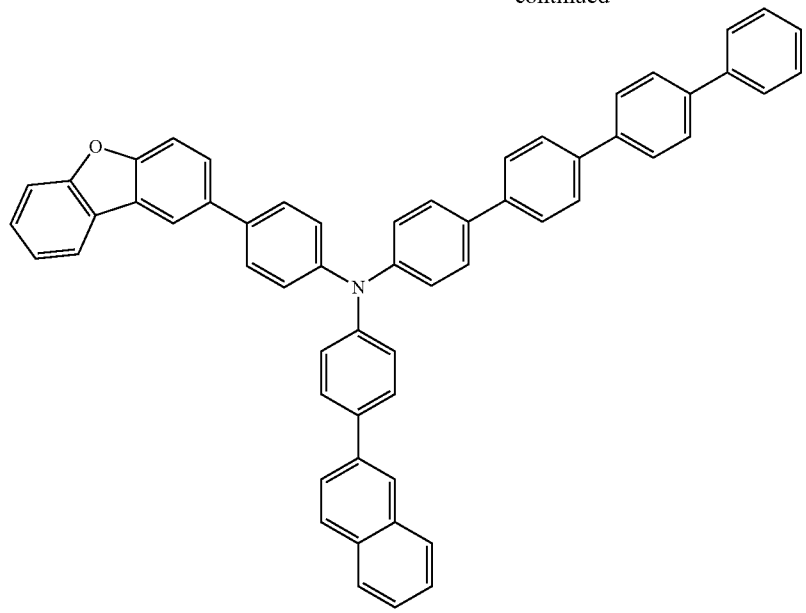
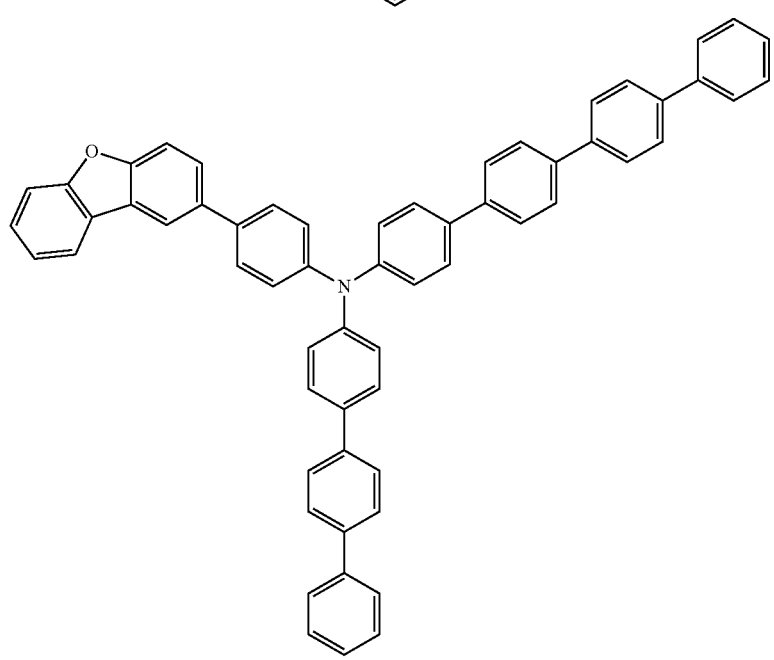
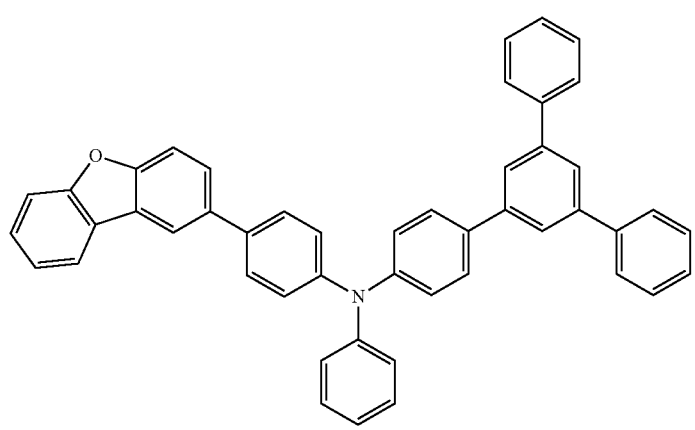

-continued
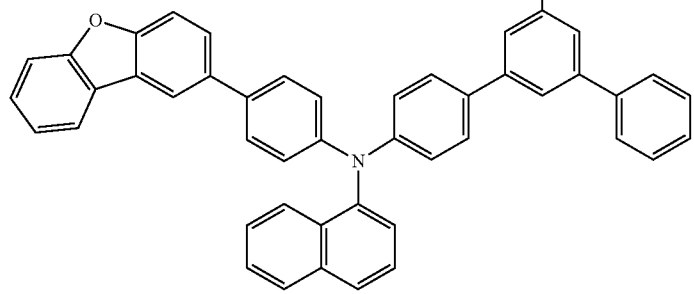
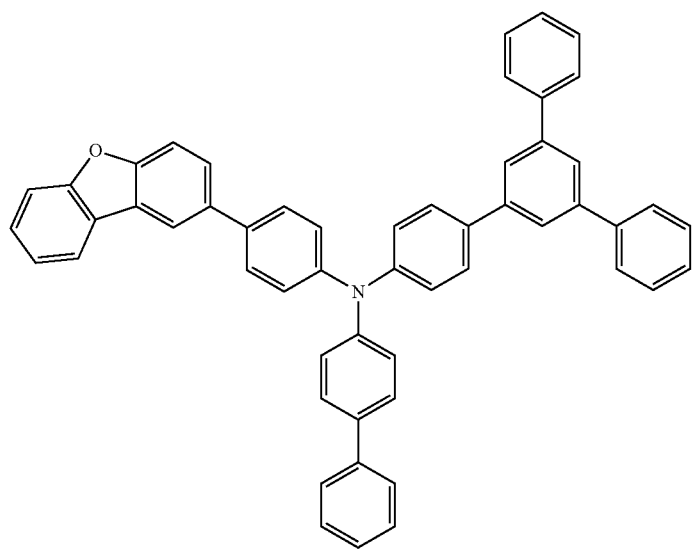
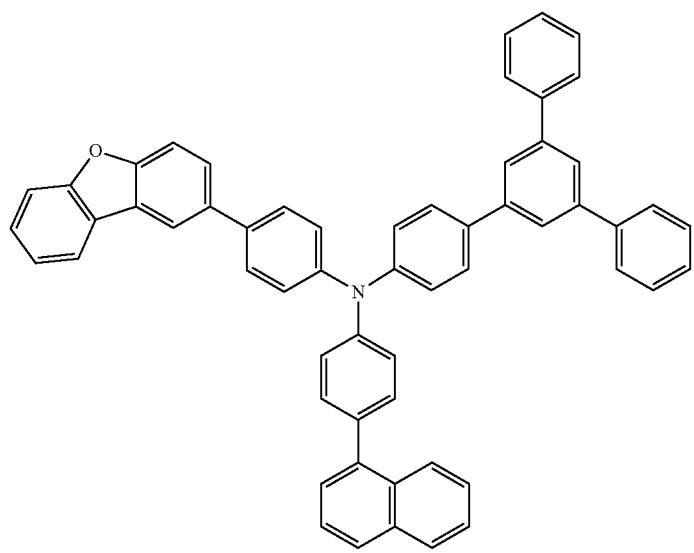

-continued
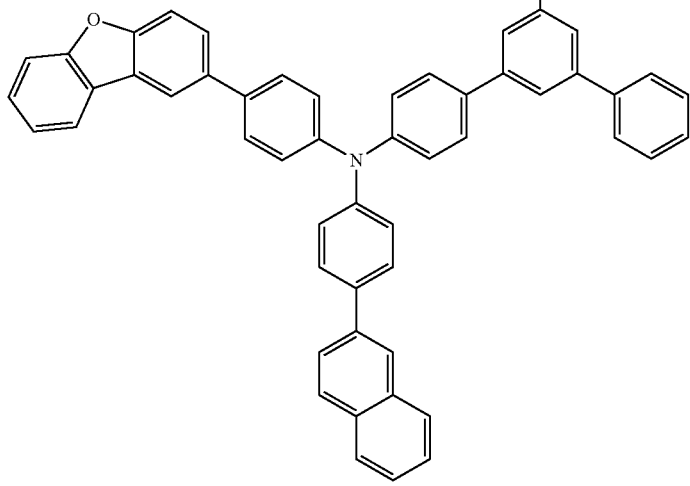
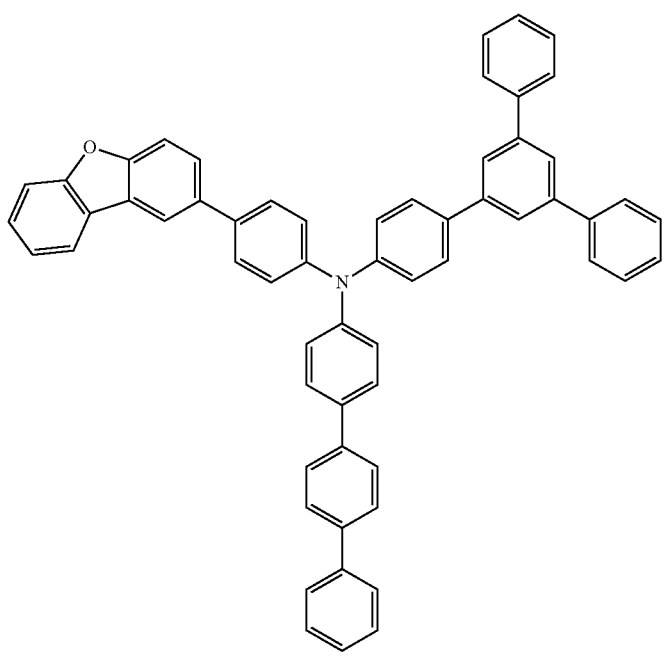

-continued
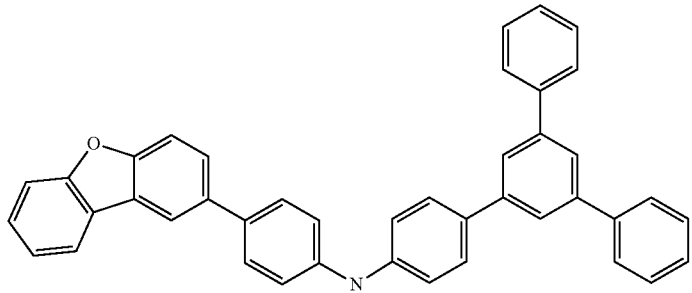
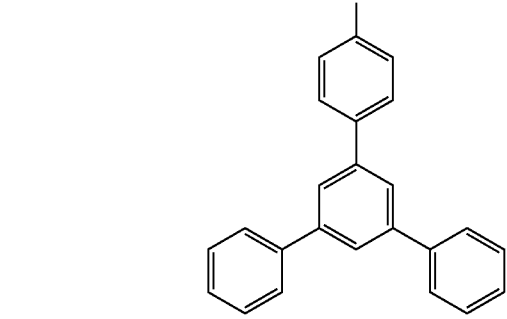
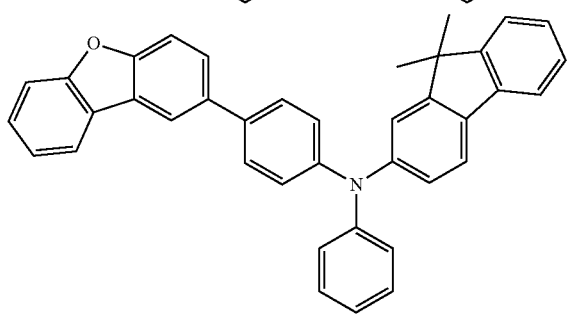
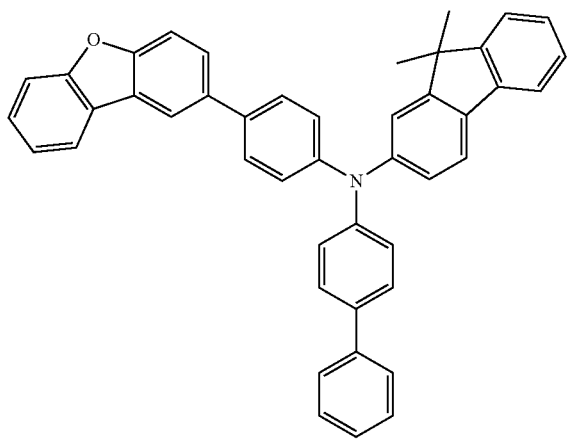

-continued
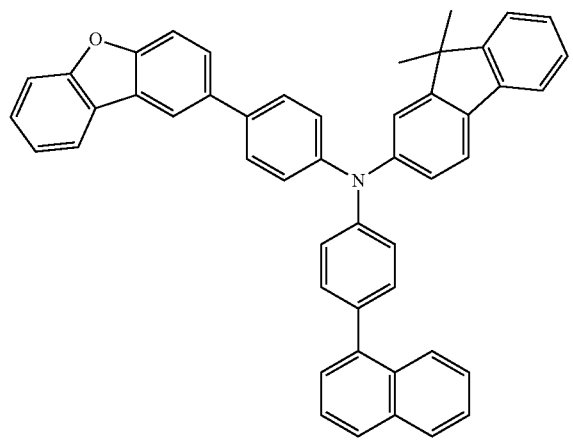
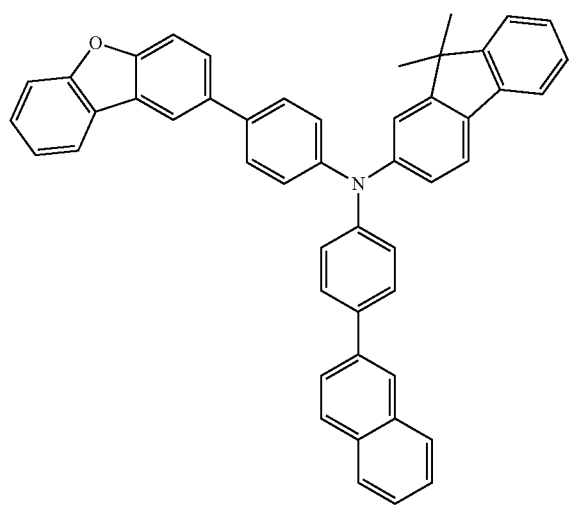
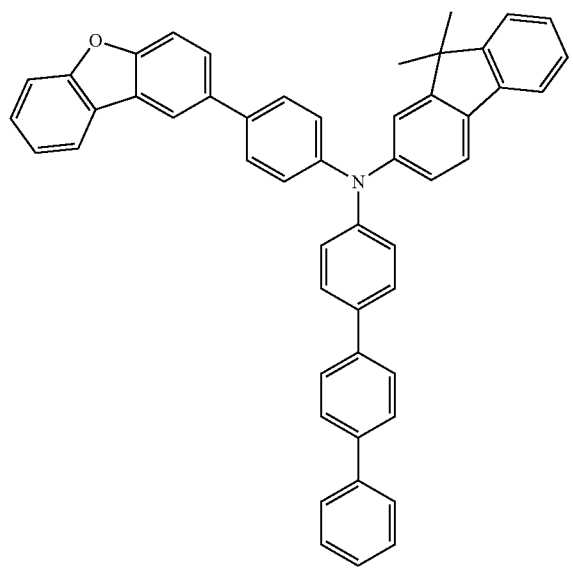

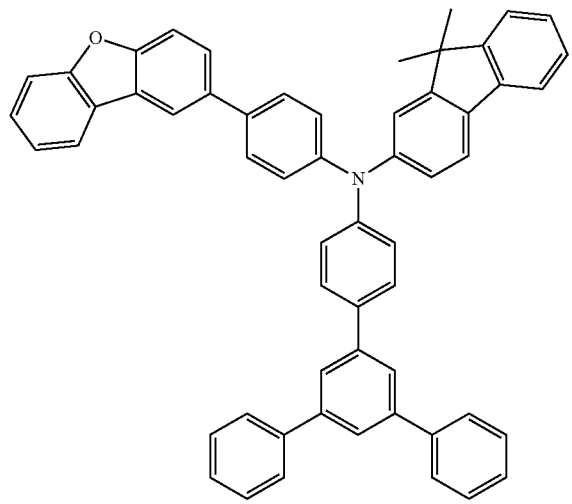
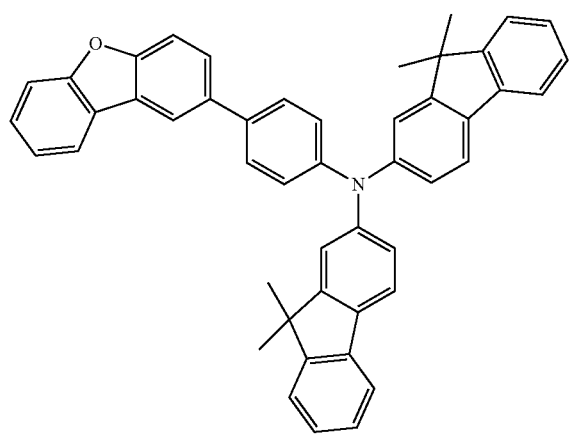
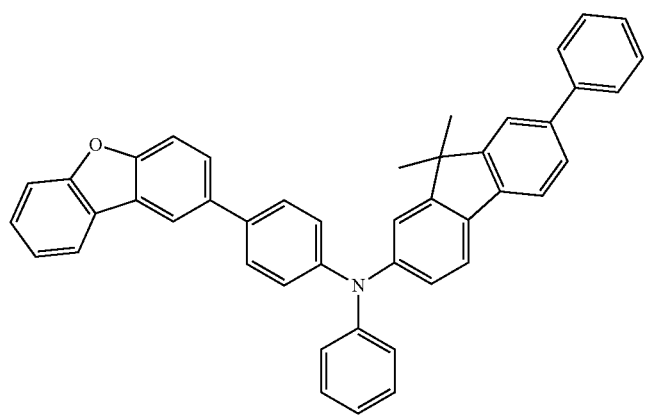

-continued
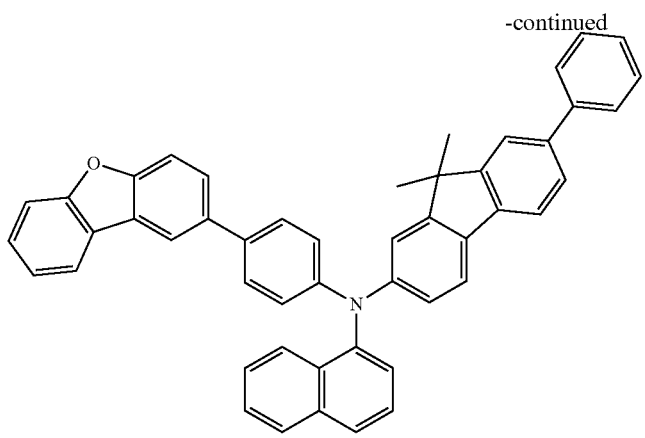
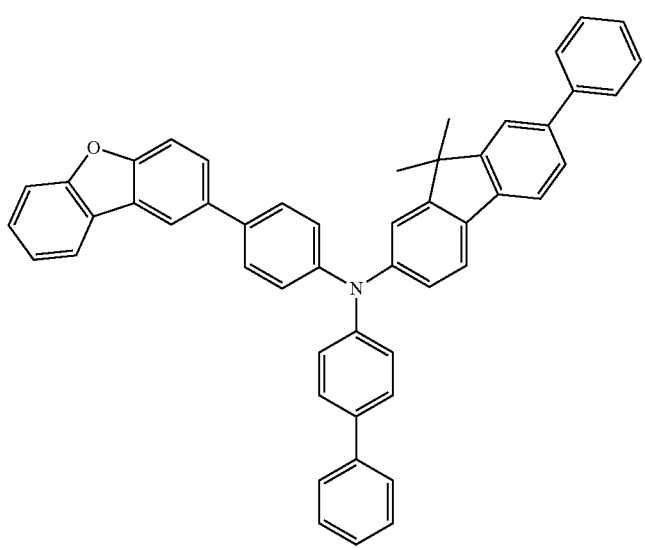
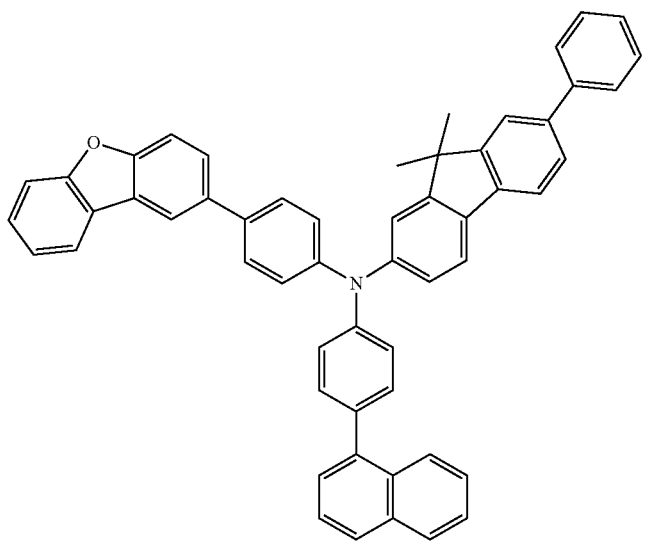

-continued
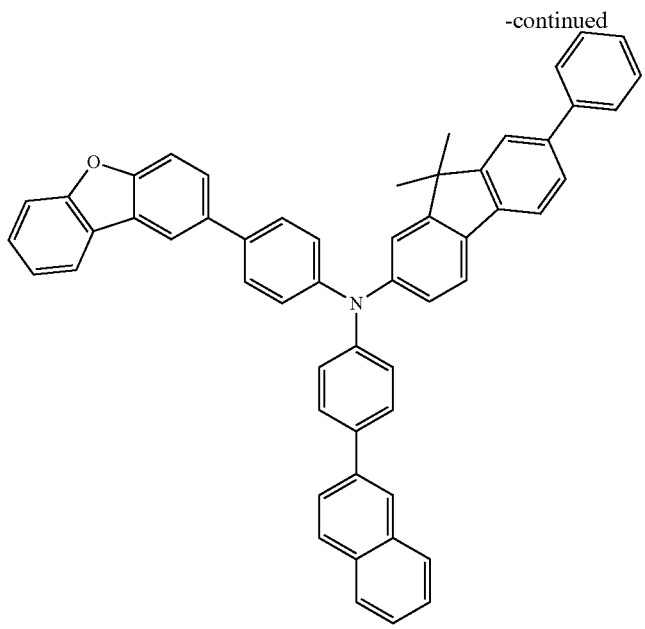
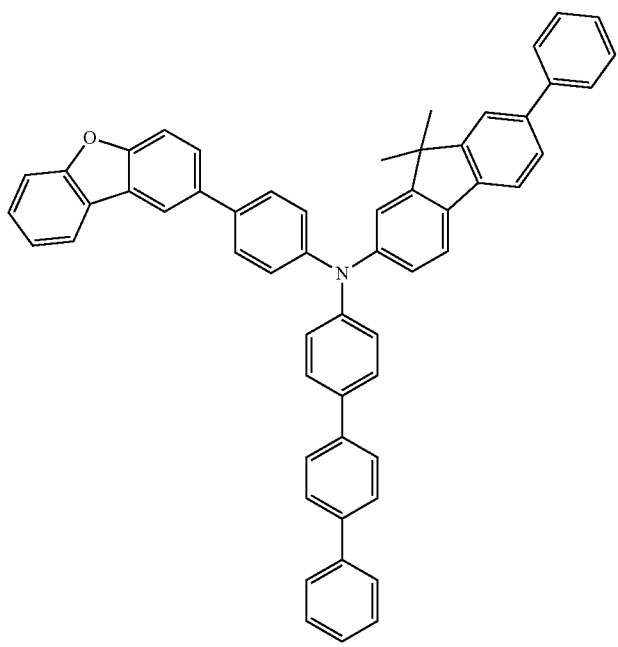

-continued
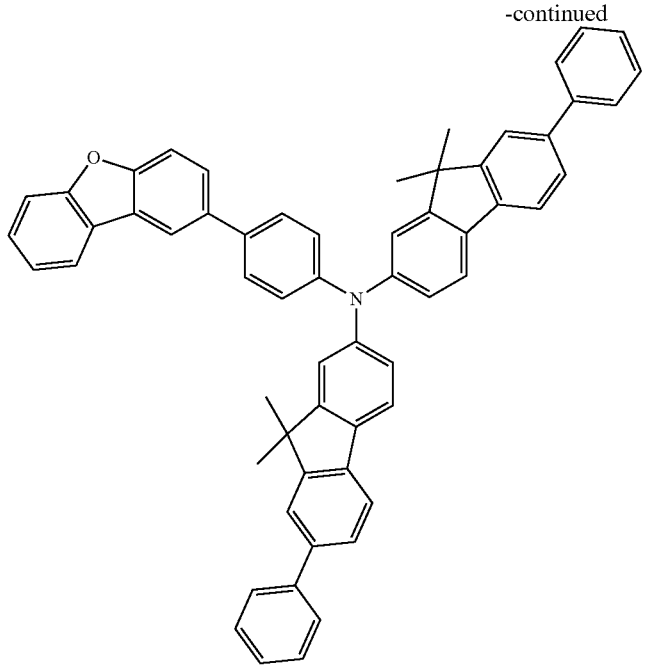
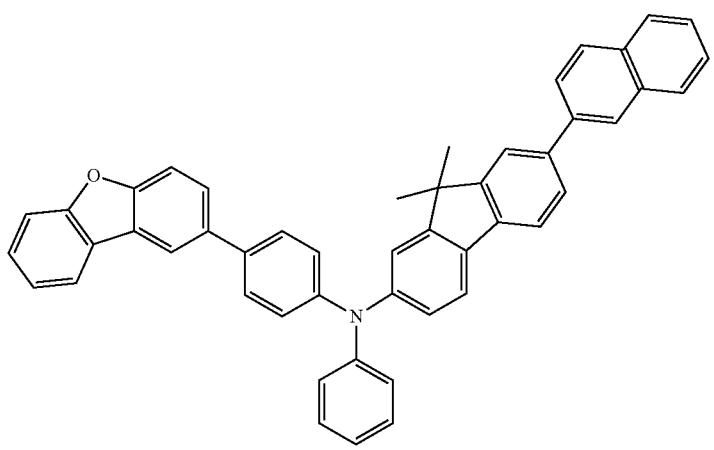
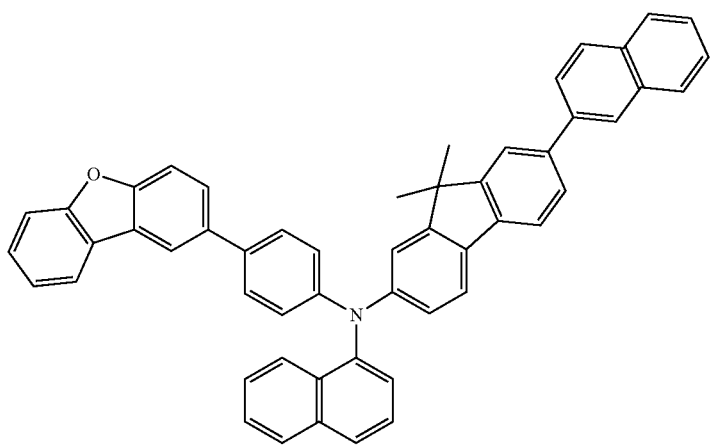

-continued
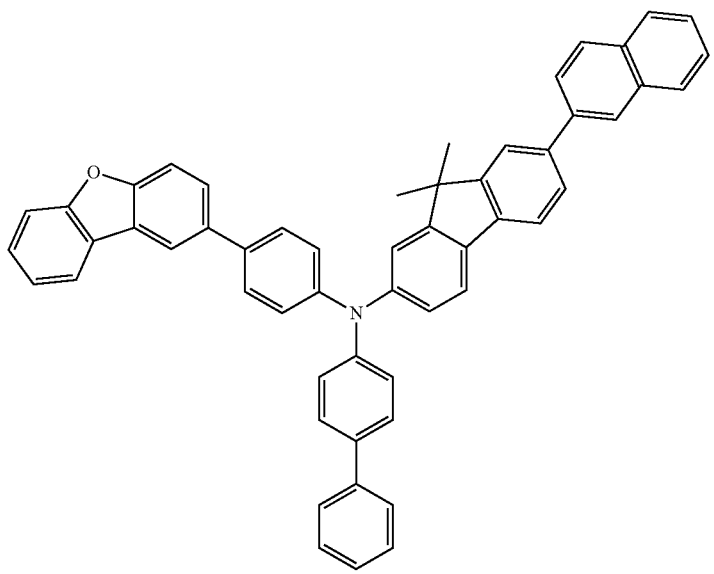
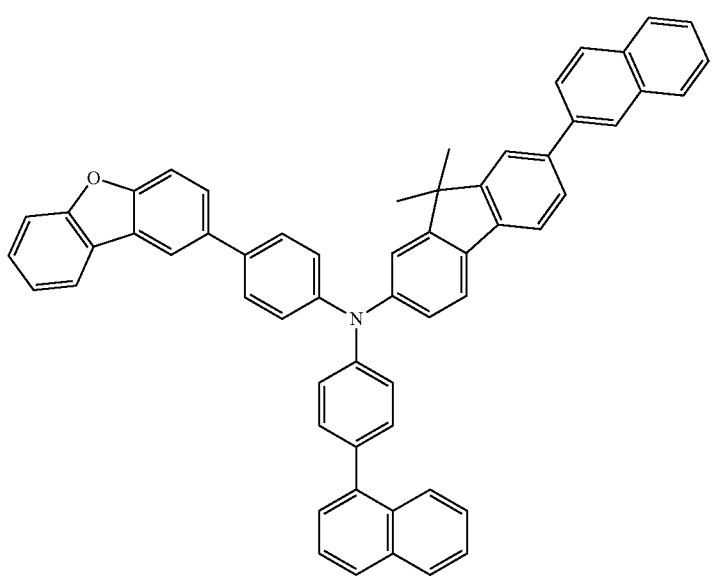

-continued
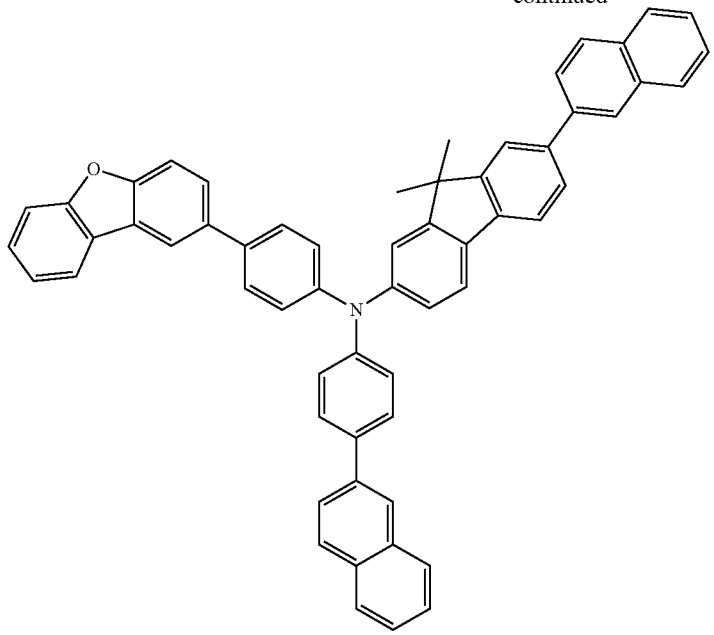
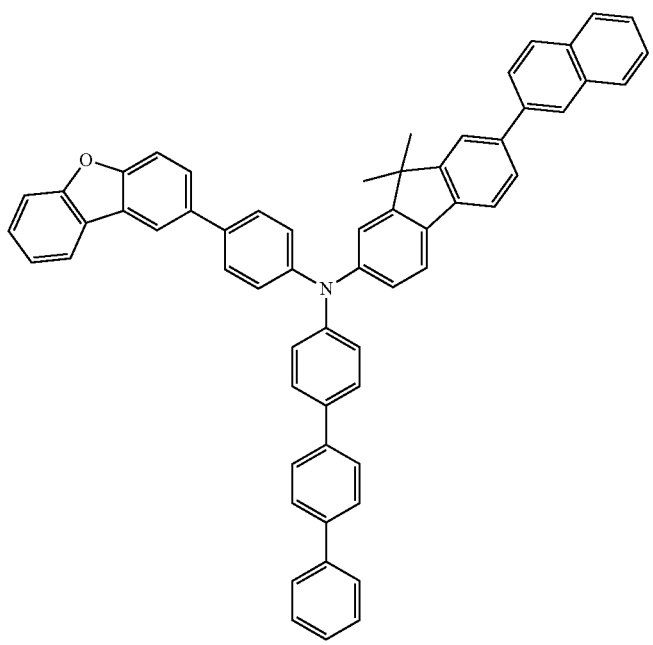

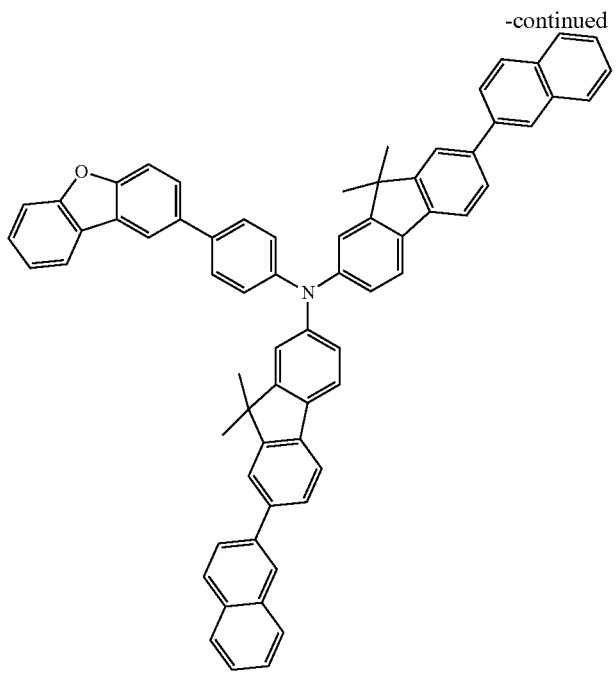
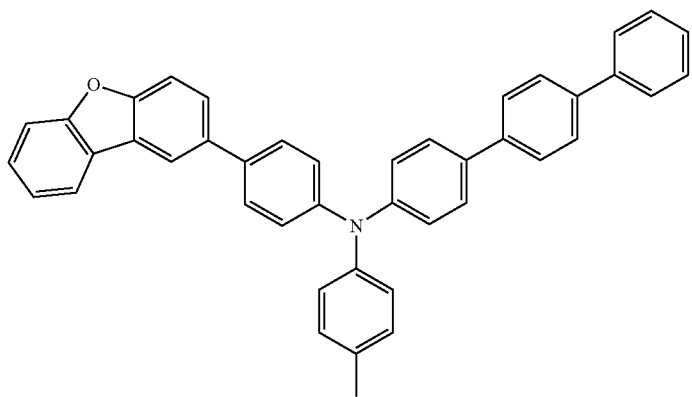
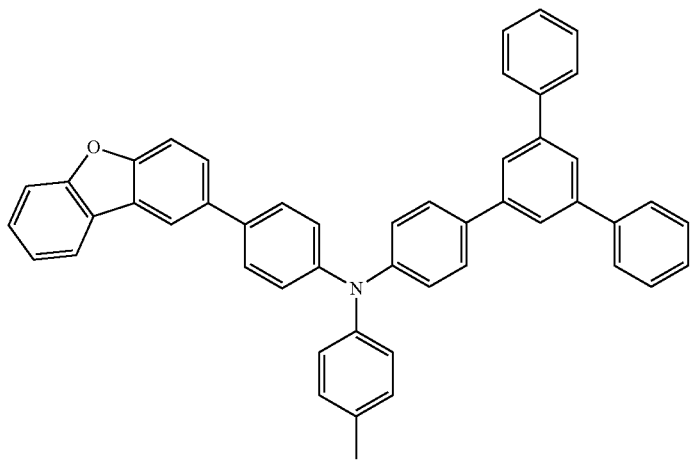

241
242
-continued
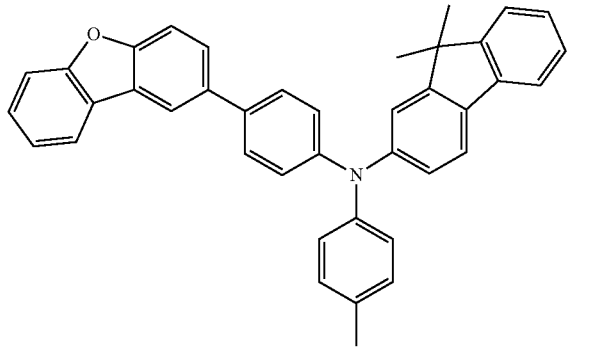
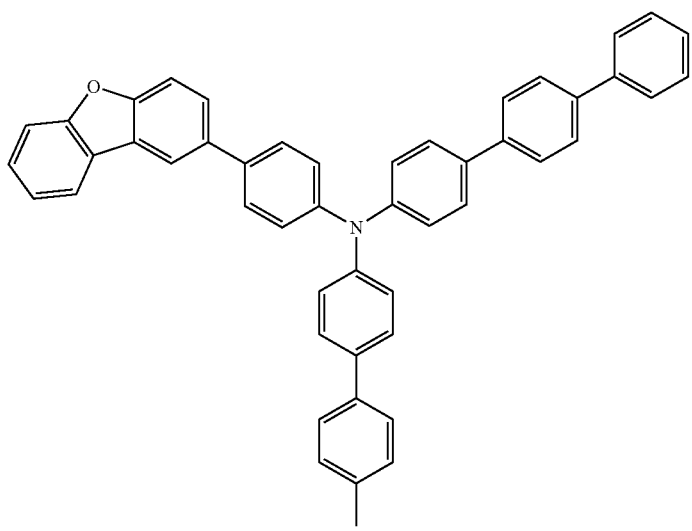
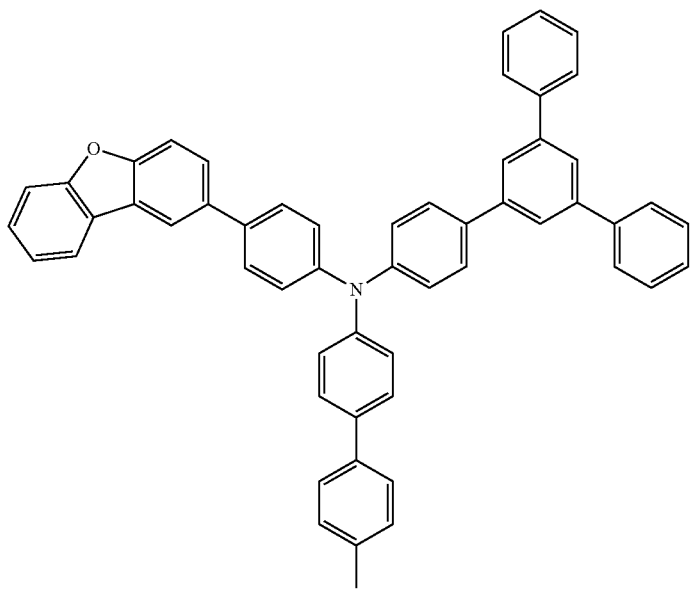

-continued
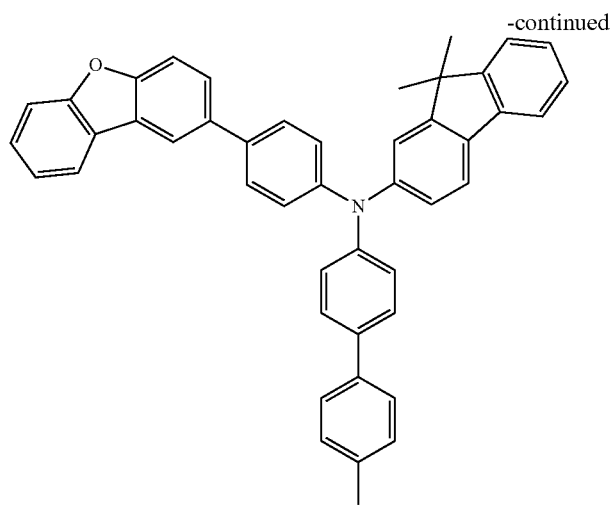
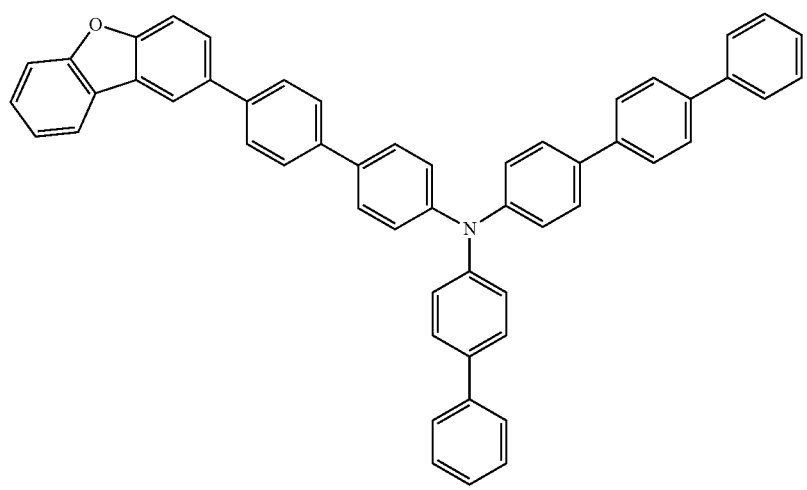
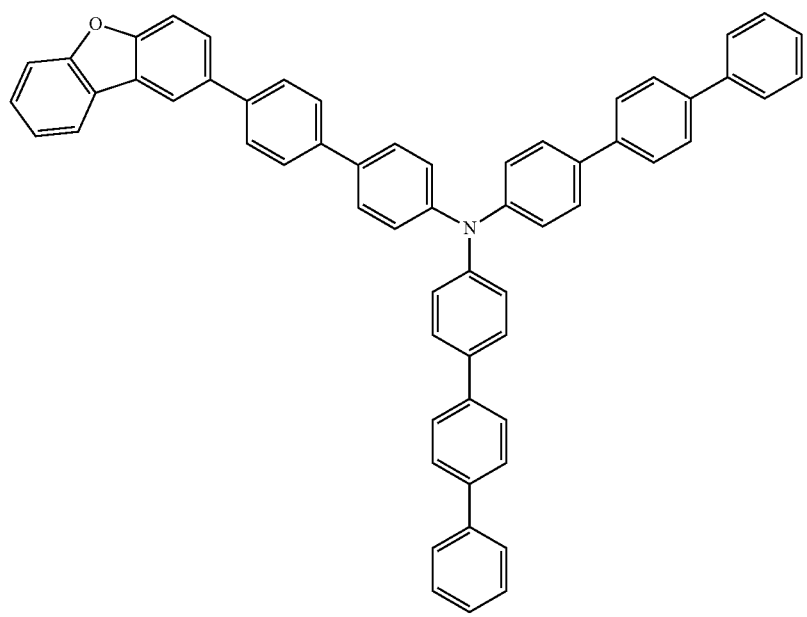

-continued
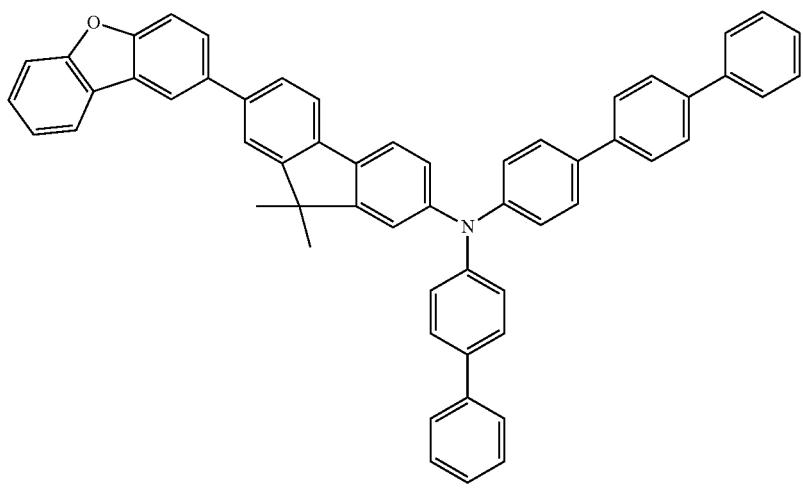
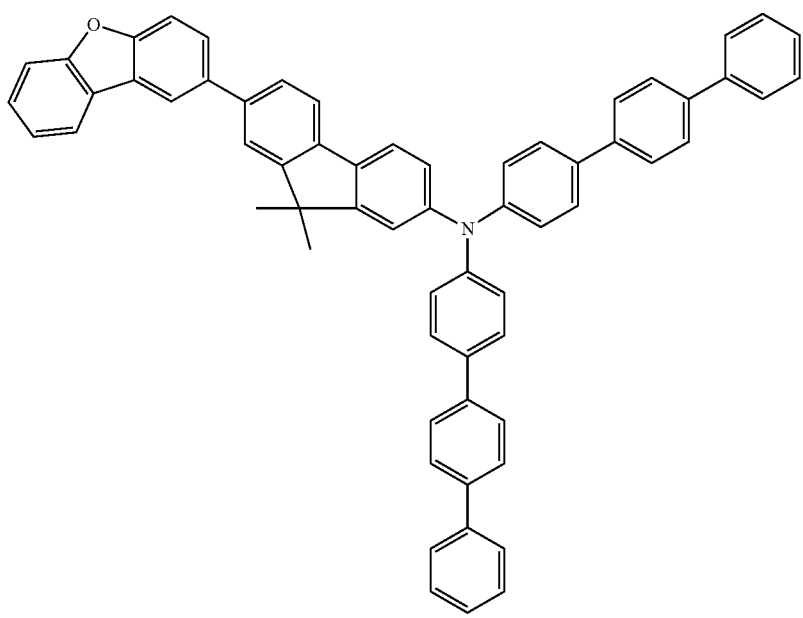
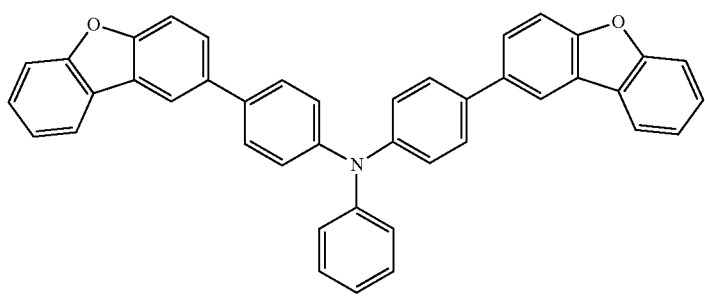
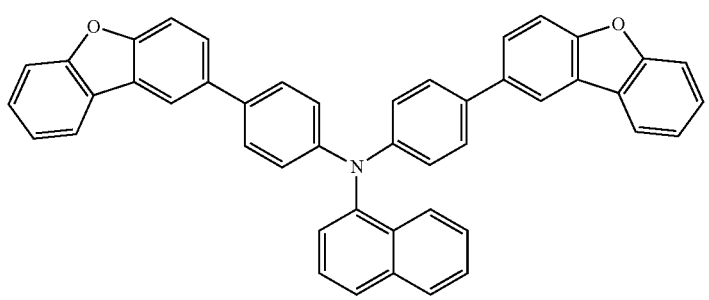

-continued
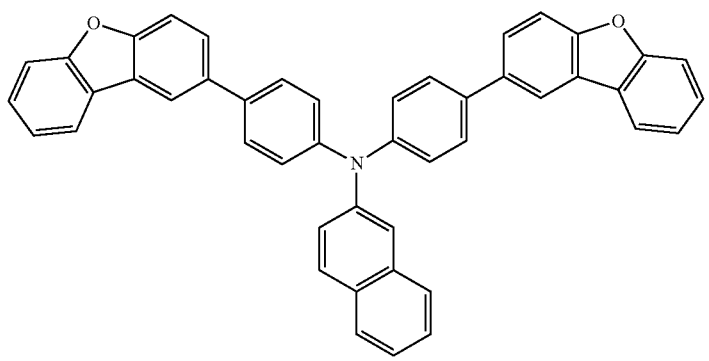
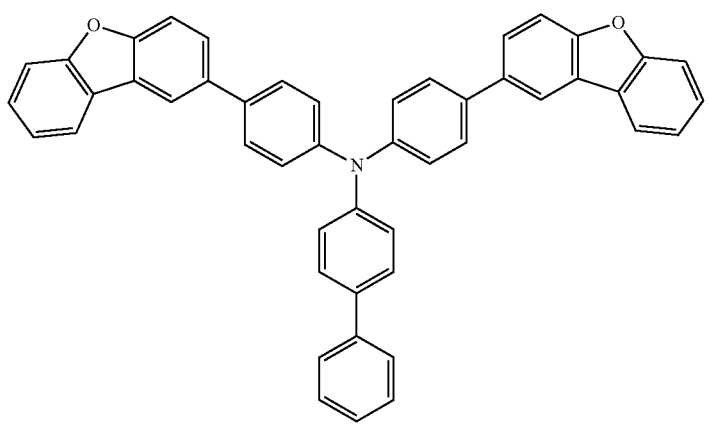
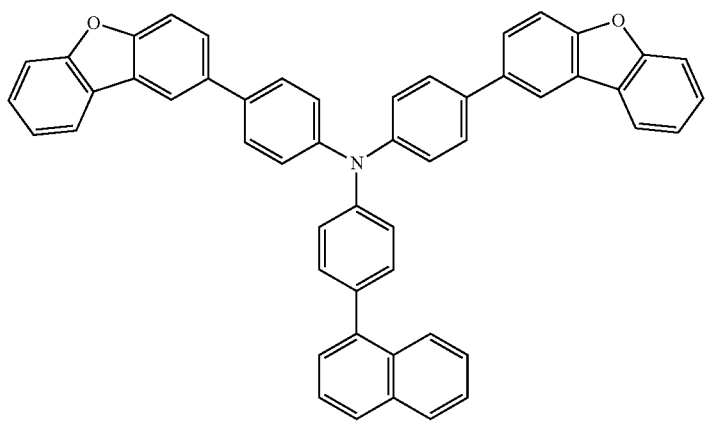
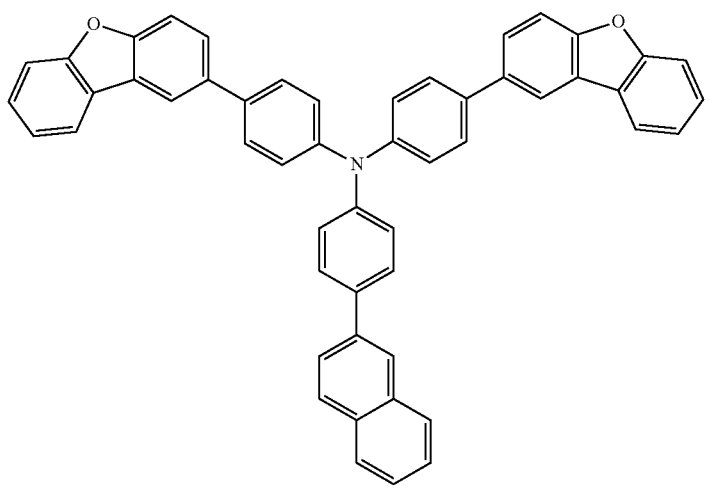

-continued
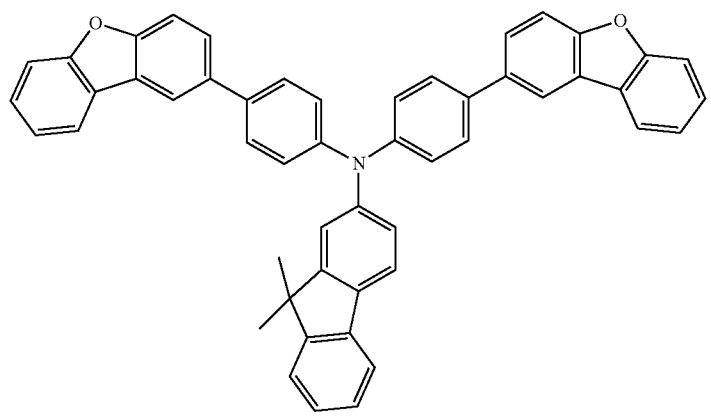
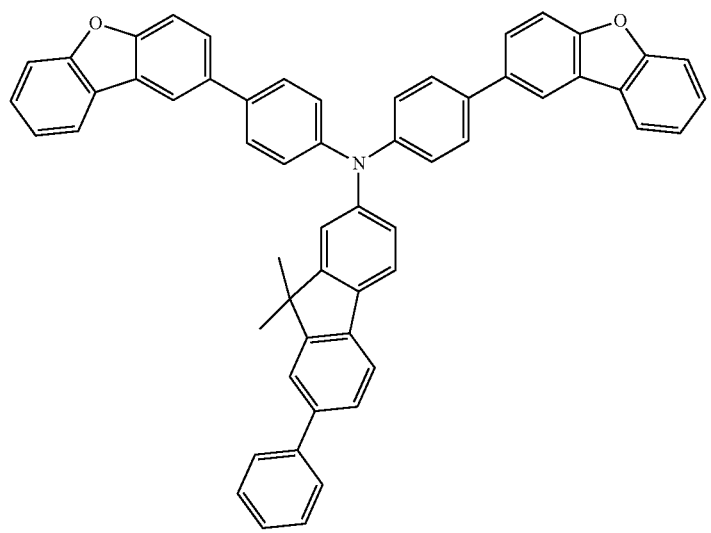
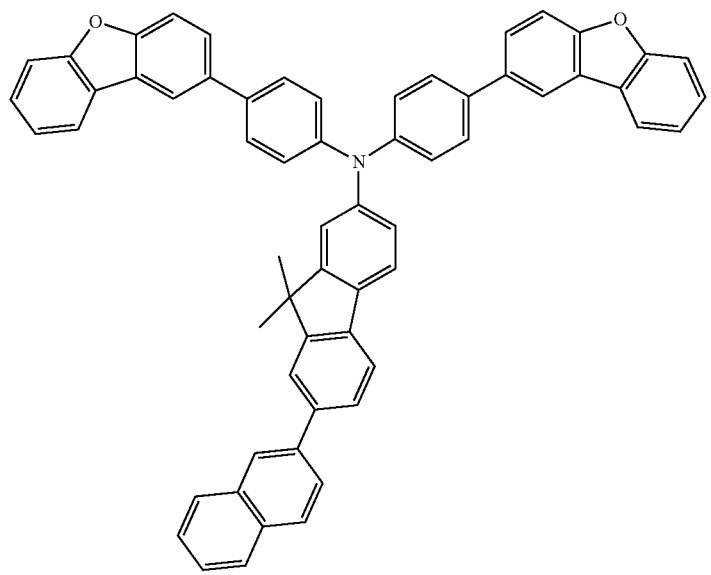

-continued
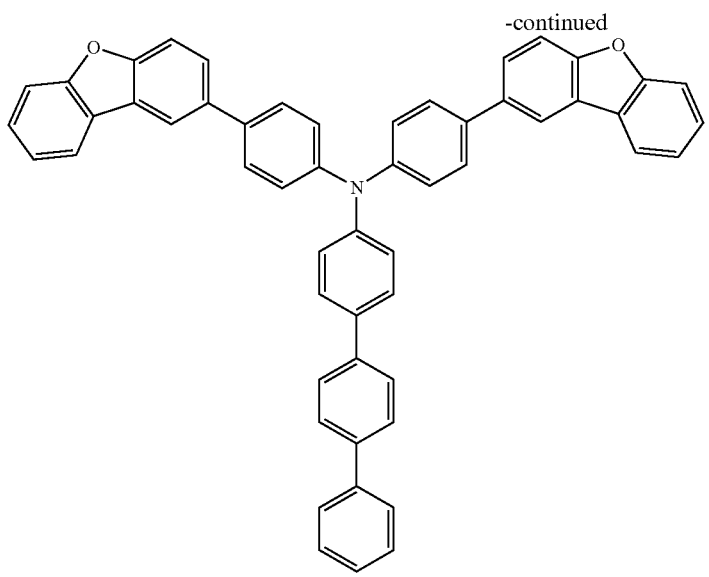
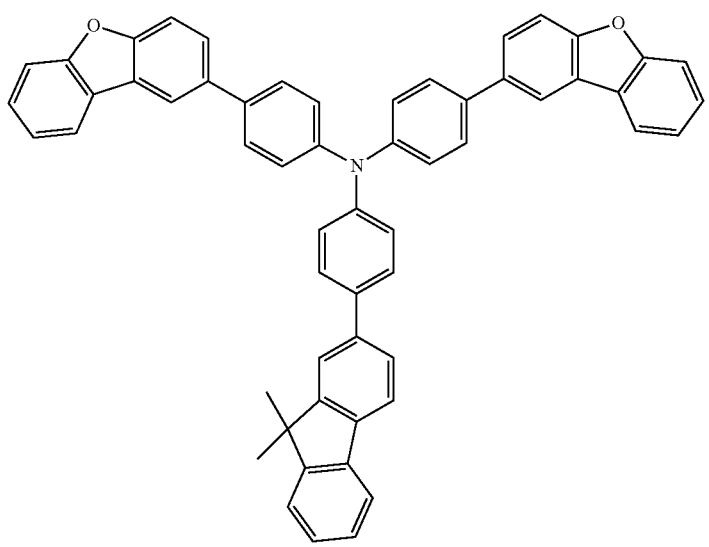
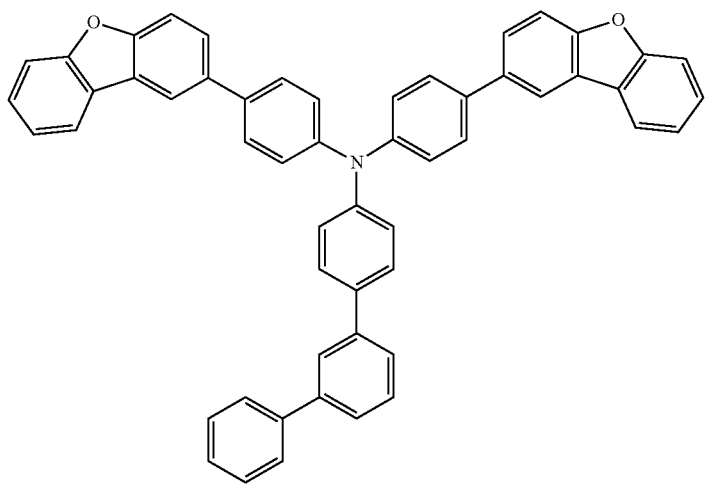

253
-continued
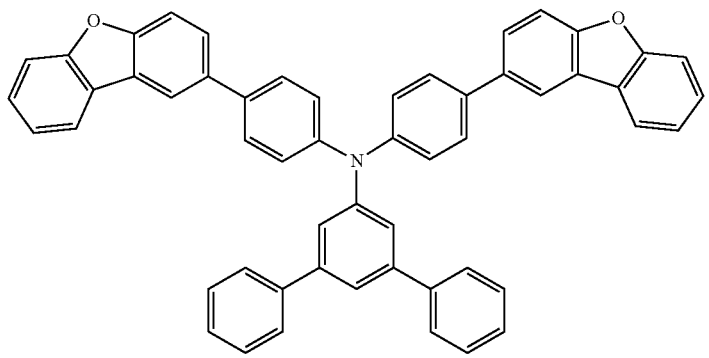
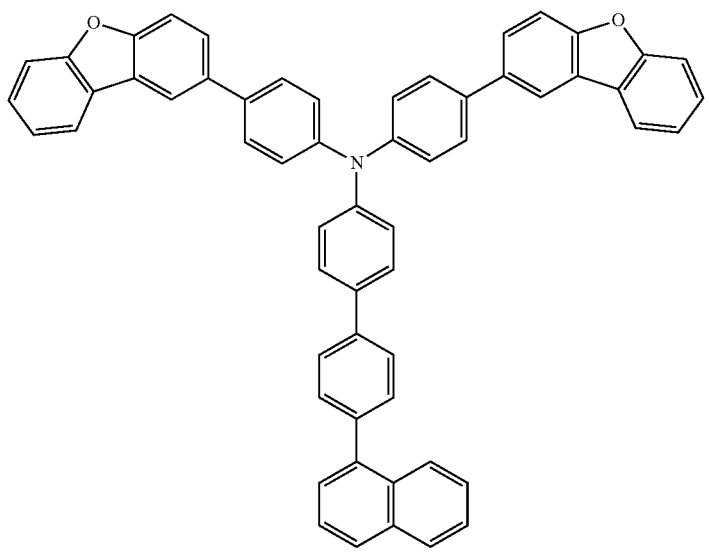
254
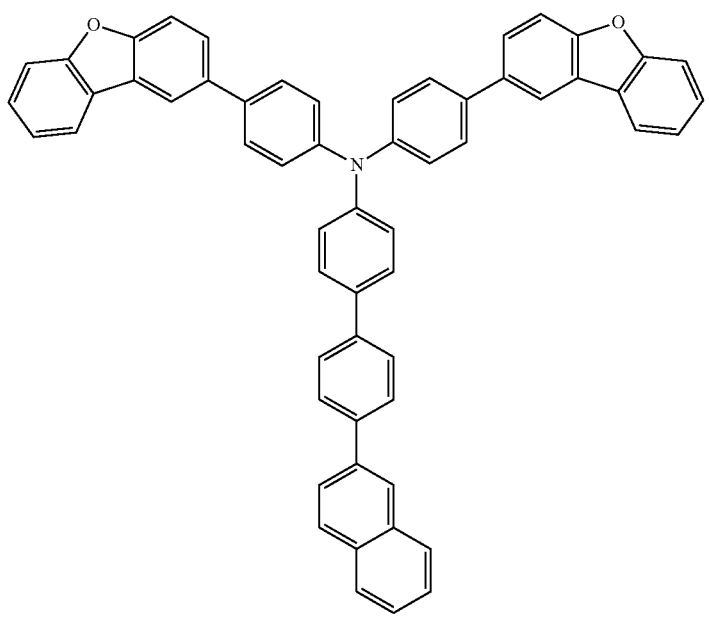

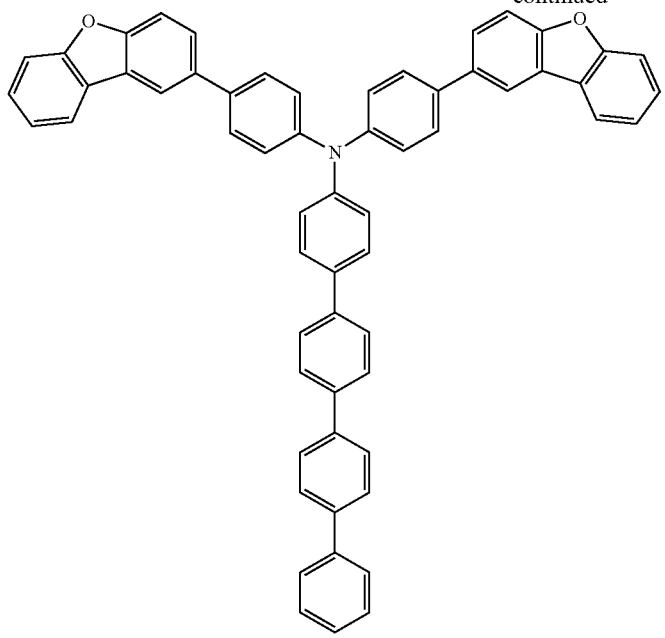
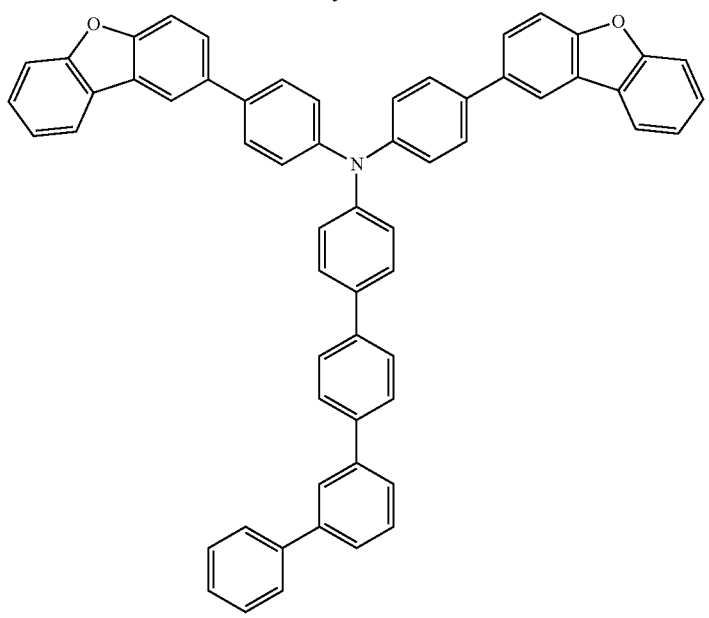
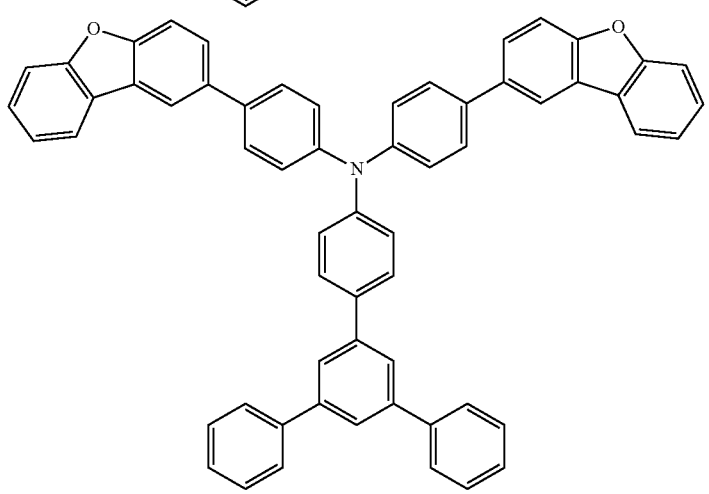

-continued
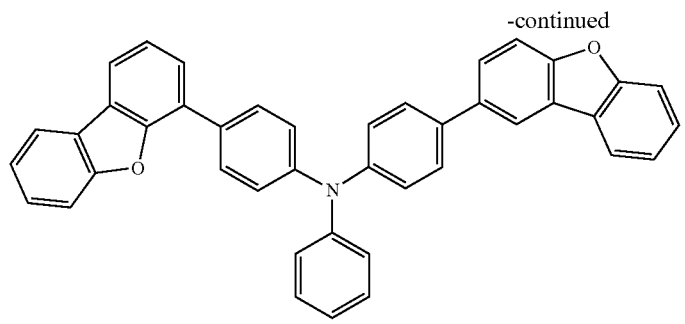
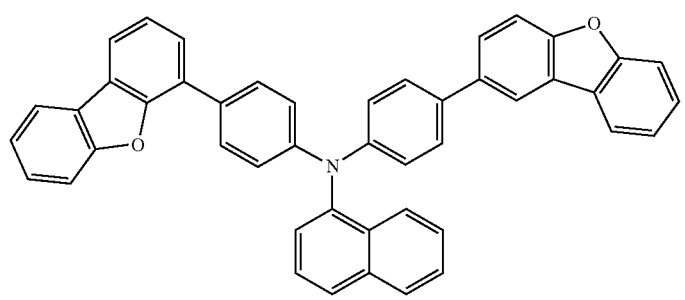
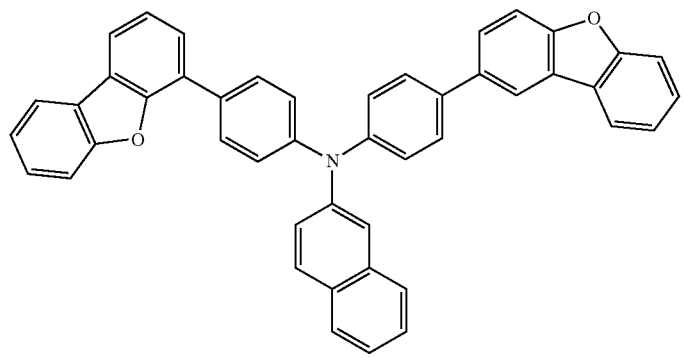
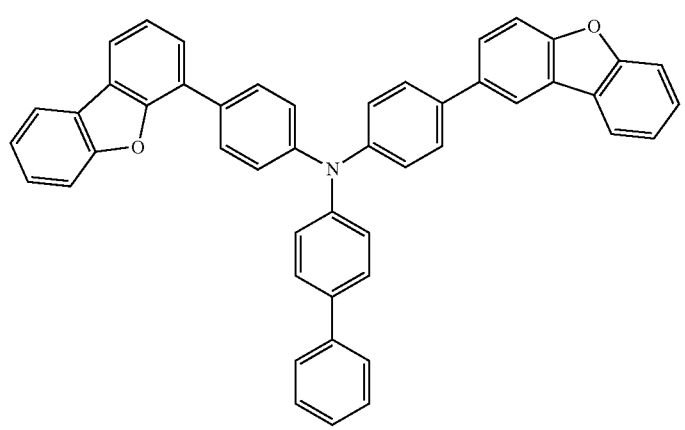

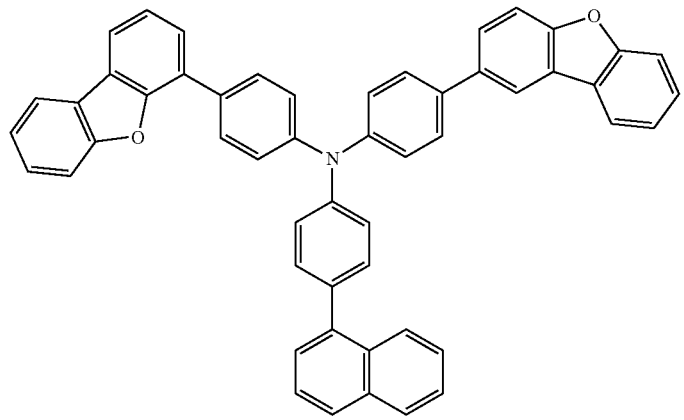
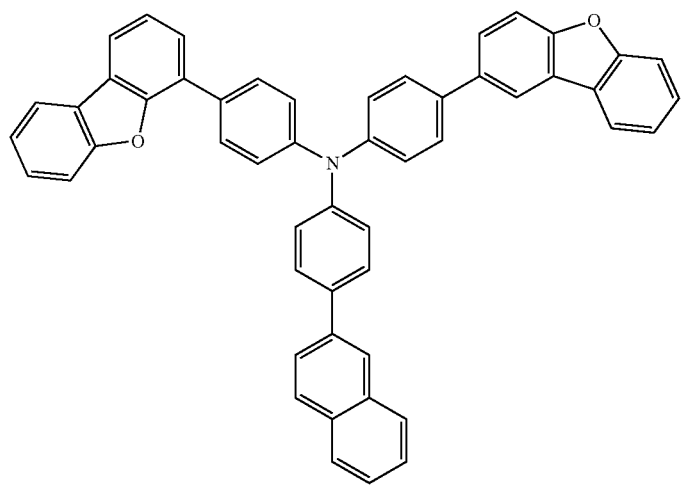
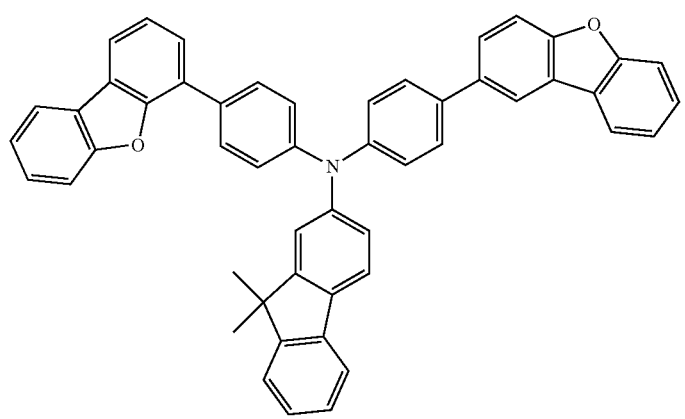

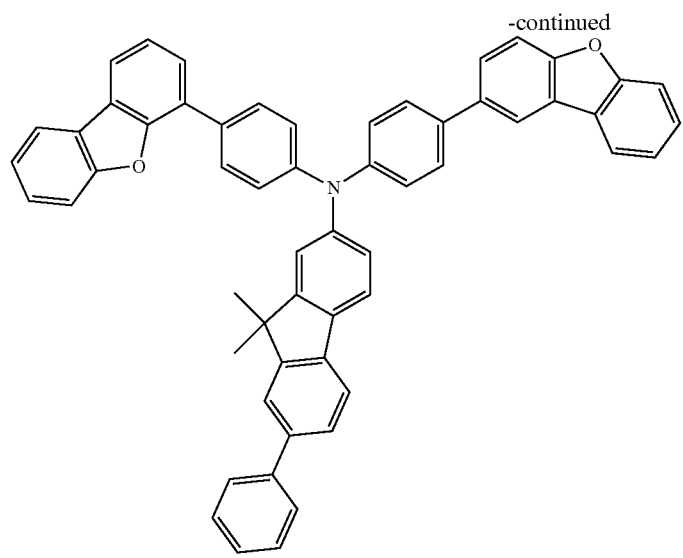
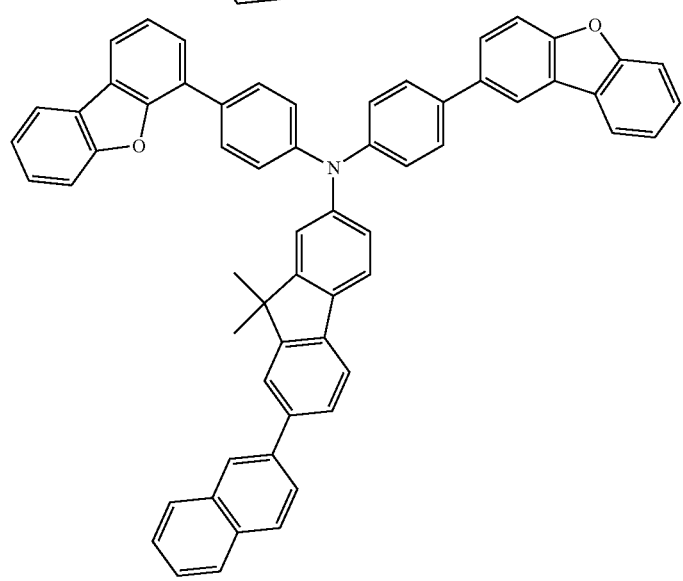
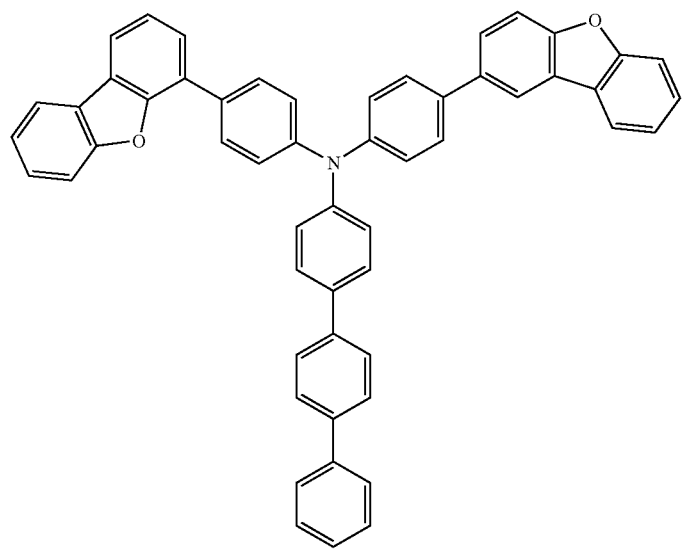

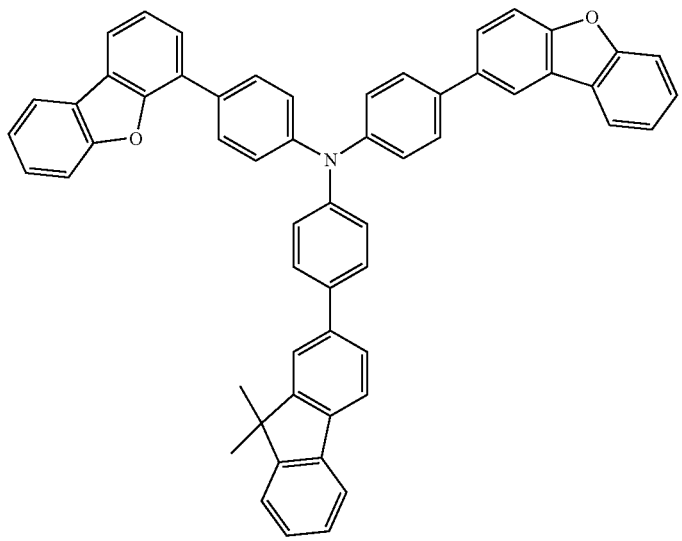
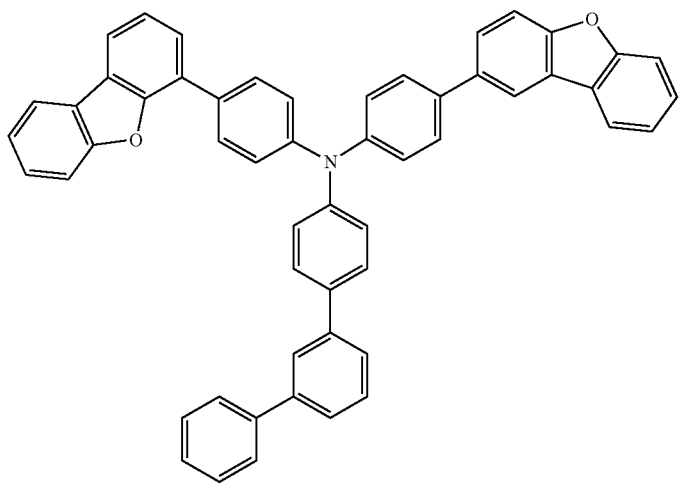
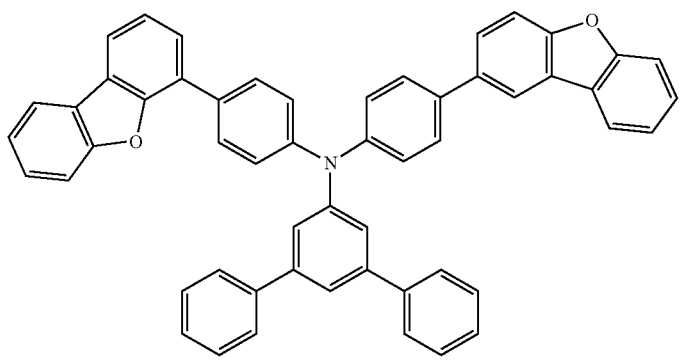

-continued
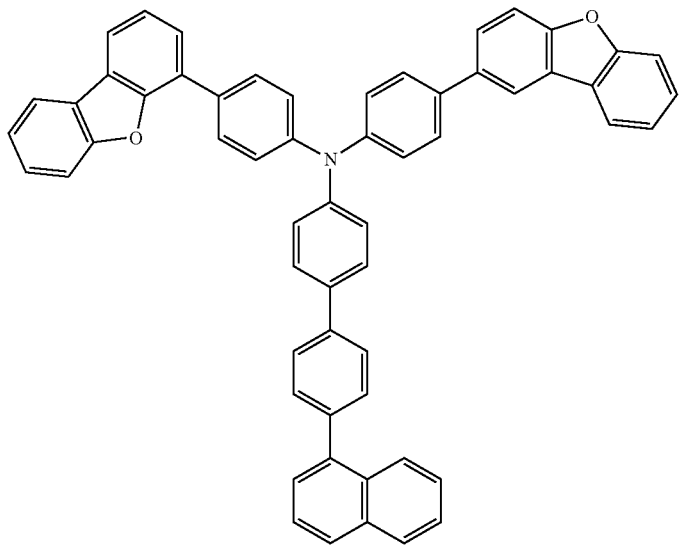
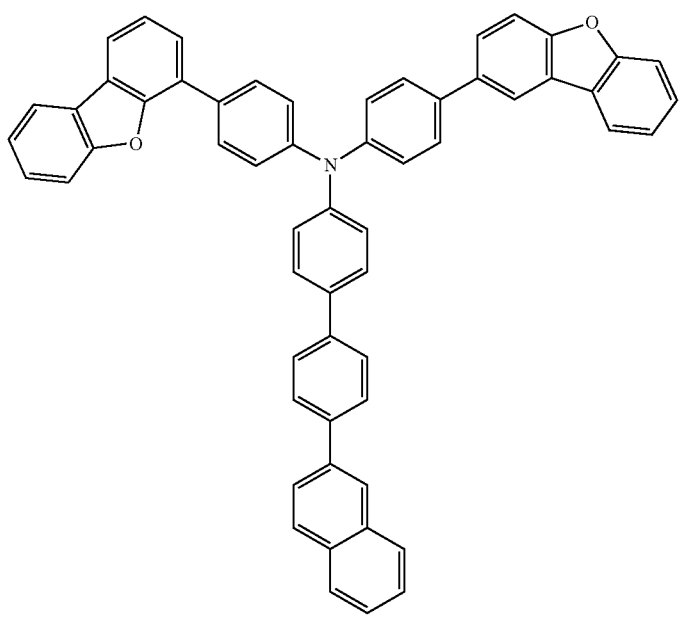

-continued
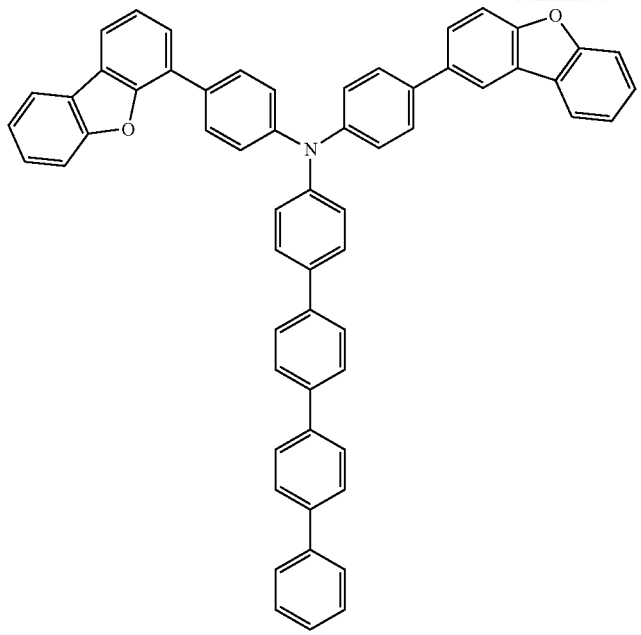
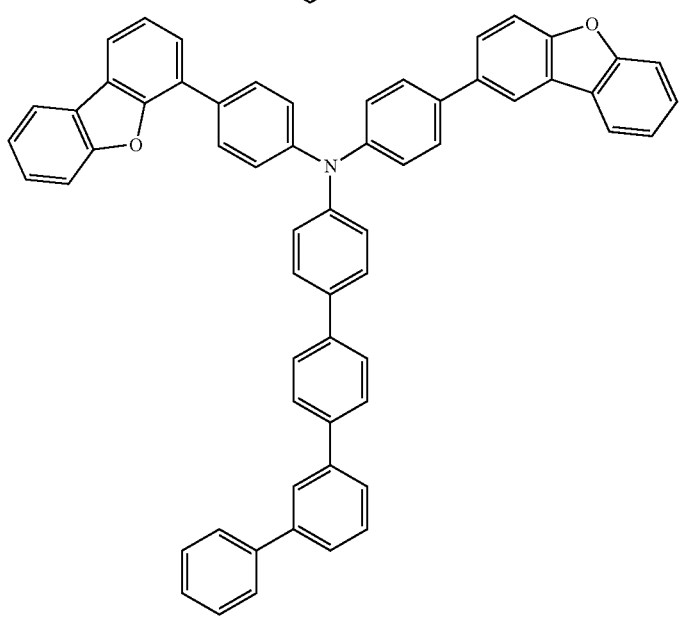
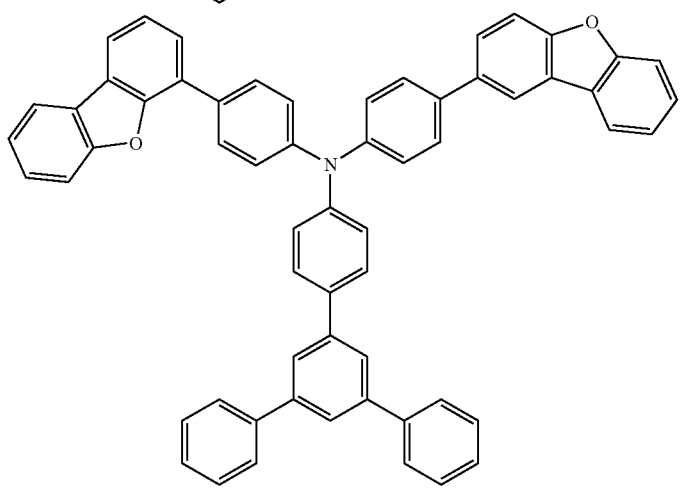

-continued
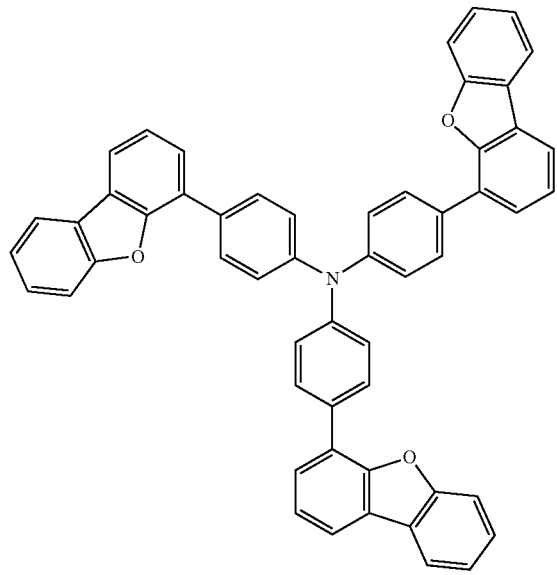
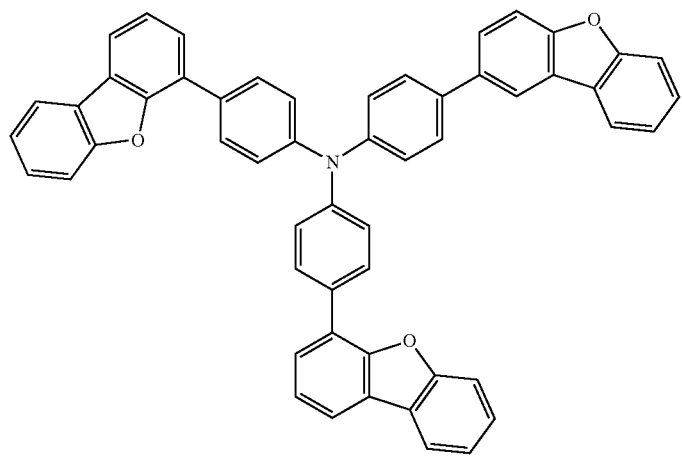
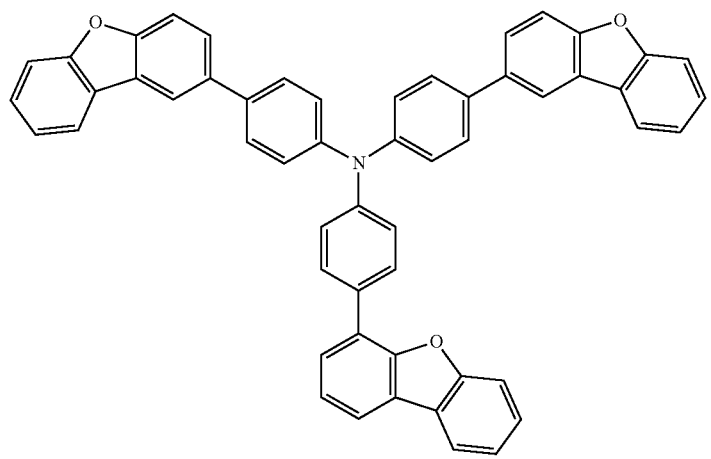

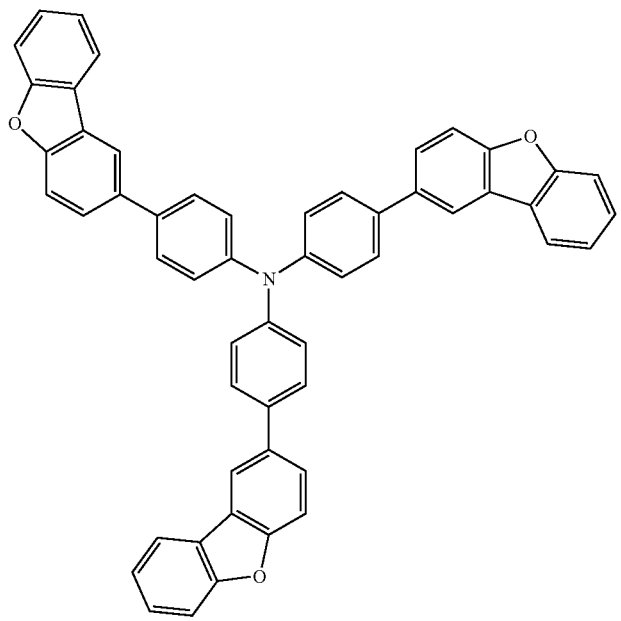
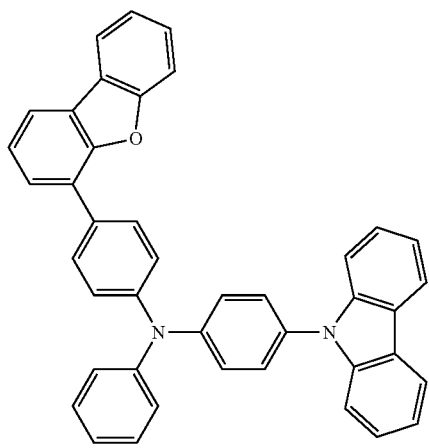
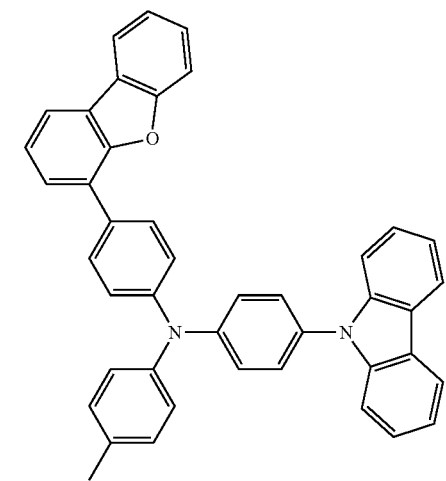
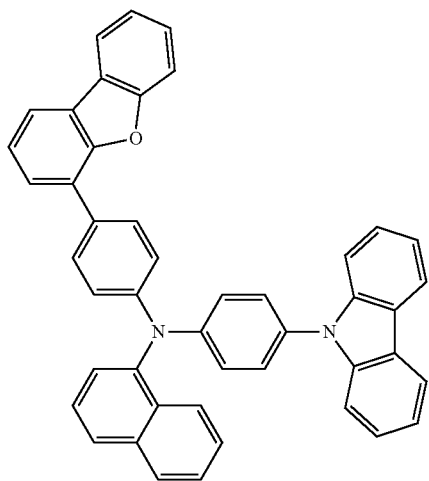
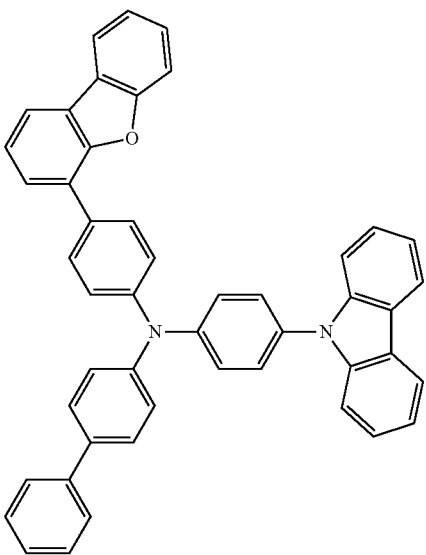

-continued
273
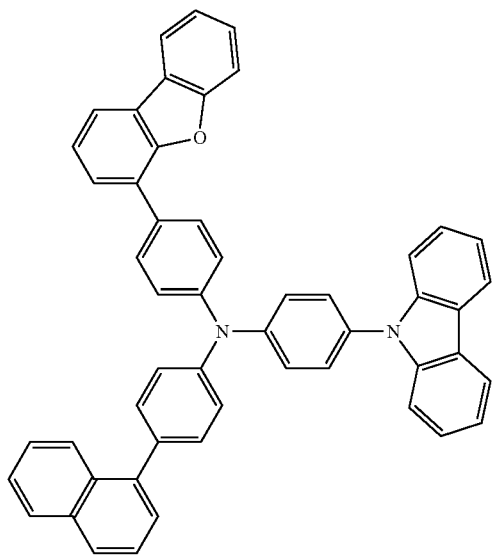
274
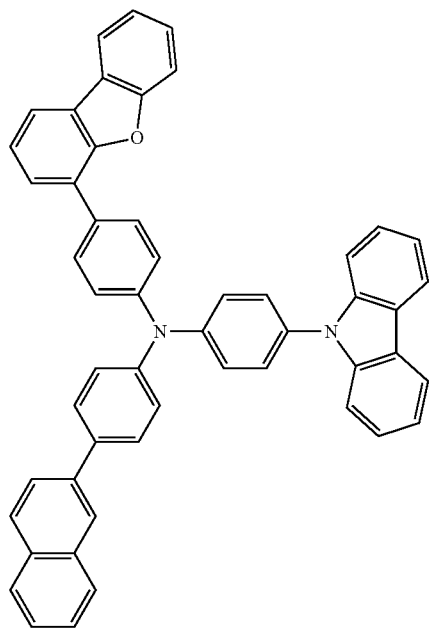
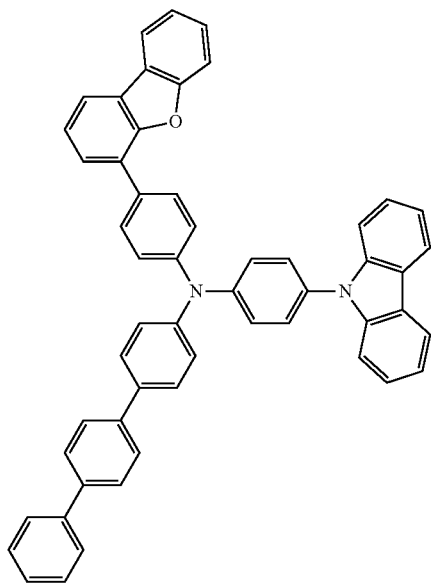
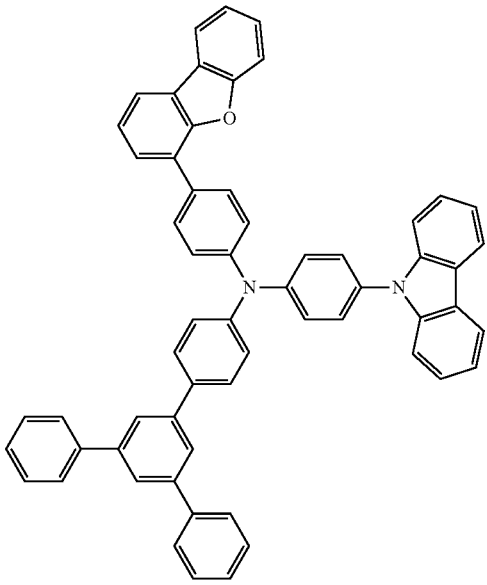

-continued
275
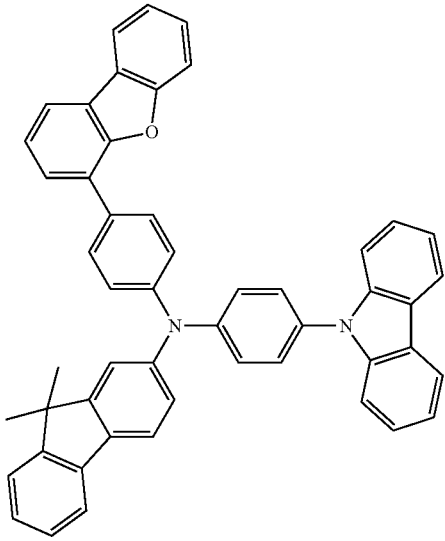
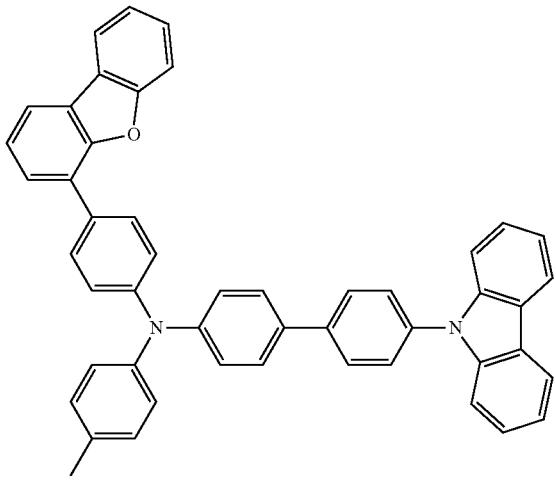
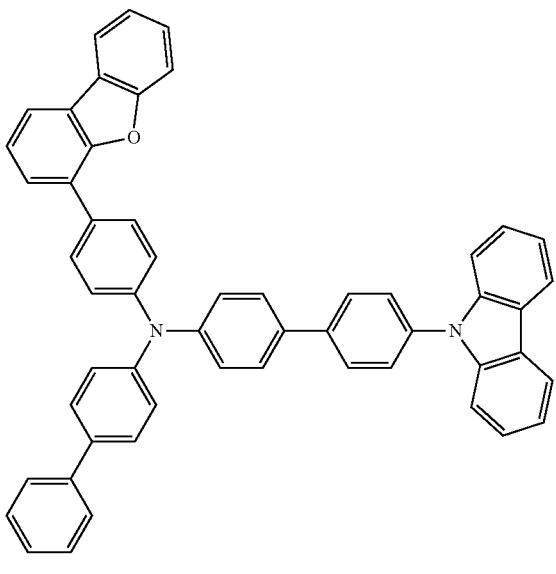
276
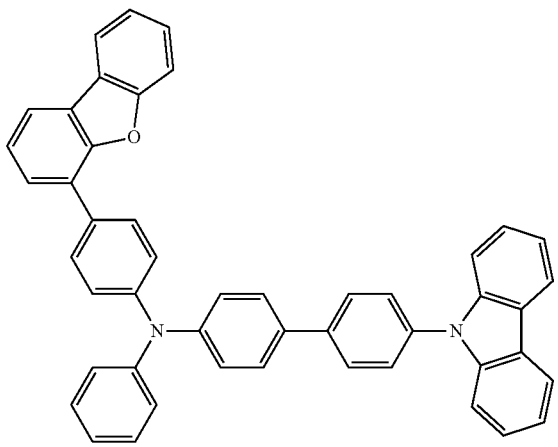
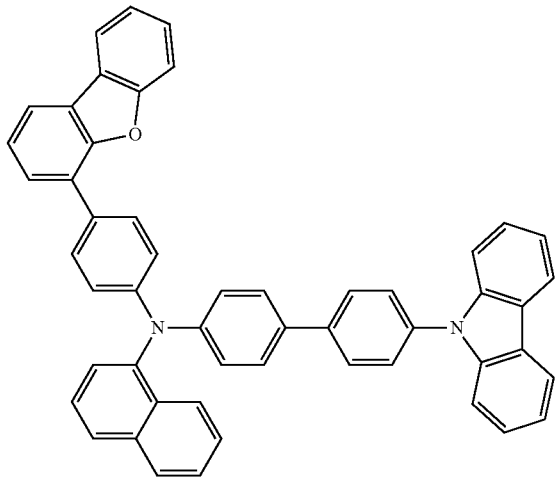
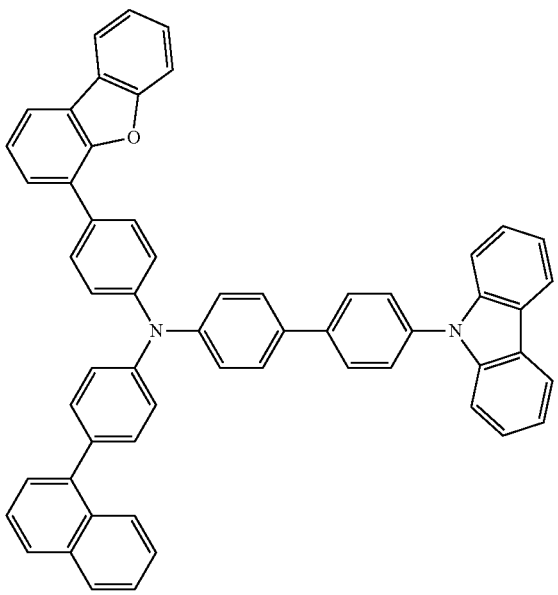

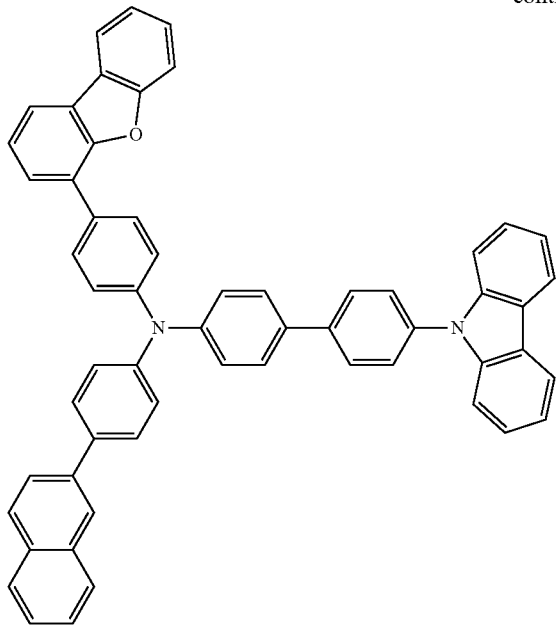
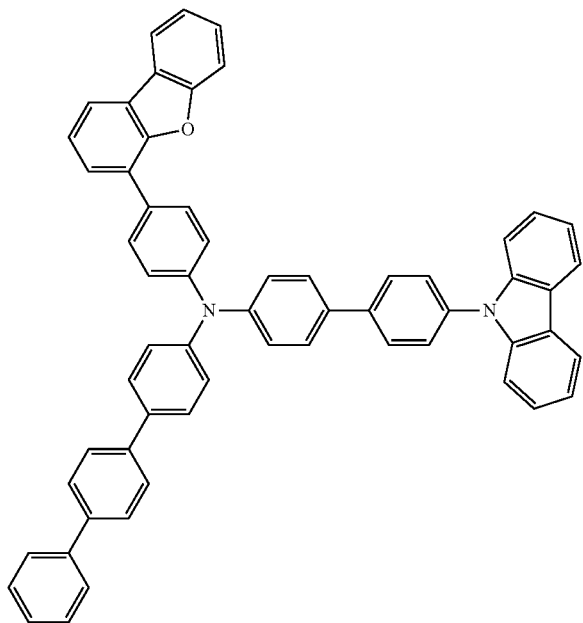

-continued
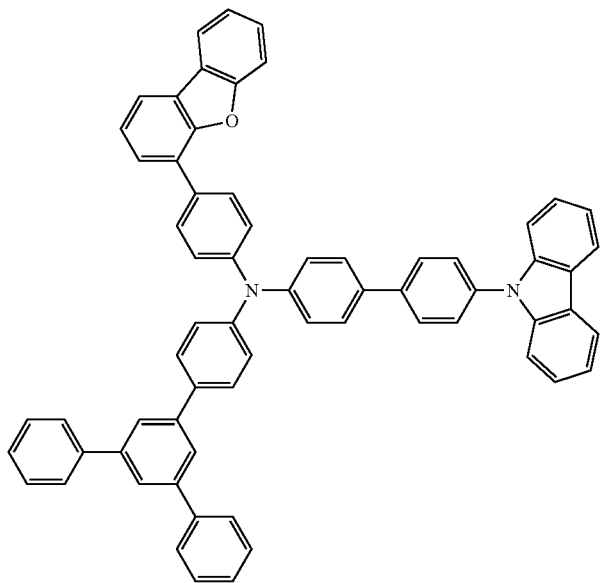
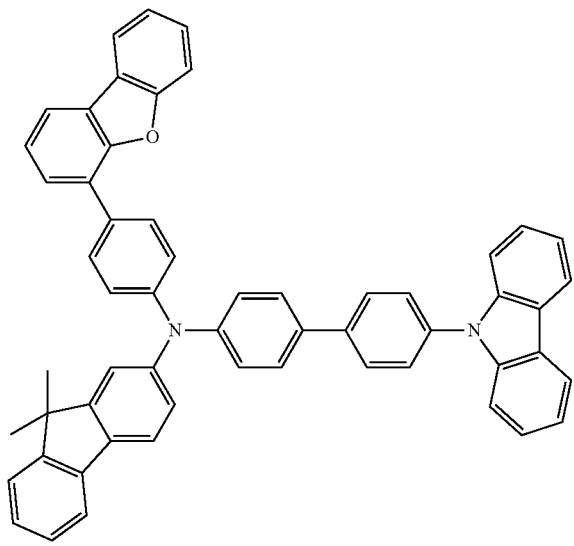
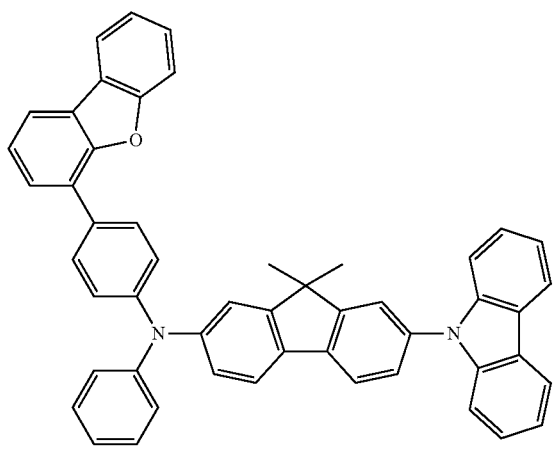

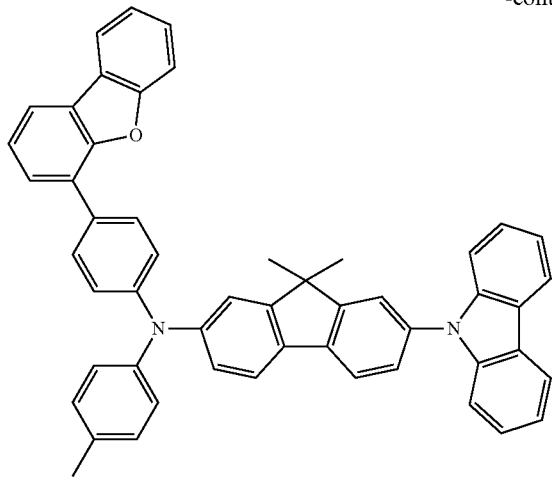
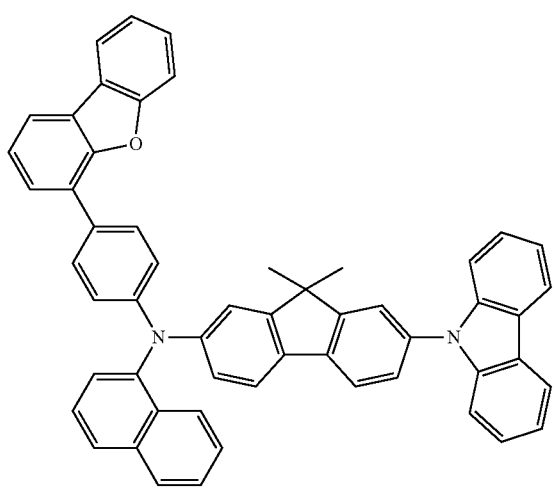
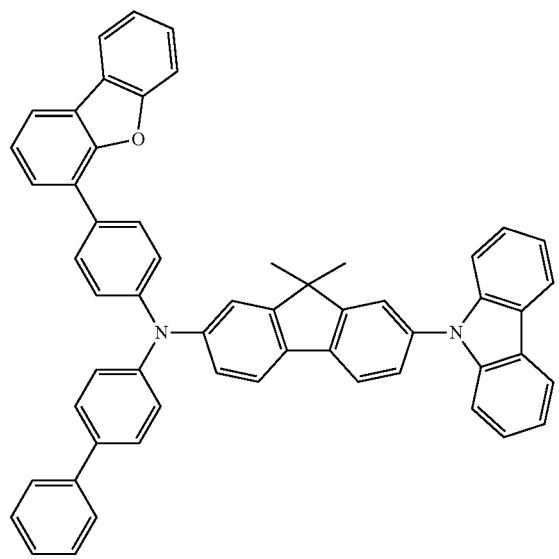
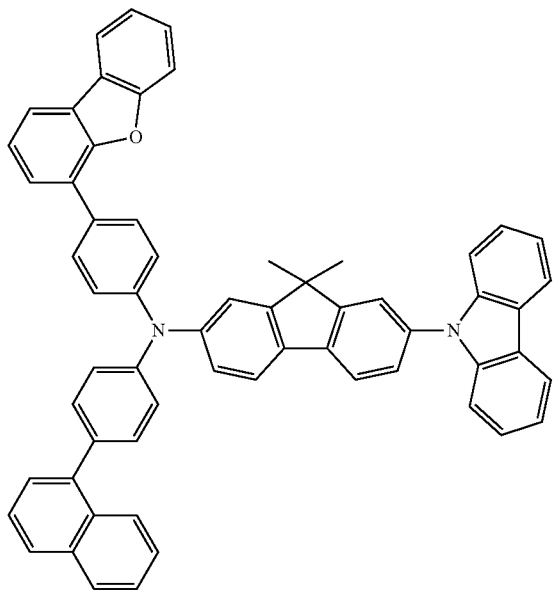
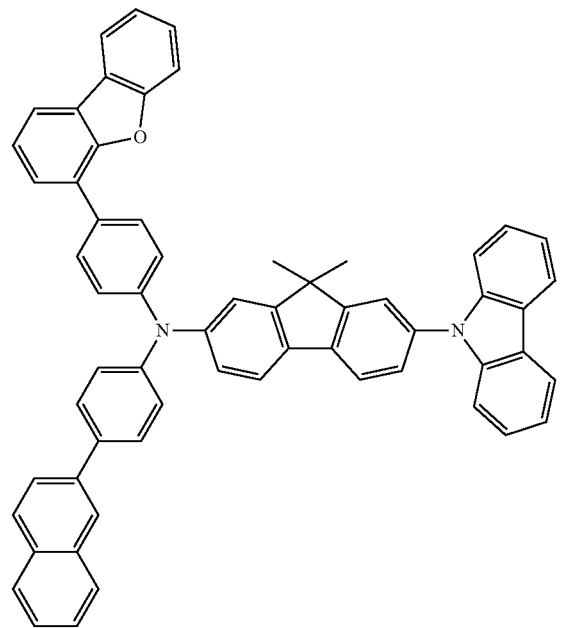

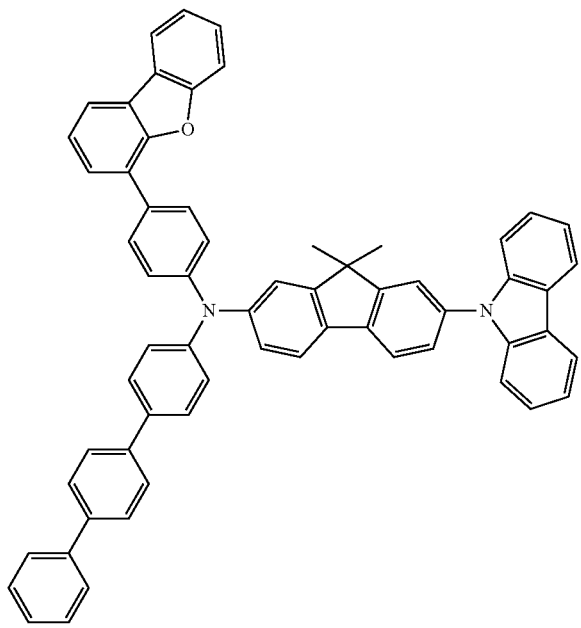
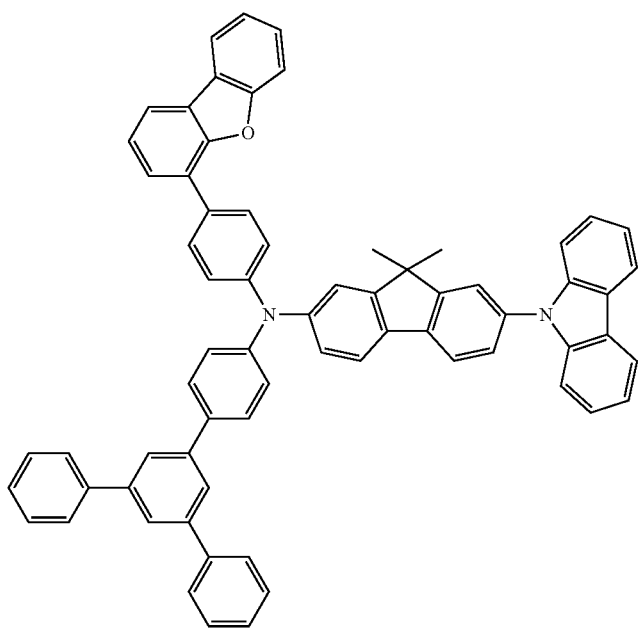

285
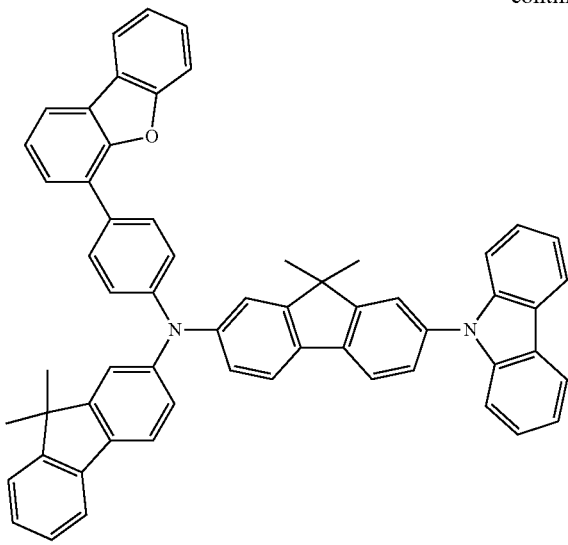
-continued
286
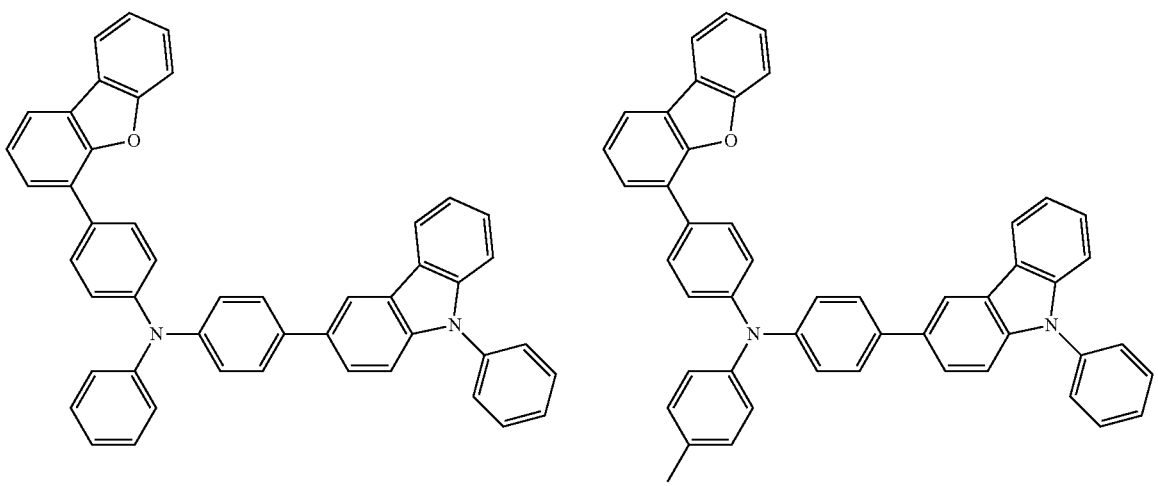
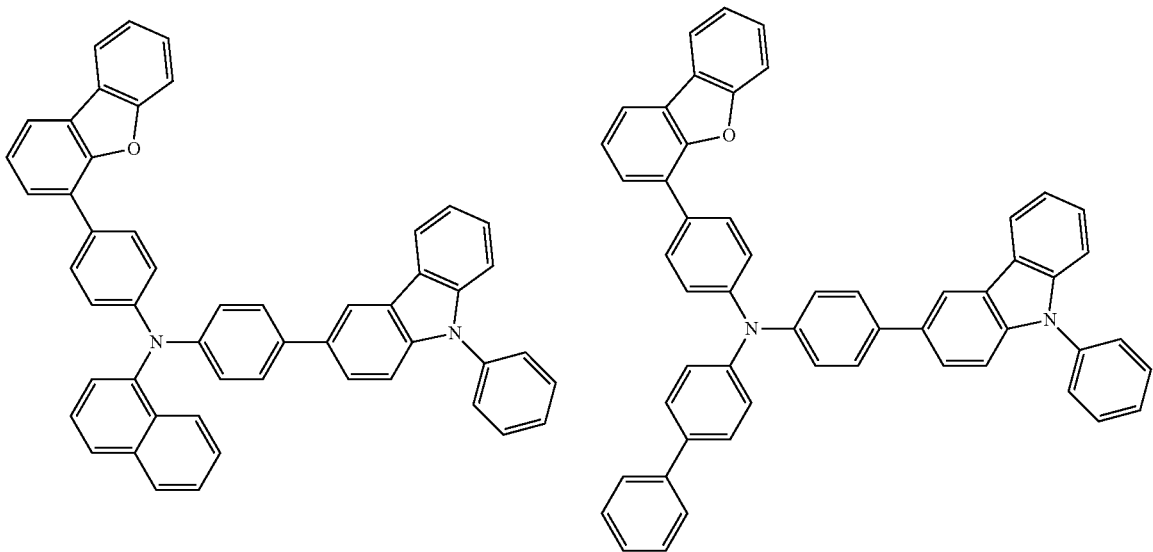

287
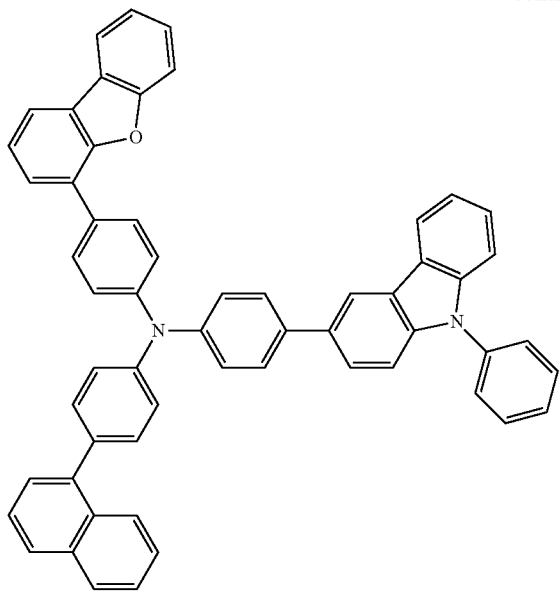
288
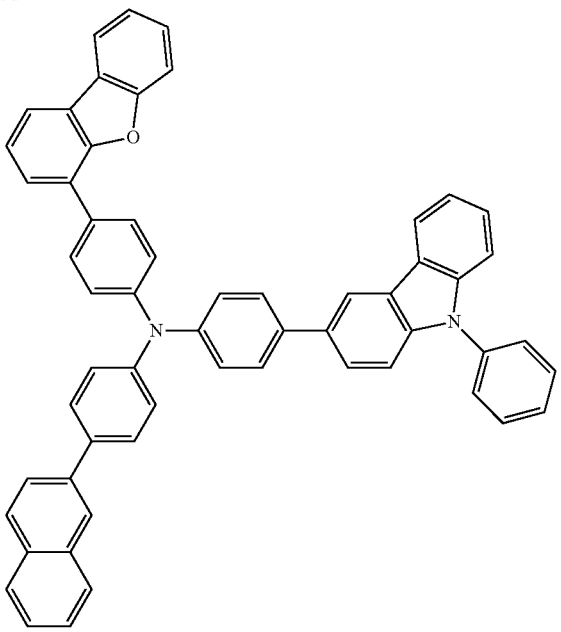
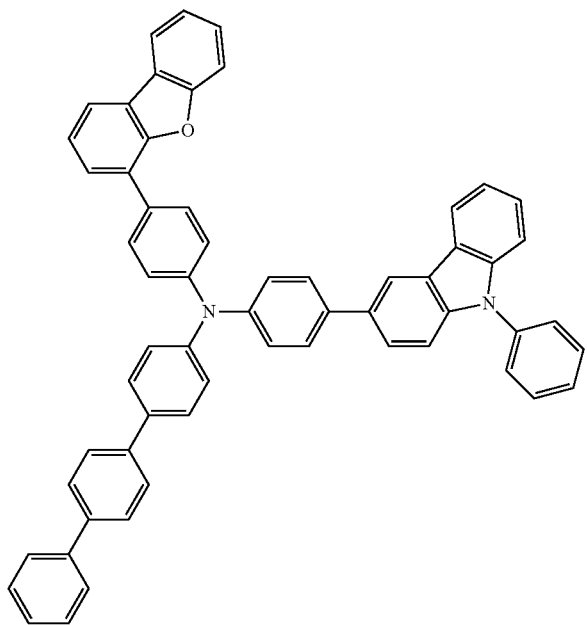

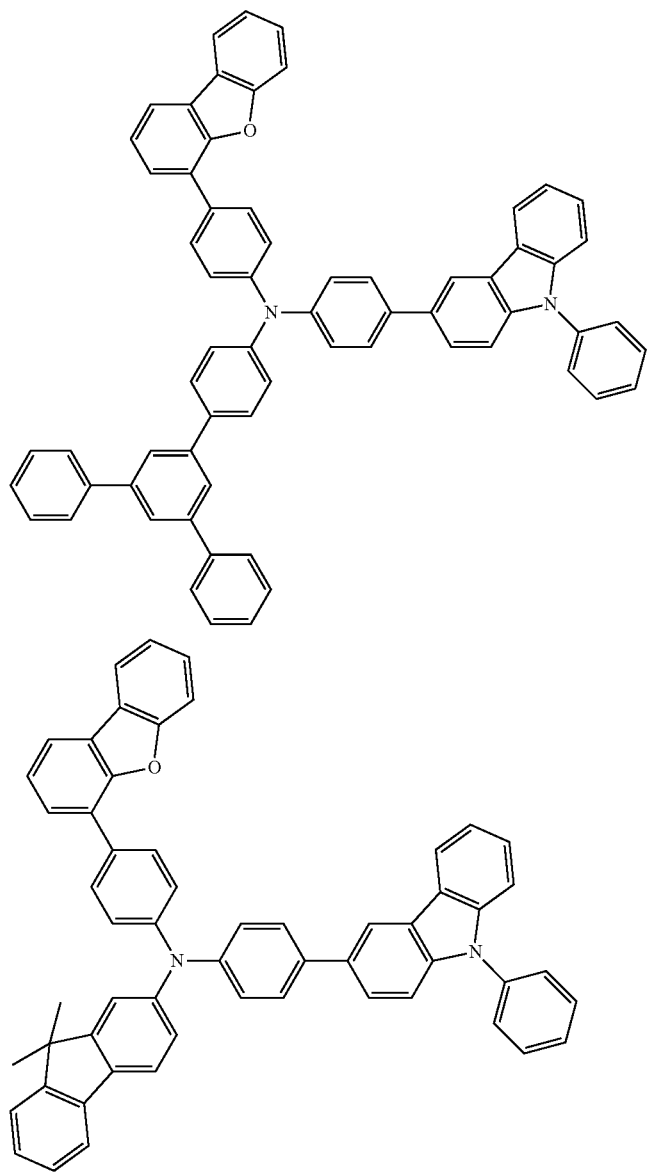
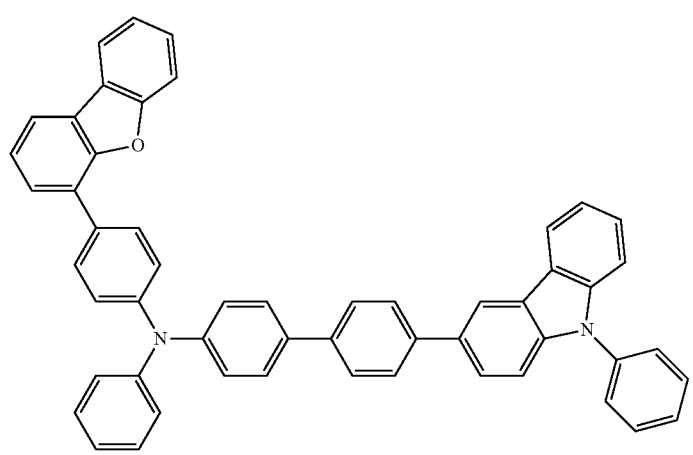

-continued
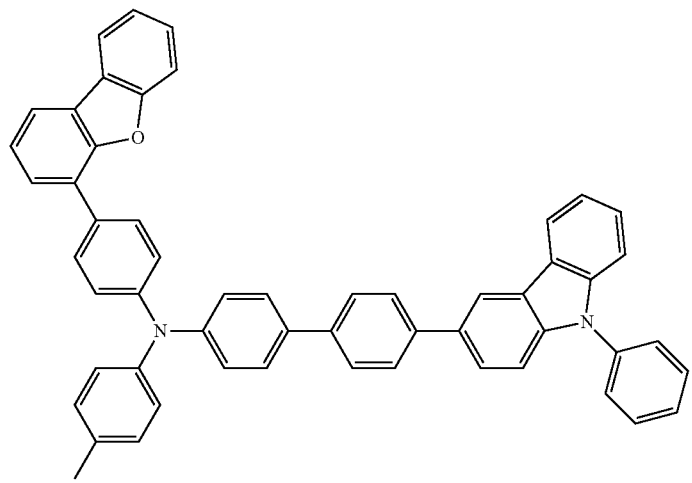
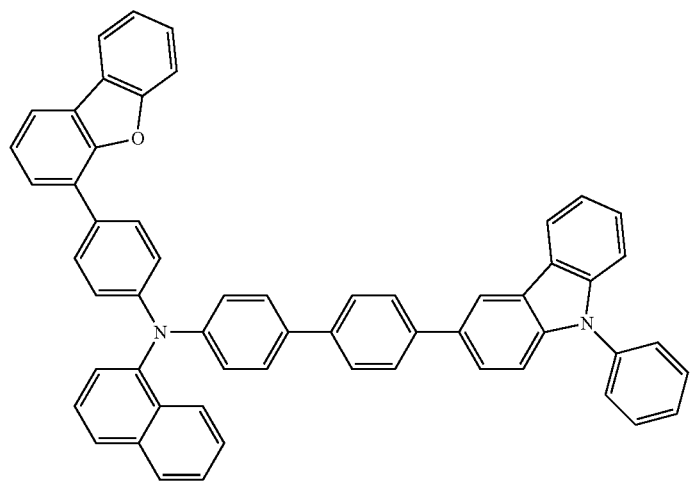
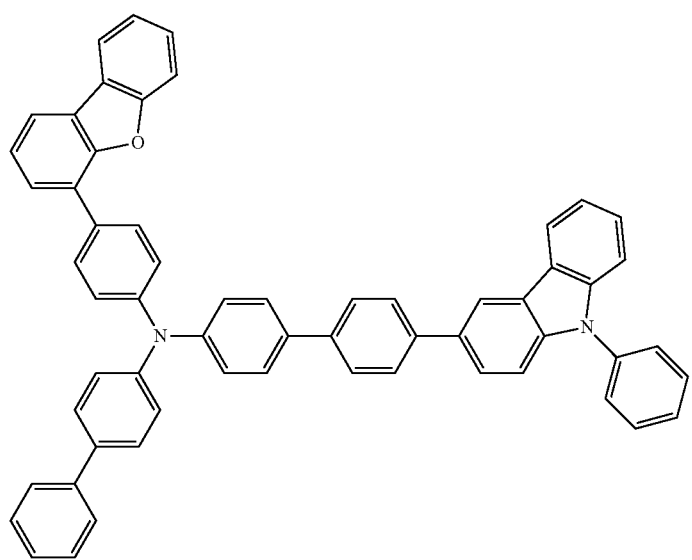

-continued
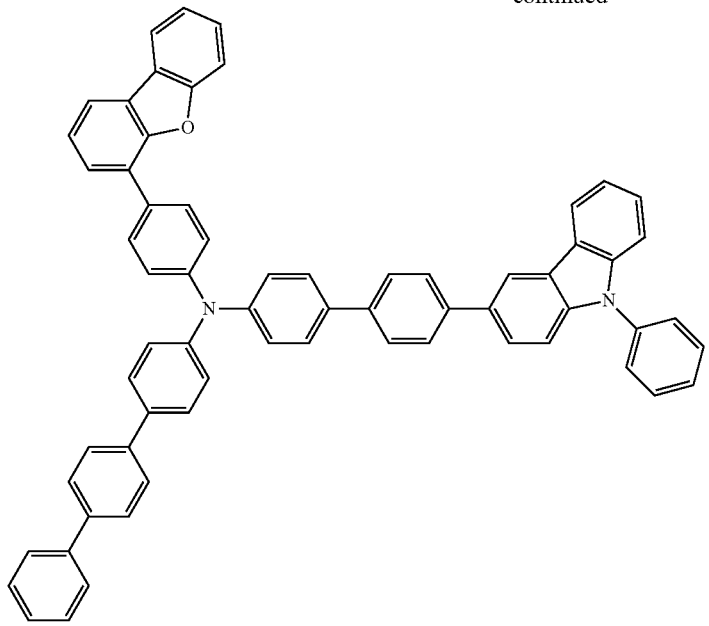
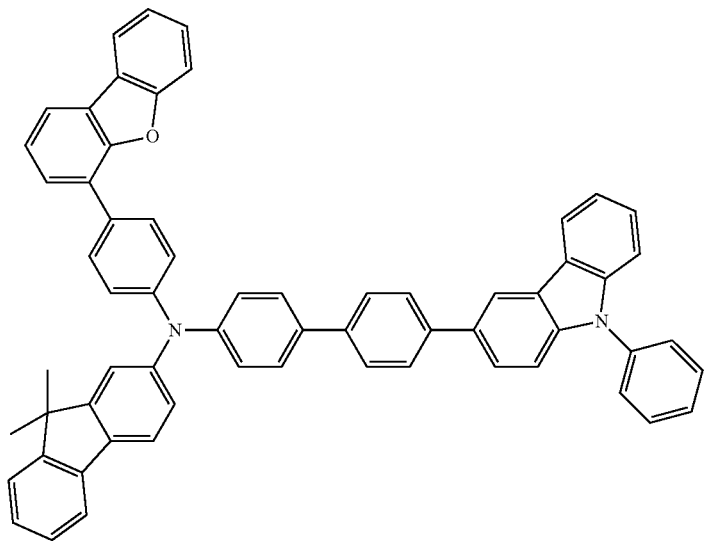
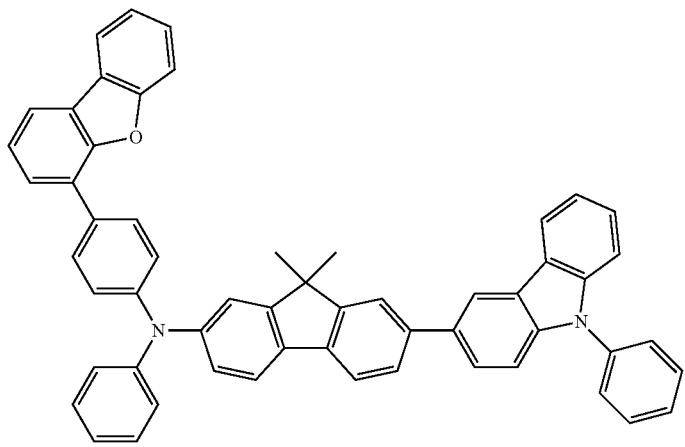

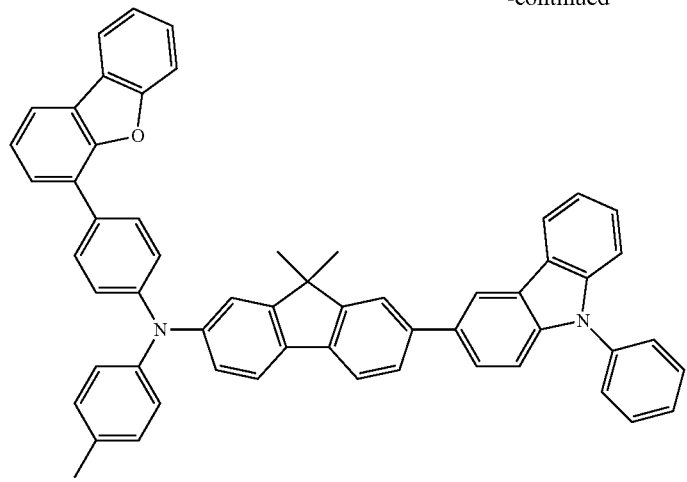
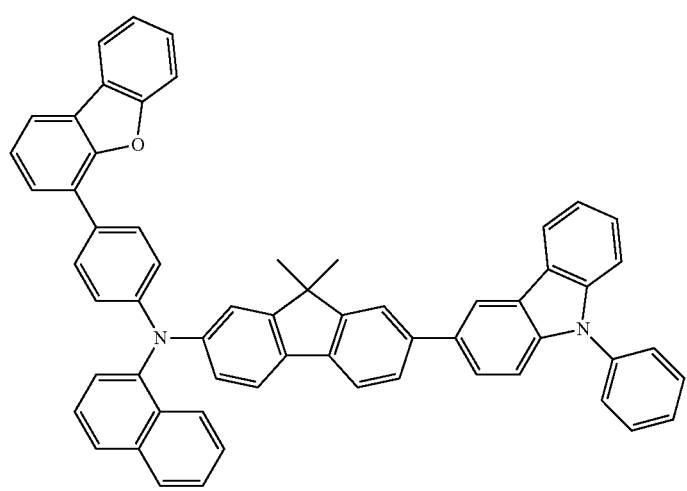
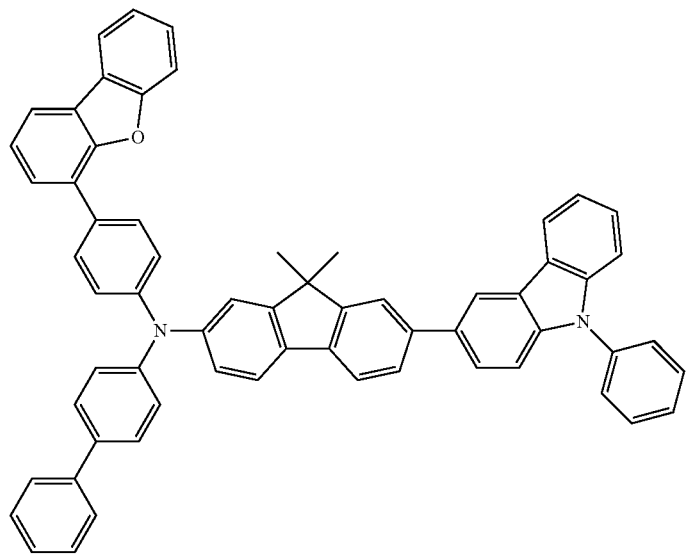

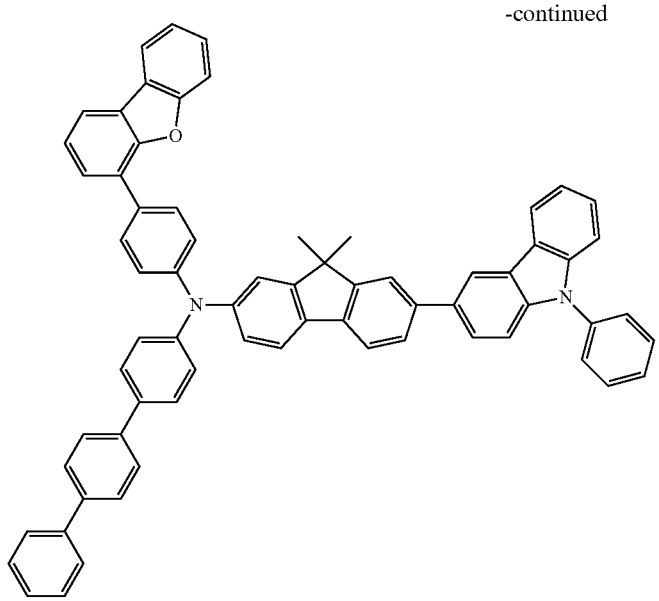
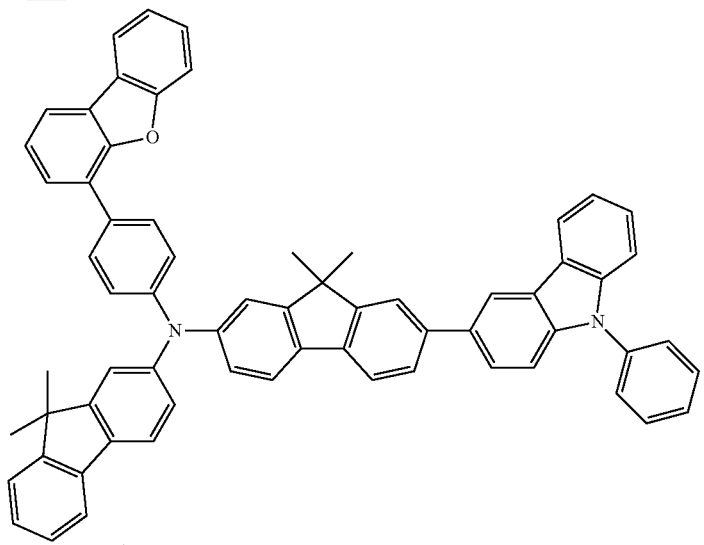
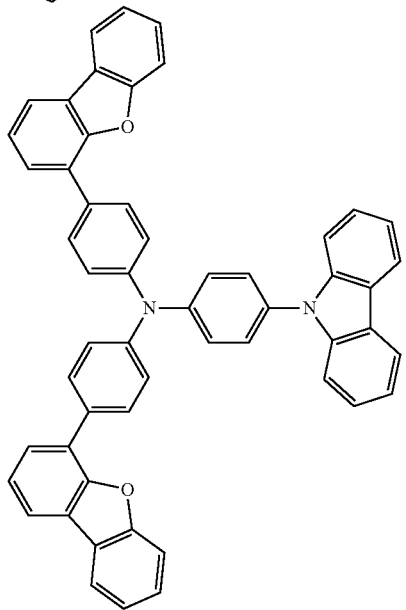
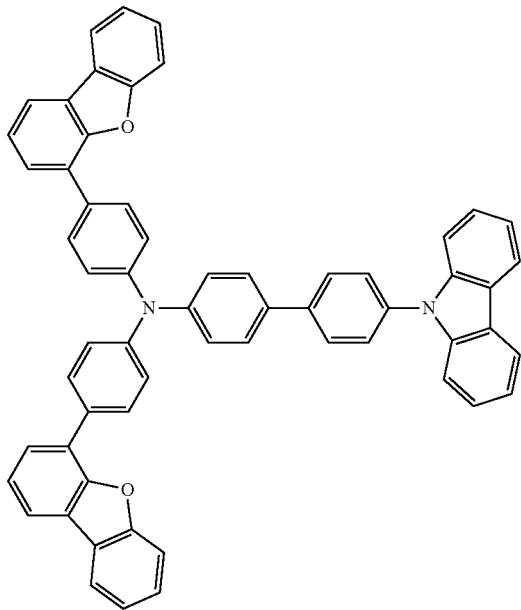

299
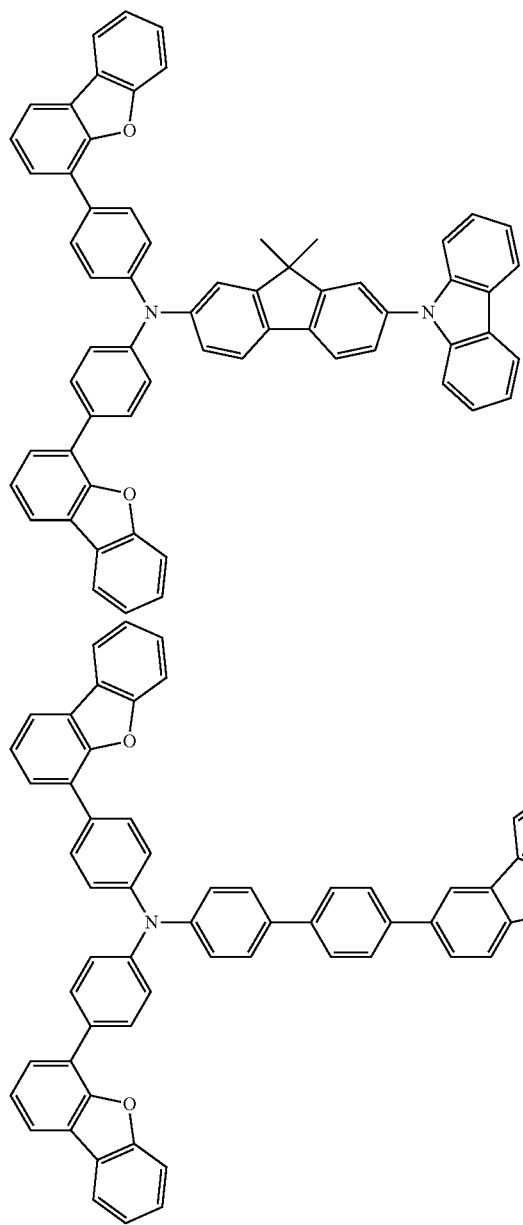
300
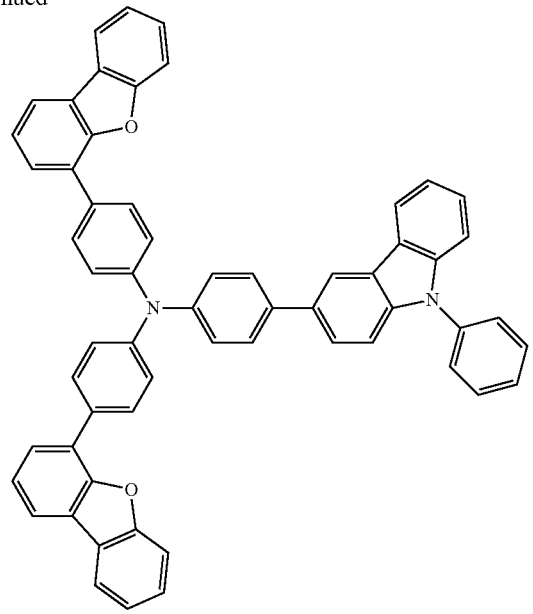
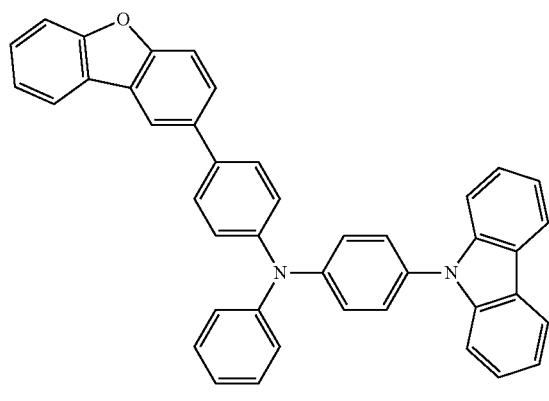
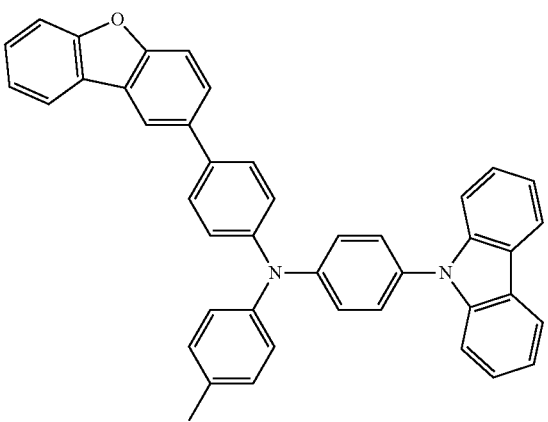

-continued
301
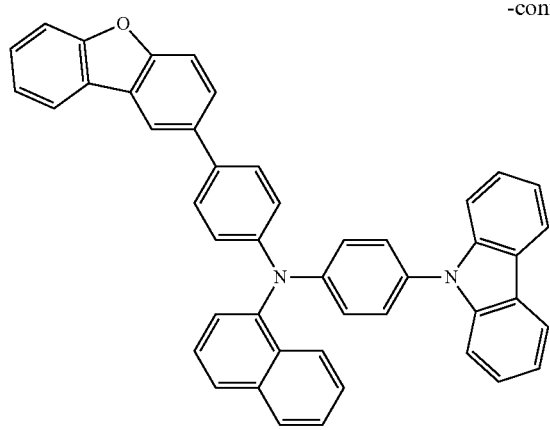
302
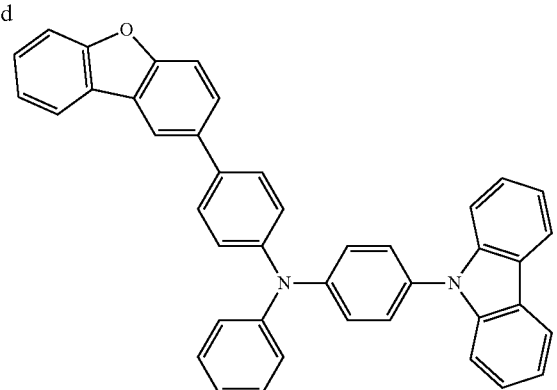
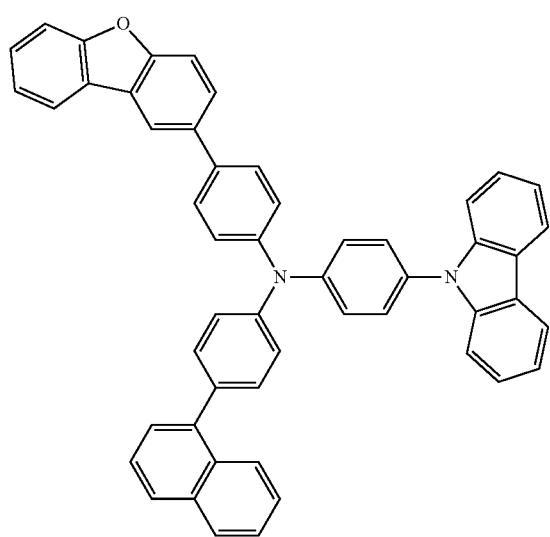
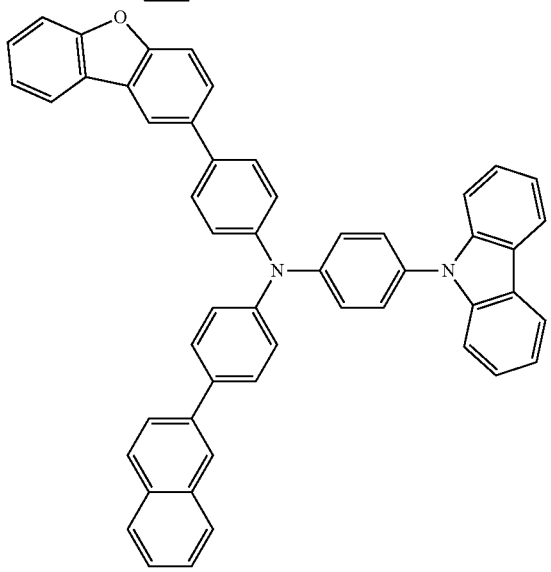
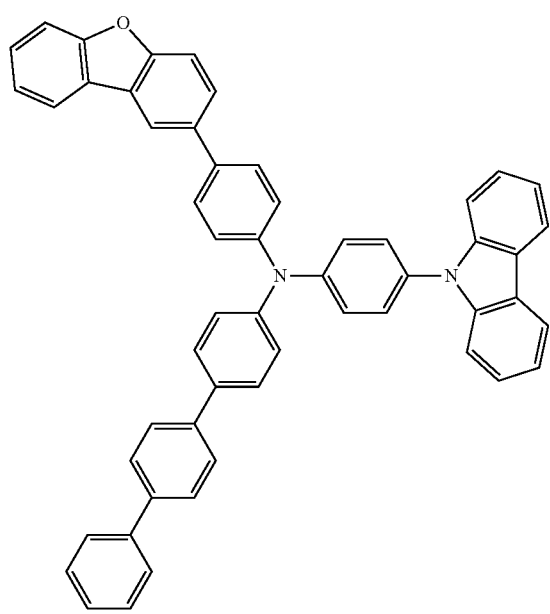

303
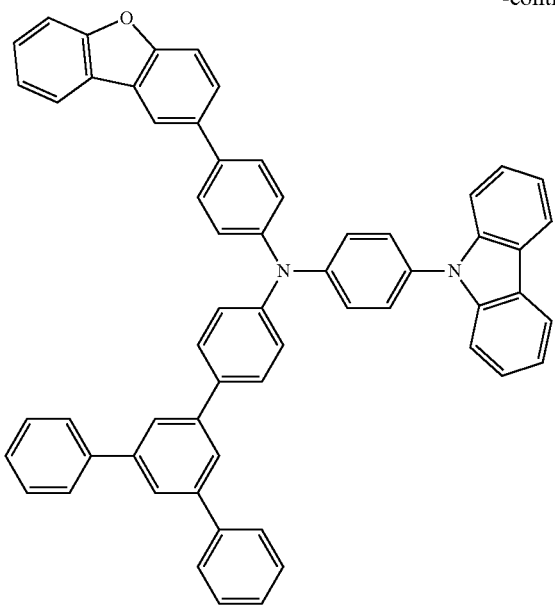
304
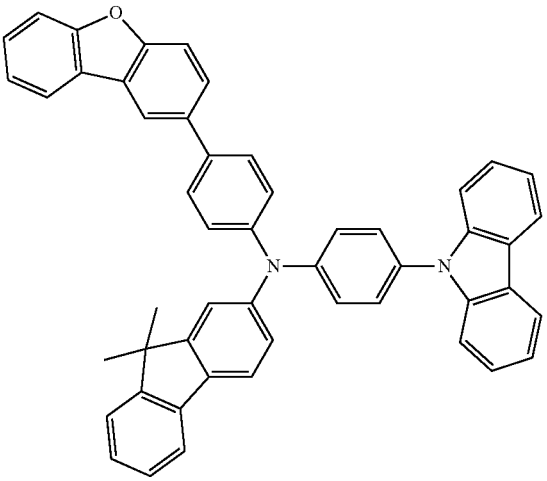
-continued
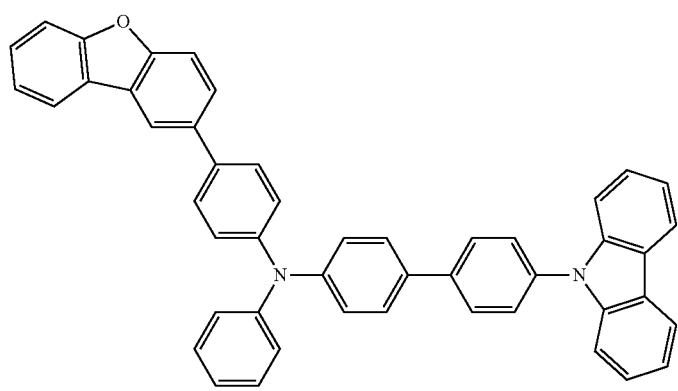
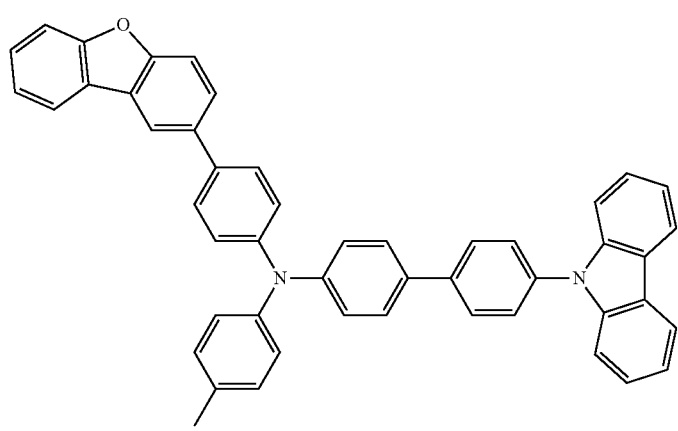

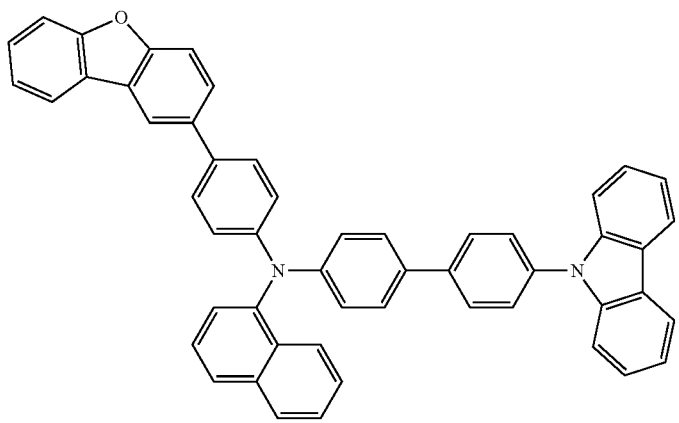
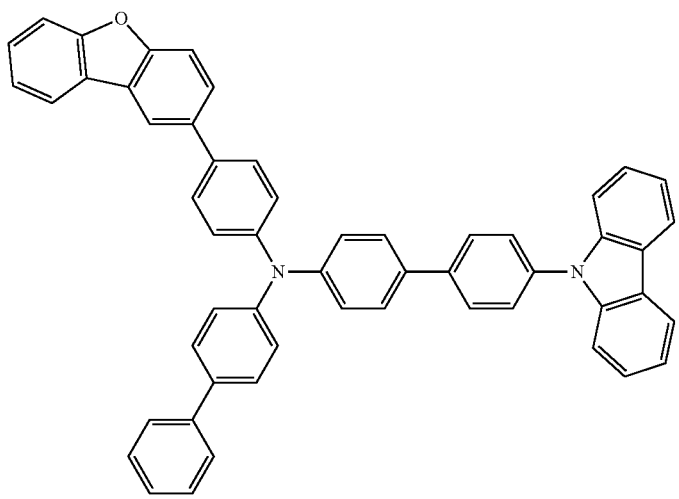
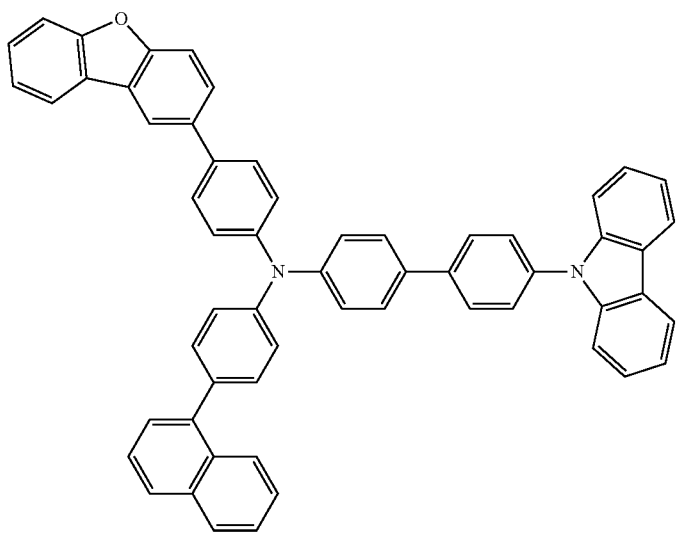

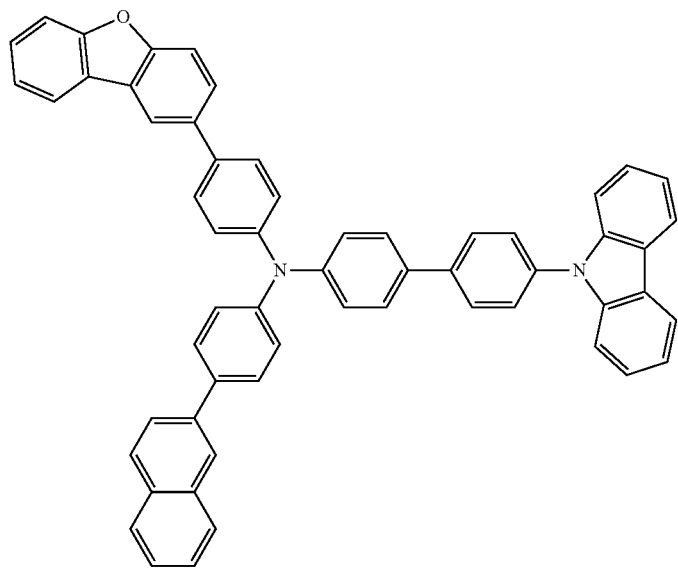
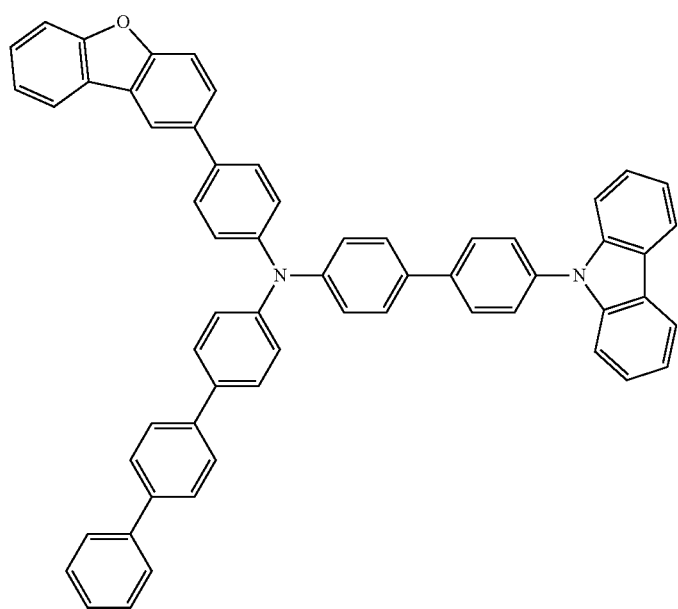

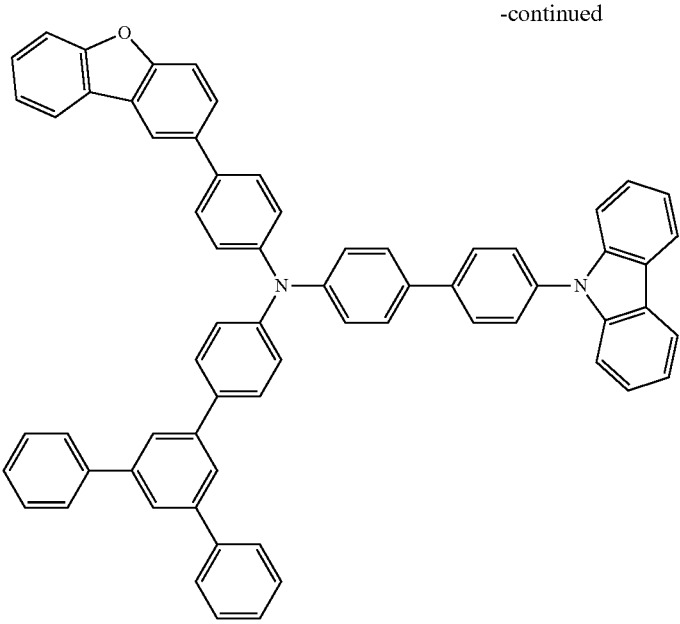
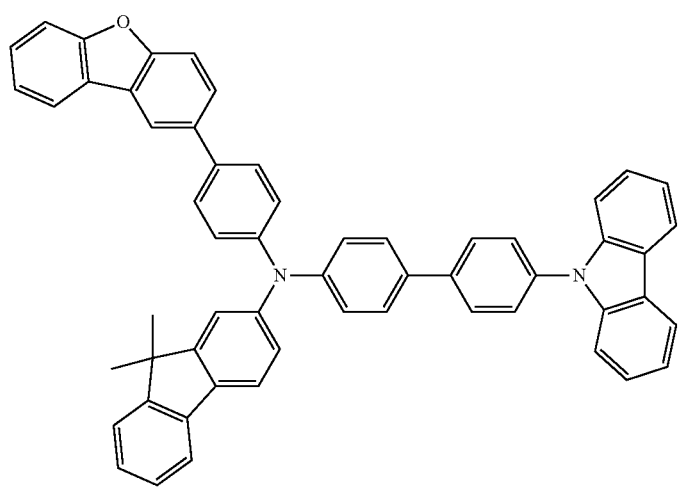
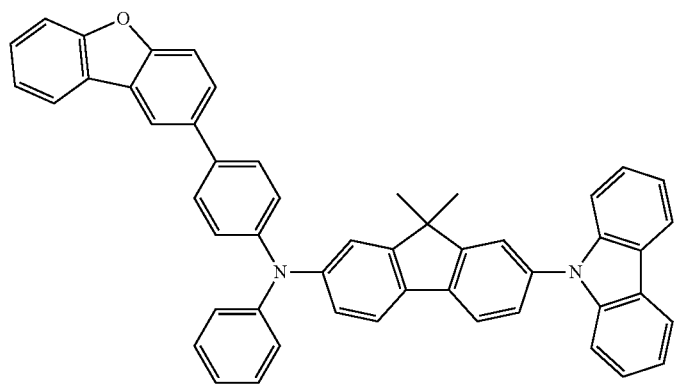

-continued
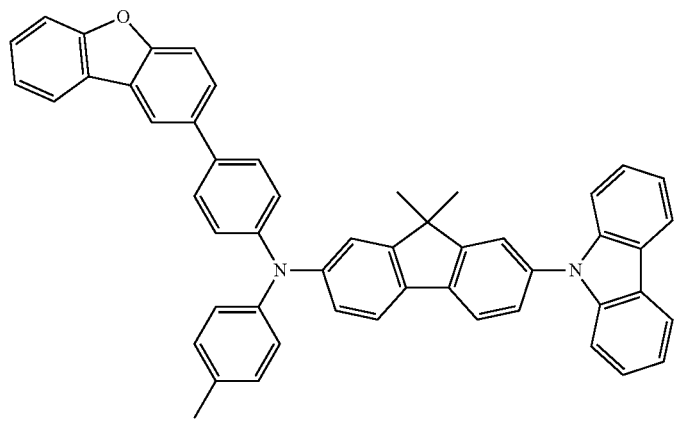
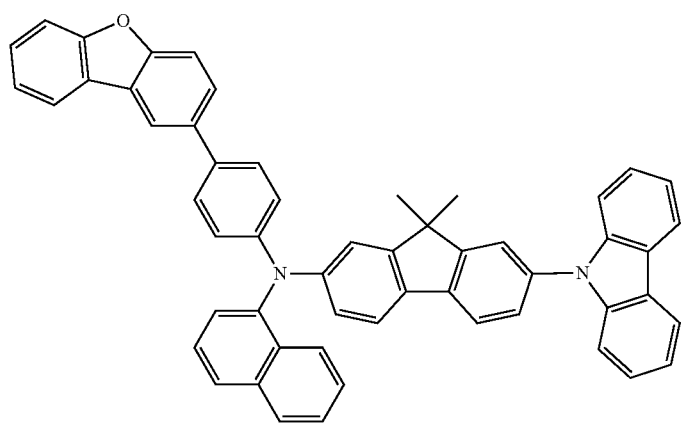
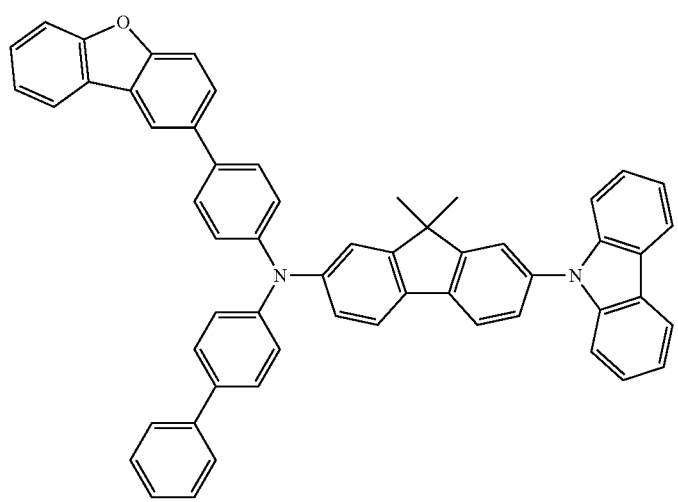

-continued
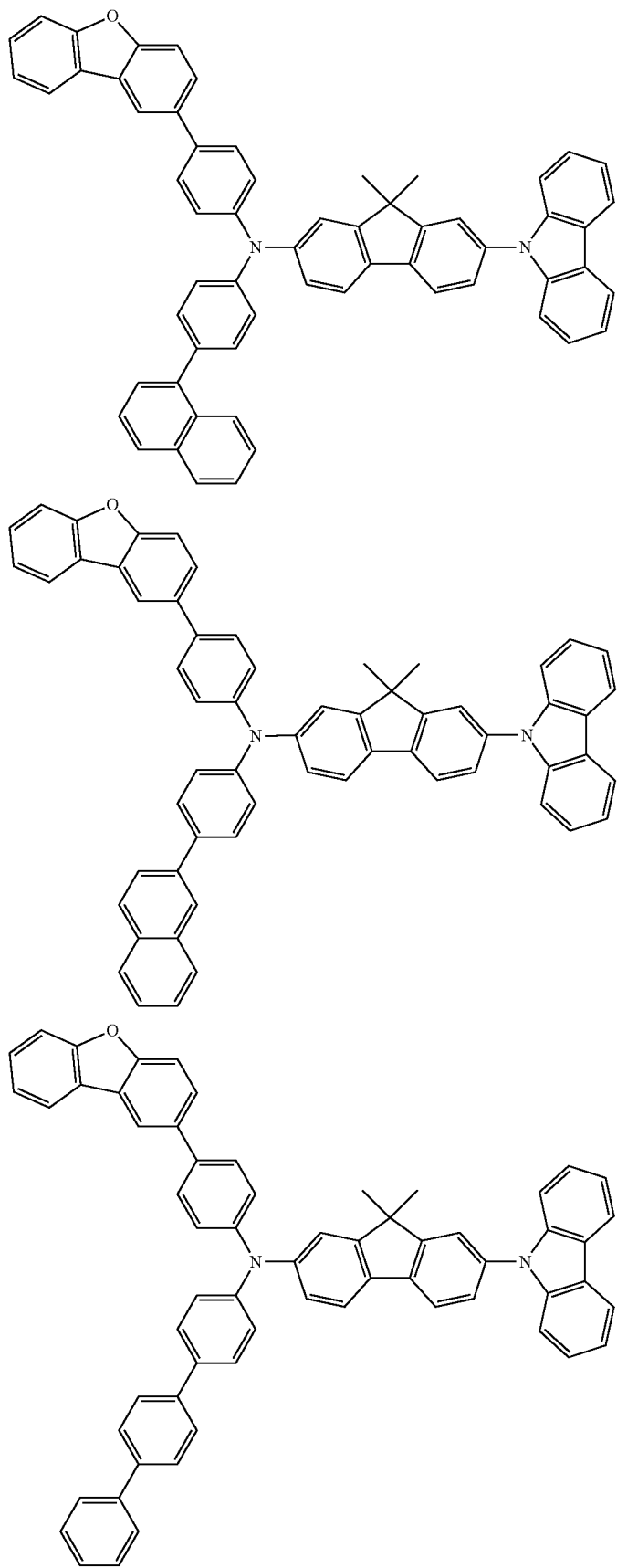

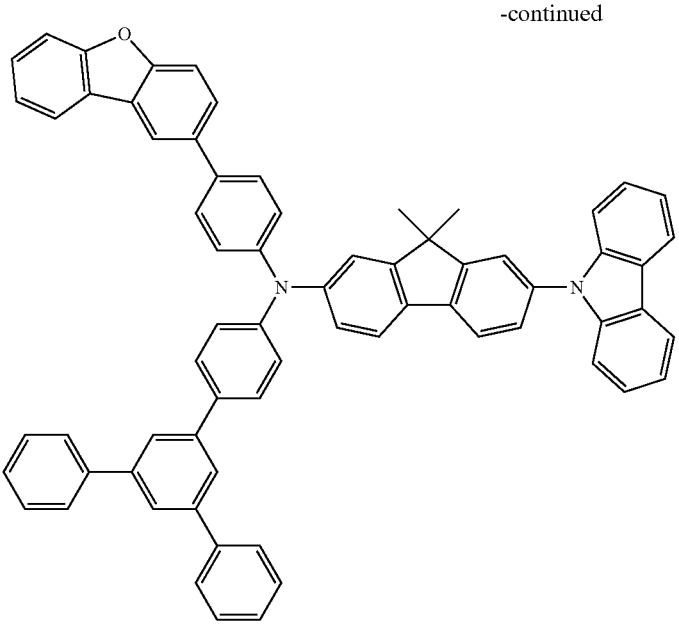
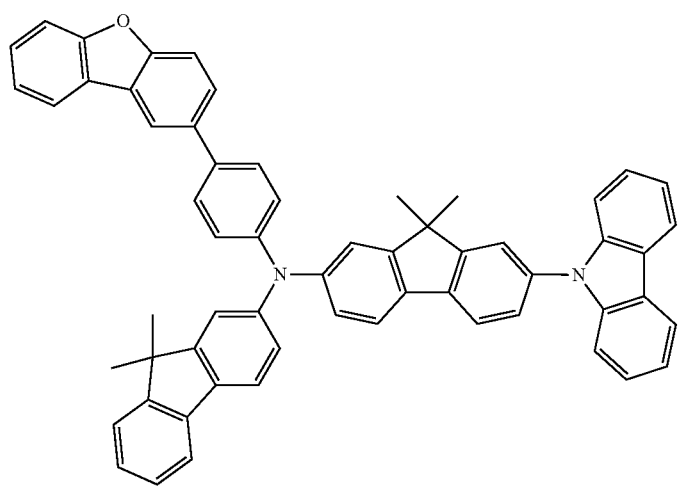
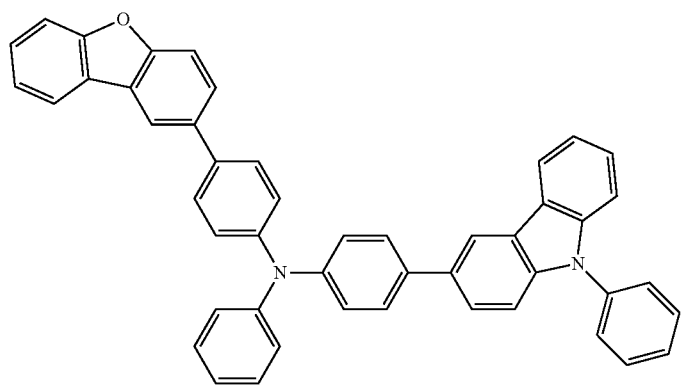

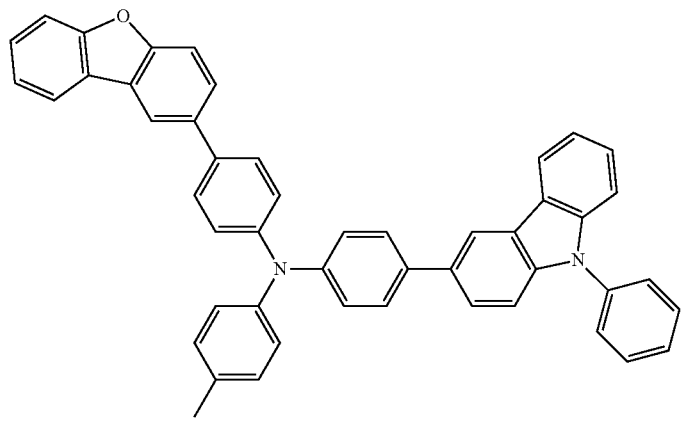
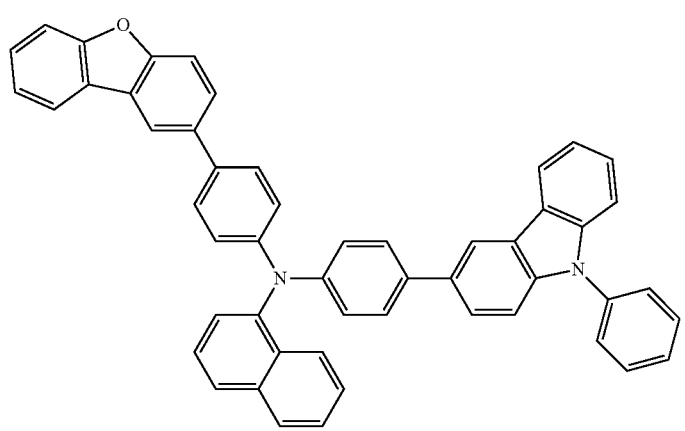
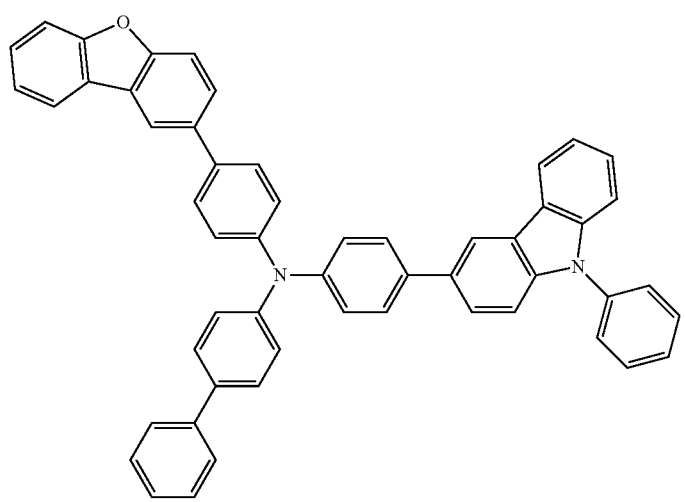

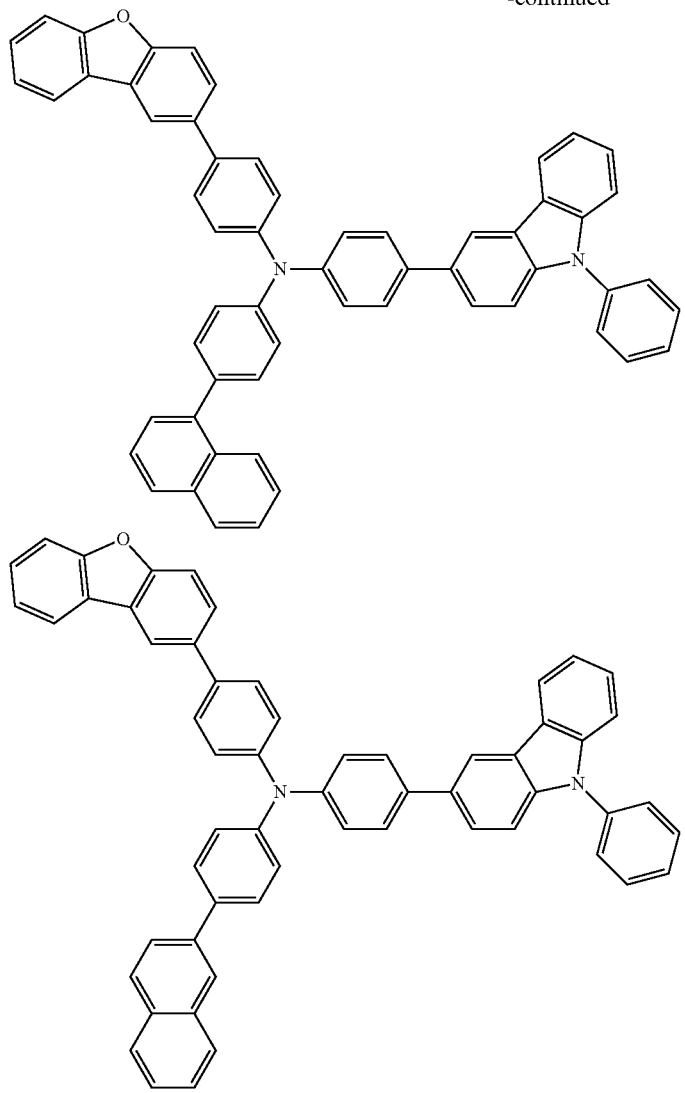
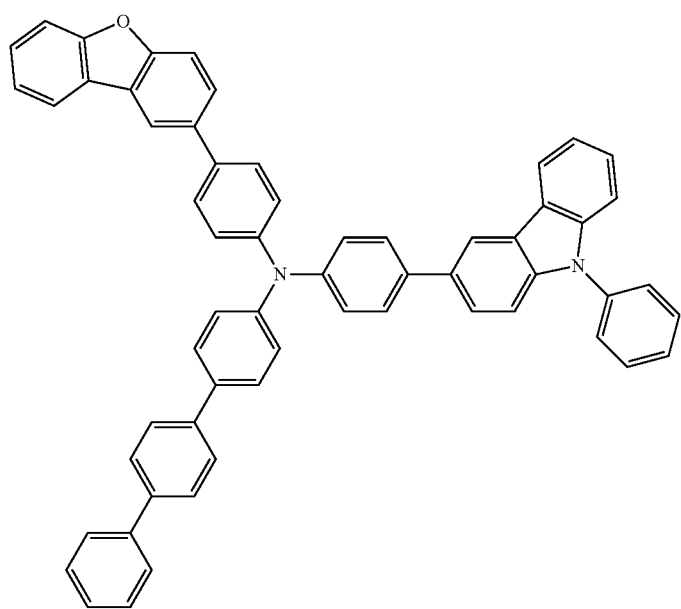

-continued
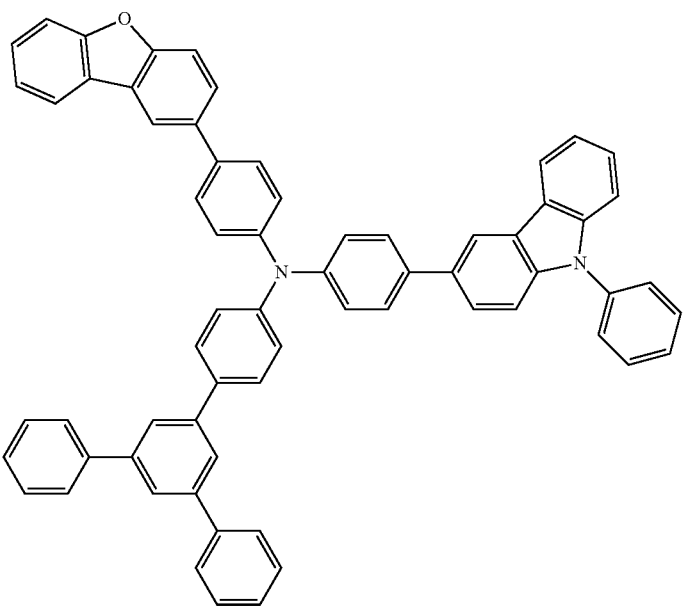
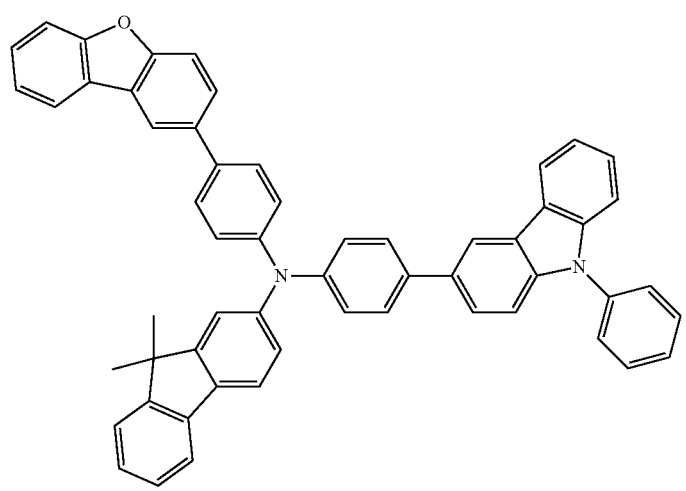
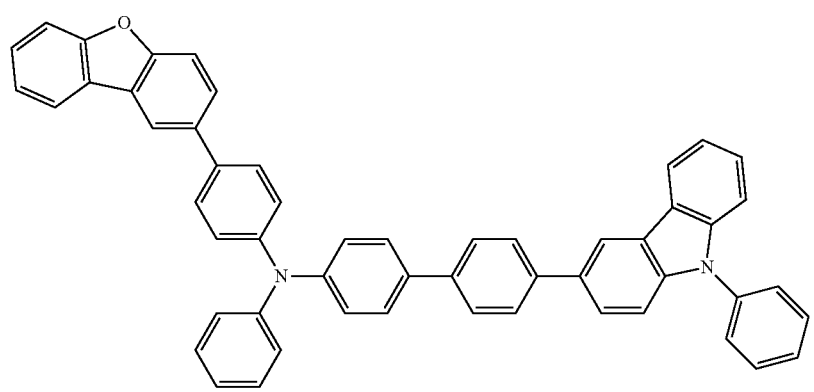

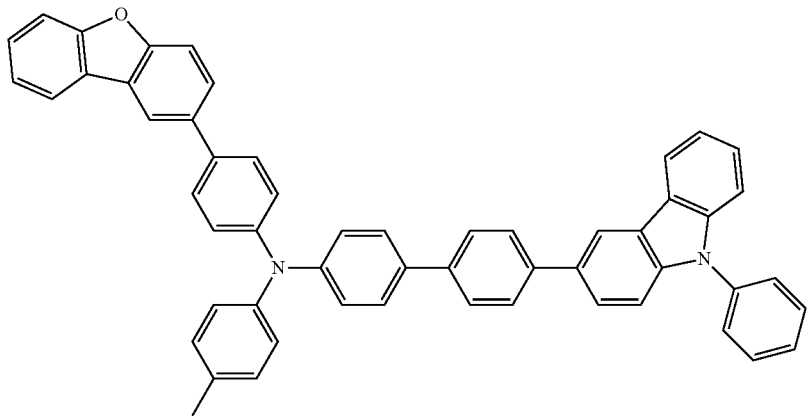
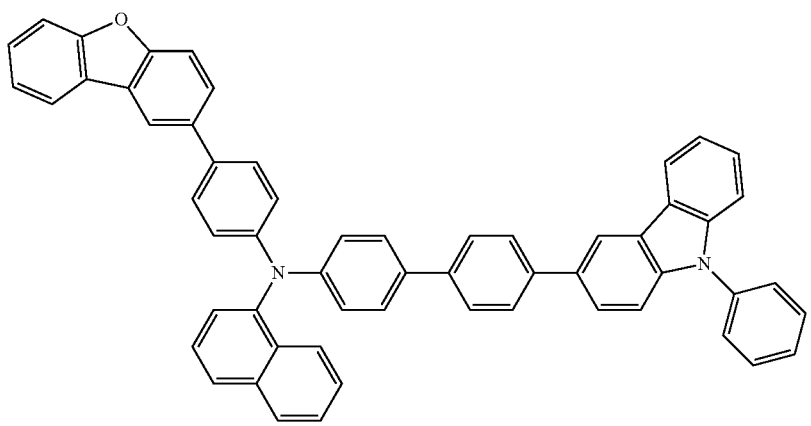
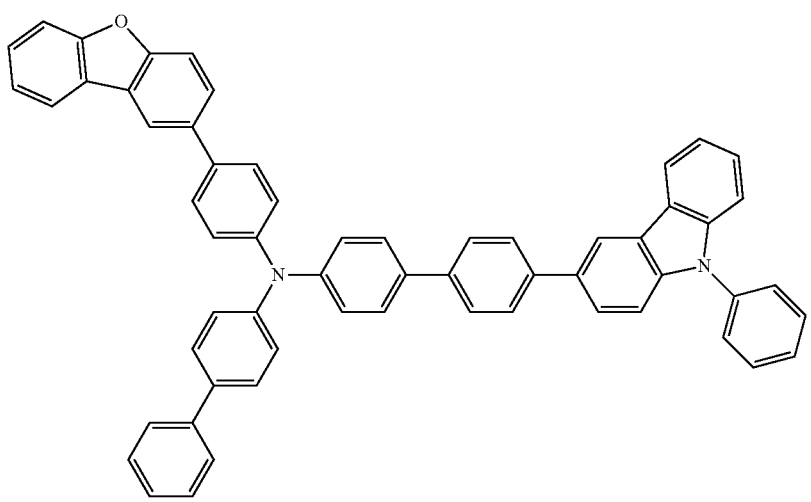

-continued
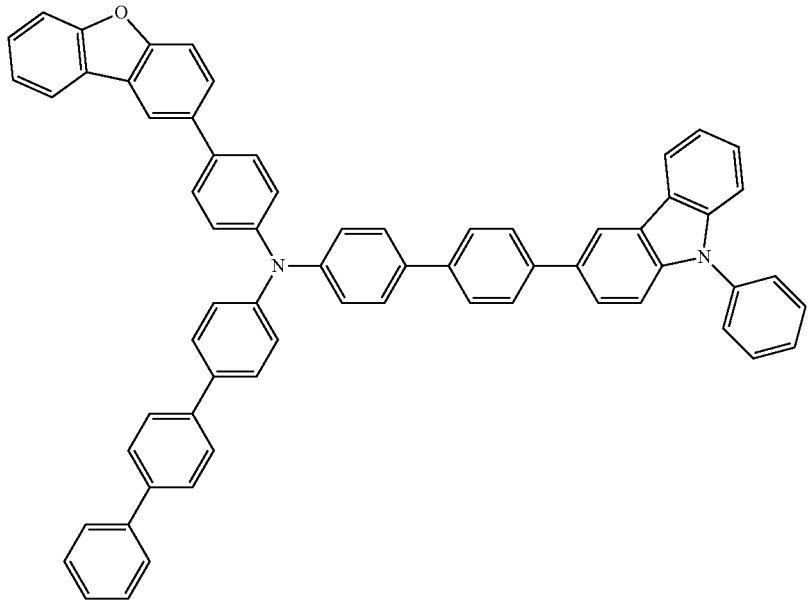
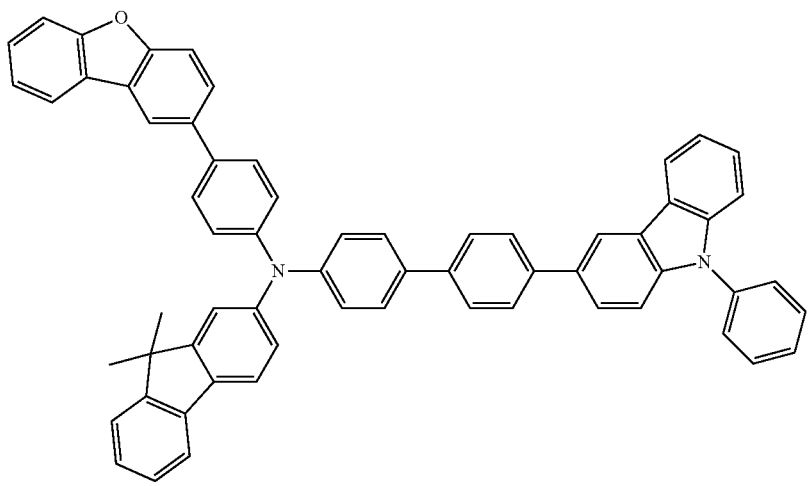
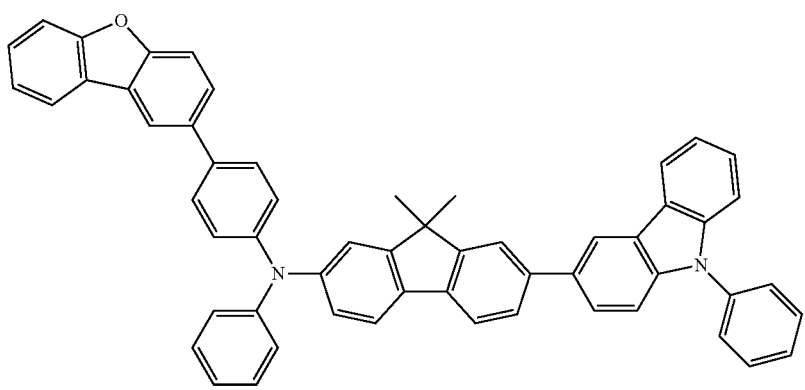

-continued
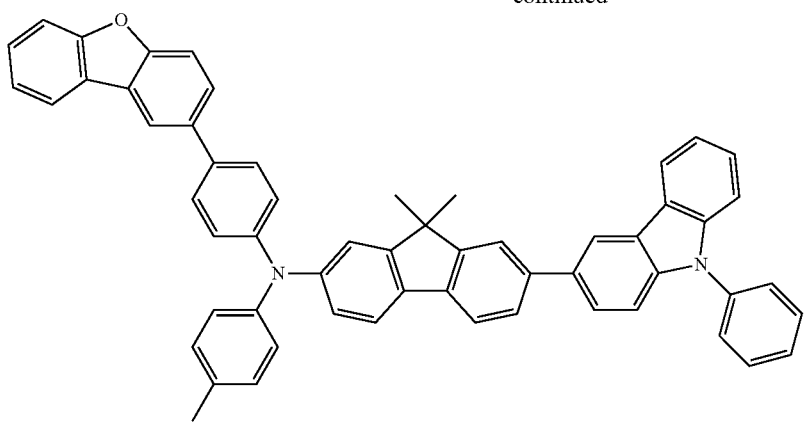
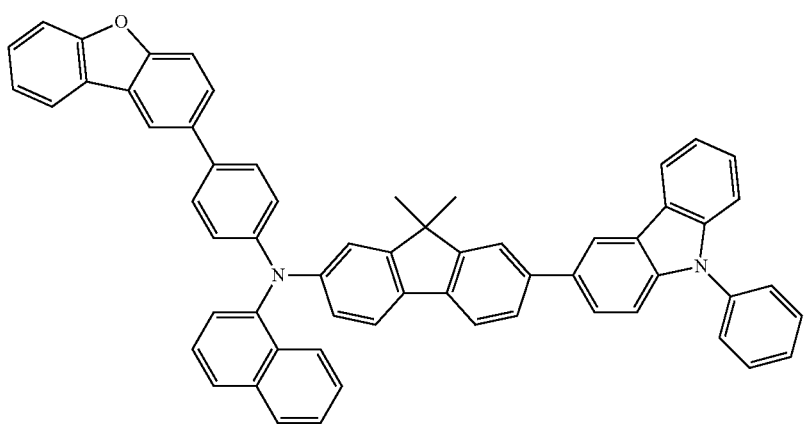
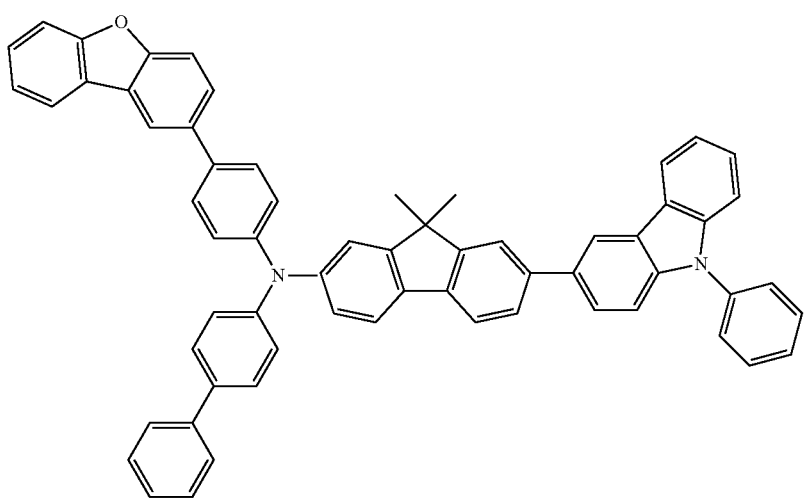

-continued
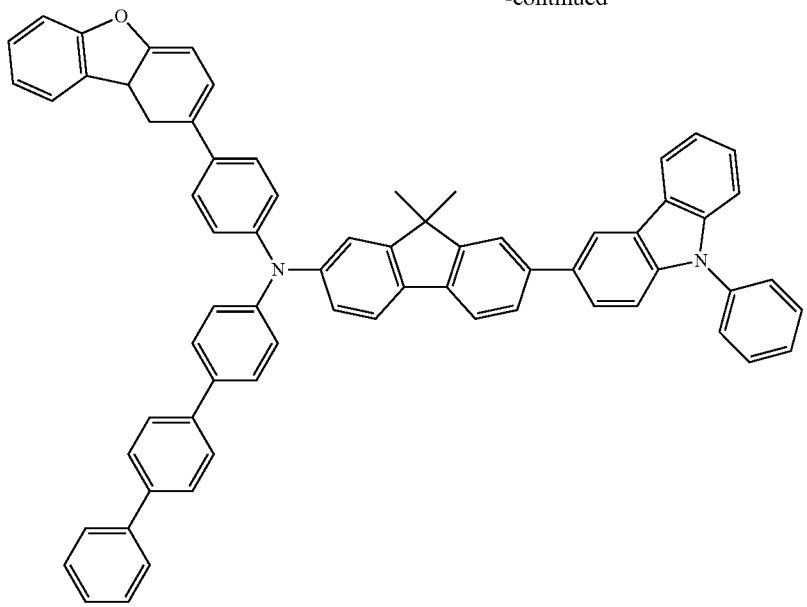
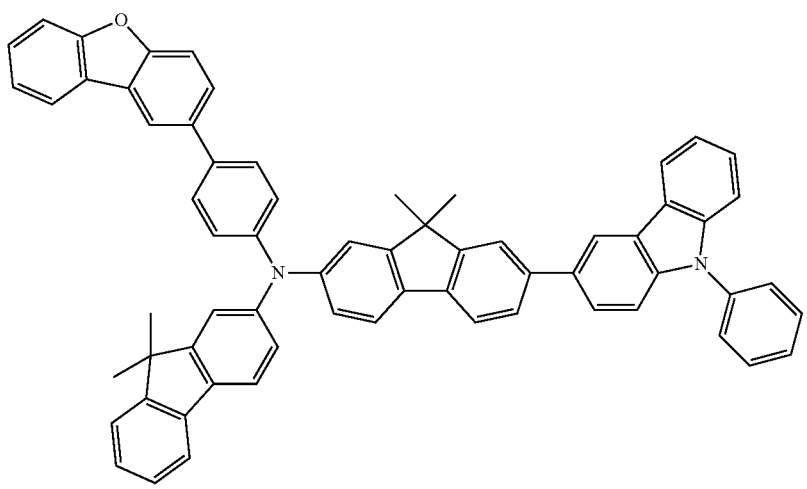
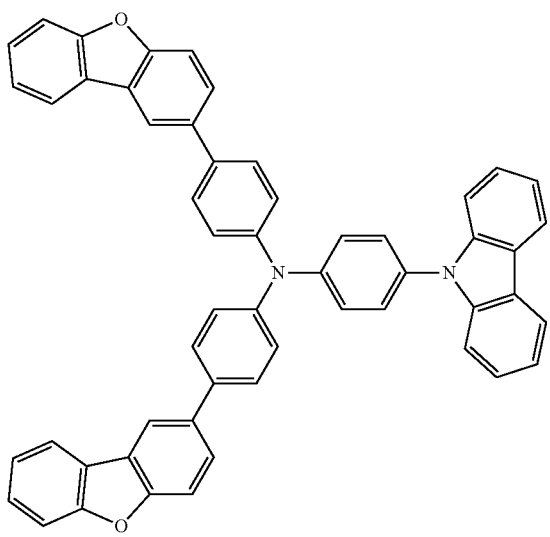

-continued
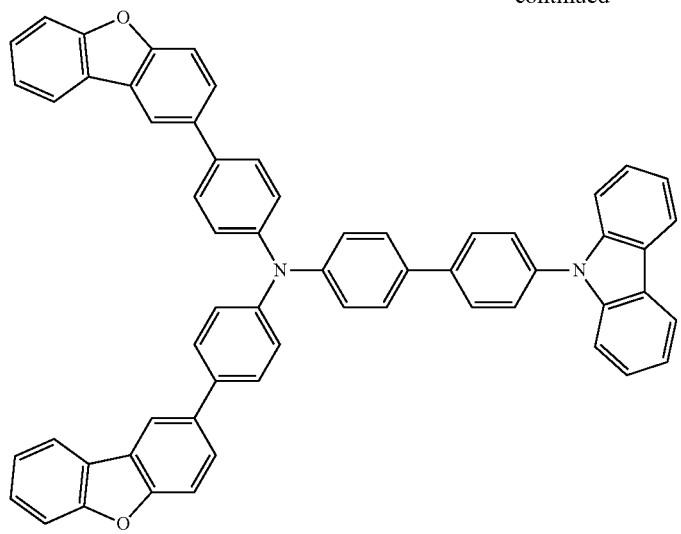
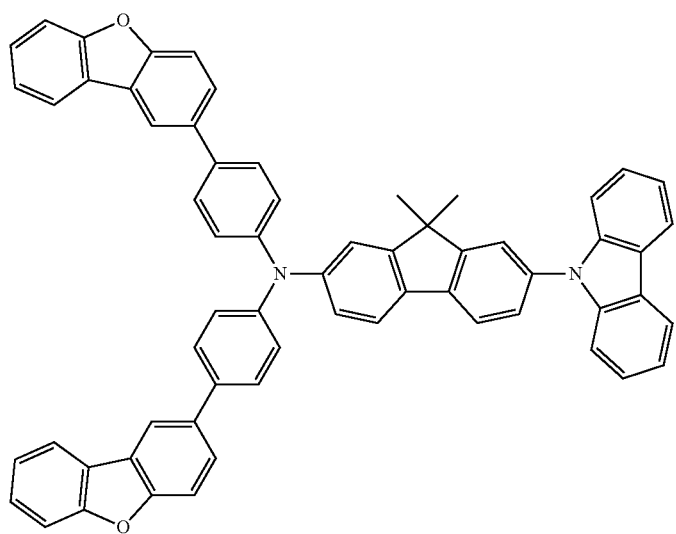
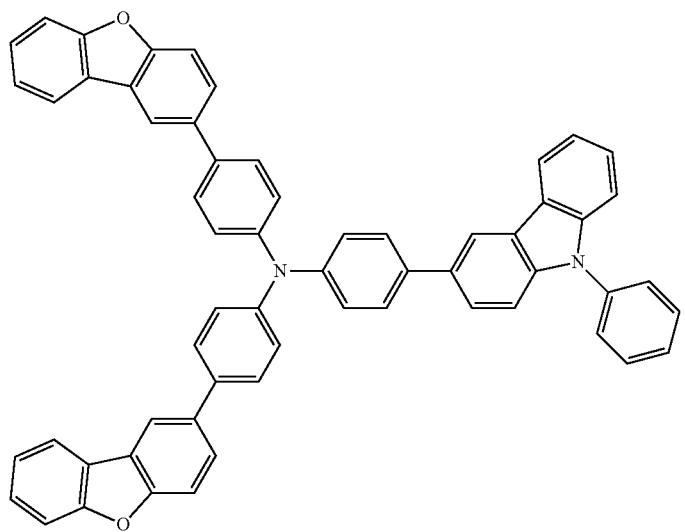

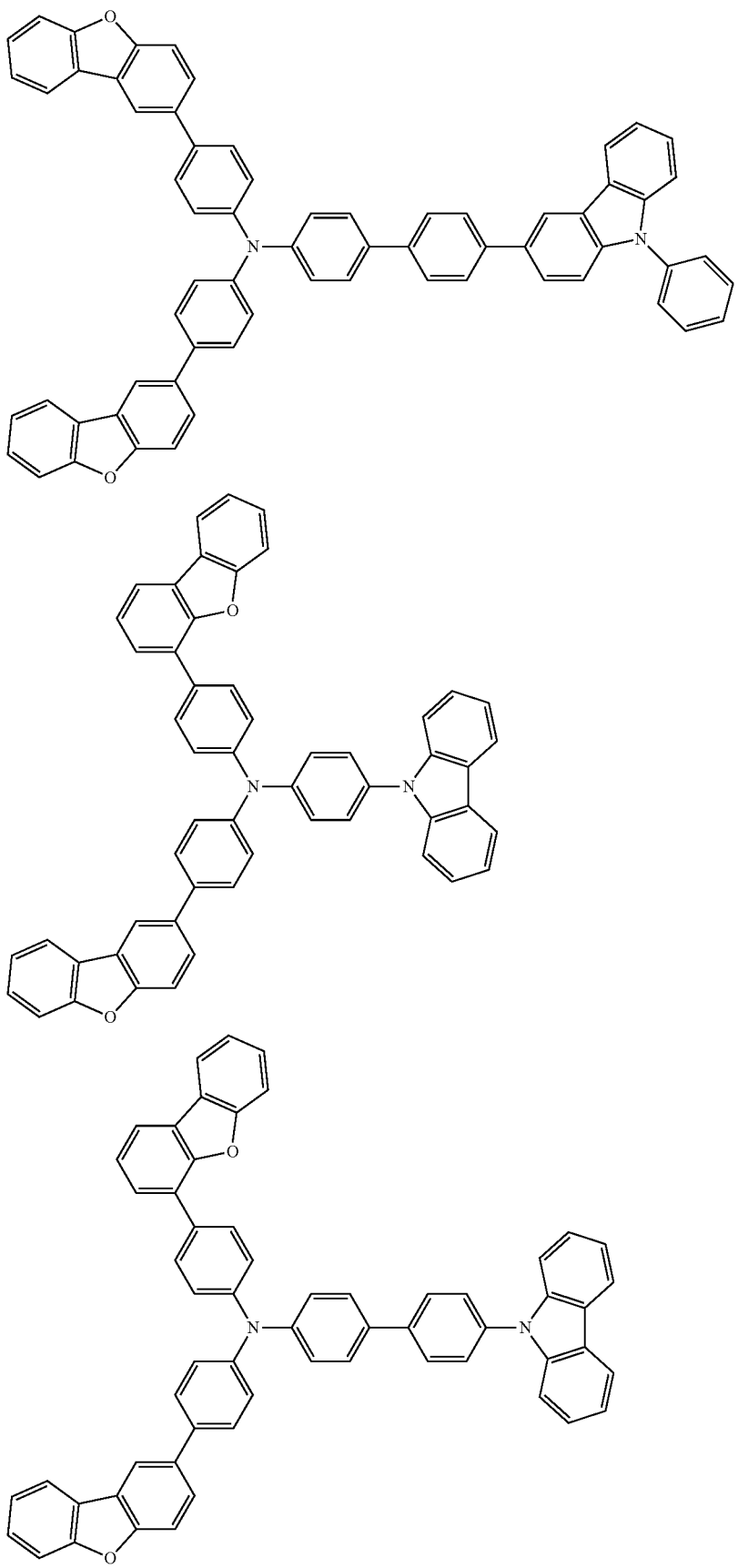

-continued
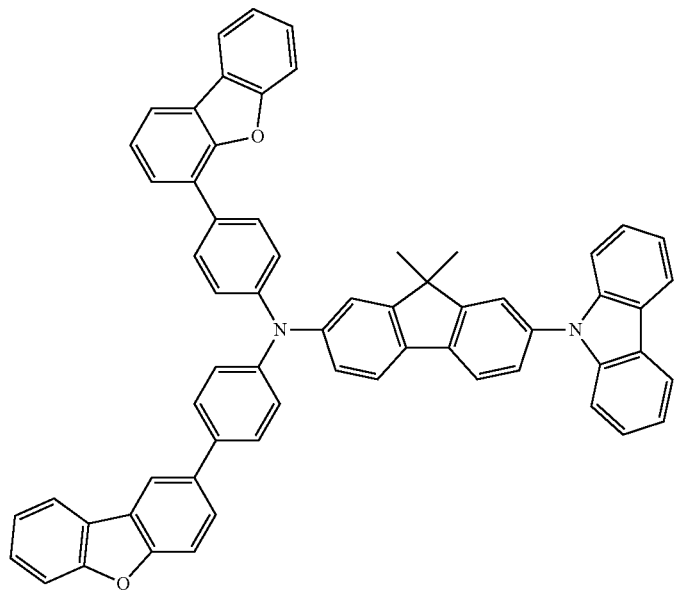
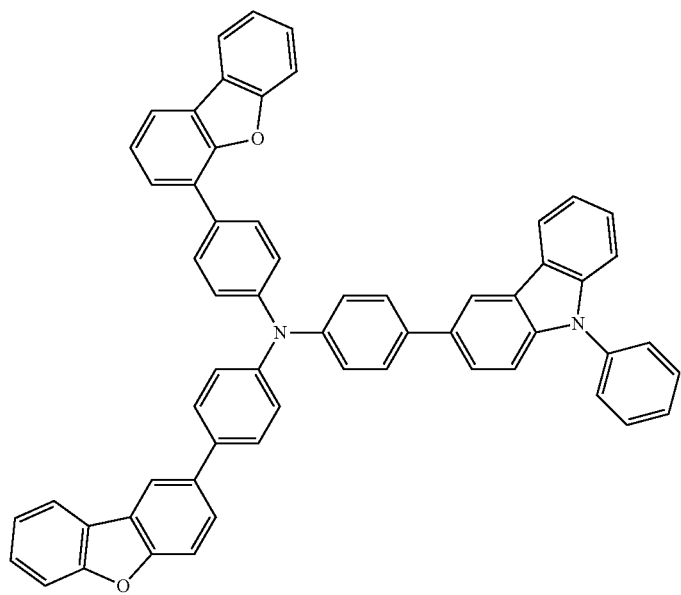

-continued
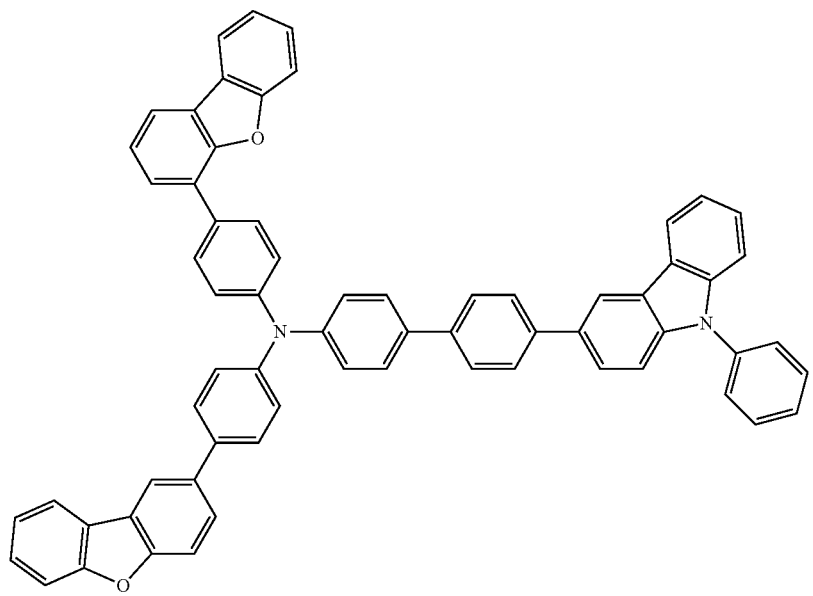

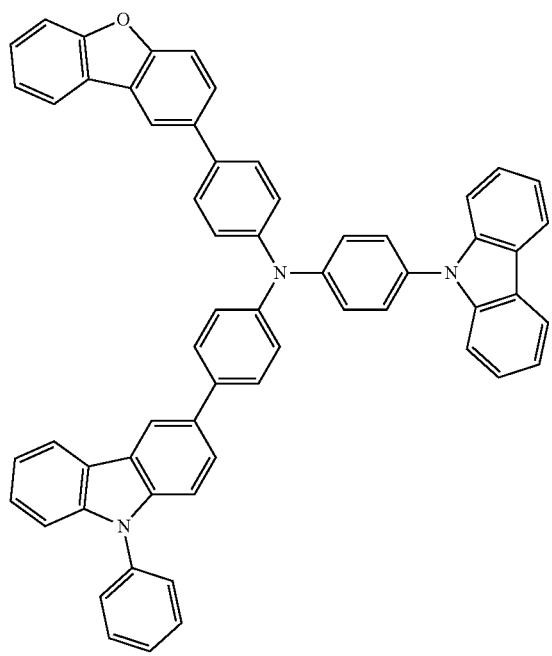
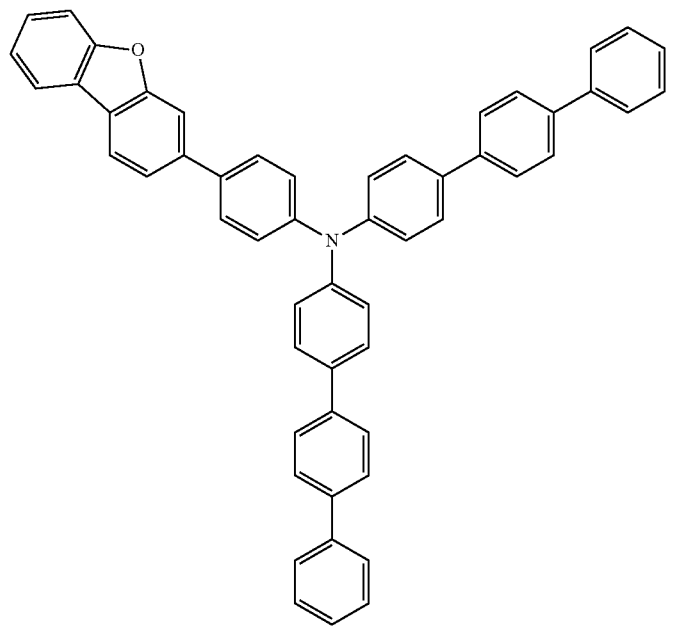

-continued
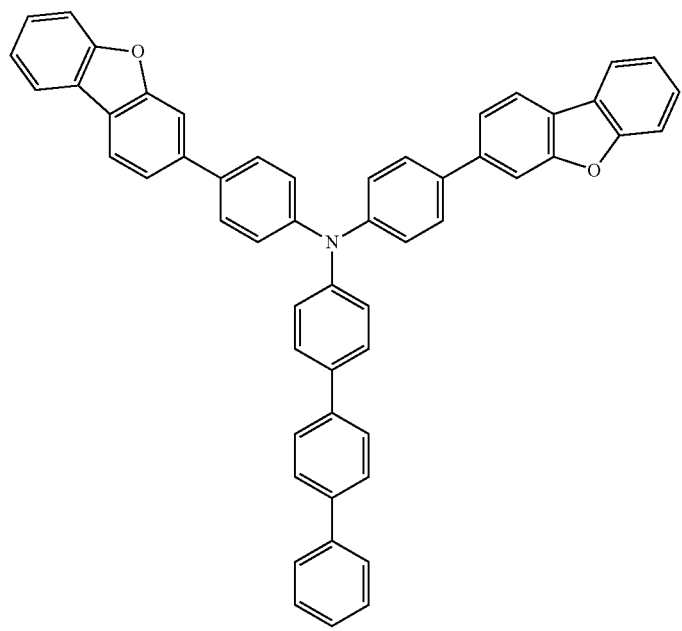
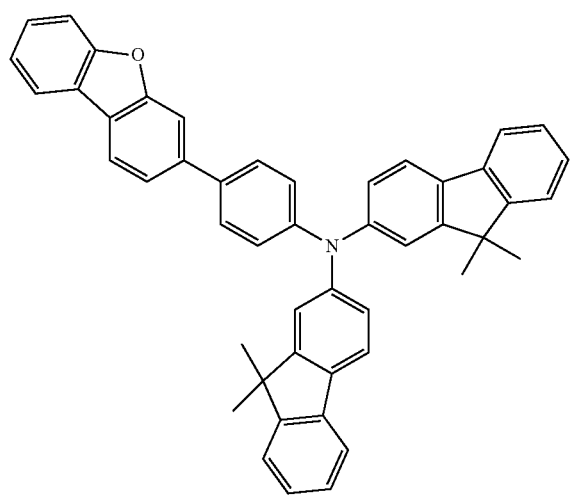
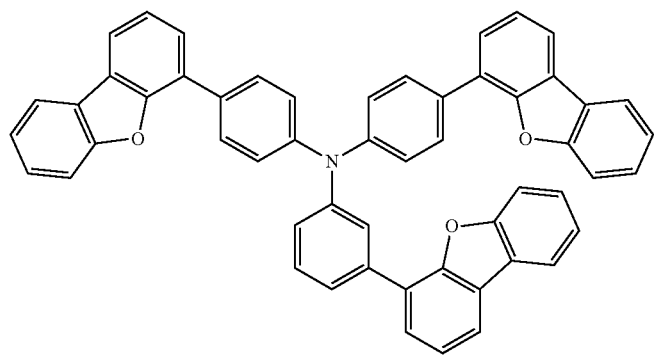

-continued
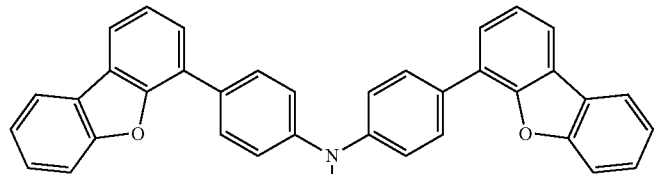
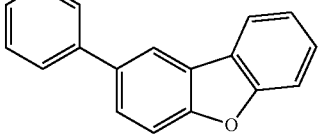
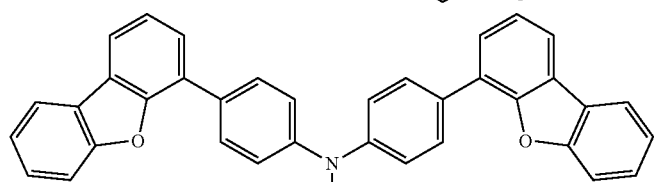
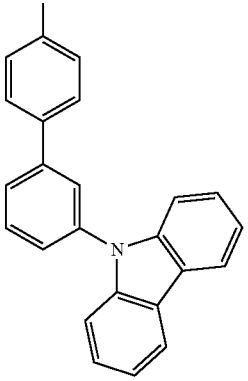
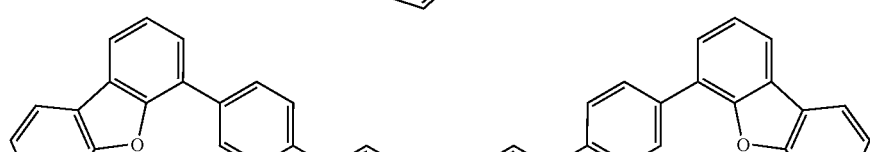
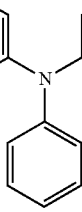
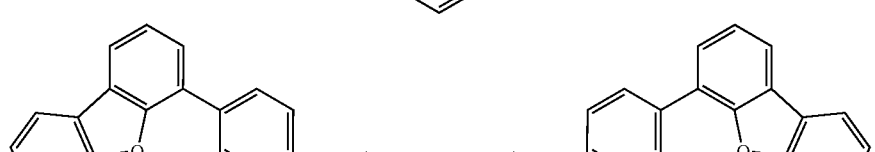
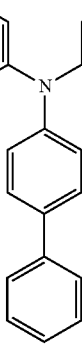

-continued
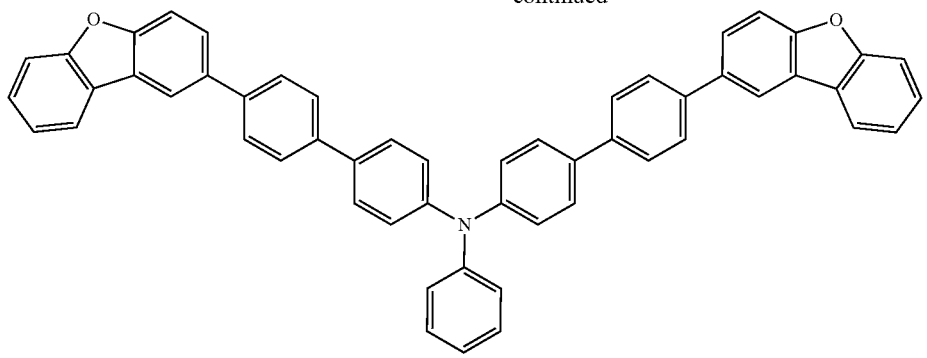
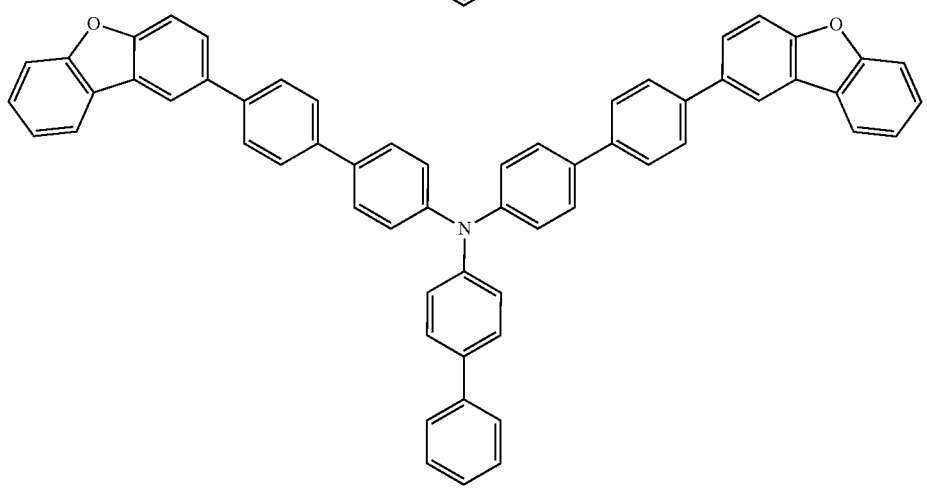
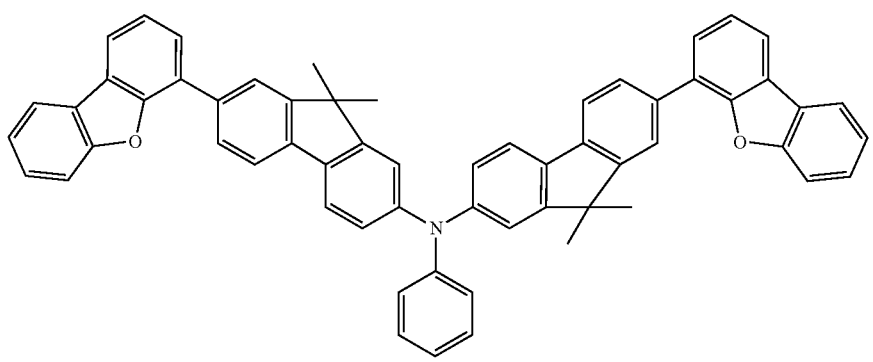
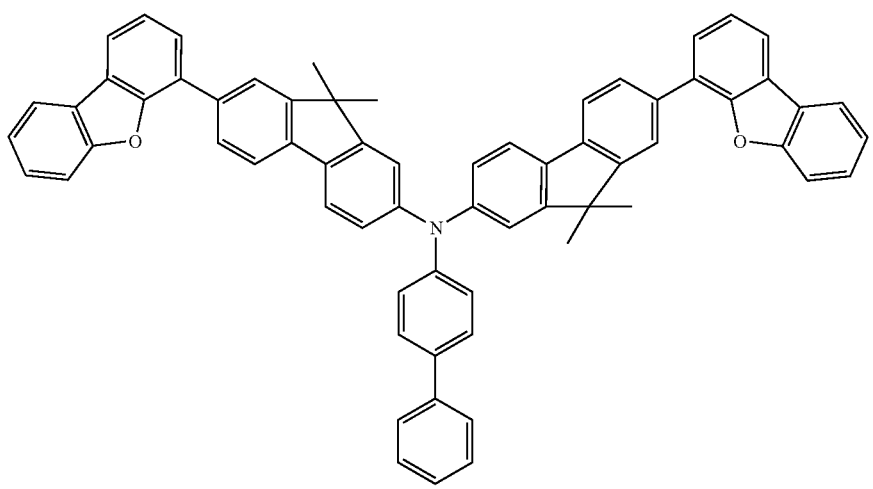

-continued

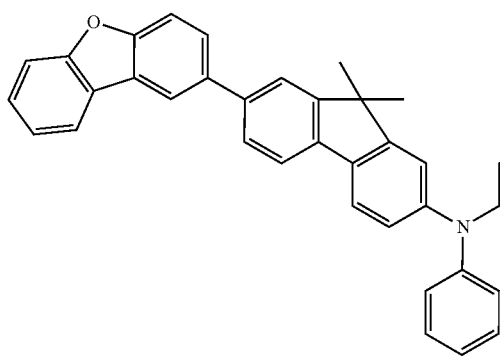

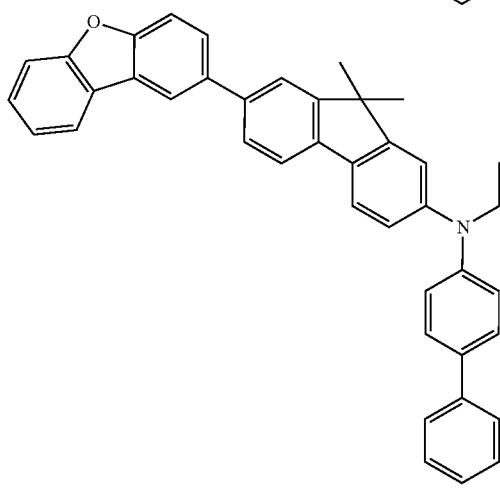

Material for hole transporting layer adjacent to light emitting layer (second hole transporting material) represented by any of formulae (5) to (7):

(5)

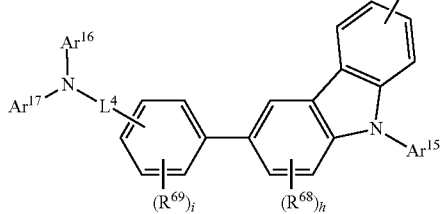

(6)

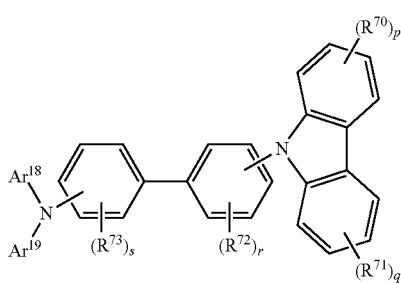

-continued (7)

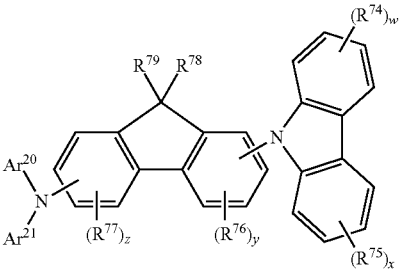

wherein:

$Ar^{15}$ to $Ar^{21}$ each independently represent a substituted or unsubstituted aryl group having 6 to 50 ring carbon atoms, a substituted or unsubstituted aromatic heterocyclic group having 5 to 50 ring carbon atoms, an aromatic amino-substituted aryl group having 8 to 50 ring carbon atoms which may have a substituent, or a heteroaryl-substituted an group having 8 to 50 ring carbon atoms which may have a substituent;

$Ar^{16}$ and $Ar^{17}$, $Ar^{18}$ and $Ar^{19}$, and $Ar^{20}$ and $Ar^{21}$ may be bonded to each other to form a ring;

$L^4$ represents a single bond or a substituted or unsubstituted arylene group having 6 to 50 ring carbon atoms, and an optional substituent of $L^4$ is a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms wherein the aryl portion has 6 to 14 ring carbon atoms, an aryl group having 6 to 50 ring carbon atoms, a halogen atom, or a cyano group;

$R^{67}$ to $R^{77}$ each independently represent a halogen atom, a substituted or unsubstituted alkyl group having 1 to 40 carbon atoms, a substituted or unsubstituted heteroaryl group having 5 to 20 ring atoms, a substituted or unsubstituted non-fused aryl group having 6 to 40 ring carbon atoms, a substituted or unsubstituted fused aryl group having 6 to 12 ring carbon atoms, a substituted or unsubstituted aralkyl group having 7 to 20 carbon atoms, a substituted or unsubstituted alkenyl group having 2 to 40 carbon atoms, a substituted or unsubstituted alkylamino group having 1 to 40 carbon atoms, a substituted or unsubstituted aralkylamino group having 7 to 60 carbon atoms, a substituted or unsubstituted alkylsilyl group having 3 to 20 carbon atoms, a substituted or unsubstituted arylsilyl group having 6 to 40 ring carbon atoms, a substituted or unsubstituted aralkylsilyl group having 8 to 40 carbon atoms, or a substituted or unsubstituted haloalkyl group having 1 to 40 carbon atoms;

$R^{78}$ and $R^{79}$ each independently represent a substituted or unsubstituted alkyl group having 1 to 40 carbon atoms, a substituted or unsubstituted heteroaryl group having 5 to 20 ring atoms, a substituted or unsubstituted non-fused aryl group having 6 to 40 ring carbon atoms, a substituted or unsubstituted fused aryl group having 6 to 12 ring carbon atoms, or a substituted or unsubstituted aralkyl group having 7 to 20 carbon atoms;

g, i, p, q, r, s, w, and x each independently represent an integer of 0 to 4; and h, y and z each independently represent an integer of 0 to 3.

Material for hole transporting layer adjacent to light emitting layer (second hole transporting material) represented by formula (8):

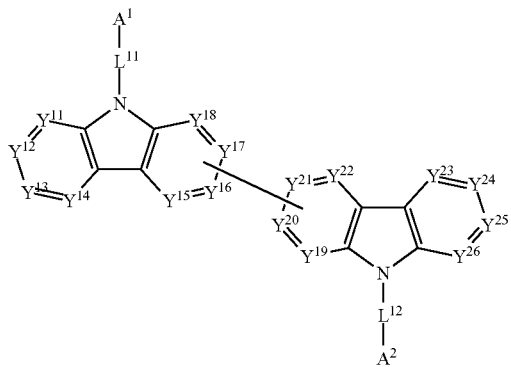

(8)

wherein:

$A^1$ and $A^2$ each independently represent a substituted or unsubstituted aryl group having 6 to 30 ring carbon atoms or a substituted or unsubstituted heteroaryl group having 2 to 30 ring carbon atoms;

$Y^{11}$ to $Y^{26}$ each independently represent C(R) or a nitrogen atom, wherein each R independently represents a hydrogen atom, a substituent, or a bond to a carbazole skeleton; and $L^{11}$ and $L^{12}$ each independently represent a single bond or a substituted or unsubstituted arylene group having 6 to 50 ring carbon atoms, and an optional substituent of the arylene group is selected from a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms wherein the aryl portion has 6 to 14 ring carbon atoms, an aryl group having 6 to 50 ring carbon atoms, a halogen atom, and a cyano group.

(5) Light Emitting Layer

The organic EL device of the invention may comprise a light emitting layer comprising a fluorescent material, i.e., a fluorescent emitting layer. The fluorescent emitting layer may be formed from a known fluorescent material, for example, at least one material selected from an anthracene derivative, a fluoranthene derivative, a styrylamine derivative, and an arylamine derivative, with the anthracene derivative and the arylamine derivative being more preferred. In particular, the anthracene derivative is preferably used as the host material and the arylamine derivative is preferably used as the dopant. The materials described in WO 2010/134350 and WO 2010/134352 are preferably used.

The organic EL device of the invention may comprise a light, emitting layer comprising a phosphorescent material, i.e., a phosphorescent emitting layer. The phosphorescent emitting layer may be formed from a known phosphorescent material, for example, those described in WO 2005/079118. The dopant in the phosphorescent material, is preferably an ortho-metallated complex of a metal, such as iridium (Ir), osmium (Os), and platinum (Pt), with an ortho-metallated complex of iridium (Ir) being more preferred. The host material in the phosphorescent material is preferably a compound comprising a carbazolyl group, more preferably a compound comprising a carbazolyl group and a triazine skeleton, and still more preferably a compound comprising two carbazolyl groups and one triazine skeleton.

The anthracene derivative for use as a fluorescent material has preferably 26 to 100, more preferably 26 to 80, and still more preferably 26 to 60 ring carbon atoms. The anthracene derivative is preferably represented by formula (10):

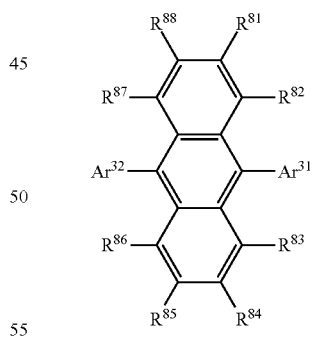

(10)

wherein:

$Ar^{31}$ and $Ar^{32}$ each independently represent a substituted or unsubstituted aryl group having 6 to 50 ring carbon atoms or a substituted or unsubstituted heterocyclic group having 5 to 50 ring atoms; and $R^{81}$ to $R^{88}$ each independently represent a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxyl group, a halogen atom, a cyano group, a nitro group, or a hydroxyl group.

The aryl group having 6 to 50 ring carbon atoms is preferably an aryl group having 6 to 40 ring carbon atoms and more preferably an aryl group having 6 to 30 ring carbon atoms.

The heterocyclic group having 5 to 50 ring atoms is preferably a heterocyclic group having 5 to 40 ring atoms and more preferably a heterocyclic group having 5 to 30 ring atoms.

The alkyl group having 1 to 50 carbon atoms is preferably an alkyl group having 1 to 30 carbon atoms, more preferably an alkyl group having 1 to 10 carbon atoms, and still more preferably an alkyl group having 1 to 5 carbon atoms.

The alkoxy group having 1 to 50 carbon atoms is preferably an alkoxy group having 1 to 30 carbon atoms, more preferably an alkoxy group having 1 to 10 carbon atoms, and still more preferably an alkoxy group having 1 to 5 carbon atoms.

The aralkyl group having 7 to 50 carbon atoms is preferably an aralkyl group having 7 to 30 carbon atoms and more preferably an aralkyl group having 7 to 20 carbon atoms.

The aryloxy group having 6 to 50 ring carbon atoms is preferably an aryloxy group having 6 to 40 ring carbon atoms and more preferably an aryloxy group having 6 to 30 ring carbon atoms.

The arylthio group having 6 to 50 ring carbon atoms is preferably an arylthio group having 6 to 40 ring carbon atoms and more preferably an arylthio group having 6 to 30 ring carbon atoms.

The alkoxycarbonyl group having 2 to 50 carbon atoms is preferably an alkoxycarbonyl group having 2 to 30 carbon atoms, more preferably an alkoxycarbonyl group having 2 to 10 carbon atoms, and still more preferably an alkoxycarbonyl group having 2 to 5 carbon atoms.

Examples of the halogen atom include a fluorine atom, a chlorine atom, and a bromine atom.

$Ar^{31}$ and $Ar^{32}$ each particularly preferably represent a substituted or unsubstituted aryl group having 6 to 50 ring carbon atoms.

The anthracene derivative represented by formula (10) is preferably represented by formula (10-1):

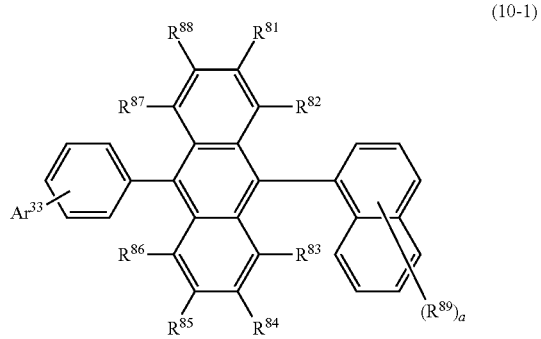

(10-1)

wherein:

$Ar^{33}$ represents a substituted or unsubstituted aryl group having 6 to 50 ring carbon atoms or a substituted or unsubstituted heterocyclic group having 5 to 50 ring atoms;

$R^{81}$ to $R^{88}$ are as defined above;

$R^{89}$ is defined in the same manner as in $R^{81}$ to $R^{88}$; and a is an integer of 1 to 7.

Preferred examples of $R^{81}$ to $R^{88}$ are as described above. Preferred examples of $R^{89}$ are the same as those of $R^{81}$ to $R^{88}$. The subscript a is preferably an integer of 1 to 3 and more preferably 1 or 2. $R^{89}$ may be bonded to either of two benzene rings of the naphthalene ring.

The aryl group having 6 to 50 ring carbon atoms for $Ar^{33}$ is preferably an aryl group having 6 to 40 ring carbon atoms, more preferably an aryl group having 6 to 30 ring carbon atoms, still more preferably an aryl group having 6 to 20 ring carbon atoms, further preferably an aryl group having 6 to 12 ring carbon atoms, and particularly preferably a naphthyl group.

The arylamine derivative for use as the fluorescent material is preferably an aryldiamine derivative, more preferably an aryldiamine derivative comprising a pyrene skeleton, and still more preferably an aryldiamine derivative comprising a pyrene skeleton and a dibenzofuran skeleton.

The aryldiamine derivative is preferably an aryldiamine derivative represented by formula (11):

(11)

wherein:

$Ar^{34}$ to $Ar^{37}$ each independently represent a substituted or unsubstituted aryl group having 6 to 50 ring carbon atoms or a substituted or unsubstituted heteroaryl group having 5 to 50 ring atoms; and $L^{21}$ represents a substituted or unsubstituted arylene group having 6 to 50 ring carbon atoms or a substituted or unsubstituted heteroarylene group having 5 to 50 ring atoms.

The aryl group having 6 to 50 ring carbon atoms is preferably an aryl group having 6 to 30 ring carbon atoms, more preferably an aryl group having 6 to 20 ring carbon atoms, still more preferably an aryl group having 6 to 12 ring carbon atoms, with a phenyl group and a naphthyl group being particularly preferred.

The heteroaryl group having 5 to 50 ring atoms is preferably a heteroaryl group having 5 to 40 ring atoms, more preferably a heteroaryl group having 5 to 30 ring atoms, and still more preferably a heteroaryl group having 5 to 20 ring atoms, for example, a carbazolyl group, a dibenzofuranyl group and dibenzothiophenyl group, with a dibenzofuranyl group being preferred. Preferred examples of the substituent of the heteroaryl group include an aryl group having 6 to 30, preferably 6 to 20, and more preferably 6 to 12 ring carbon atoms, with a phenyl group and a naphthyl group being more preferred.

The arylene group having 6 to 50 ring carbon atoms is preferably an arylene group having 6 to 40 ring carbon atoms, more preferably an arylene group having 6 to 30 ring carbon atoms, and still more preferably an arylene group having 6 to 20 ring carbon atoms, with a pyrenyl group being particularly preferred.

Examples of the compound comprising a carbazolyl group which is a preferred host material for use as the phosphorescent material are shown below.

353
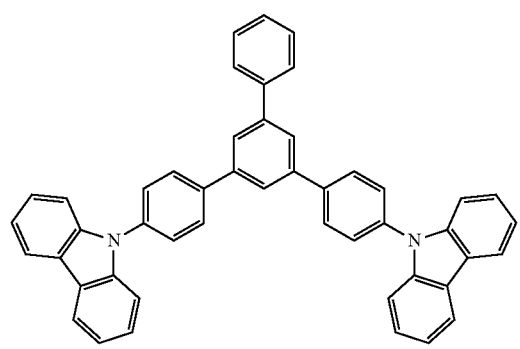
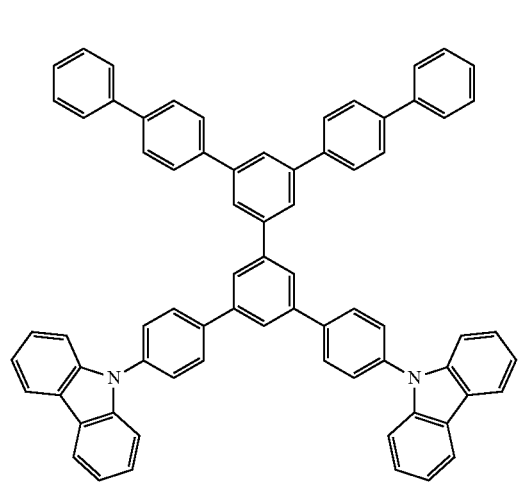
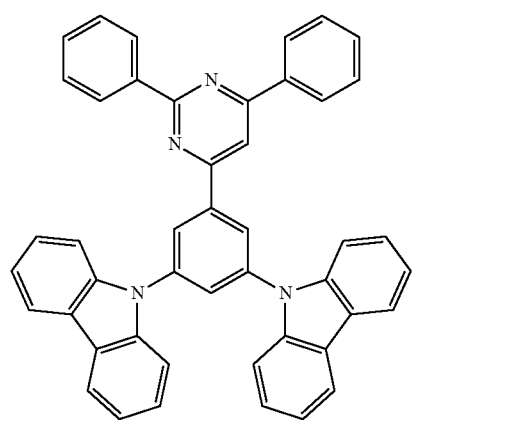
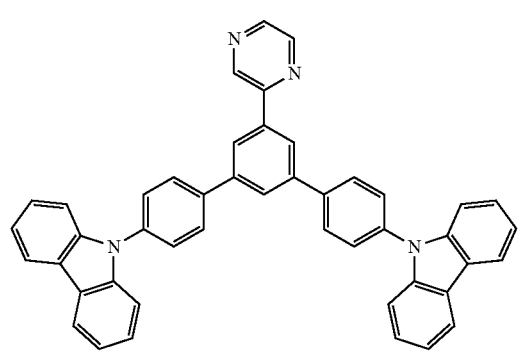
354
-continued
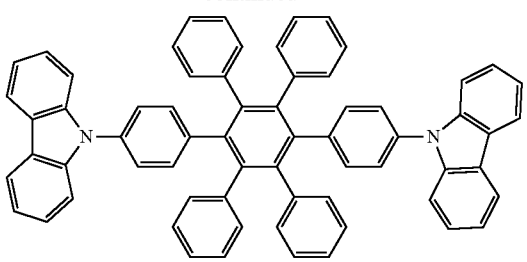
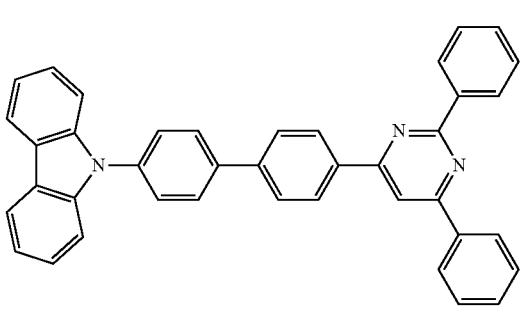
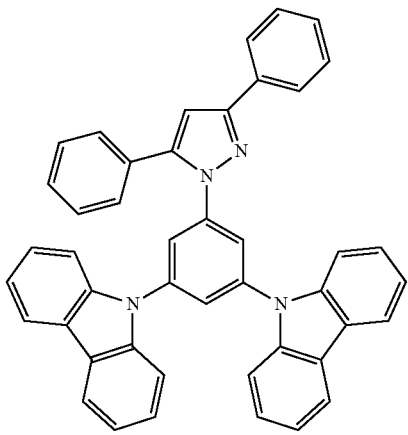
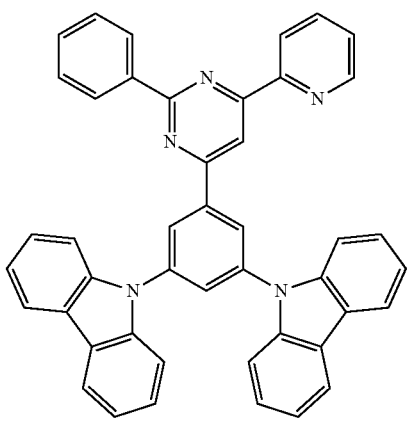

355
-continued
356
-continued
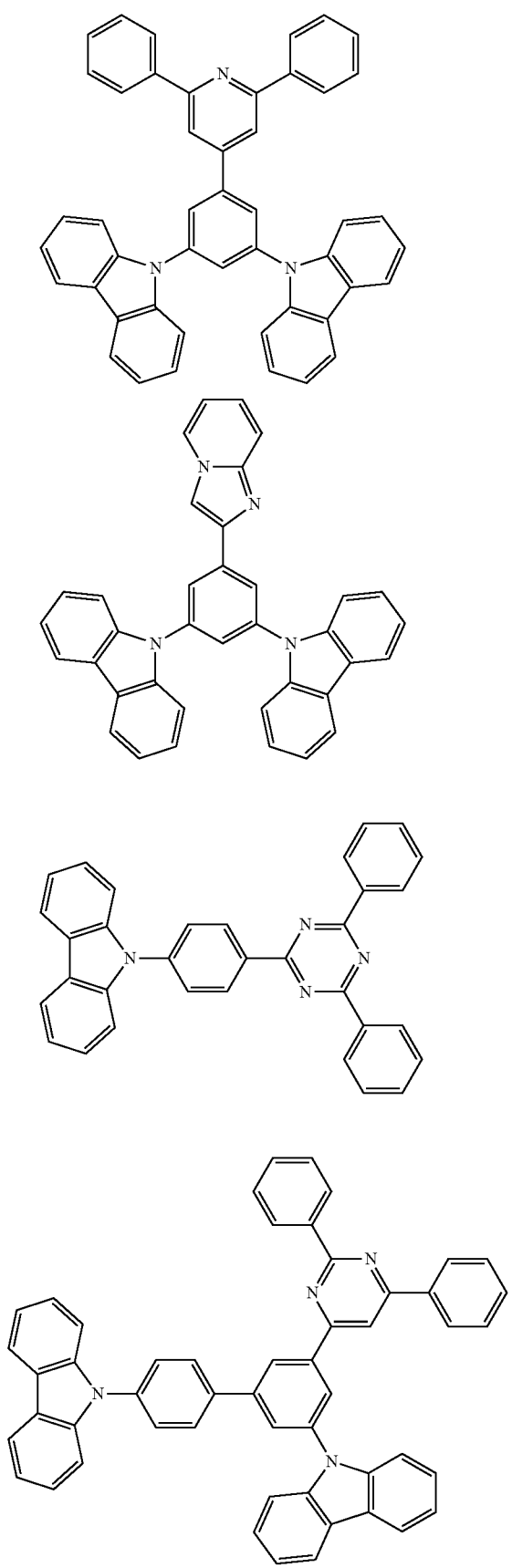
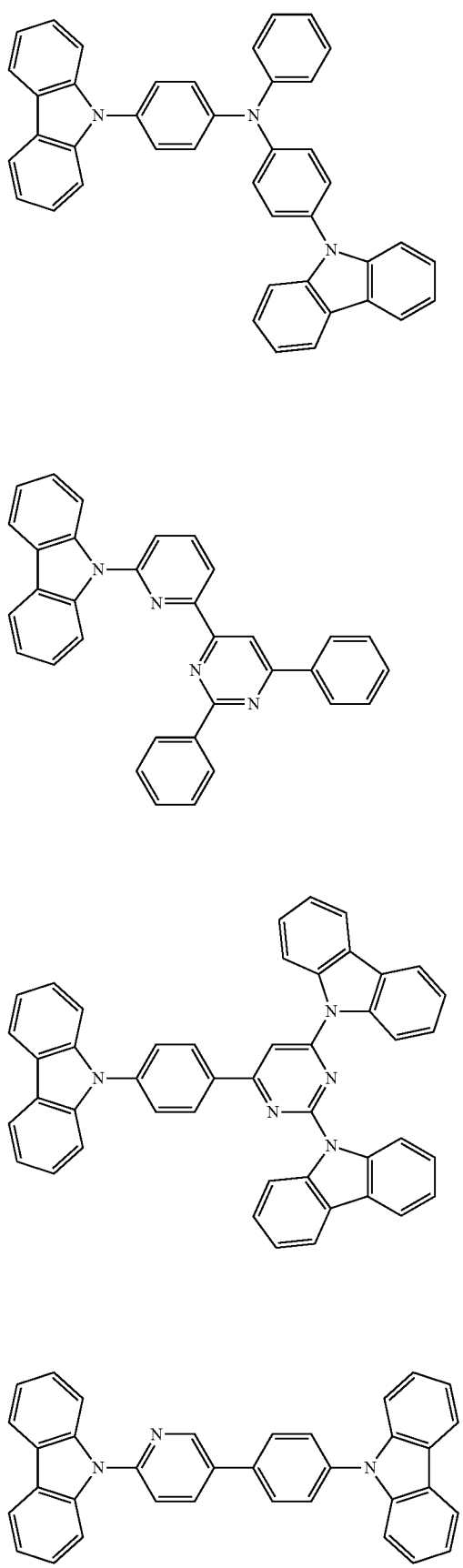

357
-continued
358
-continued
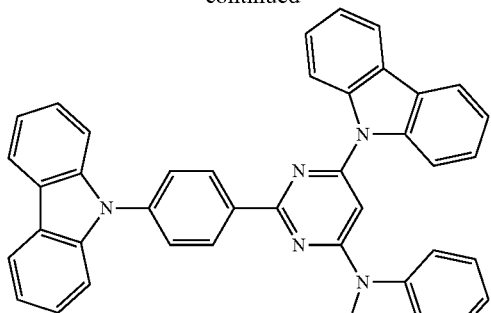
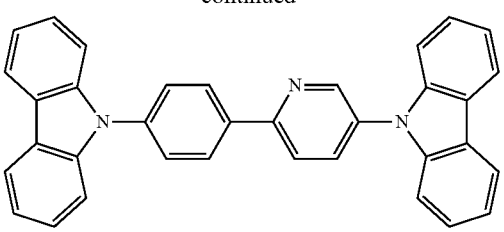
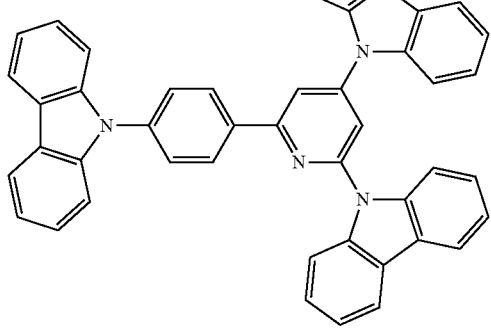
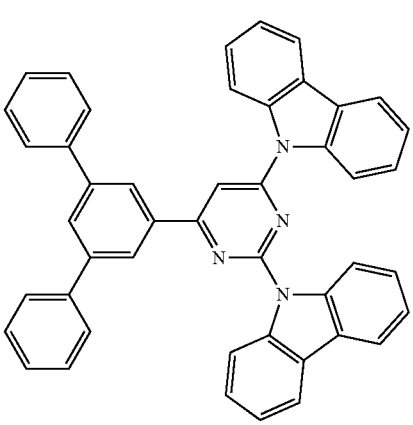
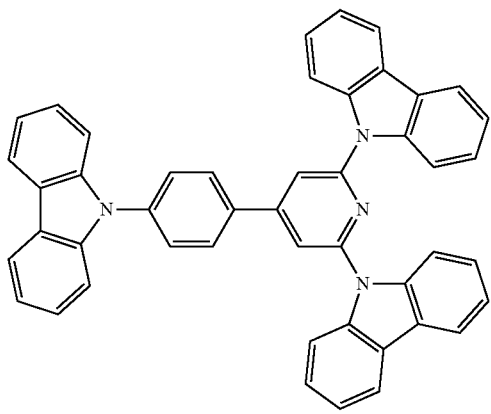
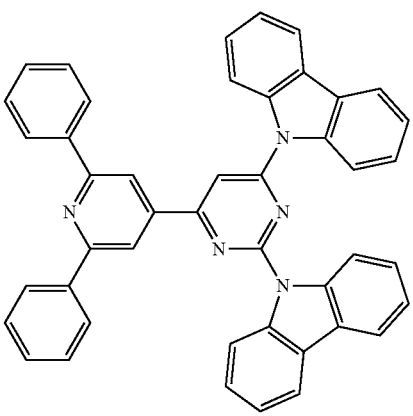
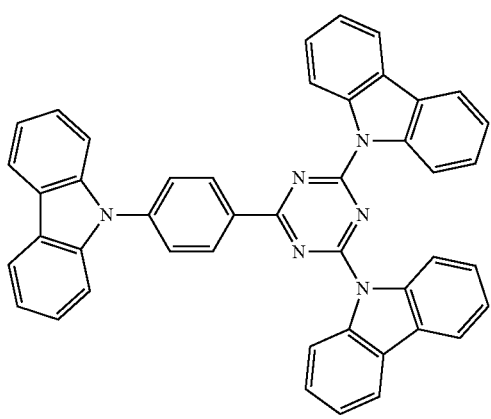
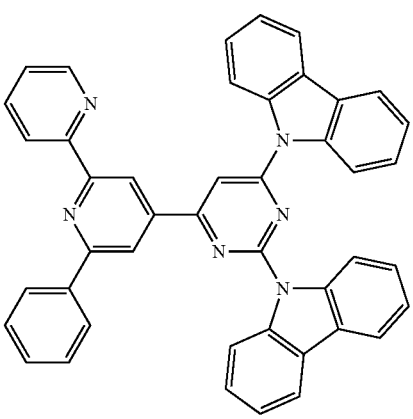

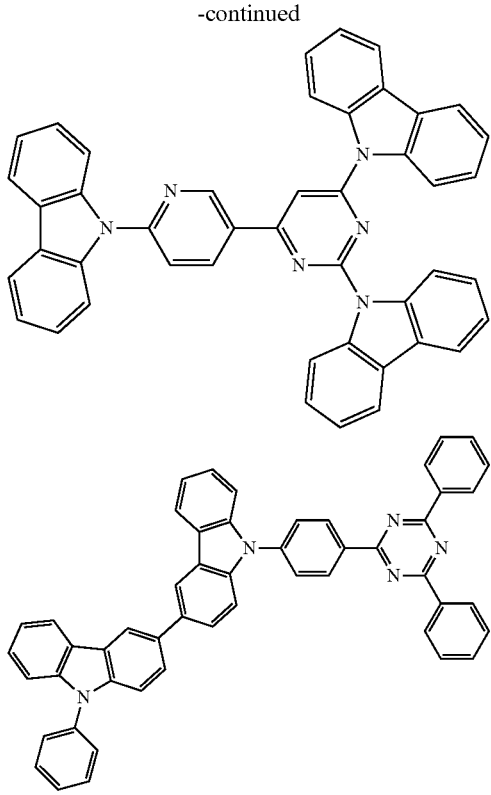

A double host (host/co-host) system may be used for the light emitting layer. For example, to control the carrier balance in the light emitting layer, an electron transporting host and a hole transporting host may be combinedly used.

The light emitting layer may be also made into a double dopant layer. When two or more kinds of dopant materials having high quantum yield are used in the light emitting layer, each dopant emits light with its own color. For example, a yellow light emitting layer can be obtained by co-depositing a host, a red-emitting dopant and a green-emitting dopant.

The light emitting layer may further comprise a hole transporting material, a electron transporting material, and a polymer binder, if necessary.

The thickness of the light emitting layer is preferably 5 to 50 nm, more preferably 7 to 50 nm and most preferably 10 to 50 nm. If less than 5 nm, the light emitting layer may be difficult to form and the color may be difficult to control. If exceeding 50 nm, the driving voltage is likely to increase.

(6) Electron Injecting/Transporting Layer

The electron injecting/transporting layer is a layer which helps the injection of electrons into the light emitting layer, transports the electrons to the light emitting region, and has a large electron mobility. The adhesion improving layer is an electron injecting/transporting layer comprising a material having a good adhesion particularly to the cathode.

The emitted light is reflected by an electrode (cathode in this case). Therefore, it has been known that the emitted light directly passing through an anode and the emitted light passing through the anode after reflected by the electrode interfere with each other. To effectively utilize this interference effect, the thickness of the electron injecting/transporting layer is appropriately selected from several nanometers to several micrometers. When the thickness is large, the electron mobility is preferably $10^{-5}$ cm$^2$/Vs or more at an electric field of $10^4$ to $10^6$ V/cm in order to avoid the increase in voltage.

A metal complex of 8-hydroxyquinoline or its derivative or an oxadiazole derivative is suitable as the material for the electron injecting/transporting layer. Specific examples of the metal complex of 8-hydroxyquinoline or its derivative include metal chelate oxynoid compounds containing a chelate of oxine (generally 8-quinolinol or 8-hydroxyquinoline), such as tris(8-quinolinol)aluminum.

Examples of the electron injecting material include the compounds represented by any of formulae (31) to (36):

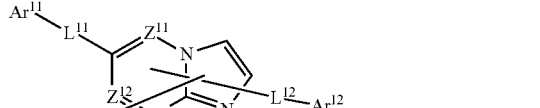

(31)

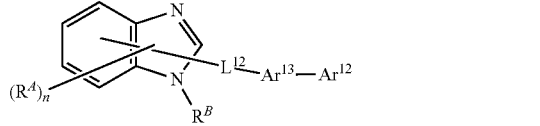

(32)

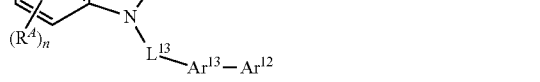

(33)

wherein:

$Z^{11}$, $Z^{12}$, and $Z^{13}$ each independently represent a nitrogen atom or a carbon atom;

$R^A$ and $R^B$ each independently represent a substituted or unsubstituted aryl group having 6 to 50, preferably 6 to 30, more preferably 6 to 20, and still more preferably 6 to 12 carbon atoms, a substituted or unsubstituted heteroaryl group having 5 to 50, preferably 5 to 30, more preferably 5 to 20, and still more preferably 5 to 12 ring atoms, an alkyl group having 1 to 20, preferably 1 to 10, and more preferably 1 to 6 carbon atoms, a haloalkyl group having 1 to 20, preferably 1 to 10, and more preferably 1 to 6 carbon atoms, or an alkoxy group having 1 to 20, preferably 1 to 10, and more preferably 1 to 6 carbon atoms, $R^A$ of formula (31) and (32) may be bonded to either of the five-membered ring and the six-membered ring, and preferably to the six-membered ring, and $R^A$ of formula (33) is bonded to the six-membered ring;

n represents an integer of 0 to 5, when n represents an integer or 2 or more, groups $R^A$ may be the same or different and adjacent groups $R^A$ may be bonded to each other to form a substituted or unsubstituted aromatic hydrocarbon ring;

$Ar^{12}$ represents a substituted or unsubstituted aryl group having 6 to 50, preferably 6 to 30, more preferably 6 to 20, and still more preferably 6 to 12 carbon atoms or a substituted or unsubstituted heteroaryl group having 5 to 50, preferably 5 to 30, more preferably 5 to 20, and still more preferably 5 to 12 ring atoms;

$Ar^{12}$ represents a hydrogen atom, an alkyl group having 1 to 20, preferably 1 to 10, and more preferably 1 to 6 carbon atoms, a haloalkyl group having 1 to 20, preferably 1 to 10, and more preferably 1 to 6 carbon atoms, an alkoxy group having 1 to 20, preferably 1 to 10, and more preferably 1 to 6 carbon atoms, a substituted or unsubstituted aryl group having 6 to 50, preferably 6 to 30, more preferably 6 to 20, and still more preferably 6 to 12 ring carbon atoms, or a substituted or unsubstituted heteroaryl group having 5 to 50, preferably 5 to 30, more preferably 5 to 20, and still more preferably 5 to 12 ring atoms;

provided that one of $Ar^{11}$ and $Ar^{12}$ represents a substituted or unsubstituted fused ring group having 10 to 50, preferably 10 to 30, more preferably 10 to 20, and still more preferably 10 to 14 ring carbon atoms or a substituted or unsubstituted fused heterocyclic group having 9 to 50, preferably 9 to 30, more preferably 9 to 20, and still more preferably 9 to 14 ring atoms;

$Ar^{13}$ represents a substituted or unsubstituted arylene group having 6 to 50, preferably 6 to 30, more preferably 6 to 20, and still more preferably 6 to 12 ring carbon atoms or a substituted or unsubstituted heteroarylene group having 5 to 50, preferably 5 to 30, more preferably 5 to 20, and still more preferably 5 to 12 ring atoms; and $L^{11}$, $L^{12}$ and $L^{13}$ each independently represent a single bond, a substituted or unsubstituted arylene group having 6 to 50, preferably 6 to 30, more preferably 6 to 20, and still more preferably 6 to 12 ring carbon atoms, a substituted or unsubstituted fused heterocyclic group having 9 to 50, preferably 9 to 30, more preferably 9 to 20, and still more preferably 9 to 14 ring atoms, or a substituted or unsubstituted fluorenylene group, and $L^{12}$ of formula (31) and $L^{13}$ or formula (32) may be bonded to either of the five-membered ring and the six membered ring, and preferably to the five-membered ring.

Examples of the aryl group and the alkyl group for $R^A$, $R^B$, $Ar^{11}$, and $Ar^{12}$ are the same as those described above with respect to $R^{21}$ to $R^{24}$ of formula (B). Examples of the alkyl group are the alkyl groups bonded with an oxygen atom. Examples of the heteroaryl group for $R^A$, $R^B$, $Ar^{11}$, and $Ar^{12}$ include a pyrrolyl group, a pyridinyl group, a pyrazinyl group, a pyrimidinyl group, an indolyl group, an isoindolyl group, a furyl group, a benzofuranyl group, an isobenzofuranyl group, a quinolinyl group, an isoquinolinyl group, a quinoxalinyl group, a carbazolyl group, a phenanthridinyl group, and an acridinyl group. Examples of the arylene groups for $Ar^{13}$, $L^{11}$, $L^{12}$, and $L^{13}$ include divalent residues of the aryl groups and examples of the fused heterocyclic group include the fused ring groups selected from the heteroaryl group having the corresponding number of carbon atoms.

  (34)

wherein X represents a fused ring comprising a nitrogen atom or a sulfur atom Y represents a single bond, an alkyl linkage, an alkylene linkage, a cycloalkyl linkage, an aryl linkage, a heterocyclic linkage, a silyl linkage, an ether linkage, a thioether linkage, or a linkage derived by combining any of the preceding linkages; and q is a natural number of 2 or more.

The molecular weight of the compound represented by formula (34) is 480 or more.

  (35)

wherein A represents a group comprising a phenanthroline skeleton or a benzoquinoline skeleton, B represents a p-valent organic group comprising a structure represented by formula (35A), and p is a natural number of 2 or more:

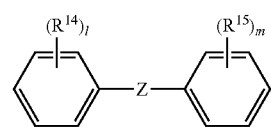

(35A)

wherein $R^{14}$ and $R^{15}$ each independently represent an alkyl group or an aryl group inclusive of an aryl group fused to a phenyl group, l and m each independently represent a natural number of 0 to 5, and Z represents at least one group selected from formula (35B):

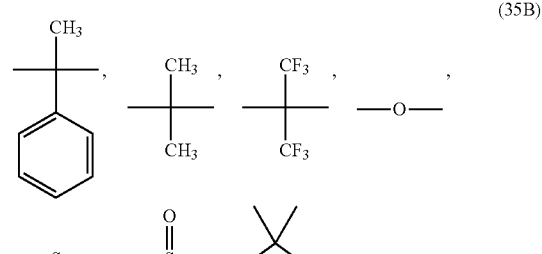

(35B)

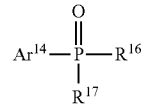

(36)

wherein $R^{16}$ and $R^{17}$ may be the same or different and each independently selected from a hydrogen atom, an alkyl group, a cycloalkyl group, a heterocyclic group, an alkenyl group, a cycloalkenyl group, an alkynyl group, an alkoxy group, an alkyithio group, an aryl ether group, an aryl thioether group, an aryl group, a heteroaryl group, a cyano group, a carbonyl group, an ester group, a carbamoyl group, an amino group, a silyl group, and a fused ring formed by adjacent groups, and $Ar^{14}$ represents an aryl group or a heteroaryl group.

The organic EL device of the present invention preferably comprises at least one selected from an electron-donating dopant and an organometallic complex in an interfacial region between the cathode and the organic thin film layer.

With such a construction, the organic EL device has an improved luminance and an elongated lifetime.

Examples of the electron-donating dopant include at least one compound selected from an alkali metal, an alkali metal compound, an alkaline earth metal, an alkaline earth metal compound, a rare earth metal, and a rare earth metal compound.

Examples of the organometallic complex include at least one complex selected from an organometallic complex containing an alkali metal, an organometallic complex containing an alkaline earth metal, and an organometallic complex containing a rare earth metal.

Examples of the alkali metal include lithium (Li) (work function: 2.93 eV), sodium (Na) (work function: 2.36 eV), potassium (K) (work function: 2.28 eV), rubidium (Rb) (work function: 2.16 eV), and cesium (Cs) (work function: 1.95 eV), with those having a work function of 2.9 eV or less being particularly preferred. Of the above, preferred are K, Rb, and Cs, more preferred are Rb and Cs, and most preferred is Cs.

Examples of the alkaline earth metal include calcium (Ca) (work function: 2.9 eV), strontium (Sr) (work function: 2.0 to 2.5 eV), and barium (Ba) (work function: 2.52 eV), with those having a work function of 2.9 eV or less being particularly preferred.

Examples of the rare earth metal include scandium (Sc), yttrium (Y), cerium (Ce), terbium (Tb), and ytterbium (Yb), with those having a work function of 2.9 eV or less being particularly preferred.

The preferred metals described above have a particularly high reducing ability. Therefore, the emission luminance and life time of an organic EL device can be improved by adding a relatively small amount of the metal to an electron injecting region.

Examples of the alkali metal compound include an alkali oxide, such as lithium oxide ($Li_2O$), cesium oxide ($Cs_2O$), and potassium oxide ($K_2O$), and an alkali halide, such as lithium fluoride (LiF), sodium fluoride (NaF), cesium fluoride (CsF), and potassium fluoride (KF), with lithium fluoride (LiF), lithium oxide ($Li_2O$), and sodium fluoride (NaF) being preferred.

Examples of the alkaline earth metal compound include barium oxide (BaO), strontium oxide (SrO), calcium oxide (CaO), and a mixture thereof, such as a barium salt of strontium acid ($Ba_xSr_{1-x}O$) (0<x<1) and a barium salt of calcium acid ($Ba_xCa_{1-x}O$) (0<x<1), with BaO, SrO, and CaO being preferred.

Examples of the rare earth metal compound include Ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$), and terbium fluoride ($TbF_3$), with $YbF_3$, $ScF_3$, and $TbF_3$ being preferred.

The organic metal complex is not particularly limited as long as it comprises at least one metal ion selected from alkali metal ions, alkaline earth metal ions, and rare earth metal ions, as described above. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, bipyridyl, phenanthroline, phthalocyanine, porphyrin, cyclopentadiene, β-diketones, azomethines, and derivative thereof.

The electron-donating dopant and organic metal complex are preferably formed into a layered form or an island form at the interfacial region. The electron-donating dopant and/or the organic metal complex is preferably co-deposited with the organic material (the light emitting material and the electron injecting material) for forming the interfacial region by a resistance heating deposition method, thereby dispersing the electron-donating dopant and/or the organic metal complex into the organic material. The disperse concentration expressed by the molar ratio of the organic material and the electron-donating dopant and/or the organic metal complex is generally 100:1 to 1:100 and preferably 5:1 to 1:5.

When the electron-donating dopant and/or the organic metal complex is formed into a layered form, a light emitting material or an electron injecting material is made into a layered form to form an interfacial organic layer, and then, the electron-donating dopant and/or the organic metal complex is deposited by a resistance heating deposition method into a layer having a thickness preferably 0.1 to 15 nm.

When the electron-donating dopant and/or the organic metal complex is formed into an island form, a light emitting material or an electron injecting material is made into an island form to form an interfacial organic layer, and then, the electron-donating dopant and/or the organic metal complex is deposited by a resistance heating deposition method into a form of island having a thickness preferably 0.05 to 1 nm.

The molar ratio of the main component and the electron-donating dopant and/or the organic metal complex in the organic EL device of the invention is preferably 5:1 to 1:5 and more preferably 2:1 to 1:2.

(7) Cathode

In view of injecting electrons into the electron injecting/transporting layer or the light emitting layer, the cathode is formed from an electrode material, such as a metal, an alloy, an electrically conductive compound and a mixture thereof, each having a small work function (4 eV or smaller). Examples of the electrode material include sodium, sodium-potassium alloy, magnesium, lithium, magnesium-silver alloy, aluminum/aluminum oxide, aluminum-lithium alloy, indium, and rare earth metal.

The cathode is formed by making the electrode material described above into a thin film by a process, such as a vapor deposition process and a sputtering process.

When the light emitted from the light emitting layer is taken through the cathode, the transmittance of the cathode to the emitted light is preferably 10% or more.

The sheet resistivity of the cathode is preferably several hundreds $\Omega/\square$ or less and the thickness of the cathode is generally 10 nm to 1 μm and preferably 50 to 200 nm.

8) Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

(9) Production of Organic EL Device

The organic EL device is produced, for example, by forming an anode, a light emitting layer, a hole transporting layer, and an optional electron injecting/transporting layer, and then forming a cathode by using the materials and production methods mentioned above. Alternatively, the organic EL device is produced by forming each layer in a reverse order from the cathode to the anode.

Example of the production of an organic EL device having a layered structure: anode/hole transporting layer/light emitting layer/electron injecting-transporting layer/cathode on a light-transmissive substrate will be described below.

First, on a suitable light-transmissive substrate, an anode is formed by making an anode material into a thin film having a thickness of 1 μm or less, preferably 10 to 200 nm by a method, such as vapor deposition and sputtering. Then, at least two hole transporting layers are formed on the anode. These hole transporting layers may be formed by a vacuum vapor deposition method, a spin coating method, a casting method or LB method, with the vacuum vapor deposition method being preferred because a uniform film is easily obtained and pinholes are hardly formed.

The conditions of the vacuum vapor deposition method for forming the hole transporting layers depend upon the compounds (hole transporting layer material) to be used and the crystalline structure and recombination structure of the intended hole transporting layers. Generally, the vacuum vapor deposition is conducted preferably under the conditions: a deposition source temperature of 50 to 450° C., a vacuum degree of $10^{-7}$ to $10^{-3}$ torr, a deposition speed of 0.01 to 50 nm/s, a substrate temperature of −50 to 300° C., and a film thickness of 5 nm to 5 μm.

Then, a light emitting layer is formed on the hole transporting layer. The light emitting layer is formed by making an organic light emitting material into a thin film by a vacuum vapor deposition method, a spin coating method, or a casting method, with the vacuum vapor deposition method being preferred because a uniform film is easily obtained and pinholes are hardly formed. The conditions of the vacuum vapor deposition method for forming the light emitting layer depend upon the kind of the compound to be used, and generally selected from those mentioned with respect to the hole transporting layer.

Next, an electron injecting/transporting layer is formed on the light emitting layer. Like the formation of the hole transporting layer and the light emitting layer, the electron transporting layer is formed preferably by the vacuum vapor deposition method because a uniform thin film is needed. The conditions of the vacuum vapor deposition are selected from those mentioned with respect to the hole transporting layer and the light emitting layer.

Finally, a cathode is formed on the electron injecting/transporting layer, to obtain an organic EL device.

The cathode is made of a metal and can be formed by the vapor deposition method or the sputtering method, with the vacuum vapor deposition method being preferred in view of preventing the underlying organic layers from being damaged during the film forming process.

In the production of organic EL device mentioned above, the layers from the anode to the cathode are successively formed preferably in a single evacuation operation.

The light emission is observed when applying a direct voltage of 5 to 40 V to the organic EL device such that the anode is charged to + polarity and the cathode is charged to − polarity. If a voltage is applied in the reverse polarity, no electric current flows and light is not emitted. When an alternating voltage is applied, the uniform light emission is observed only when the anode is charged to + polarity and the cathode is charged to − polarity. The wave shape of alternating voltage in not limited.

By using the compound of the invention in the production of an organic EL device, the thickness of the hole transporting layer can be increased to make it easy to adjust the optical thickness and the emission efficiency and lifetime of the device are improved. Therefore, the organic EL device of the invention is usable in electronic equipment, for example, as display parts, such as organic EL panel module, display devices of television sets, mobile phones, personal computer, etc., and light emitting sources of lighting equipment and vehicle lighting equipment, and particularly useful as a backlight for flat light sources and displays.

EXAMPLES

The present invention is described in more detail with reference to the examples. However, it should be noted that the scope of the invention is not limited thereto.

Synthesis 1: Synthesis of Intermediate 1-2

1. Synthesis of Intermediate 1-1

Under an argon atmosphere, 23 g (90.6 mmol) of iodine, 9.4 g (41.2 mmol) of periodic acid dihydrate, 42 ml of water, 360 ml of acetic acid, and 11 ml of sulfuric acid were added to 55 g (201.3 mmol) of 2-bromo-9,9-dimethylfluorene. The resultant mixture was stirred at 65° C. fro 30 min and further stirred at 90° C. for 6 h.

After the reaction, the reaction product was poured into iced water and the precipitated crystal was collected by filtration. After washed with water and then with methanol, 61 g of a white solid was obtained (yield: 76%), which was identified by FD-MS analysis as the following intermediate 1-1.

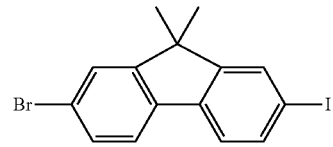

Intermediate 1-1

2. Synthesis of Intermediate 1-2

Under an argon atmosphere, 300 mL of toluene and 150 mL of a 2 M aqueous solution of sodium carbonate were added to 39.9 g of the intermediate 1, 20.8 g of 4-biphenylboronic acid, and 2.31 g of tetrakis(triphenylphosphine) palladium(0). The resultant mixture was refluxed under heating for 10 h.

After the reaction, the reaction mixture was immediately filtered and the water layer was removed. The organic layer was dried over sodium sulfate and concentrated. The residue was purified by silica gel column chromatography to obtain 34.3 g of a white crystal (yield: 81%), which was identified by FD-MS analysis as the following intermediate 1-2.

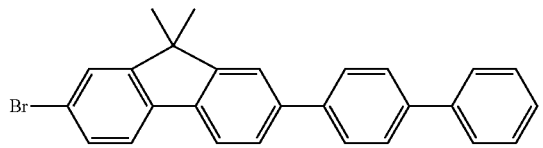

Intermediate 1-2

Synthesis 2: Synthesis of Intermediate 2-1

Under an argon atmosphere, 500 ml of dehydrated toluene was added to 23.3 g (100.0 mmol) of 2-bromobiphenyl, 20.9 g (100.0 mmol) of 9,9-dimethylaminofluorene, 13.0 g (135.3 mmol) of sodium t-butoxide, 460 mg (0.5 mmol) of tris (dibenzylideneacetone) dipalladium(0), and 210 mg (1.04 mmol) of tri-t-butylphosphine. The resultant mixture was allowed to react at 80° C. for 8 h.

After cooling, 2.5 l of water was added and the resultant mixture was filtered through celite. The filtrate was extracted with toluene, and the extract was dried over anhydrous magnesium sulfate and then concentrated under reduced pressure. The obtained residue was purified by silica gel column chromatography and recrystallized from toluene. The purified product was collected by filtration and dried to obtain 14.4 g of a pale yellow solid (yield: 40%), which was identified by FD-MS analysis as the following intermediate 2-1.

Intermediate 2-1

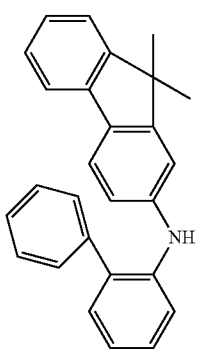

Synthesis 3: Synthesis of Intermediate 2-2

Under an argon atmosphere, 500 ml of dehydrated toluene was added to 23.3 g (100.0 mmol) of 2-bromobiphenyl, 18.3 g (100.0 mmol) of 2-aminodibenzofuran, 13.0 g (135.3 mmol) of sodium t-butoxide, 460 mg (0.5 mmol) of tris (dibenzylideneacetone) dipalladium(0), and 210 mg (1.04 mmol) of tri-t-butylphosphine. The resultant mixture was allowed to react at 80° C. for 8 h After cooling, 2.5 l of water was added and the resultant mixture was filtered through celite. The filtrate was extracted with toluene, and the extract was dried over anhydrous magnesium sulfate and then concentrated under reduced pressure. The residue was purified by silica gel column chromatography and recrystallized from toluene. The purified product was collected by filtration and dried to obtain 11.7 g of a pale yellow solid (yield: 35%), which was identified by FD-MS analysis as the following intermediate 2-2.

Intermediate 2-2

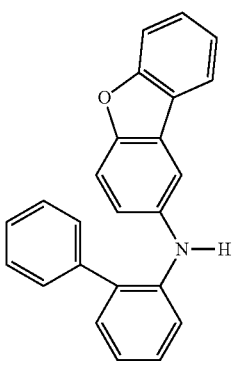

Synthesis 4: Synthesis of Intermediate 2-4

1. Synthesis of Intermediate 2-3

Under an argon atmosphere, 300 mL of toluene, 100 ml of a 1 M aqueous solution of sodium carbonate, and 100 ml of ethanol were added to 21.9 g (100.0 mmol) of 2-iodoaniline, 19.81 g (100.0 mmol) of 4-biphenylboronic acid, 0.225 g (1.00 mmol) of palladium acetate, and 0.61 g (2.00 mmol) of tri-(o-tolyl)phosphine. The resultant mixture was allowed to react at 65° C. for 2 h.

After the reaction, a hot water was added. The resultant mixture was extracted and the extract was concentrated. The residue was made into powder in methanol and the powder was collected by filtration and dried to obtain 19.15 g of a beige solid (yield: 78%), which was identified by FD-MS analysis as the following intermediate 2-3.

Intermediate 2-3

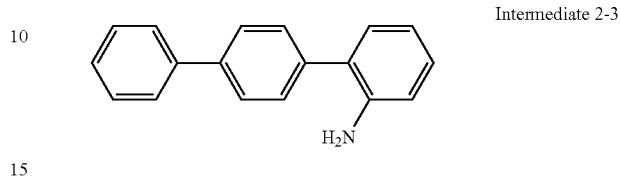

2. Synthesis of Intermediate 2-4

Under an argon atmosphere, 150 mL of dehydrated toluene was added to 15.00 g (61.14 mmol) of the intermediate 2-3, 9.41 g (59.93 mmol) of bromobenzene, 8.23 g (85.59 mmol) of sodium t-butoxide, 0.75 g (0.92 mmol) of 1,1'-bis (diphenylphosphino)ferrocene-palladium(II) dichloride dichloromethane complex, and 1.02 g (1.84 mmol) of 1,1'-bis(phenylphosphino)ferrocene phosphine. The resultant mixture was allowed to react at 85° C. for 2 h.

After the reaction, a hot water was added. The resultant mixture was extracted and the extract was treated with activated carbon and concentrated. The residue was made into powder in methanol and the powder was collected by filtration and dried to obtain 17.53 g a gray solid (yield: 91%), which was identified by FD-MS analysis as the following intermediate 2-4.

Intermediate 2-4

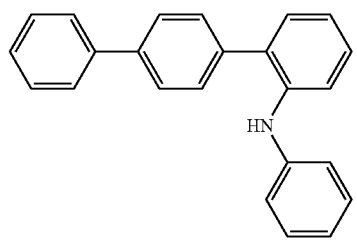

Synthesis 5: Synthesis of Intermediate 2-5

Under an argon atmosphere, 150 mL of dehydrated toluene was added to 9.8 g of the intermediate 2-3, 8.3 g of 2-bromonaphthalene, 5.5 g of sodium t-butoxide, 288 mg of [1,1'-bis(diphenylphosphino)ferrocene]palladium(II) dichloride dichloromethane adduct, and 391 mg of 1,1'-bis (diphenylphosphino)ferrocene. The resultant mixture was allowed to react at 85° C. for 4 h.

After cooling, 750 mL of water was added. The resultant mixture was filtered through celite and the filtrate was extracted with toluene. The extract was dried over anhydrous magnesium sulfate and concentrated under reduced pressure. The obtained residue was purified by silica gel column chromatography and recrystallized from toluene. The purified product was collected by filtration and dried to obtain 14.4 g of a pale yellow solid (yield: 98%), which was identified by FD-MS analysis as the following intermediate 2-5.

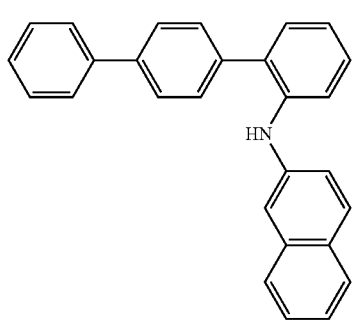

Intermediate 2-5

Synthesis 6: Synthesis of Intermediate 2-6

Under an argon atmosphere, 215 ml of dehydrated toluene was added to 23.3 g (95.0 mmol) of the intermediate 2-3, 21.5 g (92.2 mmol) of 4-bromobiphenyl, 12.7 g (132 mmol) of sodium t-butoxide, 211 mg (0.94 mmol) of palladium(II) acetate, and 1.04 g (1.88 mmol) of bis(diphenylphosphino) ferrocene. The resultant mixture was allowed to react at 80° C. for 3 h.

After cooling, 215 ml of methanol was added. The precipitated crystal was collected by filtration, purified by silica gel column chromatography, and recrystallized from toluene. The purified product was collected by filtration and dried to obtain 30.2 g a pale yellow solid (yield: 82.3%), which was identified by FD-MS analysis as the following intermediate 2-6.

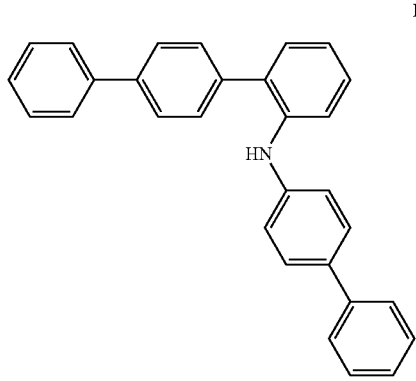

Intermediate 2-6

Synthesis 7: Synthesis of Intermediate 2-7

Under an argon atmosphere, 230 ml of dehydrated toluene was added to 25.0 g (102 mmol) of terphenyl-4-amine, 23.3 g (100 mmol) of 2-bromobiphenyl, 13.5 g (140 mmol) of sodium t-butoxide, 225 mg (1.00 mmol) of palladium(II) acetate, and 1.19 g (2.00 mmol) of bis(diphenylphosphino) ferrocene. The resultant mixture was allowed to react at 80° C. for 3 h.

After cooling, 230 ml or methanol was added. The precipitated crystal was collected by filtration. The obtained crude product was purified by silica gel column chromatography and recrystallized from toluene. The purified product was collected by filtration and dried to obtain 36.4 g of a pale yellow solid (yield: 91.6%), which was identified by FD-MS analysis as the following intermediate 2-7.

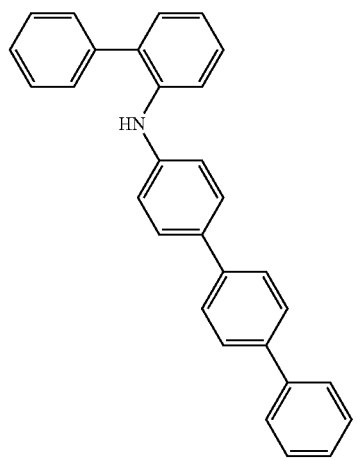

Intermediate 2-7

Synthesis Example 1: Synthesis of Compound 1

Under an argon stream, a mixture of 8.5 g of the intermediate 1-2, 7.2 g of the intermediate 2-1, 2.6 g of sodium t-butoxide, 92 mg of tris(dibenzylideneacetone) dipalladium (0), 42 mg of tri-t-butylphosphine, and 100 mL of dehydrated toluene was allowed to react at 80° C. for 8 h. After cooling, 500 mL of water was added and the resultant mixture was filtered, through celite. The filtrate was extracted with toluene. The extract was dried over anhydrous magnesium sulfate and concentrated under reduced pressure. The obtained crude product was purified by a column and recrystallized from toluene. The purified product was collected by filtration and dried to obtain 5.6 g of a pale yellow powder (yield: 40%), which was identified by FD-MS analysis as the following compound 1.

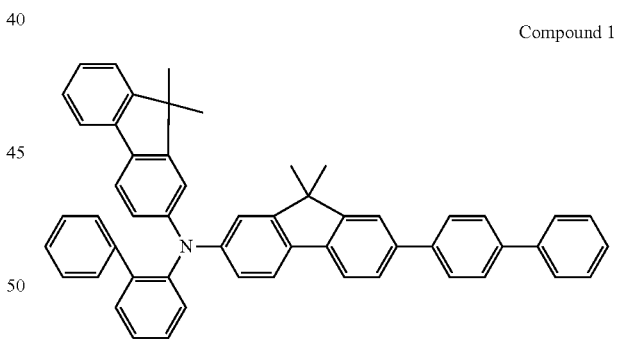

Compound 1

Synthesis Example 2: Synthesis of Compound 2

Under an argon stream, a mixture of 8.5 g of the intermediate 12, 6.7 g of the intermediate 2-2, 2.6 g of sodium t-butoxide, 92 mg of tris(dibenzylideneacetone) dipalladium (0), 42 mg of tri-t-butylphosphine, and 100 mL of dehydrated toluene was allowed to react at 80° C. for 8 h. After cooling, 500 mL of water was added and the resultant mixture was filtered through celite. The filtrate was extracted with toluene. The extract was dried over anhydrous magnesium sulfate and concentrated under reduced pressure. The obtained crude product was purified by a column and recrystallized from toluene. The purified product was collected by filtration and dried to obtain 4.7 g of a pale yellow powder (yield: 35%), which was identified by FD-MS analysis as the following compound 2.

Compound 2

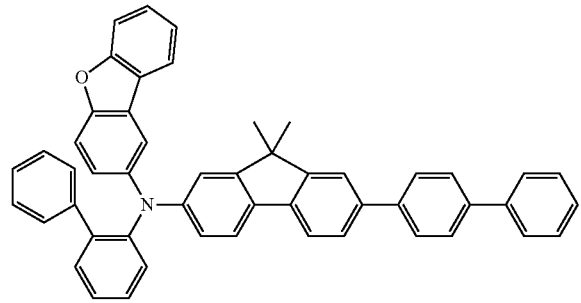

Synthesis Example 3: Synthesis of Compound 3

Under an argon stream, a mixture of 10.0 g of the intermediate 1-2, 8.0 g of the intermediate 2-4, 3.2 g of sodium t-butoxide, 106 mg of palladium acetate, 448 mg of 2-dicyclohexylphosphino-2',4',6'-triisopropylbiphenyl (Xphos), and 150 mL dehydrated toluene was allowed to react at 95° C. for 3.5 h. After cooling, 750 mL of water was added and the resultant mixture was altered through celite. The filtrate was extracted with toluene. The extract was dried over anhydrous magnesium sulfate and concentrated under reduced pressure. The obtained crude product was purified by a column and recrystallized from toluene. The purified product was collected by filtration and dried to obtain 6.7 g of a pale yellow powder (yield: 40%), which was identified by FD-MS analysis as the following compound 3.

Compound 3

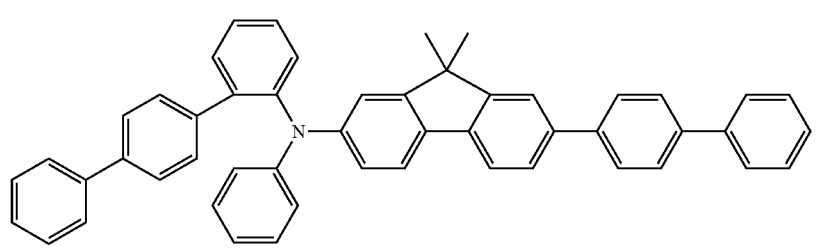

Synthesis Example 4: Synthesis of Compound 4

Under an argon stream, a mixture of 10.0 g of the intermediate 1-2, 8.7 g of the intermediate 2-5, 3.2 g of sodium t-butoxide, 106 mg of palladium acetate, 448 mg of 2-dicyclohexylphosphino-2',4',6'-triisopropylbiphenyl (Xphos), and 150 mL of dehydrated toluene was allowed to react at 95° C. for 3.5 h. After cooling, 750 mL of water was added and the resultant mixture was altered through celite. The filtrate was extracted with toluene. The extract was dried over anhydrous magnesium sulfate and concentrated under reduced pressure. The obtained crude product was purified by a column and recrystallized from toluene. The purified product was collected by filtration and dried to obtain 7.4 g of a pale yellow powder (yield: 39%), which was identified by FD-MS analysis as the following compound 4.

Compound 4

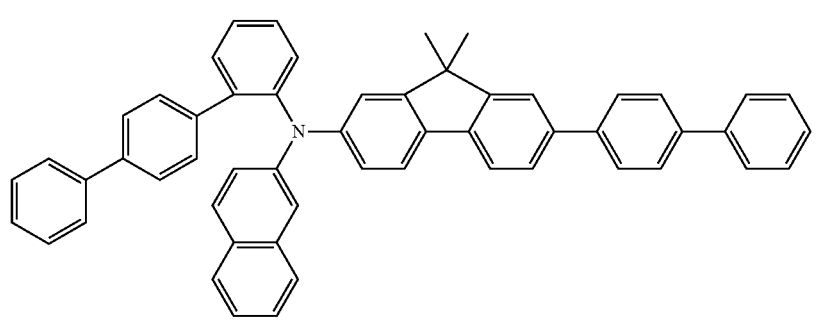

Synthesis Example 5: Synthesis of Compound 5

Under an argon stream, a mixture of 8.93 g of the intermediate 1-2, 8.35 g of the intermediate 2-6, 2.83 g of sodium t-butoxide, 48 mg of palladium(II) acetate, 201 mg of 2-dicyclohexylphosphino-2',4',6'-triisopropylbiphenyl (Xphos), and 80 mL of dehydrated toluene was allowed to react at 90° C. for 5 h. After cooling, 160 ml of methanol was added and the precipitated crystal was collected by filtration. The obtained crude product was purified by a column and recrystallized from toluene. The purified product was collected by filtration and dried to obtain 10.5 g of a white powder (yield: 67.2%), which was identified by FD-MS analysis as the following compound 5.

Synthesis Example 7: Synthesis of Compound 7

Under an argon atmosphere, a mixture of 8.09 g (25 mmol) of the intermediate 2-4, 10.12 g (25 mmol) of 9-(7-chloro-9,9-dimethyl-9H-fluorene-2-yl)phenanthrene, 3.36 g (35 mmol) of sodium t-butoxide, 56 mg (0.25 mmol) of palladium acetate, 238 mg (0.5 mmol) of 2-dicyclohexylphosphino-2',4',6'-triisopropylbiphenyl (Xphos), and 166 mL of toluene was stirred at 85° C. for 1.5 h, at 90° C. for 1.5 h, and then at 95 to 100° C. for 8 h.

After the reaction, a hot water was added. The resultant mixture was extracted and the extract was treated with activated carbon and concentrated. The residue was made into powder in methanol and the powder was collected by Compound 5

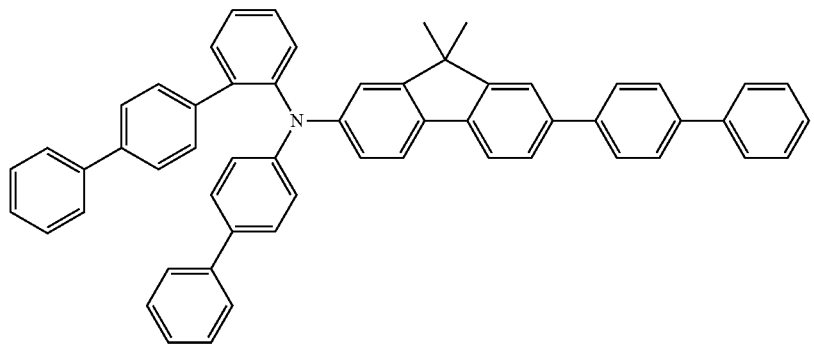

filtration and dried to obtain a crude product. The crude product was dispersed in toluene by stirring under heating and then collected by filtration and dried to obtain 4.33 g of a white powder (yield: 25%), which was identified by FD-MS analysis as the compound 7.

Synthesis Example 6: Synthesis of Compound 6

Under an argon stream, a mixture of 8.93 g of the intermediate 1-2, 8.35 g of the intermediate 2-7, 2.83 g of sodium t-butoxide, 48 mg of palladium(II) acetate, 201 mg of 2-dicyclohexylphosphino-2',4',6'-triisopropylbiphenyl (Xphos), and 80 mL of dehydrated toluene was allowed to react at 90° C. for 5 h. After cooling, 160 ml of methanol was added and the precipitated crystal was collected by filtration. The obtained crude product was purified by a column and recrystallized from toluene. The purified product was collected by filtration and dried to obtain 9.48 g of a pale yellow powder (yield: 60.8%), which was identified by FD-MS analysis as the following compound 6.

Compound 7

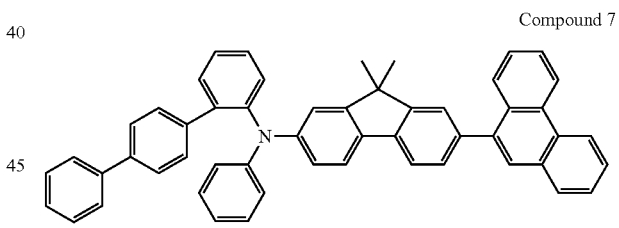

Example 1

Production of Organic EL Device

A glass substrate with an ITO transparent electrode having a size of 25 mm×75 mm×1.1 mm (manufactured by GEOMATEC Co., Ltd.) was ultrasonically cleaned in isopropyl alcohol for 5 min and then UV (ultraviolet)/ozone cleaned for 30 min.

The cleaned glass substrate with the transparent electrode line was mounted on the substrate holder of a vacuum deposition apparatus. First, the following acceptor material (A) was vapor-deposited onto the surface on the side where the transparent electrode line was formed so as to cover the transparent electrode, thereby forming an acceptor layer having a thickness of 5 nm.

Compound 6

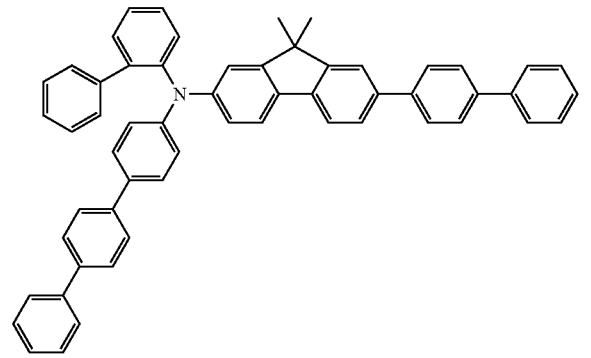

On the acceptor layer, the compound 1 obtained in Synthesis Example 1 as a first hole transporting material was vapor-deposited to form a first hole transporting layer having a thickness of 75 nm.

Successively after forming the first hole transporting layer, the following compound HT2 as a second hole transporting material was vapor-deposited to form a second hole transporting layer having a thickness of 15 nm.

On the second hole transporting layer, the following host material and the following dopant as the fluorescent materials were co-deposited to form a fluorescent emitting layer having a thickness of 25 nm. The concentration of the dopant in the fluorescent emitting layer was 5% by mass.

Then, a film of the compound ET2 having a thickness of 20 nm, a film of the compound ET1 having a thickness of 5 nm, a film of LiF having a thickness of nm, and a film of metallic Al having a thickness of 80 nm were successively deposited on the fluorescent emitting layer to form a cathode. The film of LiF as the electron injecting electrode was formed at a film-forming speed of 1 Å/min.

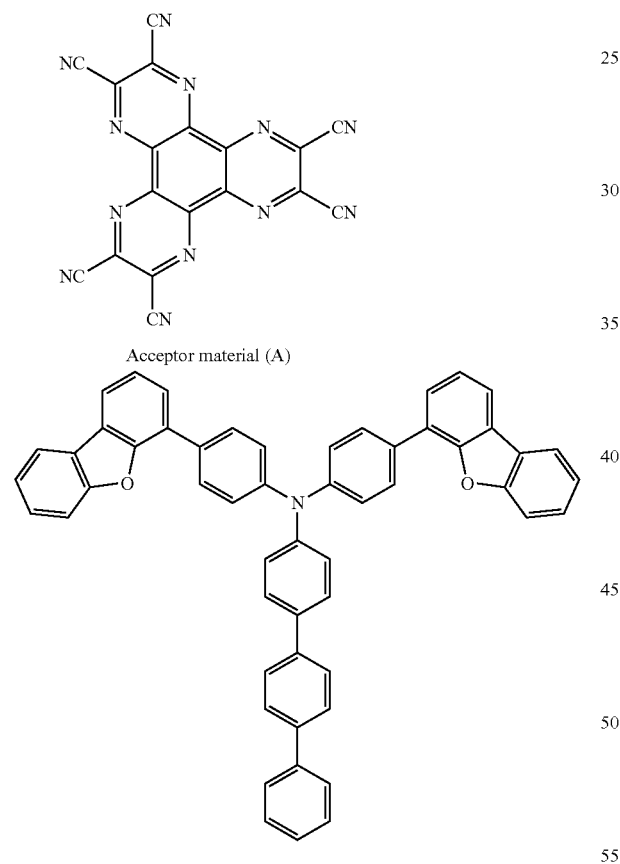

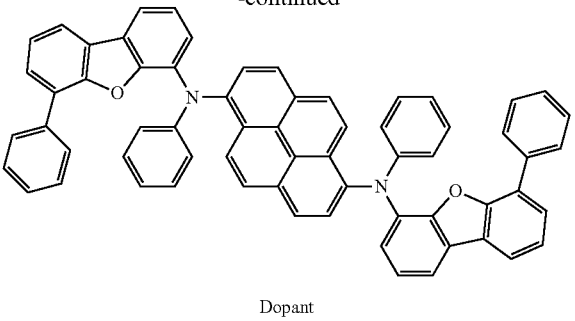

Dopant

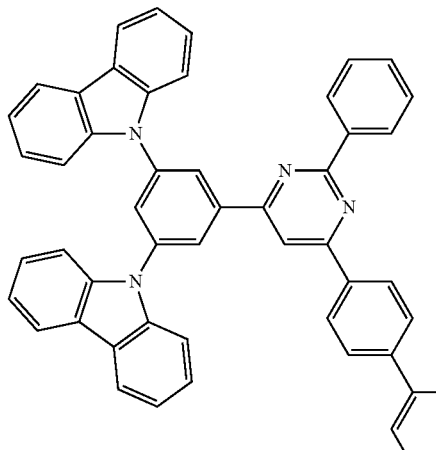

Electron transporting material (ET2)

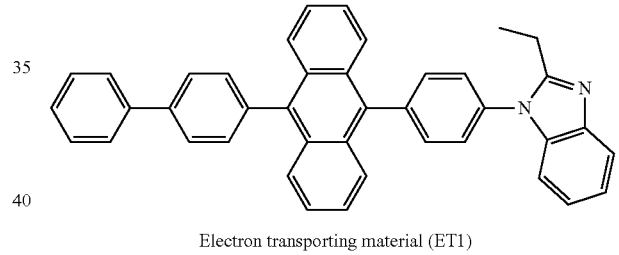

Electron transporting material (ET1)

Evaluation of Emission Performance of Organic EL Device

The organic EL device thus produced was measured for the luminance ($cd/m^2$) and the current density by driving the device at a direct current to emit light, thereby determining the emission efficiency (cd/A) and the driving voltage (V) at a current density of 10 $mA/cm^2$. The results are shown in Table 1.

Examples 2 and 3: Production of Organic EL Device

Each organic EL device was produced and evaluated in the same manner as in Example 1 except for using the compound 2 or 3 as the first hole transporting material in place of the compound 1. The results are shown in Table 1.

Comparative Example 1

Each organic EL device was produced and evaluated in the same manner as in Example 1 except for using the following comparative compound as the first hole transporting material in place of the compound 1. The results are shown in Table 1.

Comparative compound 1

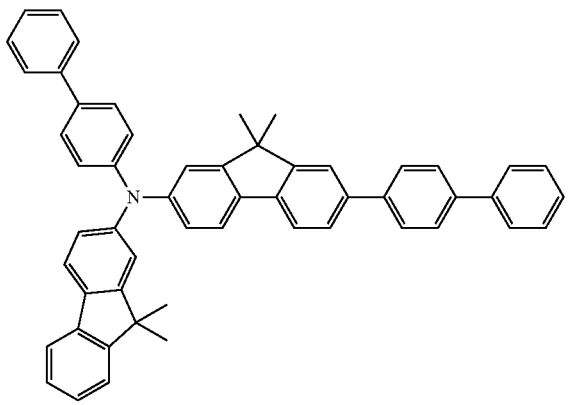

TABLE 1

| | Material of first hole transporting layer | Driving voltage (V) | Emission efficiency (cd/A) |
|---|---|---|---|
| Examples | | | |
| 1 | Compound 1 | 4.40 | 9.09 |
| 2 | Compound 2 | 4.62 | 9.00 |
| 3 | Compound 3 | 4.79 | 9.94 |
| Comparative Example | | | |
| 1 | Comparative compound 1 | 5.64 | 8.66 |

Upon comparing Examples 1 to 3 with Comparative Example 1, it can be found that the organic EL devices having first hole transporting layers comprising the compounds 1 to 3 are operated at lower voltage and have higher emission efficiency, as compared with the organic EL device having a hole transporting layer comprising a known aromatic amine derivative.

What is claimed is:

1. A compound represented by formula (1):

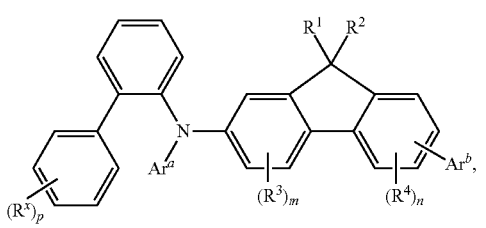

(1)

wherein:
Ar$^a$ represents an aryl group selected from the group consisting of a phenyl group, a biphenylyl group, a terphenylyl group, a naphthyl group, an anthryl group, a fluorenyl group, and a 9,9-dimethylfluorenyl group, a heteroaryl group having 5 to 50 ring atoms, or a group in which two to four groups selected from the aryl group and the heteroaryl group are linked;
R$^1$ and R$^2$ each independently represent a hydrogen atom, an alkyl group having 1 to 10 carbon atoms, or an aryl group having 6 to 12 ring carbon atoms;

R$^x$, R$^3$ and R$^4$ each represent an alkyl group having 1 to 10 carbon atoms, a cycloalkyl group having 3 to 10 ring carbon atoms, or an aryl group having 6 to 30 ring carbon atoms;
p represents an integer of 0 to 3,
m and n each independently represent an integer of 0 to 2,
R$^3$ and R$^4$ may be bonded to each other to form a hydrocarbon ring, and when m or n is 2, adjacent groups R$^3$ or adjacent groups R$^4$ may be bonded to each other to form a hydrocarbon ring; and
Ar$^b$ represents a member selected from the group consisting of a naphthyl group, a biphenylyl group, a para-terphenylyl group, a 9-phenanthryl group and an anthryl group;
with proviso that the compounds represented by above formula (1) do not include compounds of the following formulae;

Formel (101)

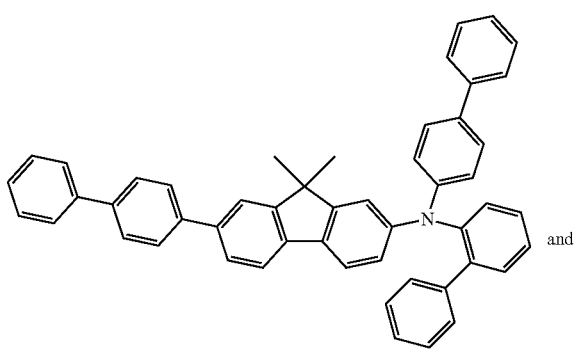

and

Formel (145)

2. The compound according to claim 1, wherein the compound is represented by formula (1'):

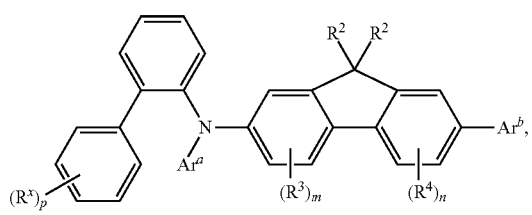

(1')

wherein Ar$^a$, Ar$^b$, R$^x$, R$^1$, R$^2$, R$^3$, R$^4$, p, m, and n are as defined in claim 1.

3. The compound according to claim 1, wherein $R^1$ and $R^2$ each independently represent a hydrogen atom or an alkyl group having 1 to 10 carbon atoms.

4. The compound according to claim 1, wherein $Ar^b$ is a biphenylyl group.

5. The compound according to claim 1, wherein p is 0 or 1.

6. The compound according to claim 1, wherein $Ar^a$ is a phenyl group.

7. The compound according to claim 1, wherein $Ar^a$ comprises a fused aryl group selected from the group consisting of a naphthyl group, an anthryl group, a fluorenyl group, a phenanthryl group and a 9,9-dimethylfluorenyl group, a non-fused aryl group selected from the group consisting of a terphenylyl group and a quaterphenylyl group, a heteroaryl group having 5 to 50 ring atoms, or a group in which two to four groups selected from the aryl group and the heteroaryl group are linked.

8. The compound according to claim 1, wherein $Ar^a$ comprises a fused aryl group selected from the group consisting of a naphthyl group, an anthryl group, a fluorenyl group, a phenanthryl group and a 9,9-dimethylfluorenyl group.

9. The compound according to claim 1, wherein $Ar^a$ is represented by formula (A-1):

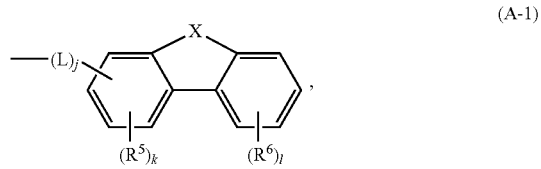

(A-1)

wherein:

L represents an arylene group having 6 to 20 ring carbon atoms or a heteroarylene group having 5 to 20 ring atoms, j is 0 or 1;

X represents an oxygen atom, a sulfur atom, or a divalent group represented by $>CR^7R^8$, wherein $R^7$ and $R^8$ each independently represent a hydrogen atom or a methyl group;

$R^5$ and $R^6$ each independently represent an alkyl group having 1 to 10 carbon atoms, a cycloalkyl group having 3 to 10 ring carbon atoms, an aryl group having 6 to 14 ring carbon atoms, or a heteroaryl group having 5 to 14 ring atoms, k represents an integer of 0 to 2, l represents an integer of 0 to 3, when k is 2, adjacent groups $R^5$ may be bonded to each other to form a hydrocarbon ring, when l is 2 or 3, adjacent groups $R^6$ may be bonded to each other to form a hydrocarbon ring, and $R^5$ and $R^6$ may be bonded to each other to form a hydrocarbon ring.

10. The compound according to claim 9, wherein $Ar^a$ is represented by any of formulae (A-1-1) to (A-1-5):

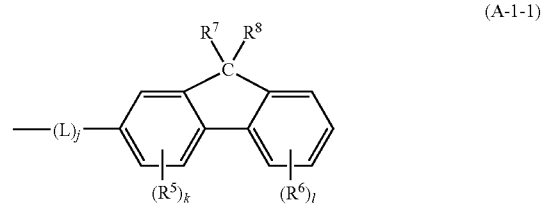

(A-1-1)

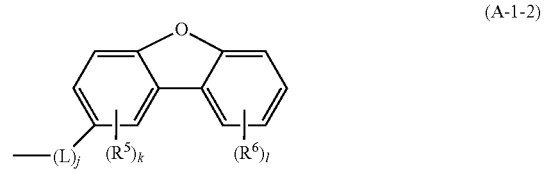

(A-1-2)

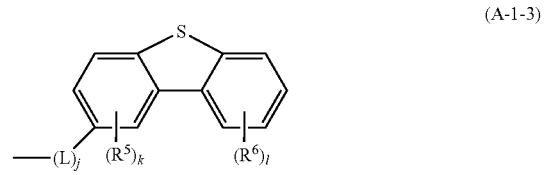

(A-1-3)

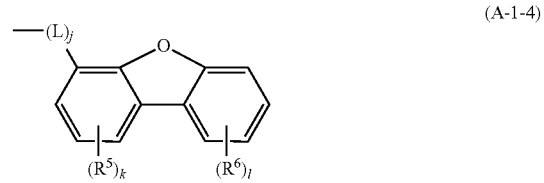

(A-1-4)

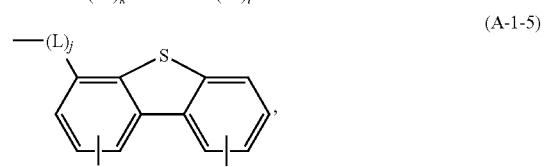

(A-1-5)

wherein L, $R^5$ to $R^8$, j, k, and l are as defined in claim 9.

11. The compound according to claim 9, wherein $Ar^a$ is represented by formula (A-2):

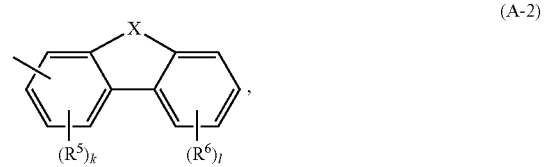

(A-2)

wherein X, $R^5$, $R^6$, k, and l are as defined in claim 9.

12. The compound according to claim 11, wherein $Ar^a$ is represented by any of formulae (A-2-1) to (A-2-3):

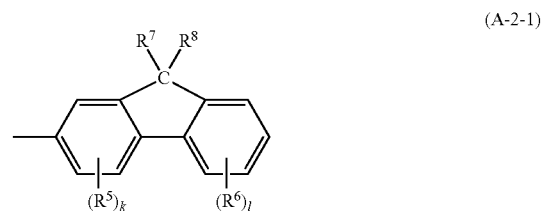

(A-2-1)

-continued (A-2-2)
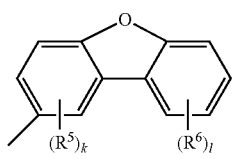

(A-2-3)
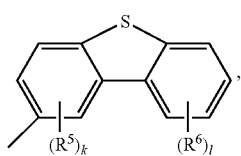

wherein R⁷ and R⁸ each independently represent a hydrogen atom or a methyl group;

$R^5$ and $R^6$ each independently represent an alkyl group having 1 to 10 carbon atoms, a cycloalkyl group having 3 to 10 ring carbon atoms, an aryl group having 6 to 14 ring carbon atoms, or a heteroaryl group having 5 to 14 ring atoms, k represents an integer of 0 to 2, l represents an integer of 0 to 3, when k is 2, adjacent groups $R^5$ may be bonded to each other to form a hydrocarbon ring, when l is 2 or 3, adjacent groups $R^6$ may be bonded to each other to form a hydrocarbon ring, and $R^5$ and $R^6$ may be bonded to each other to form a hydrocarbon ring.

13. The compound according to claim 1, wherein the compound is selected from the following group consisting of:

(H1)
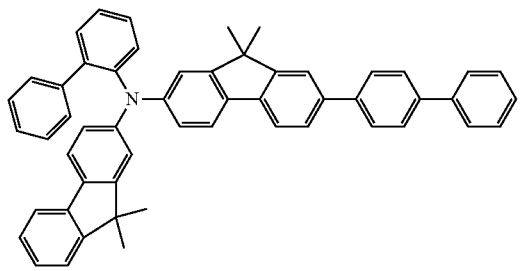

(H2)
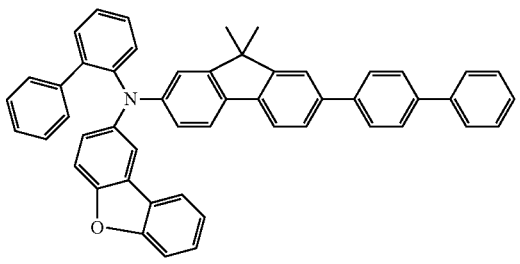

(H3)
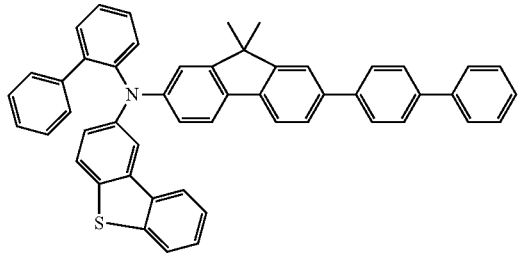

(H4)
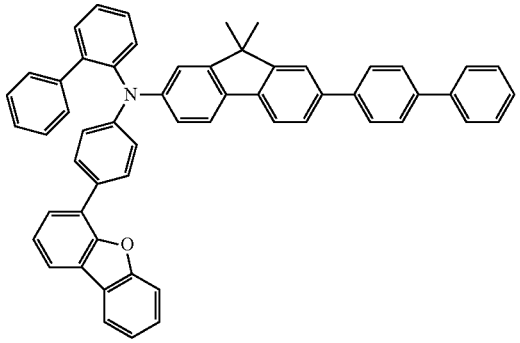

(H5)
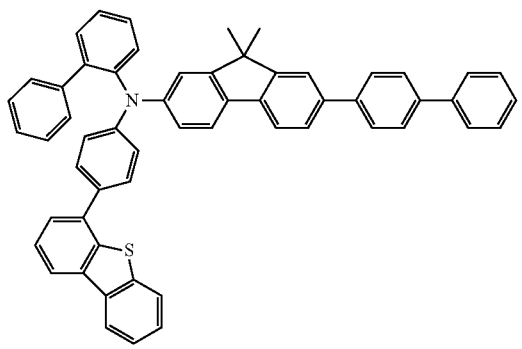

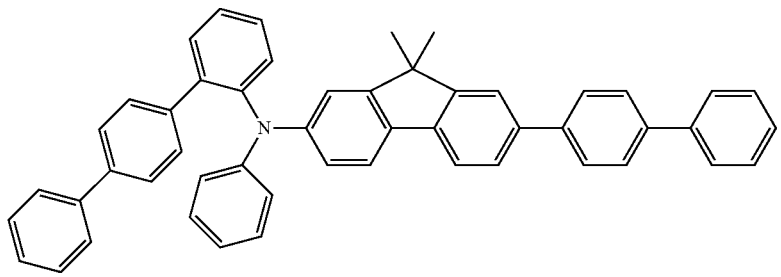
(H6)

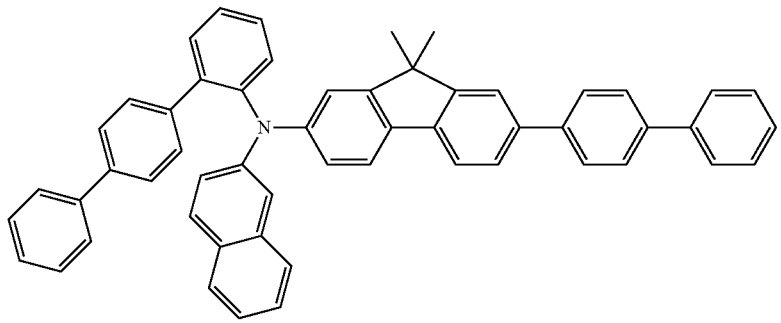
(H7)

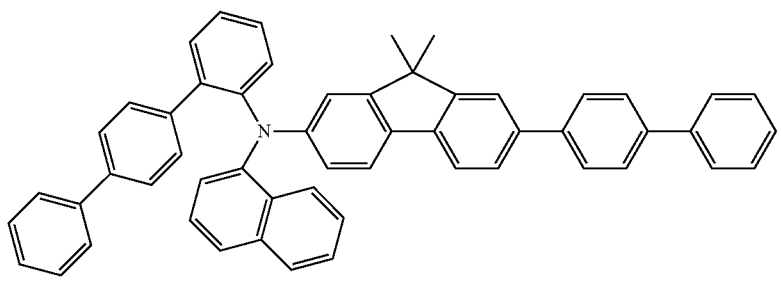
(H8)

and

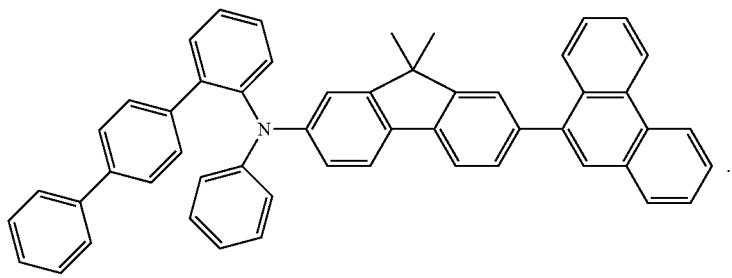
(H9)

14. A material for organic electroluminescence devices, the material comprising the compound according to claim 1.

15. A hole transporting material for an organic electroluminescence device, the hole transporting material comprising the compound according to claim 1.

16. A hole transporting material for an organic electroluminescence device comprising a hole transporting layer adjacent to an acceptor layer, wherein the hole transporting material comprises the compound according to claim 1.

17. An organic electroluminescence device which comprises an organic thin film layer between an anode and a cathode opposite to the anode, wherein at least one layer of the organic thin film layer comprises the compound according to claim 1.

18. An organic electroluminescence device which comprises at least two hole transporting layers and a light emitting layer sequentially between an anode and a cathode opposite to the anode, wherein one of the hole transporting layers comprises the compound according to claim 1 and is not adjacent to the light emitting layer.

19. The organic electroluminescence device according to claim 18, wherein the at least two hole transporting layers comprise a first hole transporting layer on an anode side and a second hole transporting layer on a light emitting layer side, and the first hole transporting layer comprises the compound.

20. The organic electroluminescence device according to claim 19, wherein the second hole transporting layer comprises a compound represented by formula (4):

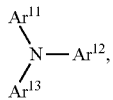

(4)

wherein at least one selected from $Ar^{11}$ to $Ar^{13}$ represents a group represented by formula (4-2) or (4-4), a group not represented by formula (4-2) represents a group represented by formula (4-3) or (4-4) or a substituted or unsubstituted aryl group having 6 to 40 ring carbon atoms, and a group not represented by formula (4-4) represents a group represented by formula (4-2) or (4-3) or a substituted or unsubstituted aryl group having 6 to 40 ring carbon atoms,

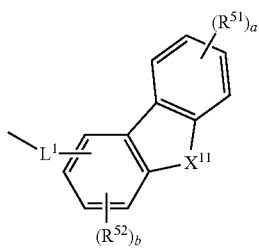

(4-2)

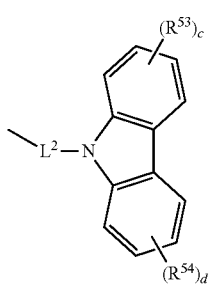

(4-3)

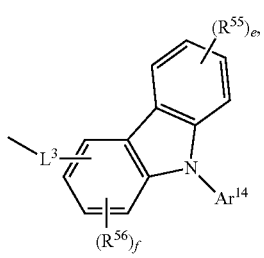

(4-4)

wherein:

$X^{11}$ represents an oxygen atom or a sulfur atom;

$L^1$ to $L^3$ each independently represent a single bond or a substituted or unsubstituted arylene group having 6 to 50 ring carbon atoms, and an optional substituent of $L^1$ to $L^3$ is selected from a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms, an aryl group having 6 to 50 ring carbon atoms, a halogen atom, and a cyano group;

$Ar^{14}$ represents a substituted or unsubstituted aryl group having 6 to 50 ring carbon atoms, and an optional substituent of $Ar^{14}$ is selected from a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms, an aryl group having 6 to 50 ring carbon atoms, a halogen atom, and a cyano group;

$R^{51}$ to $R^{56}$ each independently represent a substituted or unsubstituted, linear or branched alkyl group having 1 to 10 carbon atoms, a substituted or unsubstituted cycloalkyl group having 3 to 10 ring carbon atoms, a substituted or unsubstituted trialkylsilyl group having 3 to 10 carbon atoms, a substituted or unsubstituted triarylsilyl group having 18 to 30 ring carbon atoms, a substituted or unsubstituted alkylarylsilyl group having 8 to 15 carbon atoms, a substituted or unsubstituted aryl group having 6 to 50 ring carbon atoms, a halogen atom, and a cyano group;

adjacent groups selected from $R^{51}$ to $R^{56}$ may be bonded to each other to form a saturated or unsaturated divalent group which completes a ring;

b and f each independently represent an integer of 0 to 3; and a, c, d, and e each independently represent an integer of 0 to 4.

21. The organic electroluminescence device according to claim 20, wherein $L^1$ in formula (4-2) is a substituted or unsubstituted arylene group having 6 to 50 ring carbon atoms.

22. The organic electroluminescence device according to claim 20, wherein $L^3$ in formula (4-4) is a substituted or unsubstituted arylene group having 6 to 50 ring carbon atoms.

23. The organic electroluminescence device according to claim 20, wherein the substituted or unsubstituted aryl group having 6 to 40 ring carbon atoms for $Ar^{11}$ to $Ar^{13}$ in formula (4) is represented by any of formulae (4-5) to (4-7):

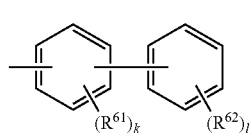

(4-5)

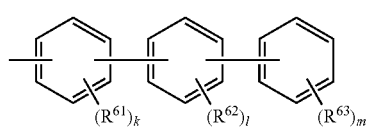

(4-6)

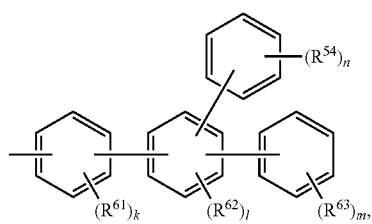

(4-7)

wherein:

$R^{61}$ to $R^{64}$ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms wherein the aryl portion has 6 to 14 ring carbon atoms, an aryl group having 6 to 50 ring carbon atoms, a halogen atom, or a cyano group;

adjacent groups selected from $R^{61}$ to $R^{64}$ may be bonded to each other to form a ring; and k, l, m, and n each independently represent an integer of 0 to 4.

24. The organic electroluminescence device according to claim 18, wherein the organic electroluminescence device comprises an acceptor layer comprising an acceptor material between the anode and the at least two hole transporting layers.

25. The organic electroluminescence device according to claim 19, wherein the first hole transporting layer comprises an acceptor material.

26. The organic electroluminescence device according to claim 24, wherein the acceptor material is represented by any of formulae (A) to (C):

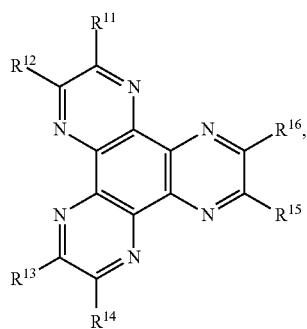

(A)

wherein $R^{11}$ to $R^{16}$ each independently represent a cyano group, —CONH$_2$, a carboxyl group, or —COOR$^{17}$, wherein $R^{17}$ represents an alkyl group having 1 to 20 carbon atoms, provided that $R^{11}$ and $R^{12}$, $R^{13}$ and $R^{14}$, or $R^{15}$ and $R^{16}$ may be bonded to each other to form a group represented by —CO—O—CO—;

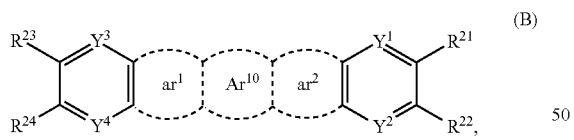

(B)

wherein
$R^{21}$ to $R^{24}$ each independently represent a hydrogen atom, a substituted or unsubstituted alkyl group having 1 to 20 carbon atoms, a substituted or unsubstituted aryl group having 6 to 50 ring carbon atoms, a substituted or unsubstituted heterocyclic group having 5 to 50 ring atoms, a halogen atom, a substituted or unsubstituted alkoxy group having 1 to 20 carbon atoms, a substituted or unsubstituted aryloxy group having 6 to 50 ring carbon atoms, or a cyano group, provided that $R^{21}$ and $R^{22}$, and $R^{23}$ and $R^{24}$ may be bonded to each other to form a ring;

$Y^1$ to $Y^4$ each independently represent —N=, —CH=, or —C(R$^{25}$)=, wherein $R^{25}$ represents a substituted or unsubstituted alkyl group having 1 to 20 carbon atoms, a substituted or unsubstituted aryl group having 6 to 50 ring carbon atoms, a substituted or unsubstituted heterocyclic group having 5 to 50 ring atoms, a halogen atom, a substituted or unsubstituted alkoxy group having 1 to 20 carbon atoms, a substituted or unsubstituted aryloxy group having 6 to 50 ring carbon atoms, or a cyano group;

$Ar^{10}$ represents a fused ring having 6 to 24 ring carbon atoms or a heterocyclic ring having 6 to 24 ring atoms, and $ar^1$ and $ar^2$ each independently represent a ring represented by formula (i) or (ii):

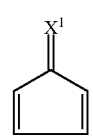

(i)

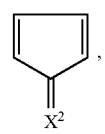

(ii)

wherein $X^1$ and $X^2$ each independently represent a divalent group represented by any of formulae (a) to (g):

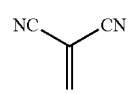

(a)

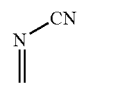

(b)

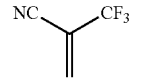

(c)

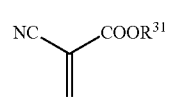

(d)

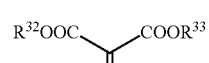

(e)

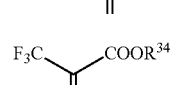

(f)

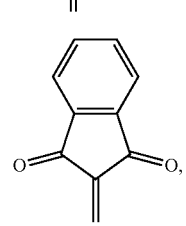

(g)

wherein $R^{31}$ to $R^{34}$ may be the same or different and each represent a hydrogen atom, a substituted or unsubstituted alkyl group having 1 to 20 carbon atoms, a substituted or unsubstituted aryl group having 6 to 50 ring carbon atoms, or a substituted or unsubstituted heterocyclic group having 5 to 50 ring atoms, and $R^{32}$ and $R^{33}$ may be bonded to each other to form a ring; and

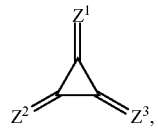
(C)

wherein $Z^1$ to $Z^3$ each independently represent a divalent group represented by formula (h):

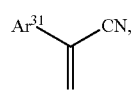
(h)

wherein $Ar^{11}$ represents a substituted or unsubstituted aryl group having 6 to 50 ring carbon atoms or a substituted or unsubstituted heteroaryl group having 5 to 50 ring atoms.

27. The organic electroluminescence device according to claim 18, wherein the light emitting layer comprises at least one fluorescent emitting material selected from the group consisting of an anthracene derivative, a fluoranthene derivative, a styrylamine derivative, and an arylamine derivative.

28. The organic electroluminescence device according to claim 18, wherein the light emitting layer comprises an phosphorescent emitting material.

29. The organic electroluminescence device according to claim 28, wherein the phosphorescent emitting material is an ortho-metallated complex of a metal selected from iridium (Ir), osmium (Os), and platinum (Pt).

30. An electronic equipment which comprises the organic electroluminescence device according to claim 17.

31. The compound according to claim 13, wherein the compound is selected from the group consisting of compounds of the following formulae H1, H6, H7, H8, and H9:

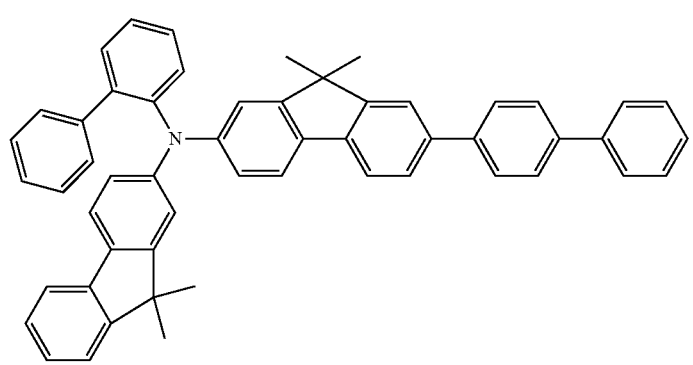
(H1)

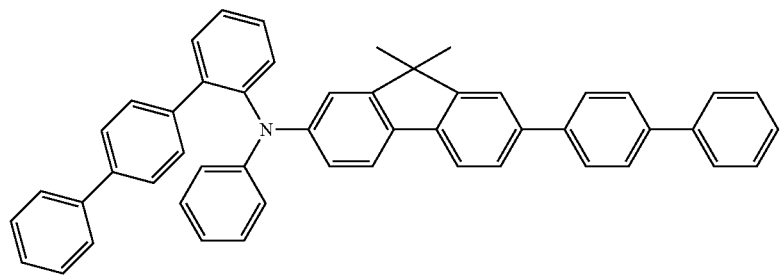
(H6)

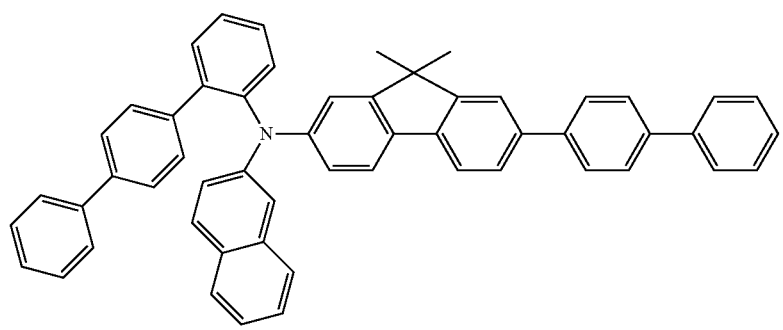
(H7)

-continued
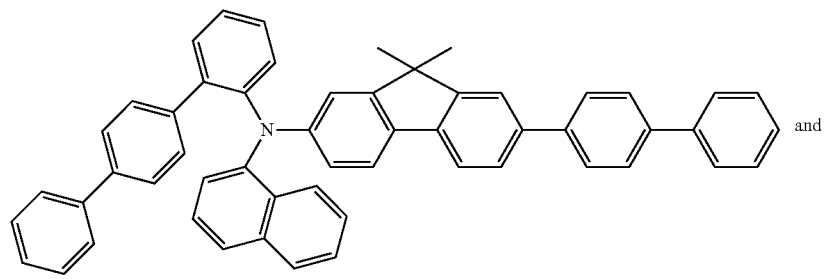
(H8)
and
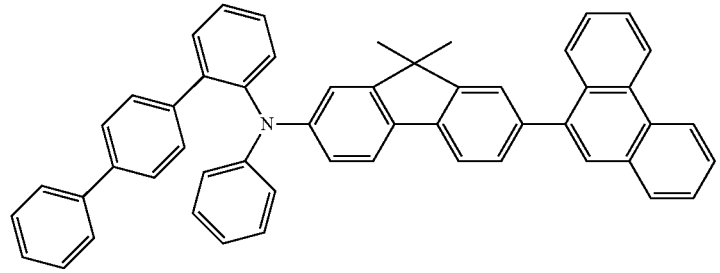
(H9)
* * * * *

UNITED STATES PATENT AND TRADEMARK OFFICE
CERTIFICATE OF CORRECTION

| | |
|---|---|
| PATENT NO. | : 10,411,192 B2 |
| APPLICATION NO. | : 14/910591 |
| DATED | : September 10, 2019 |
| INVENTOR(S) | : Tomoki Kato et al. |

It is certified that error appears in the above-identified patent and that said Letters Patent is hereby corrected as shown below:

In the Claims

Claim 1, Column 377, formula (1)

"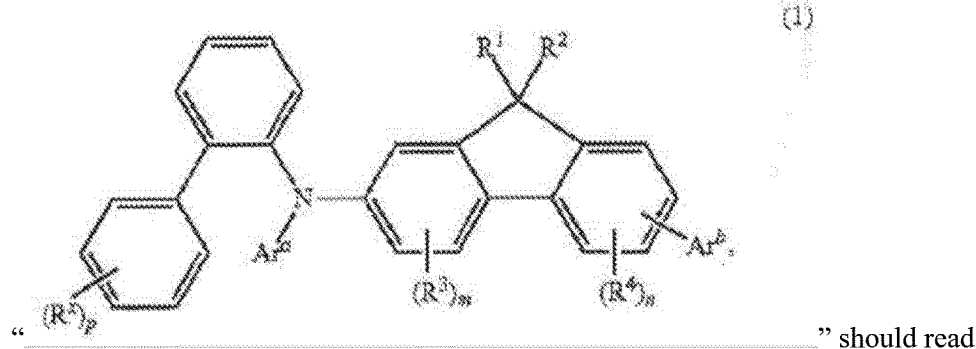" should read

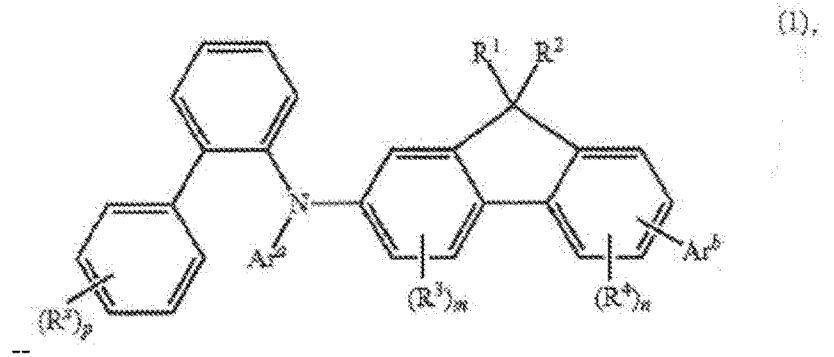

--                                                                                   --

Signed and Sealed this
Fourteenth Day of January, 2020

Andrei Iancu
*Director of the United States Patent and Trademark Office*

CERTIFICATE OF CORRECTION (continued)
U.S. Pat. No. 10,411,192 B2

Claim 1, Column 378, formula (145)

"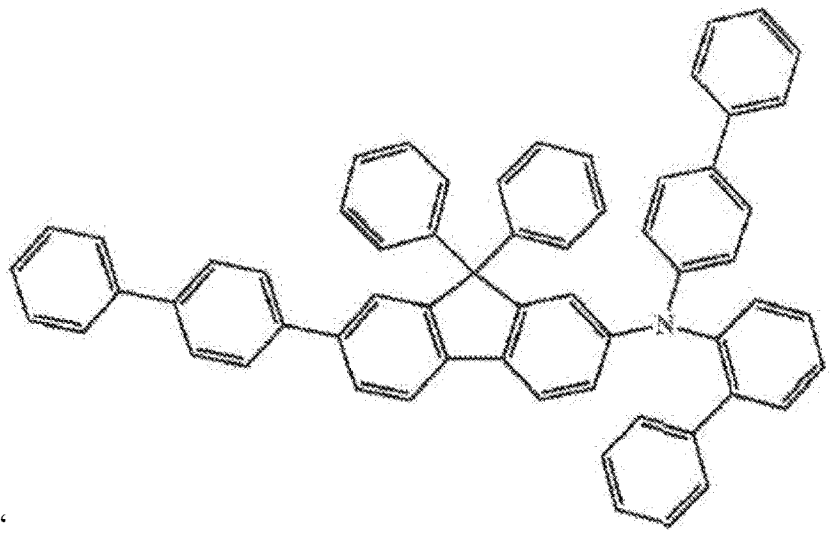" should read

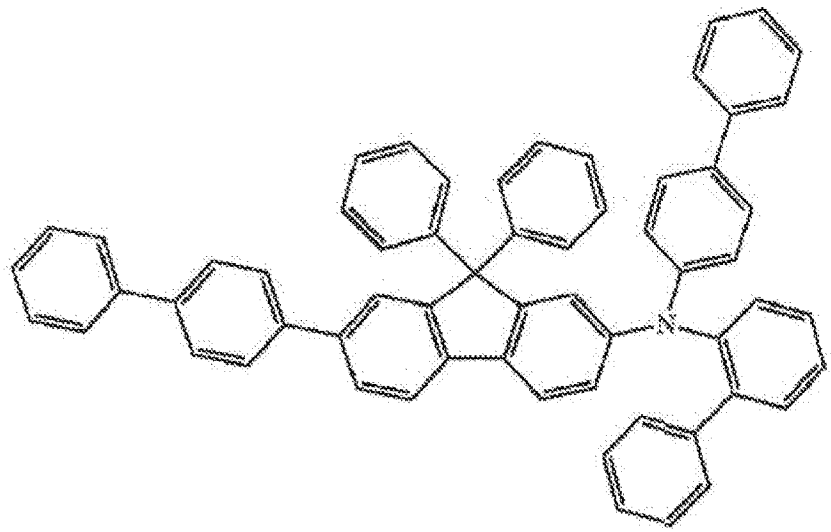
--

CERTIFICATE OF CORRECTION (continued)
U.S. Pat. No. 10,411,192 B2

Claim 2, Column 378, formula (1')

" 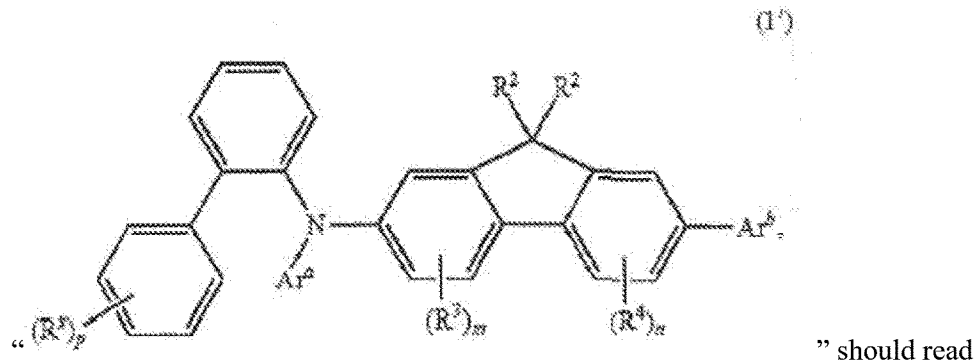 " should read

-- 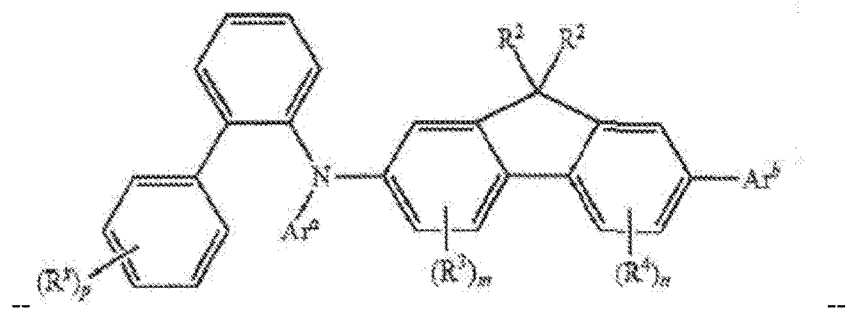 --

Claim 9, Column 379, Formula (A-1)

" 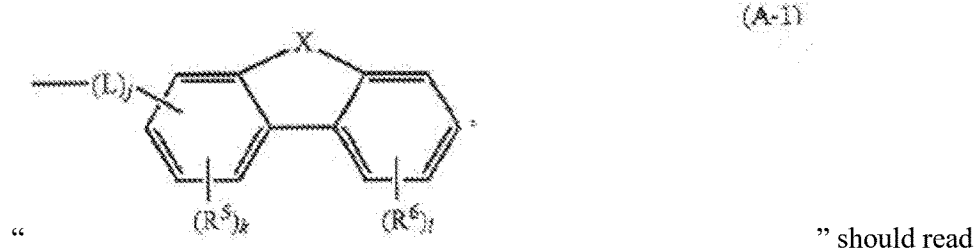 " should read

-- 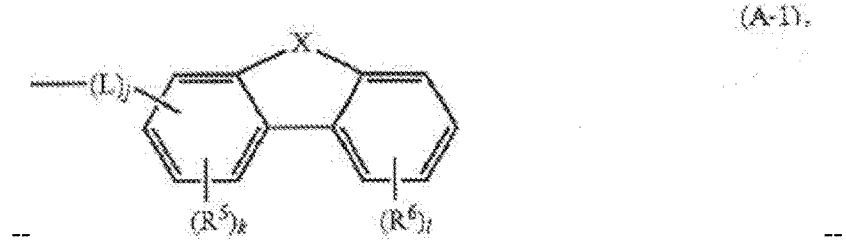 --

Claim 10, Column 380, formula (A-1-5)
" 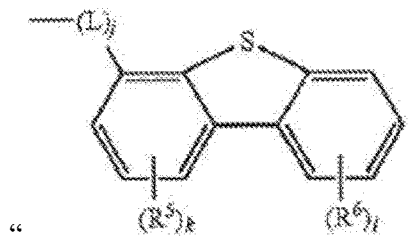 (A-1-5) " should read
-- 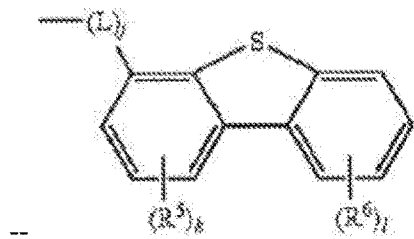 (A-1-5), --
Claim 11, Column 380, formula (A-2)
" 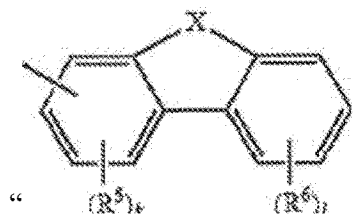 (A-2) " should read
-- 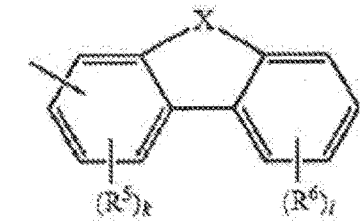 (A-2), --
Claim 12, Column 381, formula (A-2-3)
" 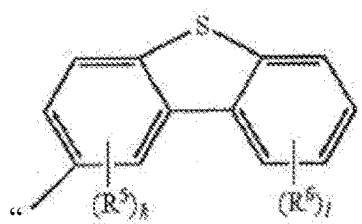 (A-2-3) " should read

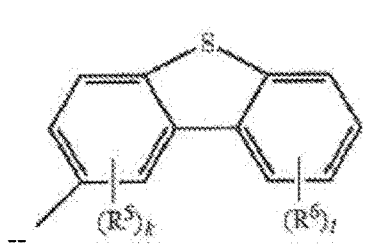
(A-2-3),
Claim 13, Column 383, formula (H9)
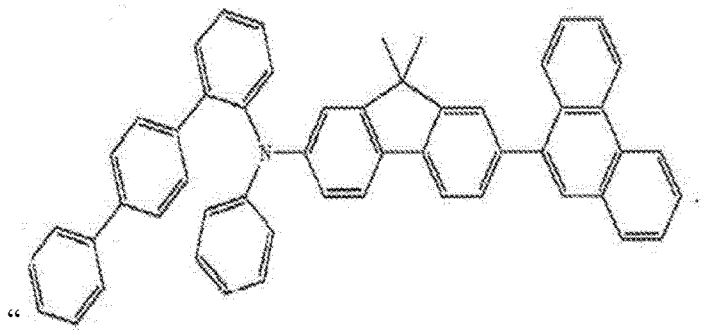
"                                                              "
should read --
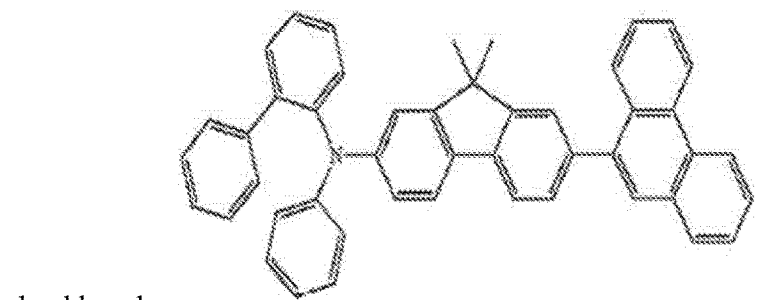
--
Claim 20, Column 385, formula (4)
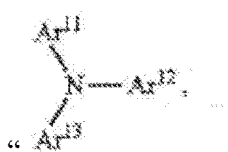
(4)
" " should read
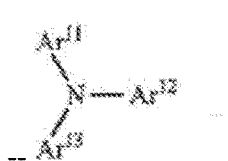
(4), --
Claim 20, Column 385, formula (4-4)

" 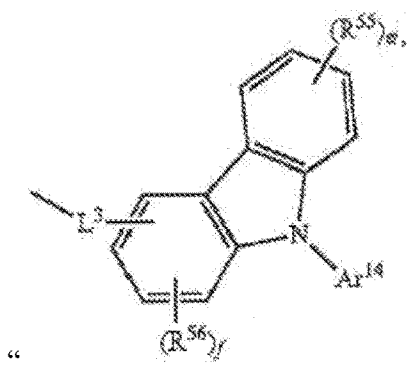 " should read (4-4),
-- 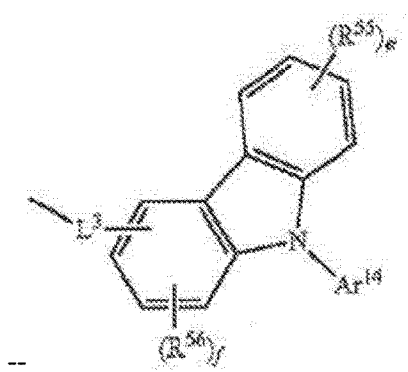 --
Claim 23, Column 386, formula (4-7)
" 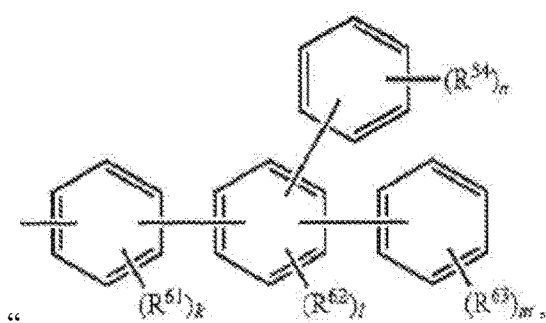 " should read (4-7),
-- 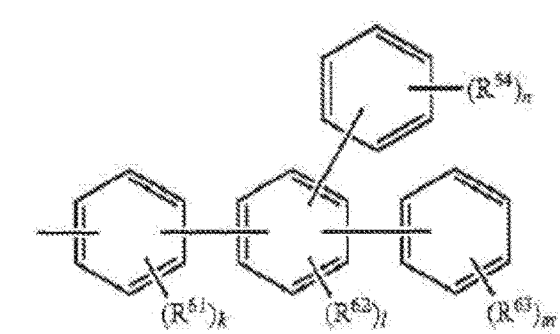 --
Claim 26, Column 387, formula (A)

"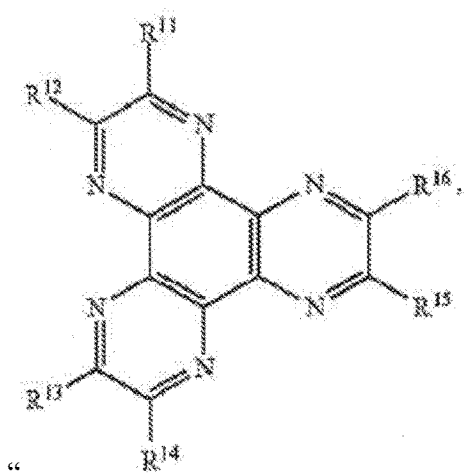" should read
--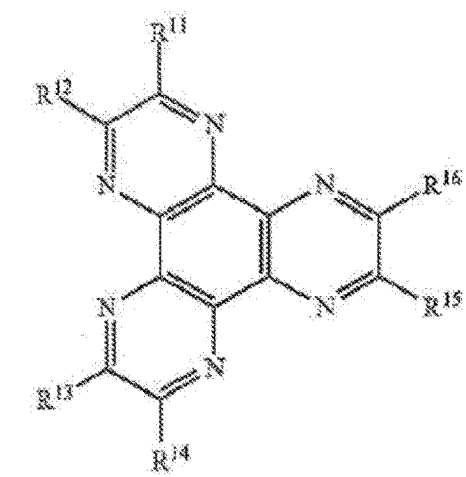--
Claim 26, Column 387, formula (B)
"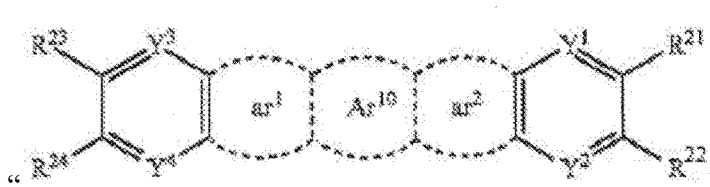" should read
--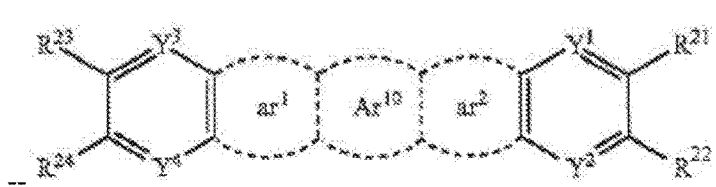--
Claim 26, Column 388, formula (ii)

CERTIFICATE OF CORRECTION (continued)
U.S. Pat. No. 10,411,192 B2

"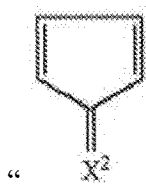" should read (ii)

--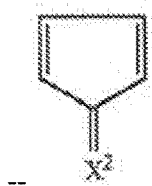--

Claim 26, Column 388, formula (g)

"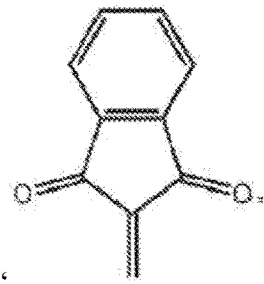" should read (g),

--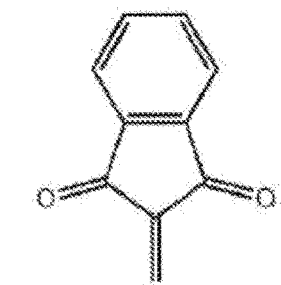--

Claim 26, Column 389, formula (C)

"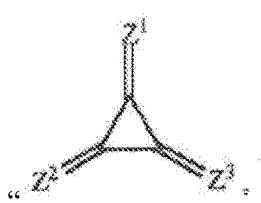" should read (C)

CERTIFICATE OF CORRECTION (continued)
U.S. Pat. No. 10,411,192 B2

Claim 26, Column 389, formula (h)

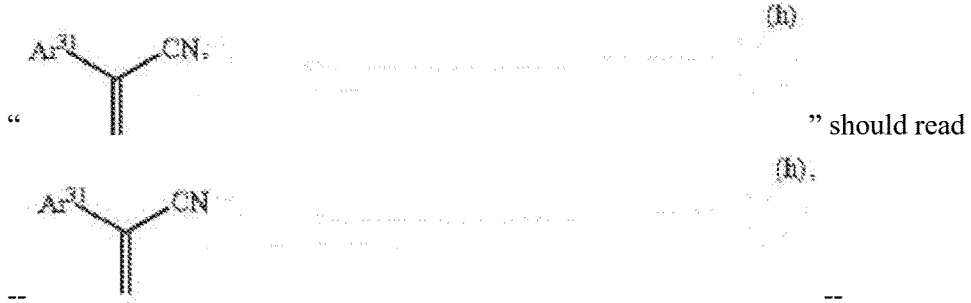

Claim 26, Column 389, Line 22, "wherein $Ar^{11}$" should read --wherein $Ar^{31}$--